United States Patent
Avila et al.

(10) Patent No.: US 10,231,907 B2
(45) Date of Patent: *Mar. 19, 2019

(54) COMPOSITIONS FOR IMPROVING THE HEALTH AND APPEARANCE OF SKIN

(71) Applicant: Algenist Holdings, Inc., Westport, CT (US)

(72) Inventors: Jeff Avila, Millbrae, CA (US); Geoffrey Brooks, Reno, NV (US); Anthony G. Day, San Francisco, CA (US); Aravind Somanchi, Redwood City, CA (US)

(73) Assignee: Algenist Holdings, Inc., Westport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/751,527

(22) Filed: Jun. 26, 2015

(65) Prior Publication Data

US 2015/0366791 A1    Dec. 24, 2015

Related U.S. Application Data

(63) Continuation of application No. 13/531,419, filed on Jun. 22, 2012, now Pat. No. 9,095,733, which is a continuation of application No. 12/176,320, filed on Jul. 18, 2008, now Pat. No. 8,298,548, which is a continuation-in-part of application No. 11/932,782, filed on Oct. 31, 2007, now Pat. No. 8,277,849, which is a continuation of application No. PCT/US2007/001653, filed on Jan. 19, 2007, which is a continuation-in-part of application No. 11/336,426, filed on Jan. 19, 2006, now abandoned, and a continuation-in-part of application No. 11/336,428, filed on Jan. 19, 2006, now abandoned, and a continuation-in-part of application No. 11/336,430, filed on Jan. 19, 2006, now abandoned, and a continuation-in-part of application No. 11/336,431, filed on Jan. 19, 2006, now abandoned, and a continuation-in-part of application No. 11/336,656, filed on Jan. 19, 2006, now abandoned, and a continuation-in-part of application No. 11/337,103, filed on Jan. 19, 2006, now abandoned, and a continuation-in-part of application No. 11/337,171, filed on Jan. 19, 2006, now abandoned.

(60) Provisional application No. 60/961,173, filed on Jul. 18, 2007, provisional application No. 60/816,967, filed on Jun. 28, 2006, provisional application No. 60/832,091, filed on Jul. 20, 2006, provisional application No. 60/838,452, filed on Aug. 17, 2006, provisional application No. 60/872,072, filed on Nov. 30, 2006.

(51) Int. Cl.
| | | |
|---|---|---|
| *A61K 8/02* | (2006.01) |
| *A61K 8/73* | (2006.01) |
| *C12R 1/89* | (2006.01) |
| *A61Q 19/08* | (2006.01) |
| *C08B 37/00* | (2006.01) |
| *C12P 19/04* | (2006.01) |
| *A61K 8/9706* | (2017.01) |

(52) U.S. Cl.
CPC .............. *A61K 8/0241* (2013.01); *A61K 8/73* (2013.01); *A61K 8/9706* (2017.08); *A61Q 19/08* (2013.01); *C08B 37/0003* (2013.01); *C12P 19/04* (2013.01); *C12R 1/89* (2013.01)

(58) Field of Classification Search
None
See application file for complete search history.

(56) References Cited

U.S. PATENT DOCUMENTS

| | | |
|---|---|---|
| 3,981,996 A | 9/1976 | Leigh |
| 3,983,008 A | 9/1976 | Shinozaki et al. |
| 4,373,434 A | 2/1983 | Alexander et al. |
| 4,417,415 A | 11/1983 | Cysewski et al. |
| 4,742,164 A | 5/1988 | Iguchi et al. |
| 4,901,635 A | 2/1990 | Williams |
| 4,906,746 A | 3/1990 | Barnier et al. |
| 5,089,481 A | 2/1992 | Muto et al. |
| 5,198,217 A | 3/1993 | Vedros |
| 5,338,673 A | 8/1994 | Thepenier et al. |
| 5,401,504 A | 3/1995 | Das et al. |
| 5,508,033 A | 4/1996 | Briand |
| 5,521,090 A | 5/1996 | Doncheck et al. |

(Continued)

FOREIGN PATENT DOCUMENTS

| | | |
|---|---|---|
| EP | 0996740 B1 | 9/2005 |
| JP | 04-222593 A | 8/1992 |

(Continued)

OTHER PUBLICATIONS

"Buffer solution," *Wikipedia, the free encyclopedia*, 1-6, (2011). [Retrieved from the Internet May 11, 2011: <http ://en.wikipedia.org/wiki/Buffer_solution>].

(Continued)

*Primary Examiner* — Shaojia A Jiang
*Assistant Examiner* — Bahar Craigo
(74) *Attorney, Agent, or Firm* — Locke Lord LLP

(57) ABSTRACT

Provided herein are microalgal skin care compositions and methods of improving the health and appearance of skin. Also provided are methods of using polysaccharides for applications such as topical personal care products, cosmetics, and wrinkle reduction compositions. The invention also provides novel decolorized microalgal compositions useful for improving the health and appearance of skin. The invention also includes insoluble polysaccharide particles for application to human skin.

15 Claims, 20 Drawing Sheets
Specification includes a Sequence Listing.

(56) References Cited

U.S. PATENT DOCUMENTS

| | | |
|---|---|---|
| 5,643,585 A | 7/1997 | Arad et al. |
| 5,658,767 A | 8/1997 | Kyle |
| 5,680,812 A | 10/1997 | Linsgeseder |
| 5,685,218 A | 11/1997 | Kemper |
| 5,826,500 A | 10/1998 | Kemper |
| 5,878,747 A | 3/1999 | Enomoto et al. |
| 5,916,577 A | 6/1999 | Golz et al. |
| 6,166,231 A | 12/2000 | Hoeksema |
| 6,328,987 B1 | 12/2001 | Marini |
| 6,440,431 B1 | 8/2002 | Yoshida et al. |
| 6,551,596 B2 | 4/2003 | Kralovec |
| 6,680,062 B2 | 1/2004 | Muizzuddin et al. |
| 6,750,048 B2 | 6/2004 | Ruecker et al. |
| 6,767,899 B1 | 7/2004 | Kay et al. |
| 7,025,966 B2 | 4/2006 | Majmudar |
| 7,037,697 B2 | 5/2006 | Kumar et al. |
| 7,063,957 B2 | 6/2006 | Chen |
| 7,135,290 B2 | 11/2006 | Dillon |
| 7,303,753 B2 | 12/2007 | Majmudar |
| 7,351,558 B2 | 4/2008 | Ruecker et al. |
| 7,662,598 B2 | 2/2010 | Ruecker et al. |
| 7,678,931 B2 | 3/2010 | Fichtali et al. |
| 7,781,193 B2 | 8/2010 | Ruecker et al. |
| 8,277,849 B2 | 10/2012 | Dillon et al. |
| 8,298,548 B2 | 10/2012 | Avila et al. |
| 8,557,249 B2 | 10/2013 | Brooks et al. |
| 8,927,522 B2 | 1/2015 | Coragliotti et al. |
| 8,932,652 B2 | 1/2015 | Dillon et al. |
| 9,095,733 B2 | 8/2015 | Avila et al. |
| 2001/0055627 A1 | 12/2001 | Guthrie et al. |
| 2003/0078233 A1 | 4/2003 | Arad et al. |
| 2003/0134803 A1 | 7/2003 | Cherr et al. |
| 2003/0198730 A1 | 10/2003 | Stewart |
| 2003/0207947 A1 | 11/2003 | Desouza et al. |
| 2004/0168648 A1 | 9/2004 | Ayers |
| 2004/0180126 A1 | 9/2004 | Kies |
| 2004/0185063 A1 | 9/2004 | Ray |
| 2004/0197790 A1 | 10/2004 | Stanton et al. |
| 2004/0228875 A1 | 11/2004 | Leclerc et al. |
| 2005/0042355 A1 | 2/2005 | Perlman et al. |
| 2005/0089501 A1 | 4/2005 | Berardesca et al. |
| 2005/0106657 A1 | 5/2005 | Rodriguez et al. |
| 2005/0123499 A1 | 6/2005 | Majmudar |
| 2005/0129831 A1 | 6/2005 | Fabritius |
| 2005/0171053 A1 | 8/2005 | Blakemore et al. |
| 2005/0239742 A1 | 10/2005 | Place et al. |
| 2005/0261240 A1 | 11/2005 | Maguire et al. |
| 2006/0122410 A1 | 6/2006 | Fichtali et al. |
| 2006/0183184 A1 | 8/2006 | Bosley et al. |
| 2006/0210523 A1 | 9/2006 | Majmudar |
| 2006/0233845 A1 | 10/2006 | Lukowski et al. |
| 2006/0286205 A1 | 12/2006 | Fichtali et al. |
| 2007/0166266 A1 | 7/2007 | Dillon et al. |
| 2007/0166449 A1 | 7/2007 | Dillon et al. |
| 2007/0166797 A1 | 7/2007 | Dillon et al. |
| 2007/0167396 A1 | 7/2007 | Dillon et al. |
| 2007/0167397 A1 | 7/2007 | Dillon et al. |
| 2007/0167398 A1 | 7/2007 | Dillon et al. |
| 2007/0191303 A1 | 8/2007 | Dillon et al. |
| 2007/0297996 A1 | 12/2007 | Tanner |
| 2008/0124286 A1 | 5/2008 | Lisson |
| 2008/0206274 A1 | 8/2008 | Majmudar et al. |
| 2009/0004715 A1 | 1/2009 | Trimbur et al. |
| 2009/0017058 A1 | 1/2009 | Arad et al. |
| 2009/0274736 A1 | 11/2009 | Dillon et al. |
| 2009/0285850 A1 | 11/2009 | Dillon et al. |
| 2009/0305942 A1 | 12/2009 | Day et al. |
| 2011/0124544 A1 | 5/2011 | He et al. |
| 2012/0149075 A1 | 6/2012 | Day et al. |
| 2014/0170184 A1 | 6/2014 | Brooks et al. |

FOREIGN PATENT DOCUMENTS

| | | |
|---|---|---|
| JP | 2002069443 A | 8/2002 |
| WO | WO 94/010131 A1 | 5/1994 |
| WO | WO 97/000689 A1 | 1/1997 |
| WO | WO 00/075282 A1 | 12/2000 |
| WO | WO 01/81603 A2 | 11/2001 |
| WO | WO 02/011746 A2 | 2/2002 |
| WO | WO 03/041679 A2 | 5/2003 |
| WO | WO 03/072775 A1 | 9/2003 |
| WO | WO 04/108941 A1 | 12/2004 |
| WO | WO 07/066340 A1 | 6/2007 |
| WO | WO 07/084769 A2 | 7/2007 |
| WO | WO 07/136428 A2 | 11/2007 |
| WO | WO 10/054322 A1 | 5/2010 |
| WO | WO 10/111710 A1 | 9/2010 |
| WO | WO 13/036726 A1 | 9/2012 |
| WO | WO 14/186395 A1 | 11/2014 |

OTHER PUBLICATIONS

"Guidance for Industry: Container Closure Systems for Packaging Human Drugs and Biologics", U.S. Department of Health and Human Services, Food and Drug Administration, 1-35, (1999).
"All Natural Food Mask," The Raw Food Institute, 2 pages, (2013). [Retrieved from the Internet May 20, 2013: <URL: http://http://therawfoodinistitute.com/raw-food-articles/all-natural-food-mask/>].
Alignments, Sequence Search report, Gen Bank ACQ5U8S3_9RHOD Dec. 7, 2004.
Allen et al., "Carotenoid Distribution in Certain Naturally Occurring Algae and in some Artificially Induced Mutants of Chlorella pyrenoidosa," J. gen. Microbial., (23)98-108, (1960).
Ansel et al., Pharmaceutical Dosage Forms and Drug Delivery Systems, published by Lippincott Williams & Wilkins, p. 55-56 (1999).
Arad et al., "Effects of Nitrogen on Polysaccharide Production in a Porphyridium," Applied and Environmental Microbiology, 54(10):2411-2414 (1988).
Baumann, "How to Prevent Photoaging?," Journal of Investigative Dermatology, 125:xii-xiii, (2005).
Becker, "Microalgae in Human and Animal Nutrition," Handbook of Microalgal Culture, Blackwell, p. 312-351, (2004).
Cesarini et al., "Immediate Effects of UV Radiation on the Skin: Modification by an Antioxidant Complex Containing Carotenoids" Photoderm., Photoimmun. & Photomed. 19:182-189 (2003).
Conti et al., "Seasonal influences on stratum corneum ceramide 1 fatty acids and the influence of topical essential fatty acids," International Journal of Cosmetics Science, 18:1-12, (1996).
Dallimore, "Perfumery," Chemistry and Technology of the Cosmetics and Toiletries Industry, edited by D.F. Williams and W.H. Schmitt, published by Chapman & Hall, 258-259, (1992).
Dvir et al., "Soluble polysaccharide and biomass of red microalgal Porphyridium sp. alter intestinal morphology and reduce serum cholesterol in rats", British J Nutrition 84(4):469-476, (2000).
El-Sheekh et al., "Variation of Some Nutritional Constituents and Fatty Acid Profiles of Chlorella vulgaris Beijerinck Grown under Auto and Heterotrophic Conditions," International Journal of Botany, 5(2):153-159, (2009).
EPO Application No. EP 10756997.2, Supplementary European Search Report and European Search Opinion, dated Jul. 23, 2014.
EPO Supplementary European Search Report and European Search Opinion for application EP07718342 dated Nov. 7, 2012.
Eteshola et al., "Red microalga exopolysaccharides: 2. Study of rheology, morphology and thermal gelation of aqueous preparations," Acta Polym., 49:549-556, (1998).
Evans et al., "A statistical analysis of hair breakage. II. Repeated grooming experiments," J. Cosmet. Sci., 61:439-455, (2010).
Fabregas et al., "In vitro inhibition of the replication of haemorrhagic septicaemia virus (VHSV) and African swine fever virus (ASFV) by extracts from marine microalgae," Antiviral Research, 44:67-73, (1999).
Ficner et al, "Isolation, Crystallization, Crystal Structure Analysis and refinement of B-Phycoerythin from the Red Alga Pophyridium sordidum at 2.2 A Resolution", J. Mol. Biol. 228(3):935-950, (1992).

(56) References Cited

OTHER PUBLICATIONS

Gennaro, *Remington: The Science and Practice of Pharmacy* Lippincott Williams & Wilkins, 20th edition, p. 1017-1020 and 1694-1699. (2000).
Geresh, et al., "Characterization of the extracelluar polysaccharide of *Porphyridium* sp. molecular weight determination and rheological properties", *Carbohydrate Polymers* 50:183-189, (2002).
Geresh, et al., "The extracellular polysaccharide of the Red Microalgae: Chemistry and Rheology", *Bioresource Technology* 38(2-3):195-201, (1991).
Gloaguen et al., "The extracellular polysaccharide of *Porphyridium* sp.: an NMR study of lithium-resistant oligosaccharidic fragments," *Carbohydrate Research*, 339:97-103, (2004).
Gourdon, D. et al. Lubrication by the red microalgae *Porphyridium* sp. polysaccharide: American Physical Society, March Meeting, Mar. 22-26, 2004, Palais des Congres de Montreal, Montreal, Quebec, Canada, Meeting ID: Mar. 2004, abstract #H8.009—English Abs.
Gourdon, D. et al. "Superlubricity of a natural polysaccharide from the alga *Porphyridium* sp.," *American Physical Society, APS March Meeting*, Mar. 21-25, 2005 abstract #V31.010—English Abstract only.
Greul et al., "Photoprotection of UV-Irradiated Human Skin: An Antioxidative Combination of Vitamins E and C, Carotenoids, Selenium and Proanthocyanidins," *Skin Pharmacology and Applied Skin Physiology*, 15:307-315, (2002).
Guerin et al., "Haematococcus astaxanthin: applications for human health and nutrition," *Trends in Biotechnology*, 21(5):210-216, (2003).
Guil-Guerrero et al., "Functional properties of the biomass of three microalgal species", *J. Food Engin.* 65:511-517, (2004).
Guzman et al., "Anti-inflammatory and Immunomodulatory Activities of Polysaccharide from Chlorella stigmatophora and Phaeodactylum tricornutum", *Phytother. Res.* 17:665-670, (2003).
Holzer, "Water, pH and buffers," *Georgia Tech Prism Web Pages*, 1-6, (2002). [Retrieved from the Internet Jan. 2011: <http://www.prism.gatech.edu/-gh19/b1510/water.htm>].
Huheihel, M. et al. "Activity of *Porphyridium* sp. polysaccharide against herpes simplex viruses in vitro and in vivo" *J. Biochem. Biophys. Methods* Jan. 4, 2002;50(2-3)189-200.
International Preliminary Report on Patentability for PCT/US2007/001653 dated Sep. 9, 2008.
International Preliminary Report on Patentability for PCT/US2007/001319 dated Oct. 21, 2008.
International Preliminary Report on Patentability for PCT/US2010/029081 dated Sep. 27, 2011.
International Search Report and Written Opinion for PCT/US2007/001319 dated Sep. 19, 2008.
International Search Report and Written Opinion for PCT/US2007/001653 dated Jul. 28, 2008.
International Search Report or PCT/US2010/029081 dated May 27, 2010.
Kamiya, "Effects of Blue Light and Ammonia on Nitrogen Metabolism in a Colorless Mutant of Chlorella," *Plant Celll Physiol.*, 30(4):513-521, (1989).
Kruckeberg et al., "The HXT2 gene of *Saccharomyces cerevisiae* is required for high-affinity glucose transport", *Mol. Cell. Biol.* 10(11):5903-5913, (1990).
Lapidot, M. et al. "Stable Chloroplast Transformation of the Unicellular Red Alga Porphyridium Species", *Plant Physiol.* May 2002;129(1):7-12.
Lee et al., "Dietary Lutein Reduces Ultraviolet Radiation-Induced Inflammation and Immunosuppression", *J. Invest. Dermatol.* 122:510-517, (2004).
Leffingwell et al., "Cooling Ingredients and Their Mechanism of Action," *Handbook of Cosmetic Science and Technology*, 3rd ed., Informa Healthcare, pp. 661-675, (2009).
Liang et al., "Current microalgal health food R&D activities in China", *Hydrobiologia* 512:45-48, (2004).

Matsui et al., "Sulfated polysaccharides from Red Microalgae Have Antiinflammatory Properties In Vitro and In Vivo," *Applied Biochemistry and Biotechnology*, 104:13-22, (2003).
Merchuk et al. "Light/Dark Cycles in the Growth of the Red Microalga *Porphyridium* Sp.". *Biotechnol Bioeng*. Sep. 20, 1998;59(6):705-13.
Mitsuhashi et al, "X-Ray Structure of Beta-Carbonic Anhydrase from the Red Alga, Porphyridium purpureum, Reveals a Novel Catalytic Site for $CO_2$ Hydration", *J. Biol. Chem.* 275(8):5521-5526, (2000).
Miyachi, *World Catalogue of Algae*, 2nd Edition. Edited by Shigetoh, Miyachi, published by the Japan Scientific Societies Press, p. 58-74 (1989).
Muggli, "Systemic evening primrose oil improves the biophysical skin parameters of healthy adults", *Intl. J. Cosmetic Sci.* 27:243-249, (2005).
NCB' submission L43357, "Chlorella vulgaris chloroplast large subunit ribosomal RNA (rrnL) gene," [online], (2005). [Retrieved from the internet May 14, 2010: <URL: http://www.ncbi.nlm.nih.gov/nuccore/17028301>].
Nghiem, et al., "Ultraviolet A Radiation Suppresses an Established Immune Response: Implications for Sunscreen Design", *J. Invest. Derm.* 117(5):1193-1198 (2001).
Olaitan et al., "Polysaccharides of Chlorella pyrenoidosa," *Biochem. J.*, 82:509-519, (1962).
PCT International Preliminary Report on Patentability (Chapter I) dated May 10, 2011 for application PCT/US09/63740.
PCT International Search Report and Written Opinion of the International Searching Authority for application PCT/US2014/037898 dated Oct. 23, 2014.
PCT Search Report dated Mar. 2, 2010 for application PCT/US09/63740.
Petit et al., "Ultrasonic depolymerization of an exopolysaccharide produced by a bacterium isolated from a deep-sea hydrothermal vent polychaete annelid," *Ultrasonics Sonochemistry*, 14(2):107-112, (2007).
Primavera et al., "Clinical and instrumental evaluation of a food supplement in improving skin hydration", *Intl. J. Cosmetic Science* 27:199-204, (2005).
Pulz et al., "Valuable products from biotechnology of micoralgae," *Appl Microbiol Biotechnol*, 65:635-648, (2004).
Rudnic et al., "Oral Solid Dosage Forms" in *Remington's Pharmaceutical Sciences*, 18th Edition, editor Alfonso R. Gennaro, published by Mack Publishing Company, p. 1633-1638 (1990).
Sansawa et al., "Production of Intracellular Phytochemicals in Chlorella under Heterotrophic Conditions," *J Biosci. Bioeng.*, 98(6):437-444, (2004).
Scipio, "A Red Marine Algae Sex Gel" website: http://www.antiviralgel.com/, download date Aug. 8, 2008.
Seffernick et al., "Melamine deaminase and atrazine chlorohydrolase: 98 percent identical but functionally different", *J. Bacteriology* 183(8):2405-2410, (2001).
Shrestha et al., "A glycoprotein noncovalently associated with cell-wall polysaccharide of the red microalga *Porphyridium* sp.(Rhodophyta)", *J. Phycol.* 40:568-580, (2004).
Sibbald et al., "Preparing the Wound Bed 2003: Focus on Infectin and Inflammation," *Ostomy/Wound Management.*, 49(11):24-51, (2003).
Simon-Bercovitch, et al., "Cell wall formation during the cell cycle of *Porphyridium* sp. (Phodophyta)", *J. Phycol.* 35:78-83, (1999).
Storey et al., "Eicosapentaenoic Acid and Docosahexaenoic Acid Reduce UVB- and TNF-$\alpha$-induced IL-8 Secretion in Keratinocytes and UVB-induced IL-8 in Fibroblasts", *J. Invest. Dermatol.* 124:248-255, (2005).
Talyshinsky et al., "Anti-viral activity of red microalgal polysaccharides against retroviruses", *Cancer Cell Int'l.* 2(8):1-7 (2002).
Tannin-Spitz et al., "Antioxidant activity of the polysaccharide of the red microalga *Porphyridium* sp," *Journal of Applied Mycology*, 17(3):215-22, (2005).
U.S. Appl. No. 11/336,426, Examiner Interview Summary Record and Restriction Requirement dated Nov. 3, 2008.
U.S. Appl. No. 11/336,426, Examiner Interview Summary Record and Advisory Action dated Sep. 9, 2009.

(56) References Cited

OTHER PUBLICATIONS

U.S. Appl. No. 11/336,426, Examiner Interview Summary Record and Advisory Action dated Oct. 14, 2009.
U.S. Appl. No. 11/336,426, Examiner Interview Summary Record dated Jun. 29, 2010.
U.S. Appl. No. 11/336,426, Examiner Interview Summary Record and Abandonment Notice dated Apr. 12, 2011.
U.S. Appl. No. 11/336,426, Final Office Action dated Jun. 22, 2009.
U.S. Appl. No. 11/336,426, Non-Final Office Action dated Feb. 26, 2010.
U.S. Appl. No. 11/336,426, Non-Final Office Action dated Aug. 3, 2010.
U.S. Appl. No. 11/336,426, Restriction Requirement dated Apr. 4, 2008.
U.S. Appl. No. 11/336,428, Examiner Interview Summary Record and Abandonment Notice dated Mar. 23, 2009.
U.S. Appl. No. 11/336,428, Non-Final Office Action dated Jul. 9, 2008.
U.S. Appl. No. 11/336,428, Restriction Requirement dated Apr. 14, 2008.
U.S. Appl. No. 11/336,430, Examiner Interview Summary Record and Abandonment Notice dated Aug. 4, 2009.
U.S. Appl. No. 11/336,430, Restriction Requirement dated Apr. 25, 2008.
U.S. Appl. No. 11/336,430, Restriction Requirement dated Sep. 26, 2008.
U.S. Appl. No. 11/336,431, Non-Final Office Action dated Nov. 2, 2007.
U.S. Appl. No. 11/336,431, Restriction Requirement dated Mar. 30, 2007.
U.S, Appl. No. 11/336,431, Restriction Requirement dated Dec. 18, 2006.
U.S. Appl. No. 11/336,656, Non-Final Office Action dated Aug. 26, 2008.
U.S. Appl. No. 11/336,656, Restriction Requirement dated Mar. 4, 2008.
U.S. Appl. No. 11/337,103, Advisory Action dated Feb. 18, 2010.
U.S. Appl. No. 11/337,103, Advisory Action dated Apr. 6, 2010.
U.S. Appl. No. 11/337,103, Advisory Action dated Dec. 18, 2009.
U.S. Appl. No. 11/337,103, Examiner Interview Summary Record and Abandonment Notice dated Apr. 26, 2011.
U.S. Appl. No. 11/337,103, Final Office Action dated Aug. 4, 2009.
U.S. Appl. No. 11/337,103, Non-Final Office Action dated Aug. 13, 2010.
U.S. Appl. No. 11/337,103, Non-Final Office Action dated Nov. 7, 2008.
U.S. Appl. No. 11/337,103, Restriction Requirement dated Mar. 18, 2008.
U.S. Appl. No. 11/337,171, Examiner Interview Summary Record and Abandonment Notice dated Apr. 29, 2009.
U.S. Appl. No. 11/337,171, Non-Final Office Action dated Aug. 13, 2008.
U.S. Appl. No. 11/337,171, Restriction Requirement dated Mar. 5, 2008.
U.S. Appl. No. 11/932,754, Examiner Interview Summary Record dated Oct. 5, 2010.
U.S. Appl. No. 11/932,754, Final Office Action dated Aug. 9, 2011.
U.S. Appl. No. 11/932,754, Non-Final Office Action dated Dec. 23, 2010.
U.S. Appl. No. 11/932,754, Restriction Requirement dated Aug. 3, 2010.
U.S. Appl. No. 11/932,782, Advisory Action dated Sep. 16, 2010.
U.S. Appl. No. 11/932,782, Election of Species Requirement dated Aug. 16, 2011.
U.S. Appl. No. 11/932,782, Final Office Action dated May 20, 2010.
U.S. Appl. No. 11/932,782, Non-Final Office Action dated Jan. 12, 2011.
U.S. Appl. No. 11/932,782, Non-Final Office Action dated Jan. 24, 2011.
U.S. Appl. No. 11/932,782, Non-Final Office Action dated Mar. 20, 2012.
U.S. Appl. No. 11/932,782, Non-Final Office Action dated Nov. 19, 2009.
U.S. Appl. No. 11/932,782, Notice of Allowance dated Jul. 18, 2012.
U.S. Appl. No. 11/932,782, Restriction Requirement dated Jun. 26, 2009.
U.S. Appl. No. 12/176,320, Final Office Action dated Sep. 22, 2011.
U.S. Appl. No. 12/176,320, Non-Final Office Action dated Mar. 15, 2011.
U.S. Appl. No. 12/176,320, Non-Final Office Action dated Dec. 14, 2011.
U.S. Appl. No. 12/176,320, Notice of Allowance dated Sep. 4, 2012.
U.S. Appl. No. 12/176,320, Restriction Requirement dated Nov. 29, 2010.
U.S. Appl. No. 12/430,036, Final Office Action dated Aug. 2, 2011.
U.S. Appl. No. 12/430,036, Non-Final Office Action dated Dec. 14, 2010.
U.S. Appl. No. 13/128,217, Non-Final Office Action dated Mar. 29, 2013.
U.S. Appl. No. 13/128,217, Notice of Allowance dated Aug. 7, 2013.
U.S. Appl. No. 13/260,546, Final Office Action dated Jan. 30, 2014.
U.S. Appl. No. 13/260,546, Non-Final Office Action dated Jul. 1, 2013.
U.S. Appl. No. 13/260,546, Notice of Allowance dated Aug. 29, 2014.
U.S. Appl. No. 13/260,546, Requirement for Restriction/Election dated Feb. 19, 2013.
U.S. Appl. No. 13/531,419, Final Office Action dated Jan. 23, 2013.
U.S. Appl. No. 13/531,419, Non-Final Office Action dated Jun. 22, 2012.
U.S. Appl. No. 13/531,419, Non-Final Office Action dated Sep. 9, 2014.
U.S. Appl. No. 13/531,419, Notice of Allowance dated Mar. 26, 2015.
U.S. Appl. No. 13/600,102, Non-Final Office Action dated May 13, 2014.
U.S. Appl. No. 13/600,102, Non-Final Office Action dated Dec. 10, 2013.
U.S. Appl. No. 13/600,102, Notice of Allowance dated Oct. 22, 2014.
U.S. Appl. No. 13/600,102, Restriction Requirement dated Sep. 26, 2013.
U.S. Appl. No. 14/015,921, Final Office Action dated May 11, 2015.
U.S. Appl. No. 14/015,921, Restriction Requirement dated May 15, 2014.
Ucko et al., "Relationship between the Unicellular Red Alga *Porphyridium* sp. and Its Predator, the Dinoflagellate *Gymnodinium* sp.," *Applied and Environmental Microbiology*, Nov. 1989, 55(11):2990-2994.
Urano, et al., "Effect of Osmotic Stabilizers on Protoplast Generation of Chlorella eilipsoidea Yellow/White Color Mutants," Journal of Bioscience and Bioengineering, 90(5):567-569, (2000).
Van Der Meeren et al., "Abdominal Radiation Exposure Elicits Inflammatory Responses and Abscopal Effects in the Lungs of Mice", *Radiation Res.* 163:144-152, (2005).
Vinson et al., "Comparative topical absorption and antioxidant effectiveness of two forms of coenzyme Q10 after a single dose and after long-term supplementation in the skin of young and middle-aged subjects", *IFSCC Magazine* 8(4):1-6, (2005).
Wells, "Additivity of mutational effects in proteins", *Biochem.* 29(37):8509-8517, (1990).
Xu et al., "High quality biodiesel production from a microalga *Chlorella protothecoides* by heterotrophic growth in fennenters," *Journal of Biotechnology*, 126:499-507. (2006).
Yamamoto et al., "Late type of daughter cell wall synthesis in one of the Chlorellaceae, Parachlorella kessleri (Chlorophyta, Trebouxiophyceae)," *Planta*, 221:766-775, (2005).

Figure 2
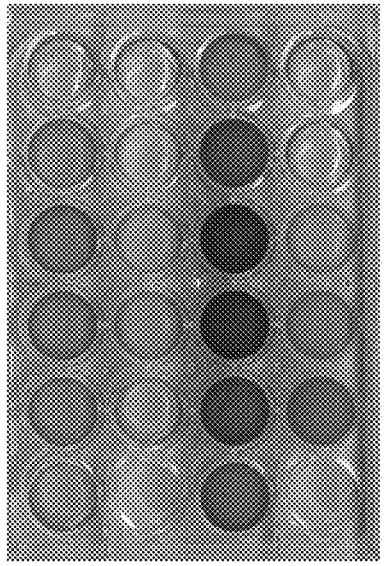
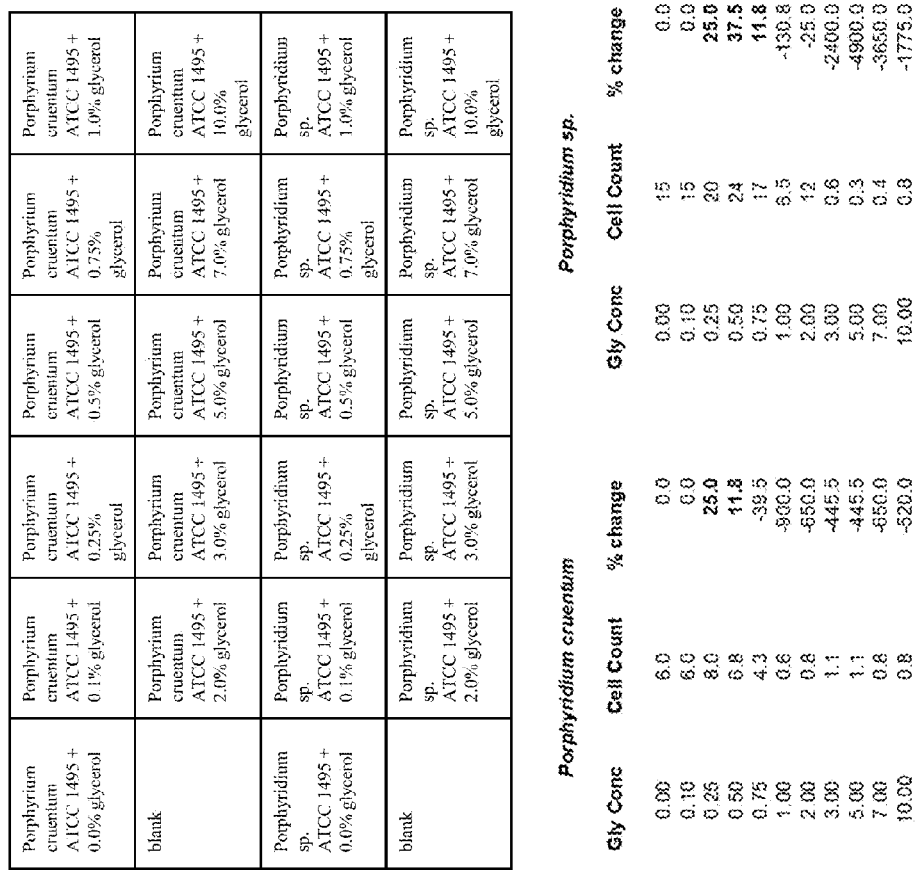

Figure 3

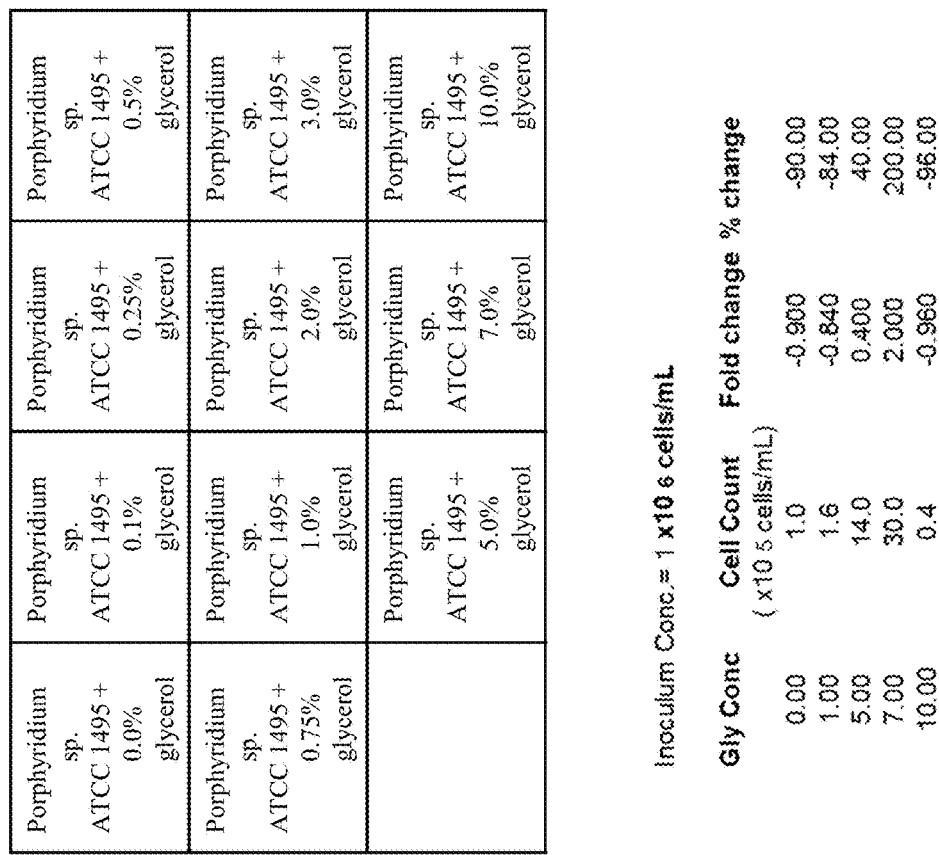

| Porphyridium sp. ATCC 1495 + 0.0% glycerol | Porphyridium sp. ATCC 1495 + 0.1% glycerol | Porphyridium sp. ATCC 1495 + 0.25% glycerol | Porphyridium sp. ATCC 1495 + 0.5% glycerol |
|---|---|---|---|
| Porphyridium sp. ATCC 1495 + 0.75% glycerol | Porphyridium sp. ATCC 1495 + 1.0% glycerol | Porphyridium sp. ATCC 1495 + 2.0% glycerol | Porphyridium sp. ATCC 1495 + 3.0% glycerol |
| Porphyridium sp. ATCC 1495 + 5.0% glycerol | Porphyridium sp. ATCC 1495 + 7.0% glycerol | Porphyridium sp. ATCC 1495 + 10.0% glycerol | |

Inoculum Conc. = 1 x10 6 cells/mL

| Gly Conc | Cell Count (x10 5 cells/mL) | Fold change | % change |
|---|---|---|---|
| 0.00 | 1.0 | -0.900 | -90.00 |
| 1.00 | 1.6 | -0.840 | -84.00 |
| 5.00 | 14.0 | 0.400 | 40.00 |
| 7.00 | 30.0 | 2.000 | 200.00 |
| 10.00 | 0.4 | -0.960 | -96.00 |

Figure 7

| Molecule | % of dry biomass | Species | Reference |
|---|---|---|---|
| Total Lipids | 10% | Porph. sp. | J. Applied Phycology 12:325-330 (2000) |
| Total Lipids | 6.53% | Porph. cruentum | Food Chemistry 70:345-353 (2000) |
| C20:4 Arachidonic Acid | 0.854% | Porph. sp. | J. Applied Phycology 12:325-330 (2000) |
| Phycoerythrin | 2.02 g/100 g | Porph. cruentum | Food Chemistry 70:345-353 (2000) |
| Chlorophyll a | 213 mg/100g | Porph. cruentum | Food Chemistry 70:345-353 (2000) |
| Carotenoids | 102 mg/100 g | Porph. cruentum | Food Chemistry 70:345-353 (2000) |
| Phycocyanin | 262 mg/100 g | Porph. cruentum | Food Chemistry 70:345-353 (2000) |
| C18:2 Linoleic Acid | 0.45% | Porph. sp. | J. Applied Phycology 12:325-330 (2000) |
| Protein | 15% | Porph. sp. | J. Applied Phycology 12:325-330 (2000) |

Porphyridium sp. (UTEX 637)

| Plate # | zeocin ug/ml | growth |
|---|---|---|
| 1 | 0 | ++++ |
| 2 | 2.5 | + |
| 3 | 5 | - |
| 4 | 7 | - |
| 5 | 8 | - |

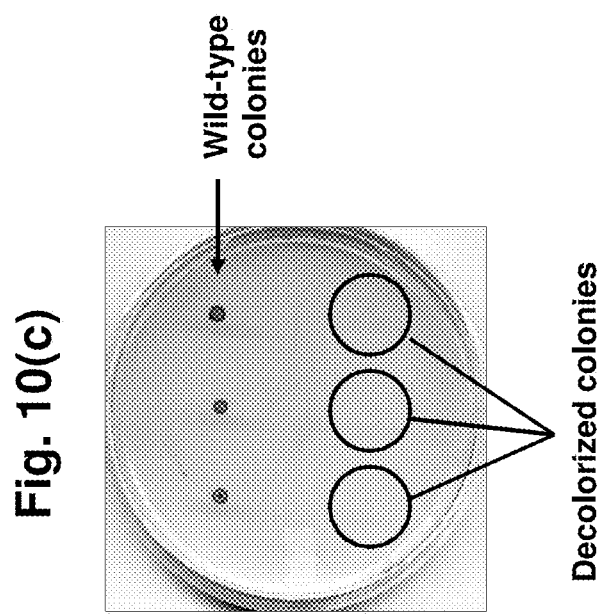
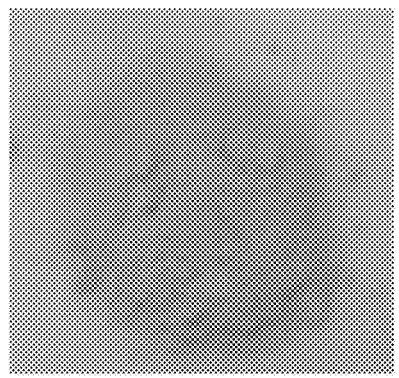
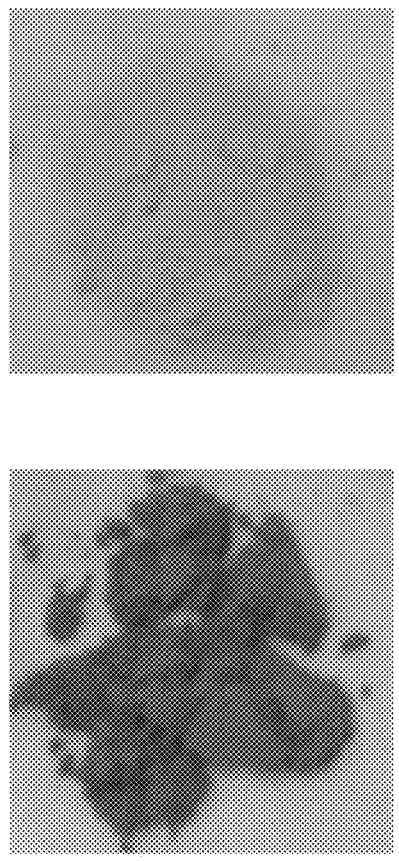

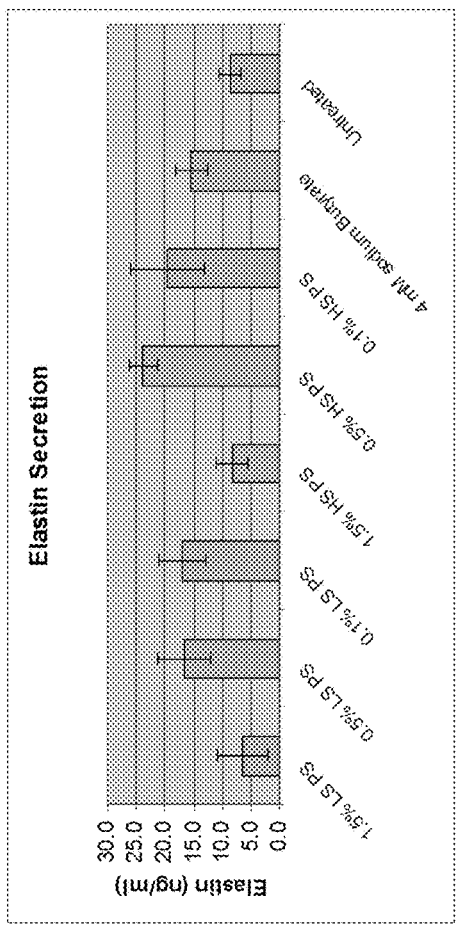
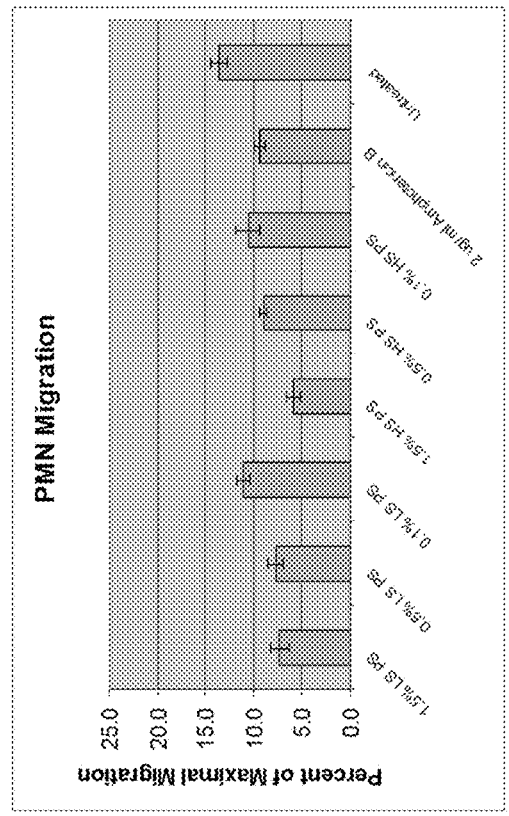
Fig. 12(a)
Fig. 12(b)

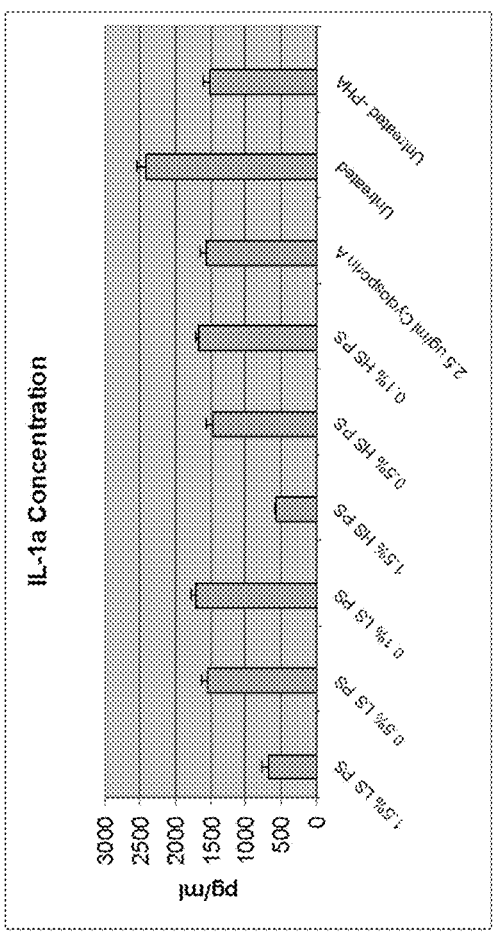
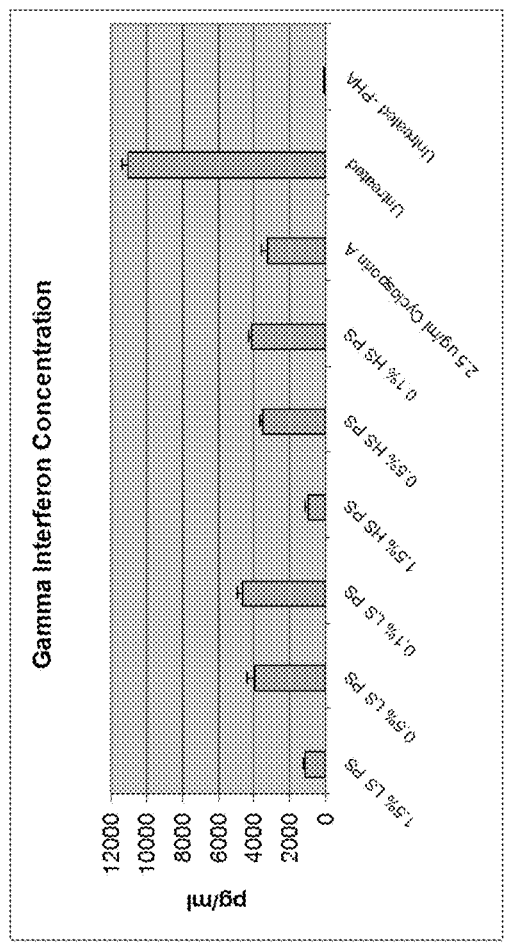
Fig. 13(a)
Fig. 13(b)

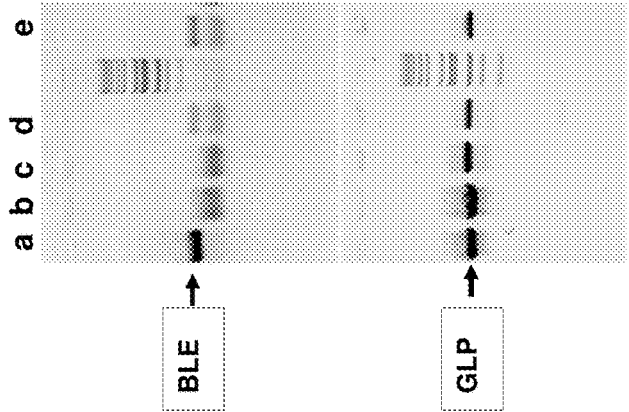
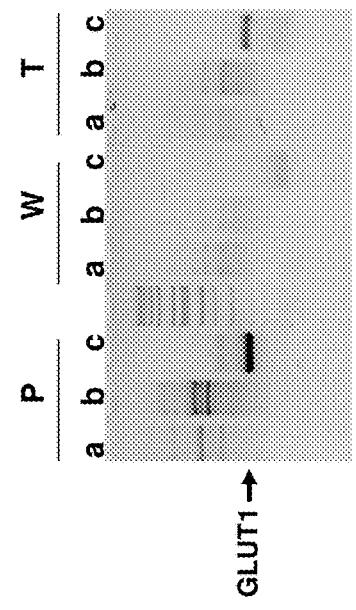
Fig. 14(a)
Fig. 14(b)
Fig. 14(c)

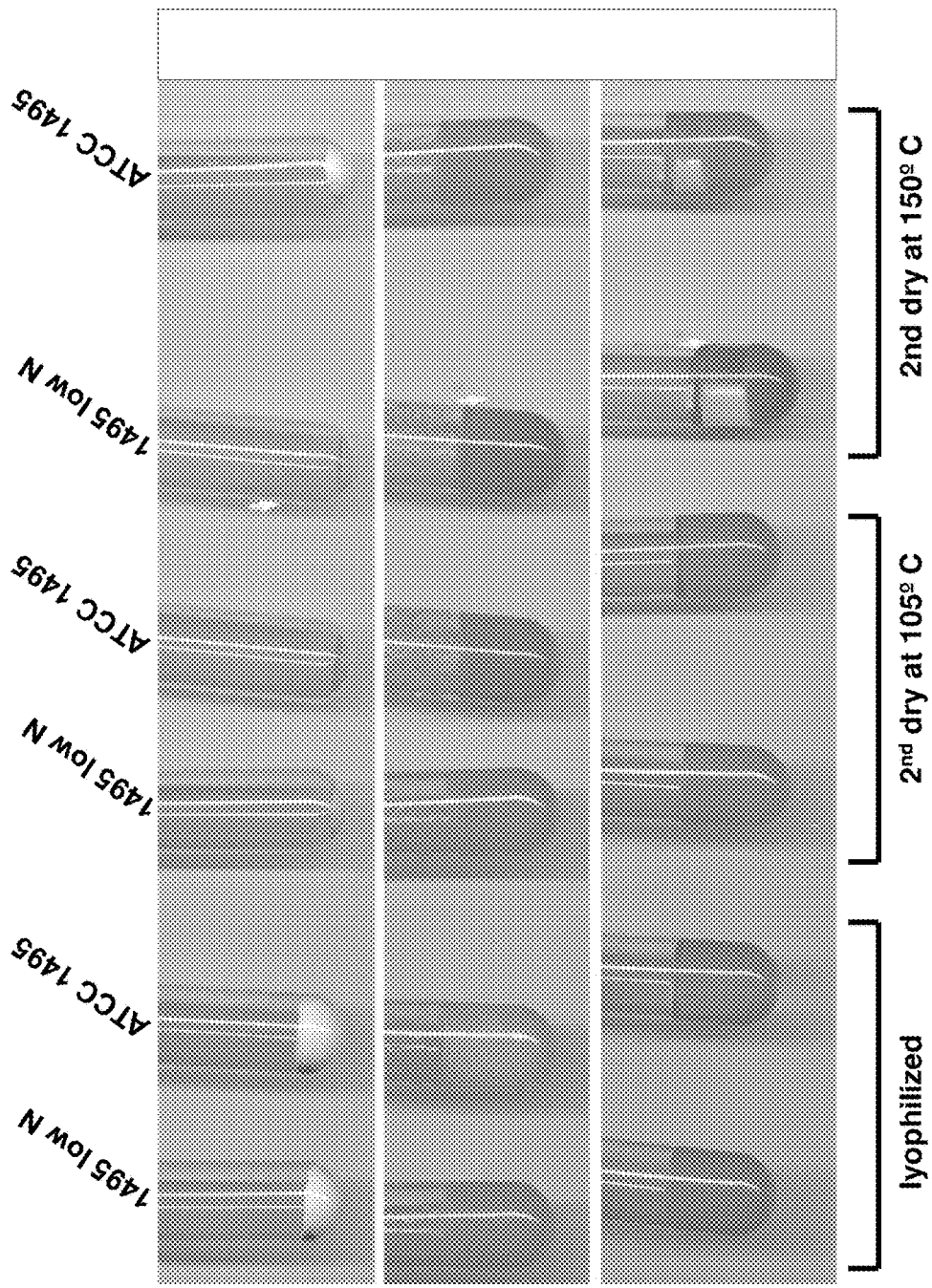
Fig. 16(a) dried
Fig. 16(b) resuspended
Fig. 16(c) centrifuged

UV-induced TT dimer protection assay
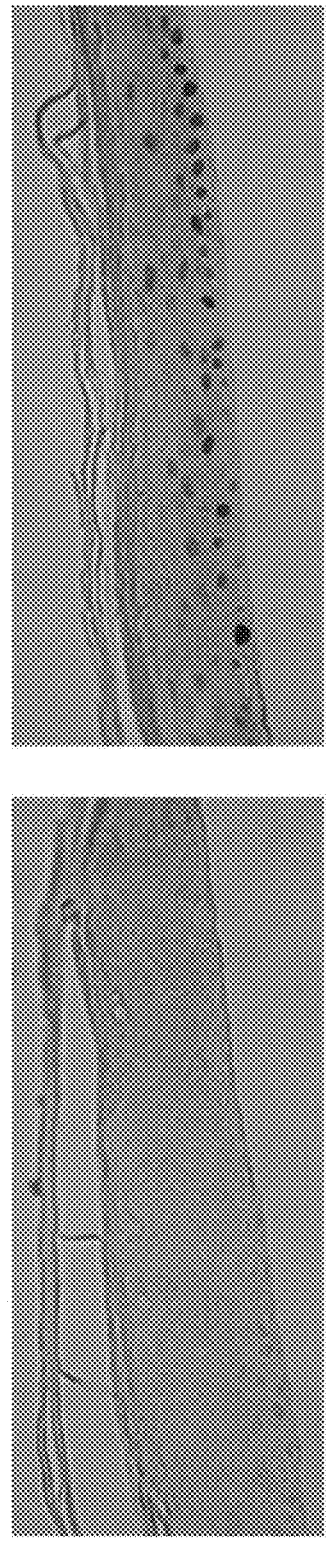
Fig. 19(a): non-UV exposed skin
Fig. 19(b): UV-exposed exposed untreated skin
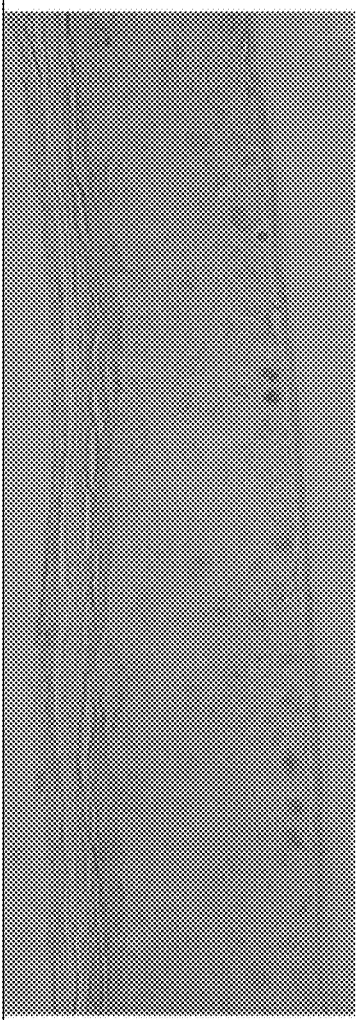
Fig. 19(c): UV-exposed exposed polysaccharide pre-treated skin

COMPOSITIONS FOR IMPROVING THE HEALTH AND APPEARANCE OF SKIN

CROSS-REFERENCE TO RELATED APPLICATIONS

This application is a continuation of U.S. application Ser. No. 13/531,419, filed Jun. 22, 2012, now U.S. Pat. No. 9,095,733, which is a continuation of U.S. application Ser. No. 12/176,320, filed Jul. 18, 2008, now U.S. Pat. No. 8,298,548, which claims the benefit under 35 USC 119(e) of U.S. Application No. 60/961,173, filed Jul. 18, 2007. U.S. application Ser. No. 12/176,320 is also a continuation-in-part of U.S. application Ser. No. 11/932,782, filed Oct. 31, 2007, now U.S. Pat. No. 8,277,849, which is a continuation of International Application No. PCT/US2007/001653, filed Jan. 19, 2007, which is a continuation-in-part of U.S. application Ser. Nos. 11/336,426, 11/336,428, 11/336,430, 11/336,431, 11/336,656, 11/337,103, and 11/337,171, each of which was filed Jan. 19, 2006. International Application No. PCT/US2007/001653 also claims the benefit under 35 USC 119(e) of U.S. Application No. 60/816,967, filed Jun. 28, 2006, U.S. Application No. 60/832,091, filed Jul. 20, 2006, U.S. Application No. 60/838,452, filed Aug. 17, 2006, and U.S. Application No. 60/872,072, filed Nov. 30, 2006, each of which is incorporated herein by reference in its entirety for all purposes.

REFERENCE TO A SEQUENCE LISTING

This application includes an electronic sequence listing in a file named "464647-Sequence.txt", created on Jun. 26, 2015 and containing 124,325 bytes, which is hereby incorporated by reference in its entirety for all purposes.

FIELD OF THE INVENTION

The invention resides in the fields of health and beauty, aquaculture, and genetic engineering.

BACKGROUND OF THE INVENTION

Carbohydrates have the general molecular formula $CH_2O$, and thus were once thought to represent "hydrated carbon". However, the arrangement of atoms in carbohydrates has little to do with water molecules. Starch and cellulose are two common carbohydrates. Both are macromolecules with molecular weights in the hundreds of thousands. Both are polymers; that is, each is built from repeating units, monomers, much as a chain is built from its links.

Three common sugars share the same molecular formula: $C_6H_{12}O_6$. Because of their six carbon atoms, each is a hexose. Glucose is the immediate source of energy for cellular respiration. Galactose is a sugar in milk. Fructose is a sugar found in honey. Although all three share the same molecular formula ($C_6H_{12}O_6$), the arrangement of atoms differs in each case. Substances such as these three, which have identical molecular formulas but different structural formulas, are known as structural isomers. Glucose, galactose, and fructose are "single" sugars or monosaccharides.

Two monosaccharides can be linked together to form a "double" sugar or disaccharide. Three common disaccharides are sucrose, common table sugar (glucose+fructose); lactose, the major sugar in milk (glucose+galactose); and maltose, the product of starch digestion (glucose+glucose). Although the process of linking the two monomers is complex, the end result in each case is the loss of a hydrogen atom (H) from one of the monosaccharides and a hydroxyl group (OH) from the other. The resulting linkage between the sugars is called a glycosidic bond. The molecular formula of each of these disaccharides is $C_{12}H_{22}O_{11} = 2 \ C_6H_{12}O_6 - H_2O$. All sugars are very soluble in water because of their many hydroxyl groups. Although not as concentrated a fuel as fats, sugars are the most important source of energy for many cells.

SUMMARY OF THE INVENTION

The present invention relates to polysaccharides and biomass produced from microalgae or other microorganisms. Representative polysaccharides include those present in the cell wall of microalgae as well as secreted polysaccharides, or exopolysaccharides. In addition to the polysaccharides themselves, such as in an isolated, purified, or semi-purified form, the invention includes a variety of compositions containing one or more microalgal polysaccharides as disclosed herein. The compositions include nutraceutical, cosmeceutical, industrial and pharmaceutical compositions which may be used for a variety of indications and uses as described herein. Other compositions include those containing one or more microalgal polysaccharides and a suitable carrier or excipient for topical or oral administration.

The present invention also relates to decolorized microalgae for formulation in skin care products as a composition of the disclosed invention. The invention thus provides highly desirable compositions of microalgal cells that do not stain human skin with red or green pigments but still provide delivery or high value cosmeceutical ingredients such as carotenoids, polyunsaturated fatty acids, moisturizing polysaccharides, superoxide dismutase, and other components.

The invention provides the insight that combinations of high light irradiance and limiting levels of nitrogen-containing compounds in the culture media allow production of biomass high in cosmeceutical/nutraceutical value but do not contain substantial amounts of pigments that stain human skin when applied as part of a skin care formulation. In addition, antioxidant, moisturizing polysaccharides are produced at higher levels in microalgae cells such as those of the genus *Porphyridium* under high light/low nitrogen conditions. The invention provides compositions of *Porphyridium* biomass that are substantially free of red coloration and contain higher amounts of exopolysaccharide than cells containing significant amounts of red coloration that are grown under nitrogen-replete conditions.

In one aspect, the disclosed invention includes a composition comprising cells of the genus *Porphyridium*, wherein an aqueous extract of the composition contains a reduced level of red pigmentation, or a reduced absorbance at 545 nm, relative to the same cells grown under different conditions. In some embodiments, the extract contains no more than about 75% to no more than about 5% of the absorbance per gram at 545 nm compared to an extract of cells of the same species grown in a photobioreactor in ATCC 1495 artificial seawater (ASW) media in the presence of 50 microeinsteins of light per second per square meter. In other embodiments, the composition comprises a carrier and/or a preservative suitable for topical administration. In additional embodiments, the carrier is suitable for human topical administration.

The invention further relates to methods of producing or preparing microalgal polysaccharides. In some disclosed methods, exogenous sugars are incorporated into the polysaccharides to produce polysaccharides distinct from those present in microalgae that do not incorporate exogenous sugars. The invention also includes methods of trophic conversion and recombinant gene expression in microalgae. In some methods, recombinant microalgae are prepared to express heterologous gene products, such as mammalian proteins as a non-limiting example, while in other embodiments, the microalgae are modified to produce more of a small molecule already made by microalgae in the absence of genetic modification.

The invention further relates to methods of growing, producing and preparing microalgal biomass. In some disclosed methods, excess light is provided as one method of removing pigmentation. In other methods, reducing the amount of nitrogen provided to microalgae cells in culture is provided as one method of removing pigmentation. In other methods, increased light irradiance combined with culture media containing limiting amounts of nitrogen are used to reduce and/or eliminate red or green pigmentation. Additionally, the invention provides decolorized strains produced through chemical mutagenesis or gene insertion/deletion methods that are used to generate biomass for skin care products.

In another aspect, the invention relates to compositions for topical application, such as a composition for application to human skin comprising a polysaccharide isolated from cells of the genus *Porphyridium*. In some embodiments, the composition comprises a polysaccharide that is part of a microalgal cell, or a homogenate thereof. In other embodiments, the polysaccharide is contained within microalgal cells, or a homogenate thereof, which is essentially free, or completely free, of red coloration. Thus, a composition of the disclosed invention may also be essentially free, or completely free, of red coloration. Non-limiting examples include compositions comprising less than about 15 milligrams, less than about 1 milligram, or less than about 0.1 milligrams of phycoerythrin per dry gram of cells in the composition.

In additional embodiments, the composition is that of a cosmetic or other skin care product. Such products may contain one or more microalgal polysaccharides, or a microalgal cell homogenate, a topical carrier, and/or a preservative. In some embodiments, the carrier may be any carrier suitable for topical application, such as, but not limited to, use on human skin or human mucosal tissue. In other embodiments, the composition may contain a purified microalgal polysaccharide, such as an exopolysaccharide, and a topical carrier. Exemplary carriers include liposome formulation, biodegradable microcapsule, lotion, spray, aerosol, dusting powder, biodegradable polymer, mineral oil, liquid petroleum, white petroleum, propylene glycol, polyoxyethylene polyoxypropylene compound, emulsifying wax, sorbitan monostearate, polysorbate 60, cetyl ester wax, cetearyl alcohol, 2-octyldodecanol, benzyl alcohol and water. Exemplary preservatives include diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, methyl paraben, sorbic acid, Germaben II, and disodium EDTA.

As a cosmeceutical, the composition may contain a microalgal polysaccharide or homogenate and other component material found in cosmetics. In some embodiments, the component material may be that of a fragrance, a colorant (e.g. black or red iron oxide, titanium dioxide and/or zinc oxide, etc.), a sunblock (e.g. titanium, zinc, etc.), and a mineral or metallic additive.

In other aspects, the invention includes methods of preparing or producing a microalgal polysaccharide. In some aspects relating to an exopolysaccharide, the invention includes methods that separate the exopolysaccharide from other molecules present in the medium used to culture exopolysaccharide producing microalgae. In some embodiments, separation includes removal of the microalgae from the culture medium containing the exopolysaccharide, after the microalgae has been cultured for a period of time. Of course the methods may be practiced with microalgal polysaccharides other than exopolysaccharides. In other embodiments, the methods include those where the microalgae was cultured in a bioreactor, optionally where a gas is infused into the bioreactor.

In one embodiment, the invention includes a method of producing an exopolysaccharide, wherein the method comprises culturing microalgae in a bioreactor, wherein gas is infused into the bioreactor; separating the microalgae from culture media, wherein the culture media contains the exopolysaccharide; and separating the exopolysaccharide from other molecules present in the culture media.

The microalgae of the invention may be that of any species, including those listed in Tables 1A and 1B herein. In some embodiments, the microalgae is a red algae, such as the red algae *Porphyridium*, which has two known species (*Porphyridium* sp. and *Porphyridium cruentum*) that have been observed to secrete large amounts of polysaccharide into their surrounding growth media. In other embodiments, the microalgae is of a genus selected from *Rhodella*, *Chlorella*, and *Achnanthes*. Non-limiting examples of species within a microalgal genus of the invention include *Porphyridium* sp., *Porphyridium cruentum*, *Porphyridium purpureum*, *Porphyridium aerugineum*, *Rhodella maculata*, *Rhodella reticulata*, *Chlorella autotrophica*, *Chlorella stigmatophora*, *Chlorella capsulata*, *Achnanthes brevipes* and *Achnanthes longipes*.

In some embodiments, a polysaccharide preparation method is practiced with culture media containing over 26.7, or over 27, mM sulfate (or total $SO_4^{2-}$). Non-limiting examples include media with more than about 28, more than about 30, more than about 35, more than about 40, more than about 45, more than about 50, more than about 55, more than about 60, more than about 65, more than about 70, more than about 75, more than about 80, more than about 85, more than about 90, more than about 95, more than about 100 mM sulfate, and in some instances more than 250 mM, more than 400 mM, more than 550 mM, and more than 750 mM, more than 900 mM, more than 1M, and more than 2 mM sulfate. Sulfate in the media may be provided in one or more of the following forms: $Na_2SO_4.10\ H_2O$, $MgSO_4.7H_2O$, $MnSO_4$, and $CuSO_4$.

Other embodiments of the method include the separation of an exopolysaccharide from other molecules present in the culture media by tangential flow filtration. Alternatively, the methods may be practiced by separating an exopolysaccharide from other molecules present in the culture media by alcohol precipitation. Non-limiting examples of alcohols to use include ethanol, isopropanol, and methanol.

In other embodiments, a method may further comprise treating a polysaccharide or exopolysaccharide with a protease to degrade polypeptide (or proteinaceous) material attached to, or found with, the polysaccharide or exopolysaccharide. The methods may optionally comprise separating the polysaccharide or exopolysaccharide from proteins, peptides, and amino acids after protease treatment.

In other embodiments, a method of formulating a cosmeceutical composition is disclosed. As one non-limiting example, the composition may be prepared by adding separated polysaccharides, or exopolysaccharides, to homogenized microalgal cells before, during, or after homogenization. Both the polysaccharides and the microalgal cells may be from a culture of microalgae cells in suspension and under conditions allowing or permitting cell division. The culture medium containing the polysaccharides is then separated from the microalgal cells followed by 1) separation of the polysaccharides from other molecules in the medium and 2) homogenization of the cells.

Other compositions of the invention may be formulated by subjecting a culture of microalgal cells and soluble exopolysaccharide to tangential flow filtration until the composition is substantially free of salts. Alternatively, a polysaccharide is prepared after proteolysis of polypeptides present with the polysaccharide. The polysaccharide and any contaminating polypeptides may be that of a culture medium separated from microalgal cells in a culture thereof. In some embodiments, the cells are of the genus *Porphyridium*.

In a further aspect, the disclosed invention includes a composition comprising particulate polysaccharides. The polysaccharides may be from any microalgal source, and with any level of sulfation, as described herein. The composition may be sterile or substantially free of endotoxins and/or proteins in some embodiments. In other embodiments, the composition further comprises hyaluronic acid or another agent suitable or desirable for treatment of skin. The particles in some embodiments are generated by first purifying the polysaccharide away from biomass, then drying the purified polysaccharide into a film, and then homogenizing and/or grinding the film into smaller particles.

In some embodiments, the polysaccharides are in the form of a purified material that was dried to be completely or partially insoluble in water. Preferably the purified material has been separated from cell biomass, for example as described in Example 2. In such purified form the polysaccharide is at least 50% polysaccharide by weight, and more preferably above 75% polysaccharide by weight. In some embodiments the polysaccharide is associated with one or more species of protein that can be endogenous to the microalgae source, and alternatively can be a fusion protein that is partially endogenous to the microalgae source as described herein. In some embodiments, the dried polysaccharide particles are in mixture with a non-aqueous solvent or material. In other embodiments, the dried polysaccharide particles are partially soluble such that they are from less than about 70% to less than about 1% soluble in water.

In additional embodiments, the polysaccharide particles increase in volume, or swell, on contact with water or water vapor. Thus the volume of the polysaccharide particles increases compared to its anhydrous or partially hydrated volume before exposure to the water or water vapor. In some embodiments, the particles increase in volume by an amount selected from at least about 5% to at least about 5000%.

In some embodiments, the polysaccharide compositions described herein further comprise at least one ingredient selected from the group consisting of beta carotene, lutein, astaxanthin, vitamin C, vitamin E, vitamin A, coenzyme Q10, a peptide, an aceylated peptide, oil soluble α-hydroxy acid, an alkyl lactate, and salicylic acid. In some cases, the compositions comprise micronized particles containing the polysaccharide and the at least one other ingredient. In some cases, the particles are of a substantially uniform size. In some embodiments, the algal polysaccharide and the at least one ingredient have been subjected to heating, drying and homogenization to form particles comprising both algal polysaccharides and the at least one ingredient. In some cases, the particles comprising both algal polysaccharides and the at least one ingredient have been processed to a substantially uniform size.

The disclosed invention further includes methods for the preparation or manufacture of the dried polysaccharide particles. In some embodiments, the method comprises formulating particles of polysaccharide material into a non-aqueous material. The particles may be formed from a film of dried polysaccharide material, wherein at least a portion (or some proportion) of the film has been made completely or partially insoluble in water. Optionally, the particles are formed by homogenization of the film into particulate form.

In some cases, the film is formed by heating a suspension of polysaccharide material until all or part of the film is insoluble. The heating may be of an aqueous suspension of the material to remove water from the suspension. Of course the polysaccharide in the suspension may be from any microalgal source as described herein. Optionally, the polysaccharide in the suspension has been isolated from microalgal biomass. Optionally, the polysaccharide in the suspension has been isolated from supernatant of a culture of microalgae.

The disclosed invention thus includes a method of preparing or manufacturing a composition for topical application, such as for improving the appearance of skin. The method may comprise 1) drying an aqueous suspension of a polysaccharide isolated from microalgae to a solid film, wherein at least some proportion of the film has been made completely or partially insoluble in water; 2) homogenizing the film into particles; and optionally 3) formulating the particles into a non-aqueous material. In some embodiments, the homogenizing is via a method selected from jet milling, ball milling, Retsch® milling, pin milling and milling in a Quadro® device. Optionally, the formulating of the particles is into the non-aqueous phase of an oil-in-water emulsion, such as an emulsion suitable for topical application. The non-aqueous phase may comprise an oil suitable for topical application, such as hexadecanoic acid as a non-limiting example. In other cases, the formulating of the particles is into a carrier suitable for topical administration as described herein. In some embodiments, the particles may be relatively uniform in size or may range in size, but in many embodiments, the particles have an average size between about 400 and 0.1 microns.

The formation of a solid film may be by heating performed between about 40 and about 180 degrees Celsius. In other embodiments, the heating is performed in two parts. The first part may comprise heating a suspension, optionally aqueous, of polysaccharide material to no more than about 60 to about 100° C. for a time period sufficient to form or produce a solid film. This may be followed by a second heating of the solid film for a (second) time period sufficient to reach no more than about 148 to about 160° C. In one embodiment the first heating is in the presence of air, which may be optionally combined with the second heating (of the solid film) being in at least a partial vacuum or in a high vacuum. Of course the second heating under reduced pressure may be used independent of the first heating in the presence of air. In other embodiments the heating is done in a single step, either in the presence of air or in the presence of a partial or full vacuum.

In some alternative embodiments, a method to render the polysaccharide material insoluble is selected from chemical cross-linking, chemical dehydration through displacement of bound water by an alcohol, precipitation from solution using an alcohol or a ketone or pH, and coating of particles by microencapsulation.

In an additional aspect, the disclosed invention includes a method of topically applying a composition comprising polysaccharides in particulate form. In some embodiments, the application is to skin, such as to mammalian or human skin. Alternatively, the application is to lips or wrinkles on human skin, or by injection into skin or a skin tissue. In many embodiments, the application is to improve the appearance of skin.

In additional embodiments, a polysaccharide containing composition (optionally with polysaccharides in particulate form) may be used in a method of cosmetic enhancement. In one embodiment, a method may include injecting a polysaccharide produced by microalgae into mammalian skin. Preferably the polysaccharide is sterile and free of protein.

In further embodiments, a method to treat skin, such as mammalian or human skin, is disclosed. In some embodiments, the method is for the treatment of human facial skin or a tissue thereof. Such methods include a method to stimulating collagen synthesis, stimulating elastin synthesis, or inhibiting collagenase activity in such skin by applying a disclosed composition of the invention to the skin. Additional methods include a method to reduce the signs of aging or reduce the appearance of aging in human skin by applying a composition of the disclosed invention to the skin. Non-limiting examples of a sign of aging or an appearance of aging include wrinkles, such as those on the forehead or around the eyes and/or lips, and liver spots (yellowish-brown flat spots that appear as large freckles). In some embodiments, a sign or appearance of aging is associated with reactive oxygen species (ROS) formation and/or activity in the skin. The use of a composition may thus be based in part on the insight that the disclosed polysaccharides possess anti-oxidant activity, and that further the high sulfated polysaccharides wherein the percent of sulfur by weight is above 4.75%.

Additional embodiments include the use of a polysaccharide containing composition in a method of reducing the effects of ultraviolet (UV) light or radiation, such as that present in sunlight, on skin or a skin tissue. One non-limiting example is a method of shielding mammalian skin from UV light. The method may comprise applying a composition of the disclosed invention to skin or a skin tissue in an effective or sufficient amount to shield, at least in part, the skin from UV radiation. In an alternative embodiment, a composition of the invention may be applied in an effective or sufficient amount to treat skin that has been damaged by UV radiation. An additional non-limiting example is a method of for treating skin to reduce the risk of skin cancer induced by sunlight or UV radiation. The method may comprise applying a composition of the invention in an effective or sufficient amount to reduce the risk of UV or sunlight induced skin cancer.

An additional non-limiting example is a method of for treating skin to reduce the risk of skin cancer induced by sunlight or UV radiation that causes erythema. Erythema is redness of the skin caused by increased blood flow to the capillaries. A subject can assess the effective amount of microalgal materials sufficient to treat erythema using methods known in the art. See for example J. Invest. Dermatol., 117 (5); 1318-1321 (2001).

In addition to the above, application of a composition of the invention to human skin may be used in a method of reducing reactive oxygen species (ROS) in the skin or a skin tissue. This is based in part on the insight that the disclosed polysaccharides possess anti-oxidant activity. In some embodiments, the method is used to prevent or treat a disease or unwanted condition associated with ROS or oxidative stress. Non-limiting examples of such a disease or unwanted condition include reducing inflammation or irritation of the skin. In some embodiments, the polysaccharide composition comprises one or more other agents or compounds with anti-oxidant activity. In further embodiments, the method may be used to lower the level of ROS, or reduce or decrease the amount of damage caused by ROS in skin or a skin tissue. The amount of the composition may be any that is effective or sufficient to produce a desired improvement or therapeutic benefit.

In other aspects, the present invention is directed to a method of reducing fine lines and/or wrinkles on human skin, a method of inducing a feel of tightening human skin, a method of reducing transepidermal water loss in human skin, a method of moisturizing human skin, and/or a method of increasing elasticity of human skin. Each method comprises administration of a composition, as disclosed herein, to human skin in an amount and at a frequency sufficient to impart the desired characteristics. The various methods and/or compositions can be combined to provide methods or compositions suitable for imparting multiple characteristics simultaneously.

The details of additional embodiments of the invention are set forth in the accompanying drawings and the description below. Other features and advantages of the invention will be apparent from the drawings and detailed description, and from the claims.

BRIEF DESCRIPTION OF THE DRAWINGS

FIG. 2 shows growth of *Porphyridium* sp. and *Porphyridium cruentum* cells grown in light in the presence of various concentrations of glycerol.

FIG. 3 shows *Porphyridium* sp. cells grown in the dark in the presence of various concentrations of glycerol.

FIG. 7 shows various amounts and ranges of amounts of compounds found per gram of cells in cells of the genus *Porphyridium*.

FIGS. 10(*a*), (*b*) and (*c*): FIGS. 10 (*a*) and (*b*) show lyophilized biomass from nitrogen-replete (FIG. 10(*a*)) and nitrogen-starved (FIG. 10(*b*)) *Porphyridium cruentum* cells.

The culture media used to grow the cells shown in FIG. 10(a) was as described in Example 1. The culture media used to grow the cells shown in FIG. 10(b) was as described in Example 1 except that the culture media contained no Tris and 0.125 g/L potassium nitrate, pH 7.6. The lyophilized biomass in FIG. 10(b) is substantially free of red coloration. FIG. 10(c) shows three colonies of wild-type *Porphyridium* sp. (top of plate) that exhibit full red pigmentation, as well as three mutagenized colonies of *Porphyridium* sp. that are substantially free of red coloration (bottom of plate).

FIG. 11(a) shows UVB-induced TT dimer formation in the presence and absence of microalgae-derived materials.

FIGS. 12(a) and (b): FIG. 12(a) shows secretion of elastin by human fibroblasts in the presence and absence of microalgae-derived materials. FIG. 12(b) shows inhibition of PMN migration in the presence and absence of microalgae-derived materials.

FIGS. 13(a) and (b): FIG. 13(a) shows secretion of IL1-α in the presence and absence of microalgae-derived materials. FIG. 13(b) shows secretion of gamma interferon in the presence and absence of microalgae-derived materials.

FIGS. 14(a), (b) and (c): FIG. 14(a) shows PCR genotyping of two *Porphyridium* transformants for the ble antibiotic resistance transgene. FIG. 14(b) shows PCR genotyping of two *Porphyridium* transformants for the endogenous glycoprotein gene promoter. FIG. 14(c) shows PCR genotyping of one *Porphyridium* transformant for an exogenous gene encoding a recoded human GLUT1 transporter.

FIGS. 16(a), (b) and (c) show insoluble and soluble polysaccharide bead preparations.

FIG. 17(a) shows swelling of polysaccharide beads over time.

FIGS. 19(a), (b) and (c) show polysaccharide protection from UV damage to human skin models.

DETAILED DESCRIPTION OF THE INVENTION

I. Definitions

Figure 1:
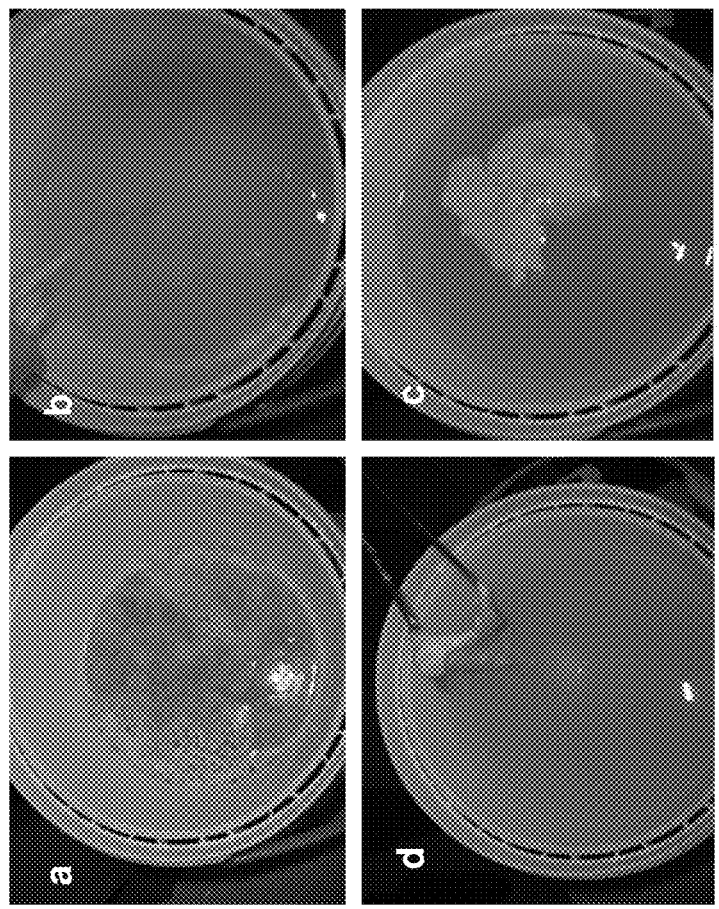
FIG. 1 shows precipitation of 4 liters of *Porphyridium cruentum* exopolysaccharide using 38.5% isopropanol. (a) supernatant; (b) addition of 38.5% isopropanol; (c) precipitated polysaccharide; (d) separating step.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Active in microalgae" means a nucleic acid that is functional in microalgae. For example, a promoter that has been used to drive an antibiotic resistance gene to impart antibiotic resistance to a transgenic microalgae is active in microalgae. Nonlimiting examples of promoters active in microalgae are promoters endogenous to certain algae species and promoters found in plant viruses.

"ARA" means Arachidonic acid.

"Associates with" means, within the context of a polysaccharide binding fusion protein, one molecule binding to another molecule. Affinity and selectivity of binding can vary when a polysaccharide and a polysaccharide binding protein are in association with each other.

"Axenic" means a culture of an organism that is free from contamination by other living organisms.

The term "biomass" refers to material produced by growth and/or propagation of cells. Biomass may contain cells and/or intracellular contents as well as extracellular material. Extracellular material includes, but is not limited to, compounds secreted by a cell.

"Bioreactor" means an enclosure or partial enclosure in which cells are cultured in suspension.

"Carrier suitable for topical administration" means a compound that may be administered, together with one or more compounds of the present invention, and which does not destroy the activity thereof and is nontoxic when administered in concentrations and amounts sufficient to deliver the compound to the skin or a mucosal tissue.

"Cellulosic material" means the products of digestion of cellulose, including glucose and xylose, and optionally additional compounds such as disaccharides, oligosaccharides, lignin, furfurals and other compounds. Nonlimiting examples of sources of cellulosic material include sugar caner bagasses, sugar beet pulp, corn stover, wood chips, sawdust and switchgrass.

The term "co-culture", and variants thereof such as "co-cultivate", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

"Combination Product" means a product that comprises at least two distinct compositions intended for human administration through distinct routes, such as a topical route and an oral route. In some embodiments the same active agent is contained in both the topical and oral components of the combination product.

"Conditions favorable to cell division" means conditions in which cells divide at least once every 72 hours.

The term "cultivated", and variants thereof, refer to the intentional fostering of growth (increases in cell size, cellular contents, and/or cellular activity) and/or propagation (increases in cell numbers via mitosis) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, and carbon source), specified temperature, oxygen tension, carbon dioxide levels, and growth in a bioreactor. The term does not refer to the growth or propagation of microorganisms in nature or otherwise without direct human intervention.

"DHA" means Docosahexaenoic acid.

"Endopolysaccharide" means a polysaccharide that is retained intracellularly.

"EPA" means eicosapentaenoic acid.

Cells or biomass that are "essentially free of red coloration" contain either no red color visible to the naked eye or a small amount of red color such that red is a minor color of the overall composition compared to at least one other color such as yellow.

Cells or biomass that are "completely free of red coloration" contain no red color visible to the naked eye.

"Exogenous gene" refers to a nucleic acid transformed into a cell. A transformed cell may be referred to as a recombinant cell, into which additional exogenous gene(s) may be introduced. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

"Exogenously provided" describes a molecule provided to the culture media of a cell culture.

"Exopolysaccharide" means a polysaccharide that is secreted from a cell into the extracellular environment.

As used herein, the terms "expression vector" or "expression construct" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"Filtrate" means the portion of a tangential flow filtration sample that has passed through the filter.

"Fixed carbon source" means molecule(s) containing carbon that are present at ambient temperature and pressure in solid or liquid form.

"Glycopolymer" means a biologically produced molecule comprising at least two monosaccharides. Examples of glycopolymers include glycosylated proteins, polysaccharides, oligosaccharides, and disaccharides.

"Homogenate" means cell biomass that has been disrupted. A homogenate is not necessarily homogeneous.

As used herein, the term "lysate" refers to a solution containing the contents of lysed cells.

As used herein, the term "lysis" refers to the breakage of the plasma membrane and optionally the cell wall of a biological organism sufficient to release at least some intracellular content, often by mechanical, viral or osmotic mechanisms that compromise its integrity.

As used herein, the term "lysing" refers to disrupting the cellular membrane and optionally the cell wall of a biological organism or cell sufficient to release at least some intracellular content.

A compound that can be "metabolized by cells" means a compound whose elemental components are incorporated into products endogenously produced by the cells. For example, a compound containing nitrogen that can be metabolized by cells is a compound containing at least one nitrogen atom per molecule that can be incorporated into a nitrogen-containing, endogenously produced metabolite such as an amino acid.

"Microalgae" means a eukarytotic microbial organism that contains a chloroplast, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae can refer to unicellular organisms that separate from sister cells shortly after cell division, such as *Chlamydomonas*, and can also refer to microbes such as, for example, *Volvox*, which is a simple multicellular photosynthetic microbe of two distinct cell types. "Microalgae" can also refer to cells such as *Chlorella* and *Dunaliella*. "Microalgae" also includes other microbial photosynthetic organisms that exhibit cell-cell adhesion, such as *Agmenellum, Anabaena*, and *Pyrobotrys*. "Microalgae" also includes obligate heterotrophic microorganisms that have lost the ability to perform photosynthesis, such as certain dinoflagellate algae species.

The terms "microorganism" and "microbe" are used interchangeably herein to refer to microscopic unicellular organisms.

"Naturally produced" describes a compound that is produced by a wild-type organism.

"Peptide" means a polypeptide of 50 or less amino acids. In some contexts, a peptide is connected to a much larger protein as a fusion protein and is referred to as a peptide to denote its independent domain as a part of the fusion protein.

"Photobioreactor" means a waterproof container, at least part of which is at least partially transparent, allowing light to pass through, in which one or more microalgae cells are cultured. Photobioreactors may be sealed, as in the instance of a polyethylene bag, or may be open to the environment, as in the instance of a pond.

"Polysaccharide material" is a composition that contains more than one species of polysaccharide, and optionally contaminants such as proteins, lipids, and nucleic acids, such as, for example, a microalgal cell homogenate.

"Polysaccharide" means a compound or preparation containing one or more molecules that contain at least two saccharide molecules covalently linked. A "polysaccharide", "endopolysaccharide" or "exopolysaccharide" can be a preparation of polymer molecules that have similar or identical repeating units but different molecular weights within the population.

"Port", in the context of a photobioreactor, means an opening in the photobioreactor that allows influx or efflux of materials such as gases, liquids, and cells. Ports are usually connected to tubing leading to and/or from the photobioreactor.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

As used herein, the term "recombinant" when used with reference, e.g., to a cell, or nucleic acid, protein, or vector, indicates that the cell, nucleic acid, protein or vector, has been modified by the introduction of an exogenous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

"Red microalgae" means unicellular algae that is of the list of classes comprising Bangiophyceae, Florideophyceae, Goniotrichales, or is otherwise a member of the Rhodophyta.

"Retentate" means the portion of a tangential flow filtration sample that has not passed through the filter.

"Small molecule" means a molecule having a molecular weight of less than 2000 daltons, in some instances less than 1000 daltons, and in still other instances less than 500 daltons or less. Such molecules include, for example, heterocyclic compounds, carbocyclic compounds, sterols, amino acids, lipids, carotenoids and polyunsaturated fatty acids.

A molecule is "solvent available" when the molecule is isolated to the point at which it can be dissolved in a solvent, or sufficiently dispersed in suspension in the solvent such that it can be detected in the solution or suspension. For example, a polysaccharide is "solvent available" when it is sufficiently isolated from other materials, such as those with which it is naturally associated, such that the polysaccharide can be dissolved or suspended in an aqueous buffer and detected in solution using a dimethylmethylene blue (DMMB) or phenol:sulfuric acid assay. In the case of a high molecular weight polysaccharide containing hundreds or thousands of monosaccharides, part of the polysaccharide can be "solvent available" when it is on the outermost layer of a cell wall while other parts of the same polysaccharide molecule are not "solvent available" because they are buried within the cell wall. For example, in a culture of microalgae in which polysaccharide is present in the cell wall, there is little "solvent available" polysaccharide since most of the cell wall polysaccharide is sequestered within the cell wall and not available to solvent. However, when the cells are disrupted, e.g., by sonication, the amount of "solvent available" polysaccharide increases. The amount of "solvent accessible" polysaccharide before and after homogenization can be compared by taking two aliquots of equal volume of cells from the same culture, homogenizing one aliquot, and comparing the level of polysaccharide in solvent from the two aliquots using a DMMB assay. The amount of solvent accessible polysaccharide in a homogenate of cells can also be compared with that present in a quantity of cells of the same type in a different culture needed to generate the same amount of homogenate.

"Substantially free of protein" means compositions that are preferably of high purity and are substantially free of potentially harmful contaminants, including proteins (e.g., at least National Food (NF) grade, generally at least analytical grade, and more typically at least pharmaceutical grade). Compositions are at least 80, at least 90, at least 99 or at least 99.9% w/w pure of undesired contaminants such as proteins are substantially free of protein. To the extent that a given compound must be synthesized prior to use, the resulting product is typically substantially free of any potentially toxic agents, particularly any endotoxins, which may be present during the synthesis or purification process. Compositions are usually made under GMP conditions. Compositions for parenteral administration are usually sterile and substantially isotonic.

A "sucrose utilization gene" is a gene that, when expressed, aids the ability of a cell to utilize sucrose as an energy source. Proteins encoded by a sucrose utilization gene are referred to herein as "sucrose utilization enzymes" and include sucrose transporters, sucrose invertases, and hexokinases such as glucokinases and fructokinases.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, $M=5$, $N=-4$, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

II. General

Polysaccharides form a heterogeneous group of polymers of different length and composition. They are constructed from monosaccharide residues that are linked by glycosidic bonds. Glycosidic linkages may be located between the $C_1$ (or $C_2$) of one sugar residue and the $C_2$, $C_3$, $C_4$, $C_5$ or $C_6$ of the second residue. A branched sugar results if more than two types of linkage are present in single monosaccharide molecule.

Monosaccharides are simple sugars with multiple hydroxyl groups. Based on the number of carbons (e.g., 3, 4, 5, or 6) a monosaccharide is a triose, tetrose, pentose, or hexose. Pentoses and hexoses can cyclize, as the aldehyde or keto group reacts with a hydroxyl on one of the distal carbons. Examples of monosaccharides are galactose, glucose, and rhamnose.

Polysaccharides are molecules comprising a plurality of monosaccharides covalently linked to each other through glycosidic bonds. Polysaccharides consisting of a relatively small number of monosaccharide units, such as 10 or less, are sometimes referred to as oligosaccharides. The end of the polysaccharide with an anomeric carbon ($C_1$) that is not involved in a glycosidic bond is called the reducing end. A polysaccharide may consist of one monosaccharide type, known as a homopolymer, or two or more types of monosaccharides, known as a heteropolymer. Examples of homopolysaccharides are cellulose, amylose, inulin, chitin, chitosan, amylopectin, glycogen, and pectin. Amylose is a glucose polymer with α(1→4) glycosidic linkages. Amylopectin is a glucose polymer with α(1→4) linkages and branches formed by α(1→6) linkages. Examples of heteropolysaccharides are glucomannan, galactoglucomannan, xyloglucan, 4-O-methylglucuronoxylan, arabinoxylan, and 4-O-Methylglucuronoarabinoxylan.

Polysaccharides can be structurally modified both enzymatically and chemically. Examples of modifications include sulfation, phosphorylation, methylation, O-acetylation, fatty acylation, amino N-acetylation, N-sulfation, branching, and carboxyl lactonization.

Glycosaminoglycans are polysaccharides of repeating disaccharides. Within the disaccharides, the sugars tend to be modified, with acidic groups, amino groups, sulfated hydroxyl and amino groups. Glycosaminoglycans tend to be negatively charged, because of the prevalence of acidic groups. Examples of glycosaminoglycans are heparin, chondroitin, and hyaluronic acid.

Polysaccharides are produced in eukaryotes mainly in the endoplasmic reticulum (ER) and Golgi apparatus. Polysaccharide biosynthesis enzymes are usually retained in the ER, and amino acid motifs imparting ER retention have been identified (Gene. 2000 Dec. 31; 261(2):321-7). Polysaccharides are also produced by some prokaryotes, such as lactic acid bacteria.

Polysaccharides that are secreted from cells are known as exopolysaccharides. Many types of cell walls, in plants, algae, and bacteria, are composed of polysaccharides. The cell walls are formed through secretion of polysaccharides. Some species, including algae and bacteria, secrete polysaccharides that are released from the cells. In other words, these molecules are not held in association with the cells as are cell wall polysaccharides. Instead, these molecules are released from the cells. For example, cultures of some species of microalgae secrete exopolysaccharides that are suspended in the culture media.

III. Methods of Producing Polysaccharides

A. Cell Culture Methods: Microalgae

Polysaccharides can be produced by culturing microalgae. Examples of microalgae that can be cultured to produce polysaccharides are shown in Tables 1A and 1B. Also listed in Table 1A are references that enable the skilled artisan to culture the microalgae species under conditions sufficient for polysaccharide production. Also listed in Table 1A are strain numbers from various publicly available algae collections, as well as strains published in journals that require public dissemination of reagents as a prerequisite for publication.

TABLE 1A

Examples of microalgae, culture parameters, and polysaccharide production.

| Species | Strain Number/ Source | Culture and polysaccharide purification method reference | Reported Monosaccharide Composition | Culture conditions |
|---|---|---|---|---|
| *Porphyridium cruentum* | UTEX[1] 161 | M. A. Guzman-Murillo and F. Ascencio., Letters in Applied Microbiology 2000, 30, 473-478 | Xylose, Glucose, Galactose, Glucoronic acid | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| *Porphyridium cruentum* | UTEX 161 | Fabregas et al., Antiviral Research 44(1999)-67-73 | Xylose, Glucose, Galactose and Glucoronic acid | Cultured in 80 ml glass tubes with aeration of 100 ml/min and 10% $CO_2$, for 10 s every ten minutes to maintain pH > 7.6. Maintained at 22° in 12:12 |

TABLE 1A-continued

Examples of microalgae, culture parameters, and polysaccharide production.

| Species | Strain Number/ Source | Culture and polysaccharide purification method reference | Reported Monosaccharide Composition | Culture conditions |
|---|---|---|---|---|
| Porphyridium sp. | UTEX 637 | Dvir, Brit. J.of Nutrition (2000), 84, 469-476. [Review: S. Geresh Biosource Technology 38 (1991) 195-201]-Huleihel, 2003, Applied Spectoscopy, v57, No. 4 2003 | Xylose, Glucose and Galactose, Methyl hexoses, Mannose, Rhamnose | Light/dark periodicity. Light at 152.3 umol/m2/s. Salinity 3.5% (nutrient enriched as Fabregas, 1984 modified in 4 mmol Nitrogen/L) Outdoor cultivation for 21 days in artficial sea water in polyethylene sleeves. See Jones (1963) and Cohen & Malis Arad, 1989) |
| Porphyridium aerugineum | SAG[2] 111.79 | Talyshinsky, Marina Cancer Cell Int'l 2002, 2; Review: S. Geresh Biosource Technology 38 (1991) 195-201] 1 See Ramus_1972 | xylose, glucose, galactose, methyl hexoses | see Dubinsky et al. Plant Physio. And Biochem. (192) 30: 409-414. Pursuant to Ramus_1972-> Axenic culutres are grown in MCYII liquid medium at 25° C. and illuminated with Cool White fluorescent tubes on a 16:8 hr light dark cycle. Cells kept in suspension by agitation on a gyrotary shaker or by a stream of filtered air. |
| Porphyridium purpurpeum | strain 1380-1a | Schmitt D., Water Research Volume 35, Issue 3, March 2001, Pages 779-785, Bioprocess Biosyst Eng. 2002 Apr; 25(1): 35-42. Epub 2002 Mar 6 | unknown | See cited reference |
| Chaetoceros sp. | USCE[3] | M. A. Guzman-Murillo and F. Ascencio., Letters in Applied Microbiology 2000, 30, 473-478 | unknown | See cited reference |
| Chlorella autotropica | USCE | M. A. Guzman-Murillo and F. Ascencio., Letters in Applied Microbiology 2000, 30, 473-478 | unknown | See cited reference |
| Chlorella autotropica | UTEX 580 | Fabregas et al., Antiviral Research 44(1999)-67-73 | unknown | Cultured in 80 ml glass tubes with aeration of 100 ml/min and 10% CO2, for 10 s every ten minutes to maintain pH > 7.6. Maintained at 22° in 12:12 Light/dark periodicity. Light at 152.3 umol/m2/s. Salinity 3.5% (nutrient enriched as Fabregas, 1984) |
| Chlorella capsulata | UTEX LB2074 | M. A. Guzman-Murillo and F. Ascencio., Letters in Applied Microbiology 2000, 30, 473-478 (species is a.k.a. Schizochlamydella capsulata) | Un known | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Chlorella stigmatophora | GGMCC[4] | S. Guzman, Phytotherapy Rscrh (2003) 17: 665-670 | glucose, glucuronic acid, xylose, ribose/fucose | Grown in 10 L of membrane filtered (0.24um) seawater and sterilized at 120° for 30 min and enriched with Erd Schreiber medium. Cultures maintained at 18 +/− 1° C. under constant 1% $CO_2$ bubbling. |
| Dunalliela tertiolecta | DCCBC[5] | Fabregas et al., Antiviral Research 44(1999)-67-73 | unknown | Cultured in 80 ml glass tubes with aeration of 100 ml/min and 10% CO2, for 10 s every ten minutes to maintain pH > 7.6. Maintained at 22° in 12:12 Light/dark periodicity. Light at 152.3 umol/m2/s. Salinity 3.5% (nutrient enriched as Fabregas, 1984) |
| Dunalliela bardawil | DCCBC | Fabregas et al., Antiviral Research 44(1999)-67-73 | unknown | Cultured in 80 ml glass tubes with aeration of 100 ml/min and 10% CO2, for 10 s every ten minutes to maintain pH > 7.6. Maintained at 22° in 12:12 Light/dark periodicity. Light at 152.3 umol/$m^2$/s. Salinity 3.5% (nutrient enriched as Fabregas, 1984) |
| Isochrysis galbana var. tahitiana | HCTMS[6] | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um millipore filter or |

TABLE 1A-continued

Examples of microalgae, culture parameters, and polysaccharide production.

| Species | Strain Number/ Source | Culture and polysaccharide purification method reference | Reported Monosaccharide Composition | Culture conditions |
| --- | --- | --- | --- | --- |
| Isochrysis galbana var. Tiso | UTEX LB 987 | Fabregas et al., Antiviral Research 44(1999)-67-73 | unknown | distilled water depending on microalgae salt tolerance. Incubated at 25° C. in flasks and illuminated with white fluorescent lamps. Cultured in 80 ml glass tubes with aeration of 100 ml/min and 10% CO2, for 10 s every ten minutes to maintain pH > 7.6. Maintained at 22° in 12:12 Light/dark periodicity. Light at 152.3 umol/m$^2$/s. Salinity 3.5% (nutrient enriched as Fabregas, 1984) |
| Isochrysis sp. | CCMP[7] | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Phaeodactylum tricornutum | UTEX 642, 646, 2089 | M. A M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Phaeodactylum tricornutum | GGMCC | S. Guzman, Phytotherapy Rscrh (2003) 17: 665-670 | glucose, glucuronic acid, and mannose | Grown in 10 L of membrane filtered (0.24 um) seawater and sterilized at 120° for 30 min and enriched with Erd Schreiber medium. Cultures maintained at 18 +/− 1° C. under constant 1% CO2 bubbling. |
| Tetraselmis sp. | CCMP 1634-1640; UTEX 2767 | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Botrycoccus braunii | UTEX 572 and 2441 | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Cholorococcum | UTEX 105 | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Hormotilopsis gelatinosa | UTEX 104 | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Neochloris oleoabundans | UTEX 1185 | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |

TABLE 1A-continued

Examples of microalgae, culture parameters, and polysaccharide production.

| Species | Strain Number/ Source | Culture and polysaccharide purification method reference | Reported Monosaccharide Composition | Culture conditions |
|---|---|---|---|---|
| Ochromonas Danica | UTEX L1298 | M. A. Guzman-Murillo and F. Ascencio., Letters in Applied Microbiology 2000, 30, 473-478 | unknown | Cultures obtained from various sources and were cultured in F/2 broth prepared with seawater filtered through a 0.45 um Millipore filter or distilled water depending on microalgae salt tolerance. Incubated at 25° C. in flasks and illuminated with white fluorescent lamps. |
| Gyrodinium impudicum | KG03; KGO9; KGJO1 | Yim, Joung Han et. Al., J. of Microbiol December 2004, 305-14; Yim, J. H. (2000) Ph.D. Dissertations, University of Kyung Hee, Seoul | Homopolysaccharide of galactose w/ 2.96% uronic acid | Isolated from seawater collected from red-tide bloom in Korean coastal water. Maintained in f/2 medium at 22° under circadian light at 100 uE/m2/sec: dark cycle of 14 h: 10 h for 19 days. Selected with neomycin and/or cephalosporin 20 ug/ml |
| Ellipsoidon sp. | See cited references | Fabregas et al., Antiviral Research 44(1999)-67-73; Lewin, R. A. Cheng, L., 1989. Phycologya 28, 96-108 | unknown | Cultured in 80 ml glass tubes with aeration of 100 ml/min and 10% CO2, for 10 s every ten minutes to maintain pH > 7.6. Maintained at 22° in 12:12 Light/dark periodicity. Light at 152.3 umol/m2/s. Salinity 3.5% (nutrient enriched as Fabregas, 1984) |
| Rhodella reticulata | UTEX 2320 | Talyshinsky, Marina Cancer Cell Int'l 2002, 2 | unknown | See Dubinsky O. et al. Composition of Cell wall polysaccharide produced by unicellular red algae Rhodella reticulata. 1992 Plant Physiology and biochemistry 30: 409-414 |
| Rhodella maculata | UTEX LB 2506 | Evans, LV., et al. J. Cell Sci 16, 1-21(1974); EVANS, L. V. (1970). Br. phycol.J. 5, 1-13. | Galactose, xylose, glucuronic acid | Grown in either SWM3 medium or ASP12, MgCl2 supplement. 100 mls in 250 mls volumetric Erlenmeyer flask with gentle shaking and 4000lx Northern Light fluorescent light for 16 hours. |
| Gymnodinium sp. | Oku-1 | Sogawa, K., et al., Life Sciences, Vol. 66, No. 16, pp. PL 227-231 (2000) AND Umemura, Ken: Biochemical Pharmacology 66 (2003) 481-487 | unknown | See cited reference |
| Spirilina platensis | UTEX LB 1926 | Kaji, T et. Al., Life Sci 2002 Mar 8; 70(16): 1841-8 Schaeffer and Krylov (2000) Review-Ectoxicology and Environmental Safety. 45, 208-227. | Na-Sp contains two disaccharide repeats: Aldobiuronic acid and Acofriose + other minor saccharides and sodium ion | See cited reference |
| Cochlodinuium polykrikoides | Oku-2 | Hasui, et. Al., Int. J. Bio. Macromol. Volume 17 No. 5 1995. | mannose, galactose, glucose and uronic acid | Precultures grown in 500 ml conicals containing 300 mls ESM (?) at 21.5° C. for 14 days in continuous light (3500 lux) in growth cabinet) and then transferred to 5 liter conical flask containing 3 liters of ESM. Grown 50 days and then filtered thru wortmann GFF filter. |
| Nostoc muscorum | PCC[8] 7413, 7936, 8113 | Sangar, VK Applied Micro. (1972) & A. M. Burja et al Tetrahydron 57 (2001) 937-9377; Otero A., J Biotechnol. 2003 Apr 24; 102(2): 143-52 | unknown | Growth in nitrogen fixing conditions in BG-11 medium in aerated cultures maintained in log phase for several months. 250 mL culture media that were disposed in a temperature controlled incubator and continuously illuminated with 70 umol photon m−2 s−1 at 30° C. |
| Cyanospira capsulata | See cited references | A. M. Burja et al. Tetrahydron 57 (2001) 937-9377 & Garozzo, D., Carbohydrate Res. 1998 307 113-124; Ascensio, F., Folia Microbiol (Praha). 2004; 49(1): 64-70., Cesaro, A., et al., Int J Biol Macromol. 1990 Apr; 12(2): 79-84 | unknown | See cited references |

TABLE 1A-continued

Examples of microalgae, culture parameters, and polysaccharide production.

| Species | Strain Number/ Source | Culture and polysaccharide purification method reference | Reported Monosaccharide Composition | Culture conditions |
|---|---|---|---|---|
| Cyanothece sp. | ATCC 51142 | Ascensio F., Folia Microbiol (Praha). 2004; 49(1): 64-70. | unknown | Maintained at 27° C. in ASN III medium with light/dark cycle of 16/8 h under fluorescent light of 3,000 lux light intensity. In Phillips each of 15 strains were grown photoautotrophically in enriched seawater medium. When required the amount of NaNO3 was reduced from 1.5 to 0.35 g/L. Strains axenically grown in an atmosphere of 95% air and 5% CO2 for 8 days under continuous illumination. with mean photon flux of 30 umol photon/m2/s for the first 3 days of growth and 80 umol photon/m/s |
| Chlorella pyrenoidosa | UTEX 343; UTEX 1806 | Cheng_2004 Journal of Medicinal Food 7(2) 146-152 | unknown | See cited reference |
| Phaeodactylum tricornutum | CCAP 1052/1A | Fabregas et al., Antiviral Research 44(1999)-67-73 | unknown | Cultured in 80 ml glass tubes with aeration of 100 ml/min and 10% CO2, for 10 s every ten minutes to maintain pH > 7.6. Maintained at 22° in 12:12 Light/dark periodicity. Light at 152.3 umol/m2/s. Salinity 3.5% (nutrient enriched as Fabregas, 1984) |
| Chlorella autotropica | USCE | M. A. Guzman-Murillo and F. Ascencio., Letters in Applied Microbiology 2000, 30, 473-478 | unknown | See cited reference |
| Chlorella sp. | CCM | M. A. Guzman-Murillo and F. Ascencio., Letters in Applied Microbiology 2000, 30, 473-478 | unknown | See cited reference |
| Dunalliela tertiolecta | USCE | M. A. Guzman-Murillo and F. Ascencio., Letters in Applied Microbiology 2000, 30, 473-478 | unknown | See cited reference |
| Isochrysis galabana | UTEX LB 987 | Fabregas et al, Antiviral Research 44(1999)-67-73 | unknown | Cultured in 80 ml glass tubes with aeration of 100 ml/min and 10% $CO_2$, for 10 s every ten minutes to maintain pH > 7.6. Maintained at 22° in 12:12 Light/dark periodicity. Light at 152.3 umol/m2/s. Salinity 3.5% (nutrient enriched as Fabregas, 1984) |
| Tetraselmis tetrathele | CCAP 66/1A-D | Fabregas et al., Antiviral Research 44(1999)-67-73 | unknown | Cultured in 80 ml glass tubes with aeration of 100 ml/min and 10% $CO_2$, for 10 s every ten minutes to maintain pH > 7.6. Maintained at 22° in 12:12 Light/dark periodicity. Light at 152.3 umol/m2/s. Salinity 3.5% (nutrient enriched as Fabregas, 1984) |
| Tetraselmis suecica | UTEX LB 2286 | M. A. Guzman-Murillo and F. Ascencio., Letters in Applied Microbiology 2000, 30, 473-478 | unknown | See cited reference |
| Tetraselmis suecica | CCAP 66/4 | Fabregas et al., Antiviral Research 44(1999)-67-73 and Otero and Fabregas-Aquaculture 159 (1997) 111-123. | unknown | Cultured in 80 ml glass tubes with aeration of 100 ml/min and 10% $CO_2$, for 10 s every ten minutes to maintain pH > 7.6. Maintained at 22° in 12:12 Light/dark periodicity. Light at 152.3 umol/m2/s. Salinity 3.5% (nutrient enriched as Fabregas, 1984) |
| Botrycoccus sudeticus | UTEX 2629 | M. A. Guzman-Murillo and F. Ascencio., Letters in Applied Microbiology 2000, 30, 473-478 | unknown | See cited reference |
| Chlamydomonas mexicana | UTEX 729 | Moore and Tisher Science. 1964 Aug. 7; 145: 586-7. | unknown | See cited reference |
| Dysmorphococcus globosus | UTEX LB 65 | M. A. Guzman-Murillo and F. Ascencio., Letters in Applied Microbiology 2000, 30, 473-478 | unknown | See cited reference |
| Rhodella reticulata | UTEX LB 2320 | S. Geresh et al., J Biochem. Biophys. Methods 50 (2002) | unknown | See cited reference |

TABLE 1A-continued

Examples of microalgae, culture parameters, and polysaccharide production.

| Species | Strain Number/ Source | Culture and polysaccharide purification method reference | Reported Monosaccharide Composition | Culture conditions |
|---|---|---|---|---|
| Anabena cylindrica | ATCC 29414 | 179-187 [Review: S. Geresh Biosource Technology 38 (1991) 195-201] Sangar, VK Appl Microbiol. 1972 Nov; 24(5): 732-4 | In Vegative wall where only 18% is carbohydrate - Glucose [35%], mannose [50%], galactose, xylose, and fucose. In heterocyst wall where 73% is carbohydrate - Glucose 73% and Mannose is 21% with some galactose and xylose | See cited reference |
| Anabena flosaquae | A37; JM Kingsbury Laboratory, Cornell University | Moore, BG [1965] Can J. Microbiol. Dec; 11(6): 877-85 | Glucose and mannose | See cited reference and APPLIED ENVIRONMENTAL MICROBIOLOGY, April 1978, 718-723) |
| Palmella mucosa | See cited references | Sangar, VK Appl Microbiol. 1972 Nov; 24(5): 732-4; Lewin RA., (1956) Can J Microbiol. 2: 665-672; Arch Mikrobiol. 1964 Aug 17; 49: 158-66 | unknown | See cited reference |
| Anacystis nidulans | PCC 6301 | Sangar, VK Appl Microbiol. 1972 Nov; 24(5): 732-4 | Glucose, galactose, mannose | See cited reference |
| Phormidium 94a | See cited reference | Vicente-Garcia V. et al., Biotechnol Bioeng. 2004 Feb 5; 85(3): 306-10 | Galactose, Mannose, Galacturonic acid, Arabinose, and Ribose | Cultivated in 2 L BG-11 medium at 28° C. Acetone was added to precipitate exopolysaccharide. |
| Anabaenaopsis circularis | 1402/1$^9$ | David KA, Fay P. Appl Environ Microbiol. 1977 Dec; 34(6): 640-6 | unknown | See cited reference |
| Aphanocapsa halophtia | MN-11 | Sudo H., et al. Current Micrcobiology Vol. 30 (1995), pp.219-222 | Rhamnose; mannose; fucose; galactose; xylose; glucose In ratio of: 15:53:3:3:25 | Cultured aerobically for 20 days in seawater-based medium, with 8% NaCl, and 40 mg/L NaHPO4. Nitrate changed the Exopolysaccharide content. Highest cell density was obtained from culture supplemented with 100 mg/l NaNO$_3$. Phosphorous (40 mg/L) could be added to control the biomass and exopolysaccharide concentration. |
| Aphanocapsa sp | See reference | De Philippis R et al., Sci Total Environ. 2005 Nov 2; | unknown | Incubated at 20 and 28° C. with artificial light at a photon flux of 5-20 umol m$^{-2}$ s$^{-1}$. |
| Cylindrotheca sp | See reference | De Philippis R et al., Sci Total Environ. 2005 Nov 2; | Glucuronic acid, Galacturonic acid, Glucose, Mannose, Arabinose, Fructose and Rhamnose | Stock enriched cultures incubated at 20 and 28° C. with artificial light at a photon flux of 5-20 umol m−2 s−1. Exopolysaccharide production done in glass tubes containing 100 mL culture at 28° C. with continuous illumination at photon density of 5-10 uE m−2 s−1. |
| Navicula sp | See reference | De Philippis R et al., Sci Total Environ. 2005 Nov 2; | Glucuronic acid, Galacturonic acid, Glucose, Mannose, Arabinose, Fructose and Rhamnose | Incubated at 20 and 28° C. with artificial light at a photon flux of 5-20 umol m−2 s−1. EPS production done in glass tubes containing 100 mL culture at 28° C. with continuous illumination at photon density of 5-10 uE m−2 s−1. |
| Gloeocapsa sp | See reference | De Philippis R et al., Sci Total Environ. 2005 Nov 2; | unknown | Incubated at 20 and 28° C. with artifical light at a photon flux of 5-20 umol m−2 s−1. |
| Gloeocapsa alpicola | See cited references | J Appl Microbiol. 2005; 98(1): 114-20; Photochem Photobiol. 1982 | unknown | See cited references |

TABLE 1A-continued

Examples of microalgae, culture parameters, and polysaccharide production.

| Species | Strain Number/ Source | Culture and polysaccharide purification method reference | Reported Monosaccharide Composition | Culture conditions |
| --- | --- | --- | --- | --- |
| Phaeocystis pouchetii | See cited references | Mar; 35(3): 359-64; J Gen Microbiol. 1977 Jan; 98(1): 277-80; Arch Microbiol. 1976 Feb; 107(1): 93-7; FEMS Microbiol Lett. 2002 Sep 10; 214(2): 229-33 Toxicology. 2004 Jul 1; 199(2-3): 207-17; Toxicon. 2003 Jun; 41(7): 803-12; Protist. 2002 Sep; 153(3): 275-82; J Virol. 2005 Jul; 79(14): 9236-43; J Bacteriol. 1961 Jul; 82(1): 72-9 | unknown | See cited references |
| Leptolyngbya sp | See reference | De Philippis R et al., Sci Total Environ. 2005 Nov 2; | unknown | Incubated at 20 and 28° C. with artificial light at a photon flux of 5-20 umol m−2 s−1. |
| Symploca sp. | See reference | De Philippis R et al., Sci Total Environ. 2005 Nov 2; | unknown | Incubated at 20 and 28° C. with artificial light at a photon flux of 5-20 umol m−2 s−1. |
| Synechocystis | PCC 6714/6803 | Jurgens UJ, Weckesser J. J Bacteriol. 1986 Nov; 168(2): 568-73 | Glucoseamine, mannosamine, galactosamine, mannose and glucose | Photoautotrophically grown in BG-11 medium, pH 7.5 at 25° C. Mass cultures prepared in a 12 liter fermentor and gassed by air and carbon dioxide at flow rates of 250 and 2.5 liters/h, with illumination from white fluorescent lamps at a constant light intensity of 5,000 lux. |
| Stauroneis decipiens | See reference | Lind, JL (1997) Planta 203: 213-221 | unknown | See cited reference |
| Achnanthes brevipes | Indiana University Culture Collection | Holdsworth, RH., Cell Biol. 1968 Jun; 37(3): 831-7; Acta Cient Venez. 2002; 53(1): 7-14.; J. Phycol 36 pp. 882-890 (2000) | unknown | See cited reference |
| Achnanthes longipes | Strain 330 from National Institute for Environmental Studies | Wang, Y., et al., Plant Physiol. 1997 Apr; 113(4): 1071-1080. | unknown | See cited reference |

Other nonlimiting examples of microalgae that can be used in accordance with the present invention can be found in Table 1B.

TABLE 1B

Examples of microalgae.

*Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora sp., Anabaena, Ankistrodesmus, Ankistrodesmus falcatus, Boekelovia hooglandii, Borodinella sp., Botryococcus braunii, Botryococcus sudeticus, Bracteococcus minor, Bracteococcus medionucleatus, Carteria, Chaetoceros gracilis, Chaetoceros muelleri, Chaetoceros muelleri subsalsum, Chaetoceros sp., Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca var. vacuolata, Chlorella glucotropha, Chlorella infusionum, Chlorella infusionum var. actophila, Chlorella infusionum var. auxenophila, Chlorella kessleri, Chlorella lobophora (strain SAG 37.88), Chlorella luteoviridis, Chlorella luteoviridis var. aureoviridis, Chlorella luteoviridis var. lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides (including any of UTEX strains 1806, 411, 264, 256, 255, 250, 249, 31, 29, 25), Chlorella protothecoides var. acidicola, Chlorella regularis, Chlorella regularis var. minima, Chlorella regularis var. umbricata, Chlorella reisiglii, Chlorella saccharophila, Chlorella saccharophila var. ellipsoidea, Chlorella salina, Chlorella simplex, Chlorella sorokiniana, Chlorella sp., Chlorella sphaerica, Chlorella stigmatophora, Chlorella vanniellii, Chlorella vulgaris, Chlorella vulgaris f. tertia,*

TABLE 1B-continued

Examples of microalgae.

*Chlorella vulgaris* var. *autotrophica*, *Chlorella vulgaris* var. *viridis*, *Chlorella vulgaris* var. *vulgaris*, *Chlorella vulgaris* var. *vulgaris f. tertia*, *Chlorella vulgaris* var. *vulgaris f. viridis*, *Chlorella xanthella*, *Chlorella zofingiensis*, *Chlorella trebouxioides*, *Chlorella vulgaris*, *Chlorococcum infusionum*, *Chlorococcum* sp., *Chlorogonium*, *Chroomonas* sp., *Chrysosphaera* sp., *Cricosphaera* sp., *Crypthecodinium cohnii*, *Cryptomonas* sp., *Cyclotella cryptica*, *Cyclotella meneghiniana*, *Cyclotella* sp., *Dunaliella* sp., *Dunaliella bardawil*, *Dunaliella bioculata*, *Dunaliella granulate*, *Dunaliella maritime*, *Dunaliella minuta*, *Dunaliella parva*, *Dunaliella peircei*, *Dunaliella primolecta*, *Dunaliella salina*, *Dunaliella terricola*, *Dunaliella tertiolecta*, *Dunaliella viridis*, *Dunaliella tertiolecta*, *Eremosphaera viridis*, *Eremosphaera* sp., *Ellipsoidon* sp., *Euglena*, *Franceia* sp., *Fragilaria crotonensis*, *Fragilaria* sp., *Gleocapsa* sp., *Gloeothamnion* sp., *Hymenomonas* sp., *Isochrysis* aff. *galbana*, *Isochrysis galbana*, *Lepocinclis*, *Micractinium*, *Micractinium* (UTEX LB 2614), *Monoraphidium minutum*, *Monoraphidium* sp., *Nannochloris* sp., *Nannochloropsis salina*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrina*, *Nitzschia communis*, *Nitzschia dissipata*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Parachlorella kessleri*, *Pascheria acidophila*, *Pavlova* sp., *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pseudochlorella aquatica*, *Pyramimonas* sp., *Pyrobotrys*, *Rhodococcus opacus*, *Sarcinoid chrysophyte*, *Scenedesmus armatus*, *Schizochytrium*, *Spirogyra*, *Spirulina platensis*, *Stichococcus* sp., *Synechococcus* sp., *Tetraedron*, *Tetraselmis* sp., *Tetraselmis suecica*, *Thalassiosira weissflogii*, and *Viridiella fridericiana*

Microalgae are preferably cultured in liquid media for polysaccharide production. Culture condition parameters can be manipulated to optimize total polysaccharide production as well as to alter the structure of polysaccharides produced by microalgae.

Microalgal culture media usually contains components such as a fixed nitrogen source, trace elements, a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

Some microalgae species can grow by utilizing a fixed carbon source such as glucose or acetate. Such microalgae can be cultured in bioreactors that do not allow light to enter. Alternatively, such microalgae can also be cultured in photobioreactors that contain the fixed carbon source and allow light to strike the cells. Such growth is known as heterotrophic growth. Any strain of microalgae, including those listed in Tables 1A and 1B, can be cultured in the presence of any one or more fixed carbon source including those listed in Tables 2 and 3.

TABLE 2

Examples of fixed-carbon sources for culturing microalgae.

2,3-Butanediol; 2-Aminoethanol; 2'-Deoxy Adenosine; 3-Methyl Glucose; Acetic Acid; Adenosine; Adenosine-5'-Monophosphate; Adonitol; Amygdalin; Arbutin; Bromosuccinic Acid; Cis-Aconitic Acid; Citric Acid; D,L-Carnitine; D,L-Lactic Acid; D,L-α-Glycerol Phosphate; D-Alanine; D-Arabitol; D-Cellobiose; Dextrin; D-Fructose; D-Fructose-6-Phosphate; D-Galactonic Acid Lactone; D-Galactose; D-Galacturonic Acid; D-Gluconic Acid; D-Glucosaminic Acid; D-Glucose; D-Glucose-6-Phosphate; D-Glucuronic Acid; D-Lactic Acid Methyl Ester; D-L-α-Glycerol Phosphate; D-Malic Acid; D-Mannitol; D-Mannose; D-Melezitose; D-Melibiose; D-Psicose; D-Raffinose; D-Ribose; D-Saccharic Acid; D-Serine; D-Sorbitol; D-Tagatose; D-Trehalose; D-Xylose; Formic Acid; Gentiobiose; Glucuronamide; Glycerol; Glycogen; Glycyl-LAspartic Acid; Glycyl-LGlutamic Acid; Hydroxy-LProline; i-Erythritol; Inosine; Inulin; Itaconic Acid; Lactamide; Lactulose; L-Alaninamide; L-Alanine; L-Alanylglycine; L-Alanyl-Glycine; L-Arabinose; L-Asparagine; L-Aspartic Acid; L-Fucose; L-Glutamic Acid; L-Histidine; L-Lactic Acid; L-Leucine; L-Malic Acid; L-Ornithine; LPhenylalanine; L-Proline; L-Pyroglutamic Acid; L-Rhamnose; L-Serine; L-Threonine; Malonic Acid; Maltose; Maltotriose; Mannan; m-Inositol; N-Acetyl-DGalactosamine; N-Acetyl-DGlucosamine; N-Acetyl-LGlutamic Acid; N-Acetyl-β-DMannosamine; Palatinose; Phenyethylamine; p-Hydroxy-Phenylacetic Acid; Propionic Acid; Putrescine; Pyruvic Acid; Pyruvic Acid Methyl Ester; Quinic Acid; Salicin; Sebacic Acid; Sedoheptulosan; Stachyose; Succinamic Acid; Succinic Acid; Succinic Acid Mono-Methyl-Ester; Sucrose; Thymidine; Thymidine-5'-Monophosphate; Turanose; Tween 40; Tween 80; Uridine; Uridine-5'-Monophosphate; Urocanic Acid; Water; Xylitol; α-Cyclodextrin; α-D-Glucose; α-D-Glucose-1-Phosphate; α-D-Lactose; α-Hydroxybutyric Acid; α-Keto Butyric Acid; α-Keto Glutaric Acid; α-Keto Valeric Acid; α-Ketoglutaric Acid; α-Ketovaleric Acid; α-Methyl-DGalactoside; α-Methyl-DGlucoside; α-Methyl-DMannoside; β-Cyclodextrin; β-Hydroxybutyric Acid; β-Methyl-DGalactoside; β-Methyl-D-Glucoside; γ-Amino Butyric Acid; and γ-Hydroxybutyric Acid

TABLE 3

Examples of fixed-carbon sources for culturing microalgae.

(2-amino-3,4-dihydroxy-5-hydroxymethyl-1-cyclohexyl)glucopyranoside; (3,4-disinapoyl)fructofuranosyl-(6-sinapoyl)glucopyranoside; (3-sinapoyl)fructofuranosyl-(6-sinapoyl)glucopyranoside; 1,10-di-O-(2-acetamido-2-deoxyglucopyranosyl)-2-azi-1,10-decanediol; 1,3-mannosylmannose; 1,6-anhydrolactose; 1,6-anhydrolactose hexaacetate; 1,6-dichlorosucrose; 1-chlorosucrose; 1-desoxy-1-glycinomaltose; 1-O-alpha-2-acetamido-2-deoxygalactopyranosyl-inositol; 1-O-methyl-di-N-trifluoroacetyl-beta-chitobioside; 1-propyl-4-O-beta galactopyranosyl-alpha galactopyranoside; 2-(acetylamino)-4-O-(2-(acetylamino)-2-deoxy-4-O-sulfogalactopyranosyl)-2-deoxyglucose; 2-(trimethylsilyl)ethyl lactoside; 2,1',3',4',6'-penta-O-acetylsucrose; 2,2'-O-(2,2'-diacetamido-2,3,2',3'-tetradeoxy-6,6'-di-O-(2-tetradecylhexadecanoyl)-alpha,alpha'-trehalose-3,3'-diyl)bis(N-lactoyl-alanyl-isoglutamine); 2,3,6,2',3',4',6'-hepta-O-acetylcellobiose; 2,3'-anhydrosucrose; 2,3-di-O-phytanyl-1-O-(mannopyranosyl-(2-sulfate)-(1-2)-glucopyranosyl)-sn-glycerol; 2,3-epoxypropyl O-galactopyranosyl(1-6)galactopyranoside; 2,3-isoprolylideneerthrofuranosyl 2,3-O-isopropylideneerythrofuranoside; 2',4'-dinitrophenyl 2-deoxy-2-fluoro-beta-xylobioside; 2,5-anhydromannitol iduronate; 2,6-sialyllactose; 2-acetamido-2,4-dideoxy-4-fluoro-3-O-galactopyranosylglucopyranose; 2-acetamido-2-deoxy-3-O-(gluco-4-enepyranosyluronic acid)glucose; 2-acetamido-2-deoxy-3-O-rhamnopyranosylglucose; 2-acetamido-2-deoxy-6-O-beta galactopyranosylgalactopyranose; 2-acetamido-2-deoxyglucosylgalactitol; 2-acetamido-3-O-(3-acetamido-3,6-dideoxy-beta-glucopyranosyl)-2-deoxy-galactopyranose; 2-amino-6-O-(2-amino-2-deoxy-glucopyranosyl)-2-deoxyglucose; 2-azido-2-deoxymannopyranosyl-(1,4)-rhamnopyranose; 2-deoxy-6-O-(2,3-dideoxy-4,6-O-isopropylidene-2,3-(N-tosylepimino)mannopyranosyl)-4,5-O-isopropylidene-1,3-di-N-tosylstreptamine; 2-deoxymaltose; 2-iodobenzyl-1-thiocellobioside; 2-N-(4-benzoyl)benzoyl-1,3-bis(mannos-4-yloxy)-2-propylamine; 2-nitrophenyl-2-acetamido-2-deoxy-6-O-beta galactopyranosyl-alpha galactopyranoside; 2-O-(glucopyranosyluronic acid)xylose; 2-O-glucopyranosylribitol-1-phosphate; 2-O-glucopyranosylribitol-4'-phosphate; 2-O-rhamnopyranosyl-rhamnopyranosyl-3-hydroxyldecanoyl-3-hydroxydecanoate; 2-O-talopyranosylmannopyranoside; 2-thiokojibiose; 2-thiosophorose; 3,3'-neotrehalosadiamine; 3,6,3',6'-dianhydro(galactopyranosylgalactopyranoside); 3,6-di-O-methyl-beta-glucopyranosyl-(1-4)-2,3-di-O-methyl-alpha-rhamnopyranose; 3-amino-3-deoxyaltropyranosyl-3-amino-3-deoxyaltropyranoside; 3-deoxy-3-fluorosucrose; 3-deoxy-5-O-rhamnopyranosyl-2-octulopyranosonate; 3-deoxyoctulosonic acid-(alpha-2-4)-3-deoxyoctulosonic acid; 3-deoxysucrose; 3-ketolactose; 3-ketosucrose; 3-ketotrehalose; 3-methyllactose; 3-O-(2-acetamido-6-O-(N-acetylneuraminyl)-2-deoxygalactosyl)serine; 3-O-(glucopyranosyluronic acid)galactopyranose; 3-O-beta-glucuronosylgalactose; 3-O-fucopyranosyl-2-acetamido-2-deoxyglucopyranose; 3'-O-galactopyranosyl-1-4-O-galactopyranosylcytarabine; 3-O-galactosylarabinose; 3-O-talopyranosylmannopyranoside; 3-trehalosamine; 4-(trifluoroacetamido)phenyl-2-acetamido-2-deoxy-4-O-beta-mannopyranosyl-beta-glucopyranoside; 4,4',6,6'-tetrachloro-4,4',6,6'-tetradeoxygalactotrehalose; 4,6,4',6'-dianhydro(galactopyranosylgalactopyranoside); 4,6-dideoxysucrose; 4,6-O-(1-ethoxy-2-propenylidene)sucrose hexaacetate; 4-chloro-4-deoxy-alpha-galactopyranosyl 3,4-anhydro-1,6-dichloro-1,6-dideoxy-beta-lyxo hexulofuranoside; 4-glucopyranosylmannose; 4-methylumbelliferylcellobioside; 4-nitrophenyl 2-fucopyranosyl-fucopyranoside; 4-nitrophenyl 2-O-alpha-D-galactopyranosyl-alpha-D-mannopyranoside; 4-nitrophenyl 2-O-alpha-D-glucopyranosyl-alpha-D-mannopyranoside; 4-nitrophenyl 2-O-alpha-D-mannopyranosyl-alpha-D-mannopyranoside; 4-nitrophenyl 6-O-alpha-D-mannopyranosyl-alpha-D-mannopyranoside; 4-nitrophenyl-2-acetamido-2-deoxy-6-O-beta-D-galactopyranosyl-beta-D-glucopyranoside; 4-O-(2-acetamido-2-deoxy-beta-glucopyranosyl)ribitol; 4-O-(2-amino-2-deoxy-alpha-glucopyranosyl)-3-deoxy-manno-2-octulosonic acid; 4-O-(glucopyranosyluronic acid)xylose; 4-O-acetyl-alpha-N-acetylneuraminyl-(2-3)-lactose; 4-O-alpha-D-galactopyranosyl-D-galactose; 4-O-galactopyranosyl-3,6-anhydrogalactose dimethylacetal; 4-O-galactopyranosylxylose; 4-O-mannopyranosyl-2-acetamido-2-deoxyglucose; 4-thioxylobiose; 4-trehalosamine; 4-trifluoroacetamidophenyl 2-acetamido-4-O-(2-acetamido-2-deoxyglucopyranosyl)-2-deoxymannopyranosiduronic acid; 5-bromoindoxyl-beta-cellobioside; 5'-O-(fructofuranosyl-2-1-fructofuranosyl)pyridoxine; 5-O-beta-galactofuranosyl-galactofuranose; 6 beta-galactinol; 6(2)-thiopanose; 6,6'-di-O-corynomycoloyl-alpha-mannopyranosyl-alpha-mannopyranoside; 6,6-di-O-maltosyl-beta-cyclodextrin; 6,6'-di-O-mycoloyl-alpha-mannopyranosyl-alpha-mannopyranoside; 6-chloro-6-deoxysucrose; 6-deoxy-6-fluorosucrose; 6-deoxy-alpha-gluco-pyranosiduronic acid; 6-deoxy-gluco-heptopyranosyl 6-deoxy-gluco-heptopyranoside; 6-deoxysucrose; 6-O-decanoyl-3,4-di-O-isobutyrylsucrose; 6-O-galactopyranosyl-2-acetamido-2-deoxygalactose; 6-O-galactopyranosylgalactose; 6-O-heptopyranosylglucopyranose; 6-thiosucrose; 7-O-(2-amino-2-deoxyglucopyranosyl)heptose; 8-methoxycarbonyloctyl-3-O-glucopyranosyl-mannopyranoside; 8-O-(4-amino-4-deoxyarabinopyranosyl)-3-deoxyoctulosonic acid; allolactose; allosucrose; allyl 6-O-(3-deoxyoct-2-ulopyranosylonic acid)-(1-6)-2-deoxy-2-(3-hydroxytetradecanamido)glucopyranoside 4-phosphate; alpha-(2-9)-disialic acid; alpha,alpha-trehalose 6,6'-diphosphate; alpha-glucopyranosyl alpha-xylopyranoside; alpha-maltosyl fluoride; aprosulate; benzyl 2-acetamido-2-deoxy-3-O-(2-O-methyl-beta-galactosyl)-beta-glucopyranoside; benzyl 2-acetamido-2-deoxy-3-O-beta fucopyranosyl-alpha-galactopyranoside; benzyl 2-acetamido-6-O-(2-acetamido-2,4-dideoxy-4-fluoroglucopyranosyl)-2-deoxygalactopyranoside; benzyl gentiobioside; beta-D-galactosyl(1-3)-4-nitrophenyl-N-acetyl-alpha-D-galactosamine; beta-methylmelibiose; calcium sucrose phosphate; camiglibose; cellobial; cellobionic acid; cellobionolactone; Cellobiose; cellobiose octaacetate; cellobiosyl bromide heptaacetate; Celsior; chitobiose; chondrosine; Cristolax; deuterated methyl beta-mannobioside; dextrin maltose; D-glucopyranose, O-D-glucopyranosyl; Dietary Sucrose; difructose anhydride I; difructose TABLE 3-continued Examples of fixed-carbon sources for culturing microalgae.

anhydride III; difructose anhydride IV; digalacturonic acid; DT 5461; ediol; epilactose;
epsilon-N-1-(1-deoxylactulosyl)lysine; feruloyl arabinobiose; floridoside; fructofuranosyl-
(2-6)-glucopyranoside; FZ 560; galactosyl-(1-3)galactose; garamine; gentiobiose; geranyl
6-O-alpha-L-arabinopyranosyl-beta-D-glucopyranoside; geranyl 6-O-xylopyranosyl-
glucopyranoside; glucosaminyl-1,6-inositol-1,2-cyclic monophosphate; glucosyl (1-4) N-
acetylglucosamine; glucuronosyl(1-4)-rhamnose; heptosyl-2-keto-3-deoxyoctonate;
inulobiose; Isomaltose; isomaltulose; isoprimeverose; kojibiose; lactobionic acid; lacto-N-
biose II; Lactose; lactosylurea; Lactulose; laminaribiose; lepidimoide; leucrose; levanbiose;
lucidin 3-O-beta-primveroside; LW 10121; LW 10125; LW 10244; maltal; maltitol;
Maltose; maltose hexastearate; maltose-maleimide; maltosylnitromethane heptaacetate;
maltosyltriethoxycholesterol; maltotetraose; Malun 25; mannosucrose; mannosyl-(1-4)-N-
acetylglucosaminyl-(1-N)-urea; mannosyl(2)-N-acetyl(2)-glucose; melibionic acid;
Melibiose; melibiouronic acid; methyl 2-acetamido-2-deoxy-3-O-(alpha-
idopyranosyluronic acid)-4-O-sulfo-beta-galactopyranoside; methyl 2-acetamido-2-deoxy-
3-O-(beta-glucopyranosyluronic acid)-4-O-sulfo-beta-galactopyranoside; methyl 2-
acetamido-2-deoxy-3-O-glucopyranosyluronoylglucopyranoside; methyl 2-O-alpha-
rhamnopyranosyl-beta-galactopyranoside; methyl 2-O-beta-rhamnopyranosyl-beta-
galactopyranoside; methyl 2-O-fucopyranosylfucopyranoside 3 sulfate; methyl 2-O-
mannopyranosylmannopyranoside; methyl 2-O-mannopyranosyl-rhamnopyranoside; methyl
3-O-(2-acetamido-2-deoxy-6-thioglucopyranosyl)galactopyranoside; methyl 3-O-
galactopyranosylmannopyranoside; methyl 3-O-mannopyranosylmannopyranoside; methyl
3-O-mannopyranosyltalopyranoside; methyl 3-O-talopyranosyltalopyranoside; methyl 4-O-
(6-deoxy-manno-heptopyranosyl)galactopyranoside; methyl 6-O-acetyl-3-O-benzoyl-4-O-
(2,3,4,6-tetra-O-benzoylgalactopyranosyl)-2-deoxy-2-phthalimidoglucopyranoside; methyl
6-O-mannopyranosylmannopyranoside; methyl beta-xylobioside; methyl fucopyranosyl(1-
4)-2-acetamido-2-deoxyglucopyranoside; methyl laminarabioside; methyl O-(3-deoxy-3-
fluorogalactopyranosyl)(1-6)galactopyranoside; methyl-2-acetamido-2-
deoxyglucopyranosyl-1-4-glucopyranosiduronic acid; methyl-2-O-
fucopyranosylfucopyranoside 4-sulfate; MK 458; N(1)-2-carboxy-4,6-dinitrophenyl-N(6)-
lactobionoyl-1,6-hexanediamine; N-(2,4-dinitro-5-fluorophenyl)-1,2-bis(mannos-4'-
yloxy)propyl-2-amine; N-(2'-mercaptoethyl)lactamine; N-(2-nitro-4-azophenyl)-1,3-
bis(mannos-4'-yloxy)propyl-2-amine; N-(4-azidosalicylamide)-1,2-bis(mannos-4'-
yloxy)propyl-2-amine; N,N-diacetylchitobiose; N-acetylchondrosine; N-acetyldermosine;
N-acetylgalactosaminyl-(1-4)-galactose; N-acetylgalactosaminyl-(1-4)-glucose; N-
acetylgalactosaminyl-1-4-N-acetylglucosamine; N-acetylgalactosaminyl-1-4-N-
acetylglucosamine; N-acetylgalactosaminyl-alpha(1-3)galactose; N-acetylglucosamine-N-
acetylmuramyl-alanyl-isoglutaminyl-alanyl-glycerol dipalmitoyl; N-acetylglucosaminyl
beta(1-6)N-acetylgalactosamine; N-acetylglucosaminyl-1-2-mannopyranose; N-
acetylhyalobiuronic acid; N-acetylneuraminoyllactose; N-acetylneuraminoyllactose sulfate
ester; N-acetylneuraminyl-(2-3)-galactose; N-acetylneuraminyl-(2-6)-galactose; N-benzyl-
4-O-(beta-galactopyranosyl)glucamine-N-carbodithioate; neoagarobiose; N-
formylkansosaminyl-(1-3)-2-O-methylrhamnopyranose; O-((Nalpha)-acetylglucosamine 6-
sulfate)-(1-3)-idonic acid; O-(4-O-feruloyl-alpha-xylopyranosyl)-(1-6)-glucopyranose; O-
(alpha-idopyranosyluronic acid)-(1-3)-2,5-anhydroalditol-4-sulfate; O-(glucuronic acid 2-
sulfate)-(1--3)-O-(2,5)-andydrotalitol 6-sulfate; O-(glucuronic acid 2-sulfate)-(1--4)-O-
(2,5)-anhydromannitol 6-sulfate; O-alpha-glucopyranosyluronate-(1-2)-galactose; O-beta-
galactopyranosyl-(1-4)-O-beta-xylopyranosyl-(1-0)-serine; octyl maltopyranoside; O-
demethylpaulomycin A; O-demethylpaulomycin B; O-methyl-di-N-acetyl beta-
chitobioside; Palatinit; paldimycin; paulomenol A; paulomenol B; paulomycin A;
paulomycin A2; paulomycin B; paulomycin C; paulomycin D; paulomycin E; paulomycin
F; phenyl 2-acetamido-2-deoxy-3-O-beta-D-galactopyranosyl-alpha-D-galactopyranoside;
phenyl O-(2,3,4,6-tetra-O-acetylgalactopyranosyl)-(1-3)-4,6-di-O-acetyl-2-deoxy-2-
phthalimido-1-thioglucopyranoside; poly-N-4-vinylbenzyllactonamide; pseudo-cellobiose;
pseudo-maltose; rhamnopyranosyl-(1-2)-rhamnopyranoside-(1-methyl ether); rhoifolin;
ruberythric acid; S-3105; senfolomycin A; senfolomycin B; solabiose; SS 554;
streptobiosamine; Sucralfate; Sucrose; sucrose acetate isobutyrate; sucrose caproate;
sucrose distearate; sucrose monolaurate; sucrose monopalmitate; sucrose monostearate;
sucrose myristate; sucrose octaacetate; sucrose octabenzoic acid; sucrose octaisobutyrate;
sucrose octasulfate; sucrose polyester; sucrose sulfate; swertiamacroside; T-1266;
tangshenoside I; tetrahydro-2-((tetrahydro-2-furanyl)oxy)-2H-pyran; thionigerose;
Trehalose; trehalose 2-sulfate; trehalose 6,6'-dipalmitate; trehalose-6-phosphate; rehalulose;
trehazolin; trichlorosucrose; tunicamine; turanose; U 77802; U 77803; xylobiose; xylose-
glucose; and xylosucrose Microalgae contain photosynthetic machinery capable of metabolizing photons, and transferring energy harvested from photons into fixed chemical energy sources such as monosaccharide. Glucose is a common monosaccharide produced by microalgae by metabolizing light energy and fixing carbon from carbon dioxide. Some microalgae can also grow in the absence of light on a fixed carbon source that is exogenously provided (for example see Plant Physiol. 2005 February; 137(2):460-74). In addition to being a source of chemical energy, monosaccharides such as glucose are also substrate for production of polysaccharides (see Example 14). The invention provides methods of producing polysaccharides with novel monosaccharide compositions. For example, microalgae is cultured in the presence of culture media that contains exogenously provided monosaccharide, such as glucose. The monosaccharide is taken up by the cell by either active or passive transport and incorporated into polysaccharide molecules produced by the cell. This novel method of polysaccharide composition manipulation can be performed with, for example, any microalgae listed in Table 1A or Table 1B using any monosaccharide or disaccharide listed in Tables 2 or 3.

In some embodiments, the fixed carbon source is one or more selected from glucose, galactose, xylose, mannose, rhamnose, N-acetylglucosamine, glycerol, floridoside, and glucuronic acid. The methods may be practiced cell growth in the presence of at least about 5.0 µM, at least about 10 µM, at least about 15.0 µM, at least about 20.0 µM, at least about 25.0 µM, at least about 30.0 µM, at least about 35.0 µM, at least about 40.0 µM, at least about 45.0 µM, at least about 50.0 µM, at least about 55.0 µM, at least about 60.0 µM, at least about 75.0 µM, at least about 80.0 µM, at least about 85.0 µM, at least about 90.0 µM, at least about 95.0 µM, at least about 100.0 µM, or at least about 150.0 µM, of one or more exogenously provided fixed carbon sources selected from Tables 2 and 3.

In some embodiments using cells of the genus Porphyridium, the methods include the use of approximately 0.5-0.75% glycerol as a fixed carbon source when the cells are cultured in the presence of light. Alternatively, a range of glycerol, from approximately 4.0% to approximately 9.0% may be used when the Porphyridium cells are cultured in the dark, more preferably from 5.0% to 8.0%, and more preferably 7.0%.

After culturing the microalgae in the presence of the exogenously provided carbon source, the monosaccharide composition of the polysaccharide can be analyzed as described in Example 5.

Microalgae culture media can contain a fixed nitrogen source such as $KNO_3$. Alternatively, microalgae are placed in culture conditions that do not include a fixed nitrogen source. For example, Porphyridium sp. cells are cultured for a first period of time in the presence of a fixed nitrogen source, and then the cells are cultured in the absence of a fixed nitrogen source (see for example Adda M., Biomass 10:131-140. (1986); Sudo H., et al., Current Microbiology Vol. 30 (1995), pp. 219-222; Marinho-Soriano E., Bioresour Technol. 2005 February; 96(3):379-82; Bioresour. Technol. 42:141-147 (1992)). While the invention is not limited by theory, it is well accepted by those skilled in the art that the red color of Porphyridium is due to the red pigmented light harvesting protein phycoerythrin (for example see Fujimori and Pecci, Distinct subunits of phycoerythrin from Porphyridium cruentum and their spectral characteristics, Arch. Biochem. Biophys. 118, 448-55 1967). Culture of Porphyridium in the presence of reduced levels of nitrogen causes cells to degrade phycoerythrin, resulting in a significant decrease in the amount of red pigmentation. Because phycoerythrin constitutes over 2% of the dry weight of Porphyridium cells under nitrogen-replete conditions (see for example M. M. Rebolloso Fuentes 2000, Food Chemistry, 70; 345-353), this catabolic process allows a significant amount of fixed nitrogen to be recycled. Again while the invention is not limited by theory, providing excess light also causes Porphyridium cells to degrade phycoerythrin to reduce the amount of light harvesting per cell. This process reduces oxidative stress caused by excess photon flux in the thylakoid membrane. Porphyridium biomass grown in nitrogen-limited conditions, particularly when grown under high light, lose red coloration and turn yellow with occasional shades of light brown, referred to as "decolorized biomass". The invention provides novel methods of production of compositions for topical application including culturing cells of the genus Porphyridium under reduced levels of nitrogen (such as, for example, no Tris and less than 20% of the $KNO_3$ per liter of ATCC 1495 ASW media) and optionally also under relatively light conditions such as, for example, 130 µE $m^{-2}$ $s^{-1}$. In other embodiments, the culture media contains no more than 300 mg/L of one or more nitrate-containing compounds that can be metabolized by the cells (such as, for example, but not limited to $KNO_3$) at inoculation, no more than 250 mg/L at inoculation, no more than 200 mg/L at inoculation, no more than 175 mg/L at inoculation, no more than 150 mg/L at inoculation, no more than 135 mg/L at inoculation, no more than 125 mg/L at inoculation, no more than 50 mg/L at inoculation, no more than 25 mg/L at inoculation, and no more than 12.5 mg/L at inoculation. In some methods the nitrate-containing compounds are provided in the culture media at inoculation at approximately 180 mg/L, approximately 160 mg/L, approximately 140 mg/L, approximately 130 mg/L, approximately 125 mg/L, approximately 110 mg/L, approximately 100 mg/L, and approximately 90 mg/L. In other embodiments, the culture media contains no more than 300 millimolar of one or more nitrate-containing compounds that can be metabolized by the cells (such as, for example, but not limited to $KNO_3$) at inoculation, no more than 250 millimolar at inoculation, no more than 200 millimolar at inoculation, no more than 175 millimolar at inoculation, no more than millimolar at inoculation, no more than millimolar at inoculation, no more than millimolar at inoculation, no more than 50 millimolar at inoculation, no more than 25 millimolar at inoculation, and no more than 12.5 millimolar at inoculation. In some methods the nitrate-containing compounds are provided in the culture media at inoculation at approximately 180 millimolar, approximately 160 millimolar, approximately 140 millimolar, approximately 130 millimolar, approximately 125 millimolar, approximately 110 millimolar, approximately 100 millimolar, and approximately 90 millimolar. Inoculation can mean when seed cells are infused into a bioreactor, and can also mean when cells grown in nitrogen-replete media that have been pelleted, optionally washed, and are resuspended in culture media that has limiting amounts of nitrogen-containing compounds or no nitrogen-containing compounds. Cells inoculated into media containing limiting amounts of nitrogen-containing compounds, such as 125 mg/L, will typically undergo cell division until nitrogen is used up (assuming other nutrients are not limiting), and then begin the "bleaching" process in which phycoerythrin is degraded. This process is accelerated as light intensity is increased. Cells grown in nitrogen-replete media can also be harvested and washed and resuspended in culture media that contains no nitrogen or a limited amount of nitrogen such as the amounts listed above. In addition, nitrogen-replete media can be exchanged with nitrogen-limited media through tangential flow filtration using a filter that has a pore size smaller than the diameter of the cells. The diameter of Porphyridium cells is approximately 4-8 microns. This method avoids centrifugation and reduces the possibility of contamination.

Other methods include removing red coloration from different species of microalgae through mutagenesis. For example, species of the genus Porphyridium are subjected to chemical mutagenesis, followed by screening for colonies lacking red coloration. See for example Sivan and Arad, Phycologia 32(1), pp. 68-72 (1993). Examples of novel strains of Porphyridium sp. lacking red pigment, generated through chemical mutagenesis as described in Sivan and Arad, are shown in FIG. 10(c). Such genetically decolorized strains are used to generate non-red biomass for formulation as skin care products. In a preferred embodiment the genetically decolorized biomass is homogenized. In another preferred embodiment the polysaccharide contains more than 4.75% sulfur by weight. While the invention is not limited by theory, production of phycoerythrin is reduced in some mutagenized strains due to mutations in various regions of the genome including promoters, coding regions, and other functional elements. Both bleaching through nutrient limitation and excess light, as well as through mutagenesis, can be performed on any microalgae species, including those listed in Tables 1A and 1B.

Some methods further comprise formulating decolorized *Porphyridium* biomass, generated through any or all of the methods nutrient limitation, excess light, and mutagenesis, with a carrier suitable for topical administration. The methods also optionally include formulating decolorized *Porphyridium* biomass with one or more preservatives, such as for example diiodomethyl-p-tolylsulfone, 2-Bromo-2-nitropropane-1,3-diol, cis isomer 1-(3-chloroallyl)-3,5,7-triaza-1-azoniaadamantane chloride (a.k.a. Dowicil 200), glutaraldehyde, 4,4-dimethyl oxazolidine, 7-Ethylbicyclooxazolidine, methyl paraben, sorbic acid, methyl paraben, Germaben II, and disodium EDTA.

Other culture parameters can also be manipulated, such as the pH of the culture media, the identity and concentration of trace elements such as those listed in Table 3, and other media constituents. One non-limiting example is the inclusion of at least one source of sulfate in the culture media to increase the level of sulfation in the polysaccharides produced. In some embodiments, a polysaccharide preparation method is practiced with culture media containing more than about 100, more than about 150, more than about 200, more than about 250, more than about 300, more than about 350, more than about 400, more than about 450, more than about 500, more than about 550, more than about 600, more than about 650, more than about 700, or more than about 750, more than about 800, more than about 850, more than about 900, more than about 950, or more than about 1 or 2 M sulfate (or total $SO_4^{2-}$). Increasing the sulfation has been demonstrated to increase the antioxidant apacity of the polysaccharide (see Example 23 and Spitz et al. (J. Appl. Phycology (2005) 17:215-222). Without being bound by theory, and offered to improved the understanding of certain aspects of the disclosed invention, it is possible that an increased level of sulfation may increase the anti-cholesterol characteristics of the homogenized cell material or polysaccharide preparation disclosed herein. The correlation between higher amounts of sulfation and antioxidant activity demonstrated herein was unexpected given the weak antioxidant activity of carrageenan, which contains as much as 40% sulfate.

It is believed that microalgae of the genus *Porphyridium* have not been grown or propagated under conditions with sulfate concentrations of 100 mM to 2 M. Thus the invention includes the surprising discovery that microalgae are capable of growth under such conditions. Additionally, the invention is based in part on the surprising discovery that growth under higher sulfate concentrations can produce polysaccharides with higher levels of sulfation. This allows for the production of cells (and so biomass) containing highly sulfated polysaccharides that may be used in the form of purified polysaccharides, a homogenate of cells (biomass), intact cells (biomass) per se, or a combination thereof.

The discovery that *Porphyridium* can survive above 100 mM sulfate was surprising for a number of reasons. First, it is known that sulfate can alter the rate of uptake of toxic metal ions in algae, such as chromium, and that increasing metal accumulation can lead to toxicity (see for example Kaszycki et al, Plant, Cell & Environment, 28(2): p. 260, 2005). Second, it is also known that sulfate can inhibit the uptake of metal ions required for nitrogen fixation such as molybdenum, and that increasing sulfate concentrations negatively affects algae such as cyanobacteria even at sulfate concentrations in estuarine (>8-10 mM) and seawater (28 mM) levels of sulfate (see for example Marino et al, Hydrobiologia 500: pp. 277-293, 2004). Third, sulfate at high levels can often be taken up and reduced and sulfide, which is toxic to photosynthesis because it attacks photosystem II (see for example Khanal et al., J. Envir. Engrg., 129(12); pp. 1104-1111, 2003). Fourth, high sulfate levels alter the osmotic pressure of the growth media, and many organisms cannot survive at such an elevated osmoticum. For example, it is well established that photosynthesis of algae is inhibited by hyperosmotic and salt stresses. See for example "Suppression of Quantum Yield of Photosystem II by Hyperosmotic Stress in *Chlamydomonas reinhardtii*" Plant Cell Physiol. 36: pp. 1253-1258 (1995); and "The Effect of Osmotic and Ionic Stress on the Primary Processes of Photosynthesis in *Dunaliella tertiolecta*", J. Exp. Bot. 1984 35(1): 18-27 (1984).

By use of methods described above, the disclosed invention includes a preparation of cells, cell biomass, or cell homogenate containing a reduced level of green pigmentation, or a reduced absorbance at 545 nm, relative to the same cells grown under different conditions. The cells may be those of any microalgae as described herein, including those of the genus *Porphyridium*. The cells, cell biomass, or cell homogenate may be formulated into a composition of the disclosure such that an aqueous extract of the composition would contain the same reduced level of green pigmentation.

In some embodiments, an aqueous extract of the composition contains no more than about 75%, no more than about 70%, no more than about 65%, no more than about 60%, no more than about 55%, no more than about 50%, no more than about 45%, no more than about 40%, no more than about 35%, no more than about 30%, no more than about 25%, no more than about 20%, no more than about 15%, no more than about 10%, or no more than about 5% of the absorbance per gram at 545 nm compared to an extract of cells of the same species grown in a photobioreactor in ATCC 1495 ASW media (as described in Example 1) in the presence of 50 microeinsteins of light per second per square meter. One non-limiting means for detection of absorbance is by use of a spectrophotometer.

Microalgae can be grown in the presence of light. The number of photons striking a culture of microalgae cells can be manipulated, as well as other parameters such as the wavelength spectrum and ratio of dark:light hours per day. Microalgae can also be cultured in natural light, as well as simultaneous and/or alternating combinations of natural light and artificial light. For example, microalgae of the genus *Chlorella* be cultured under natural light during daylight hours and under artificial light during night hours.

The gas content of a photobioreactor can be manipulated. Part of the volume of a photobioreactor can contain gas rather than liquid. Gas inlets can be used to pump gases into the photobioreactor. Any gas can be pumped into a photobioreactor, including air, air/$CO_2$ mixtures, noble gases such as argon and others. The rate of entry of gas into a photobioreactor can also be manipulated. Increasing gas flow into a photobioreactor increases the turbidity of a culture of microalgae. Placement of ports conveying gases into a photobioreactor can also affect the turbidity of a culture at a given gas flow rate. Air/$CO_2$ mixtures can be modulated to generate different polysaccharide compositions by manipulating carbon flux. For example, air:$CO_2$ mixtures of about 99.75% air:0.25% $CO_2$, about 99.5% air:0.5% $CO_2$, about 99.0% air:1.00% $CO_2$, about 98.0% air:2.0% $CO_2$, about 97.0% air:3.0% $CO_2$, about 96.0% air:4.0% $CO_2$, and about 95.00% air:5.0% $CO_2$ can be infused into a bioreactor or photobioreactor.

Microalgae cultures can also be subjected to mixing using devices such as spinning blades and propellers, rocking of a culture, stir bars, and other instruments.

Microalgae can be cultured in liquid media. The culture can be contained within a bioreactor. Optionally, the bioreactor does not allow light to enter. Alternatively, microalgae can also be cultured in photobioreactors that contain a fixed carbon source and allow light to strike the cells. Exposure of microalgae cells to light, even in the presence of a fixed carbon source that the cells transport and utilize (i.e., mixotrophic growth), nonetheless accelerates growth compared to culturing cells in the dark. Culture condition parameters can be manipulated to optimize total hydrocarbon production, the combination of hydrocarbon species produced, and/or production of a hydrocarbon species. In some instances it is preferable to culture cells in the dark, such as, for example, when using extremely large (40,000 liter and higher) fermentors that do not allow light to strike the culture.

Microalgal culture media typically contains components such as a fixed nitrogen source, trace elements, optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

For organisms able to grow on a fixed carbon source, the fixed carbon source can be, for example, glucose, fructose, sucrose, galactose, xylose, mannose, rhamnose, N-acetylglucosamine, glycerol, floridoside, and/or glucuronic acid. The one or more carbon source(s) can be supplied at a concentration of at least about 50 µM, at least about 100 µM, at least about 500 µM, at least about 5 mM, at least about 50 mM, and at least about 500 mM, of one or more exogenously provided fixed carbon source(s). Some microalgae species can grow by utilizing a fixed carbon source such as glucose or acetate in the absence of light. Such growth is known as heterotrophic growth.

Other culture parameters can also be manipulated, such as the pH of the culture media, the identity and concentration of trace elements and other media constituents.

B. Cell Culture Methods: Photobioreactors

Microalgae can be grown and maintained in closed photobioreactors made of different types of transparent or semitransparent material. Such material can include Plexiglas® enclosures, glass enclosures, bags bade from substances such as polyethylene, transparent or semitransparent pipes, and other materials. Microalgae can also be grown in open ponds.

Photobioreactors can have ports allowing entry of gases, solids, semisolids and liquids into the chamber containing the microalgae. Ports are usually attached to tubing or other means of conveying substances. Gas ports, for example, convey gases into the culture. Pumping gases into a photobioreactor can serve to both feed cells $CO_2$ and other gases and to aerate the culture and therefore generate turbidity. The amount of turbidity of a culture varies as the number and position of gas ports is altered. For example, gas ports can be placed along the bottom of a cylindrical polyethylene bag. Microalgae grow faster when $CO_2$ is added to air and bubbled into a photobioreactor. For example, a 5% $CO_2$:95% air mixture is infused into a photobioreactor containing cells of the genus *Porphyridium* (see for example Biotechnol Bioeng. 1998 Sep. 20; 59(6):705-13; textbook from office; U.S. Pat. Nos. 5,643,585 and 5,534,417; Lebeau, T., et. al. Appl. Microbiol Biotechnol (2003) 60:612-623; Muller-Fuega, A., Journal of Biotechnology 103 (2003 153-163; Muller-Fuega, A., Biotechnology and Bioengineering, Vol. 84, No. 5, Dec. 5, 2003; Garcia-Sanchez, J. L., Biotechnology and Bioengineering, Vol. 84, No. 5, Dec. 5, 2003; Garcia-Gonzales, M., Journal of Biotechnology, 115 (2005) 81-90. Molina Grima, E., Biotechnology Advances 20 (2003) 491-515).

Photobioreactors can be exposed to one or more light sources to provide microalgae with light as an energy source via light directed to a surface of the photobioreactor. Preferably the light source provides an intensity that is sufficient for the cells to grow, but not so intense as to cause oxidative damage or cause a photoinhibitive response. In some instances a light source has a wavelength range that mimics or approximately mimics the range of the sun. In other instances a different wavelength range is used. Photobioreactors can be placed outdoors or in a greenhouse or other facility that allows sunlight to strike the surface. Photon intensities are typically measured in microeinsteins of light per square meter per second (uE $m^{-2}$ $s^{-1}$) although other measurements such as lux and footcandles are sometimes used. Preferred photon intensities for culturing species of the genus *Porphyridium* are between 50 and 300 uE $m^{-2}$ $s^{-1}$ (see for example Photosynth Res. 2005 June; 84(1-3):21-7), although in cases of inducing *Porphyridium* cells to degrade phycoerythrin preferred light intensities can be higher, such as for example 400-700 uE $m^{-2}$ $s^{-1}$.

Photobioreactors preferably have one or more parts that allow media entry. It is not necessary that only one substance enter or leave a port. For example, a port can be used to flow culture media into the photobioreactor and then later can be used for sampling, gas entry, gas exit, or other purposes. In some instances a photobioreactor is filled with culture media at the beginning of a culture and no more growth media is infused after the culture is inoculated. In other words, the microalgal biomass is cultured in an aqueous medium for a period of time during which the microalgae reproduce and increase in number; however quantities of aqueous culture medium are not flowed through the photobioreactor throughout the time period. Thus in some embodiments, aqueous culture medium is not flowed through the photobioreactor after inoculation.

In other instances culture media can be flowed though the photobioreactor throughout the time period during which the microalgae reproduce and increase in number. In some instances media is infused into the photobioreactor after inoculation but before the cells reach a desired density. In other words, a turbulent flow regime of gas entry and media entry is not maintained for reproduction of microalgae until a desired increase in number of said microalgae has been achieved, but instead a parameter such as gas entry or media entry is altered before the cells reach a desired density.

Photobioreactors preferably have one or more ports that allow gas entry. Gas can serve to both provide nutrients such as $CO_2$ as well as to provide turbulence in the culture media. Turbulence can be achieved by placing a gas entry port below the level of the aqueous culture media so that gas entering the photobioreactor bubbles to the surface of the culture. One or more gas exit ports allow gas to escape, thereby preventing pressure buildup in the photobioreactor. Preferably a gas exit port leads to a "one-way" valve that prevents contaminating microorganisms to enter the photobioreactor. In some instances cells are cultured in a photobioreactor for a period of time during which the microalgae reproduce and increase in number, however a turbulent flow regime with turbulent eddies predominantly throughout the culture media caused by gas entry is not maintained for all of the period of time. In other instances a turbulent flow regime with turbulent eddies predominantly throughout the culture media caused by gas entry can be maintained for all of the period of time during which the microalgae reproduce and increase in number. In some instances a predetermined range of ratios between the scale of the photobioreactor and the scale of eddies is not maintained for the period of time during which the microalgae reproduce and increase in number. In other instances such a range can be maintained.

Photobioreactors preferably have at least one port that can be used for sampling the culture. Preferably a sampling port can be used repeatedly without altering compromising the axenic nature of the culture. A sampling port can be configured with a valve or other device that allows the flow of sample to be stopped and started. Alternatively a sampling port can allow continuous sampling. Photobioreactors preferably have at least one port that allows inoculation of a culture. Such a port can also be used for other purposes such as media or gas entry.

Microalgae that produce polysaccharides can be cultured in photobioreactors. Microalgae that produce polysaccharide that is not attached to cells can be cultured for a period of time and then separated from the culture media and secreted polysaccharide by methods such as centrifugation and tangential flow filtration. Preferred organisms for culturing in photobioreactors to produce polysaccharides include *Porphyridium* sp., *Porphyridium cruentum*, *Porphyridium purpureum*, *Porphyridium aerugineum*, *Rhodella maculata*, *Rhodella reticulata*, *Chlorella autotrophica*, *Chlorella stigmatophora*, *Chlorella capsulata*, *Achnanthes brevipes*, *Achnanthes longipes*, *Gloeocapsa alpicola* and *Phaeocysstis pouchettii*.

C. Cell Culture Methods: Heterotrophic Growth

As an alternative to photosynthetic growth of microorganisms, as described above, some microorganisms can be cultured under heterotrophic growth conditions in which a fixed carbon source provides energy for growth and polysaccharide production.

For polysaccharide production, cells, including recombinant cells of the invention described herein, are preferably cultured or fermented in large quantities. The culturing may be in large liquid volumes, such as in suspension cultures as an example. Other examples include starting with a small culture of cells which expand into a large biomass in combination with cell growth and propagation as well as polysaccharide production. Bioreactors or steel fermentors can be used to accommodate large culture volumes. A fermentor similar those used in the production of beer and/or wine is suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other Starch (glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp.

A fermentor can be used to allow cells to undergo the various phases of their growth cycle. As an example, an inoculum of polysaccharide-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

In an alternate heterotrophic growth method in accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstock have been found to be inhibitory to yeast growth, and yeast cannot use the 5-carbon sugars produced from cellulosic materials (e.g., xylose from hemicellulose). By contrast, microalgae can grow on processed cellulosic material. Accordingly, the invention provides a method of culturing a microalgae in the presence of a cellulosic material and/or a 5-carbon sugar. Cellulosic materials generally include:

| Component | Percent Dry Weight |
| --- | --- |
| Cellulose | 40-60% |
| Hemicellulose | 20-40% |
| Lignin | 10-30% |

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

In still another alternative heterotrophic growth method in accordance with the present invention, which itself may optionally be used in combination with the methods described above, sucrose, produced by example from sugar cane or sugar beet, is used as a feedstock. Microalgae can be engineered to utilize sucrose as a carbon source. For example, expression of a sucrose transporter and a sucrose invertase allows microalgae, e.g., *Chlorella protothecoides*, to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable sucrose invertases are Genbank accession numbers CAB95010, NP_012104 and CAA06839. Examples of suitable fructokinases are Genbank accession numbers P26984, P26420 and CAA43322. Vectors for transformation of microalgae, including Chlorella, encoding one or more of such genes can be designed as described herein, or as described in U.S. patent application Ser. No. 12/131,783, filed Jun. 2, 2008, titled "Use of Cellulosic Materials for Cultivation of Microorganisms," and incorporated herein by reference in its entirety.

Secretion of a sucrose invertase can obviate the need for expression of a transporter that can transport sucrose into the cell. This is because a secreted invertase catalyzes the conversion of a molecule of sucrose into a molecule of glucose and a molecule of fructose, both of which can be transported and utilized by microbes disclosed herein. For example, expression of a sucrose invertase with a secretion signal generates invertase activity outside the cell. See Hawkins et al., Current Microbiology Vol. 38 (1999), pp. 335-341 for examples of secretion signals active in Chlorella. Expression of such a protein, as enabled by the genetic engineering methodology disclosed herein, allows cells already capable of utilizing extracellular glucose as an energy source to utilize sucrose as an extracellular energy source.

Alternatively, a sucrose invertase can also be expressed intracellularly in cells that express a sucrose transporter, as well as in cells that express any carbohydrate transporter that allows sucrose to enter the cell.

Bioreactors can be employed for use in heterotrophic growth methods. As will be appreciated, provisions made to make light available to the cells in photosynthetic growth methods are unnecessary when using a fixed-carbon source in the heterotrophic growth methods described herein.

The specific examples of process conditions and heterotrophic growth methods described herein can be combined in any suitable manner to improve efficiencies of microbial growth and lipid production. In addition, the invention includes the selection and/or genetic engineering of microbes, such as microalgae, to produce microbes that are even more suitable for use in the above-described methods. For example, the microbes having a greater ability to utilize any of the above-described feedstocks for increased proliferation and/or polysaccharide production are within the scope of the invention.

D. Mixotrophic Growth

Mixotrophic growth is the use of both light and fixed carbon source(s) as energy sources for cells to grow and produce polysaccharides. Mixotrophic growth can be conducted in a photobioreactor. Microalgae can be grown and maintained in closed photobioreactors made of different types of transparent or semitransparent material. Such material can include Plexiglas® enclosures, glass enclosures, bags made from substances such as polyethylene, transparent or semitransparent pipes, and other materials. Microalgae can be grown and maintained in open photobioreactors such as raceway ponds, settling ponds, and other non-enclosed containers.

E. Growth Media

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin for its culture collection of algae (UTEX).

In a particular example, a medium suitable for culturing Chlorella protothecoides (UTEX 31) comprises Proteose Medium. This medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use.

Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic).

F. Non-Microalgal Polysaccharide Production

Organisms besides microalgae can be used to produce polysaccharides, such as lactic acid bacteria (see for example Stinglee, F., Molecular Microbiology (1999) 32(6), 1287-1295; Ruas_Madiedo, P., J. Dairy Sci. 88:843-856 (2005); Laws, A., Biotechnology Advances 19 (2001) 597-625; Xanthan gum bacteria: Pollock, T J., J. Ind. Microbiol Biotechnol., 1997 August; 19(2):92-7; Becker, A., Appl. Micrbiol. Bioltechnol. 1998 August; 50(2):92-7; Garcia-Ochoa, F., Biotechnology Advances 18 (2000) 549-579, seaweed: Talarico, L B., et al., Antiviral Research 66 (2005) 103-110; Dussealt, J., et al., J Biomed Mater Res A., (2005) November 1; Melo, F. R., J Biol Chem 279:20824-35 (2004)).

G. Ex Vivo Methods

Microalgae and other organisms can be manipulated to produce polysaccharide molecules that are not naturally produced by methods such as feeding cells with monosaccharides that are not produced by the cells (Nature. 2004 Aug. 19; 430(7002):873-7). For example, species listed in Table 1A are grown according to the referenced growth protocols, with the additional step of adding to the culture media a fixed carbon source that is not in the culture media as published and referenced in Table 1A and is not produced by the cells in a detectable amount.

H. In Vitro Methods

Polysaccharides can be altered by enzymatic and chemical modification. For example, carbohydrate modifying enzymes can be added to a preparation of polysaccharide and allowed to catalyze reactions that alter the structure of the polysaccharide. Chemical methods can be used to, for example, modify the sulfation pattern of a polysaccharide (see for example Carbohydr. Polym. 63:75-80 (2000); Pomin V H., Glycobiology. 2005 December; 15(12):1376-85; Naggi A., Semin Thromb Hemost. 2001 October; 27(5): 437-43 Review; Habuchi, O., Glycobiology. 1996 January; 6(1); 51-7; Chen, J., J. Biol. Chem. In press; Geresh., S et al., J. Biochem. Biophys. Methods 50 (2002) 179-187).

I. Polysaccharide Purification Methods

Exopolysaccharides can be purified from microalgal cultures by various methods, including those disclosed herein.

1. Precipitation

For example, polysaccharides can be precipitated by adding compounds such as cetylpyridinium chloride, isopropanol, ethanol, or methanol to an aqueous solution containing a polysaccharide in solution. Pellets of precipitated polysaccharide can be washed and resuspended in water, buffers such as phosphate buffered saline or Tris, or other aqueous solutions (see for example Farias, W. R. L., et al., J. Biol. Chem. (2000) 275; (38)29299-29307; U.S. Pat. No. 6,342,367; U.S. Pat. No. 6,969,705).

2. Dialysis

Polysaccharides can also be dialyzed to remove excess salt and other small molecules (see for example Gloaguen, V., et al., Carbohydr Res. 2004 Jan. 2; 339(1):97-103; Microbiol Immunol. 2000; 44(5):395-400).

3. Tangential Flow Filtration

Filtration can be used to concentrate polysaccharide and remove salts. For example, tangential flow filtration (TFF), also known as cross-flow filtration, can be used)). For a preferred filtration method see Geresh, Carb. Polym. 50; 183-189 (2002), which discusses use of a MaxCell A/G technologies 0.45 uM hollow fiber filter. Also see for example Millipore Pellicon® devices, used with 100 kD, 300 kD, 1000 kD (catalog number P2C01MC01), 0.1 uM (catalog number P2VVPPV01), 0.22 uM (catalog number P2GVPPV01), and 0.45 uM membranes (catalog number P2HVMPV01). It is preferred that the polysaccharides do not pass through the filter at a significant level. It is also preferred that polysaccharides do not adhere to the filter material. TFF can also be performed using hollow fiber filtration systems.

Non-limiting examples of tangential flow filtration include use of a filter with a pore size of at least about 0.1 micrometer, at least about 0.12 micrometer, at least about 0.14 micrometer, at least about 0.16 micrometer, at least about 0.18 micrometer, at least about 0.2 micrometer, at least about 0.22 micrometer, or at least about 0.45 micrometer. Preferred pore sizes of TFF allow contaminants to pass through but not polysaccharide molecules.

4. Ion Exchange Chromatography

Anionic polysaccharides can be purified by anion exchange chromatography. (Jacobsson, I., Biochem J. 1979 Apr. 1; 179(1):77-89; Karamanos, N K., Eur J Biochem. 1992 Mar. 1; 204(2):553-60).

5. Protease Treatment

Polysaccharides can be treated with proteases to degrade contaminating proteins. In some instances the contaminating proteins are attached, either covalently or noncovalently to polysaccharides. In other instances the polysaccharide molecules are in a preparation that also contains proteins. Proteases can be added to polysaccharide preparations containing proteins to degrade proteins (for example, the protease from *Streptomyces griseus* can be used (SigmaAldrich catalog number P5147). After digestion, the polysaccharide is preferably purified from residual proteins, peptide fragments, and amino acids. This purification can be accomplished, for example, by methods listed above such as dialysis, filtration, and precipitation.

Heat treatment can also be used to eliminate proteins in polysaccharide preparations (see for example Biotechnol Lett. 2005 January; 27(1):13-8; 1-EMS Immunol Med Microbiol. 2004 Oct. 1; 42(2):155-66; Carbohydr Res. 2000 Sep. 8; 328(2):199-207; J Biomed Mater Res. 1999; 48(2): 111-6; Carbohydr Res. 1990 Oct. 15; 207(1):101-20).

The invention thus includes production of an exopolysaccharide comprising separating the exopolysaccharide from contaminants after proteins attached to the exopolysaccharide have been degraded or destroyed. The proteins may be those attached to the exopolysaccharide during culture of a microalgal cell in media, which is first separated from the cells prior to proteolysis or protease treatment. The cells may be those of the genus *Porphyridium* as a non-limiting example.

In one non-limiting example, a method of producing an exopolysaccharide is provided wherein the method comprises culturing cells of the genus *Porphyridium*; separating cells from culture media; destroying protein attached to the exopolysaccharide present in the culture media; and separating the exopolysaccharide from contaminants. In some methods, the contaminant(s) are selected from amino acids, peptides, proteases, protein fragments, and salts. In other methods, the contaminant is selected from NaCl, $MgSO_4$, $MgCl_2$, $CaCl_2$, $KNO_3$, $KH_2PO_4$, $NaHCO_3$, Tris, $ZnCl_2$, $H_3BO_3$, $CoCl_2$, $CuCl_2$, $MnCl_2$, $(NH_4)_6Mo_7O_{24}$, FeCl3 and EDTA.

6. Whole Cell Extraction

Intracellular polysaccharides and cell wall polysaccharides can be purified from whole cell mass (see form example U.S. Pat. No. 4,992,540; U.S. Pat. No. 4,810,646; J Sietsma J H., et al., Gen Microbiol. 1981 July; 125(1): 209-12; Fleet G H, Manners D J., J Gen Microbiol. 1976 May; 94(1):180-92).

J. Drying Methods

After purification of methods such as those above, polysaccharides can be dried using methods such as lyophilization and heat drying (see for example Shastry, S., Brazilian Journal of Microbiology (2005) 36:57-62; Matthews K H., Int J Pharm. 2005 Jan. 31; 289(1-2):51-62. Epub 2004 Dec. 30; Gloaguen, V., et al., Carbohydr Res. 2004 Jan. 2; 339(1):97-103).

Tray dryers accept moist solid on trays. Hot air (or nitrogen) can be circulated to dry. Shelf dryers can also employ reduced (below atmospheric at sea level, such as at about 25 in Hg or less) pressure or vacuum to dry at room temperature when products are temperature sensitive and are similar to a freeze-drier but less costly to use and can be easily scaled-up. In some embodiments drying in oven tray dryers is performed under vacuum.

Spray dryers are relatively simple in operation, which accept feed in fluid state and convert it into a dried particulate form by spraying the fluid into a hot drying medium.

Rotary dryers operate by continuously feeding wet material, which is dried by contact with heated air, while being transported along the interior of a rotating cylinder, with the rotating shell acting as the conveying device and stirrer.

Spin flash dryers are used for drying of wet cake, slurry, or paste which is normally difficult to dry in other dryers. The material is fed by a screw feeder through a variable speed drive into the vertical drying chamber where it is heated by air and at the same time disintegrated by a specially designed disintegrator. The heating of air may be direct or indirect depending upon the application. The dry powder is collected through a cyclone separator/bag filter or with a combination of both.

K. Microalgae Homogenization Methods

A pressure disrupter pumps a slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method is applied mainly for the release of intracellular molecules. According to Hetherington et al., cell disruption (and consequently the rate of protein release) is a first-order process, described by the relation: log [Rm/(Rm−R)]=K N P72.9. R is the amount of soluble protein; Rm is the maximum amount of soluble protein K is the temperature dependent rate constant; N is the number of passes through the homogenizer (which represents the residence time). P is the operating pressure.

In a ball mill, cells are agitated in suspension with small abrasive particles. Cells break because of shear forces, grinding between beads, and collisions with beads. The beads disrupt the cells to release biomolecules. The kinetics of biomolecule release by this method is also a first-order process.

Another widely applied method is the cell lysis with high frequency sound that is produced electronically and transported through a metallic tip to an appropriately concentrated cellular suspension, ie: sonication. The concept of ultrasonic disruption is based on the creation of cavities in cell suspension. Homogenization can also be performed with a Microfluidizer® device (such as the M-110Y Microfluidizer® model, Microfluidics Inc., Newton, Mass.).

Blending (high speed or Waring), the french press, or even centrifugation in the case of weak cell walls, also disrupt the cells by using the same concepts.

Cells can also be ground after drying in devices such as a colloid mill.

Because the percentage of polysaccharide as a function of the dry weight of a microalgae cell can frequently be in excess of 50%, microalgae cell homogenates can be considered partially pure polysaccharide compositions. Cell disruption aids in increasing the amount of solvent-accessible polysaccharide by breaking apart cell walls that are largely composed of polysaccharide.

Homogenization as described herein can increase the amount of solvent-available polysaccharide significantly. For example, homogenization can increase the amount of solvent-available polysaccharide by at least a factor of 0.25, at least a factor of 0.5, at least a factor of 1, at least a factor of 2, at least a factor of 3, at least a factor of 4, at least a factor of 5, at least a factor of 8, at least a factor of 10, at least a factor of 15, at least a factor of 20, at least a factor of 25, and at least a factor of 30 or more compared to the amount of solvent-available polysaccharide in an identical or similar quantity of non-homogenized cells of the same type. One way of determining a quantity of cells sufficient to generate a given quantity of homogenate is to measure the amount of a compound in the homogenate and calculate the gram quantity of cells required to generate this amount of the compound using known data for the amount of the compound per gram mass of cells. The quantity of many such compounds per gram of particular microalgae cells are know. For examples, see FIG. 7. Given a certain quantity of a compound in a composition, the skilled artisan can determine the number of grams of intact cells necessary to generate the observed amount of the compound. The number of grams of microalgae cells present in the composition can then be used to determine if the composition contains at least a certain amount of solvent-available polysaccharide sufficient to indicate whether or not the composition contains homogenized cells, such as for example five times the amount of solvent-available polysaccharide present in a similar or identical quantity of unhomogenized cells.

L. Analysis Methods

Assays for detecting polysaccharides can be used to quantitate starting polysaccharide concentration, measure yield during purification, calculate density of secreted polysaccharide in a photobioreactor, measure polysaccharide concentration in a finished product, and other purposes.

The phenol: sulfuric acid assay detects carbohydrates (see Hellebust, Handbook of Phycological Methods, Cambridge University Press, 1978; and Cuesta G., et al., J Microbiol Methods. 2003 January; 52(1):69-73). The 1,6 dimethylmethylene blue assay detects anionic polysaccharides. (see for example Braz J Med Biol Res. 1999 May; 32(5):545-50; Clin Chem. 1986 November; 32(11):2073-6).

Polysaccharides can also be analyzed through methods such as HPLC, size exclusion chromatography, and anion exchange chromatography (see for example Prosky L, Asp N, Schweizer T F, DeVries J W & Furda I (1988) Determination of insoluble, soluble and total dietary fiber in food and food products: Interlaboratory study. Journal of the Association of Official Analytical Chemists 71, 1017±1023; Int J Biol Macromol. 2003 November; 33(1-3):9-18)

Polysaccharides can also be detected using gel electrophoresis (see for example Anal Biochem. 2003 Oct. 15; 321(2):174-82; Anal Biochem. 2002 Jan. 1; 300(1):53-68).

Monosaccharide analysis of polysaccharides can be performed by combined gas chromatography/mass spectrometry (GC/MS) of the per-O-trimethylsilyl (TMS) derivatives of the monosaccharide methyl glycosides produced from the sample by acidic methanolysis (see Merkle and Poppe (1994) Methods Enzymol. 230: 1-15; York, et al. (1985) Methods Enzymol. 118:3-40).

The determination of protein concentration may be by use of any known procedure, such as the Lowry assay, the Biuret assay, the Bradford assay, or the bicinchoninic acid (BCA) assay. As a non-limiting example, the BCA assay is based on the formation of a $Cu^{2+}$-protein complex under alkaline conditions. The $Cu^{2+}$ is then reduced to $Cu^{1+}$ where the amount of protein present is proportional to the amount reduction. The reduction has been shown to be mediated by amino acids such as cysteine, cystine, tryptophan, and tyrosine as well as the peptide bond. The result of the assay is a purple-blue complex with $Cu^{1+}$ under alkaline conditions. The color complex is stable, even in the presence of other components possibly present with the proteins, such as detergents. The amount of reduction can be monitored by absorbance at 562 nm. The BCA assay is sensitive and accurate over a broad range of protein concentrations.

IV. Compositions

Compositions of the invention include a microalgal polysaccharide or homogenate as described herein. In embodiments relating to polysaccharides, including exopolysaccharides, the composition may comprise a homogenous or a heterogeneous population of polysaccharide molecules, including sulfated polysaccharides as non-limiting embodiments. Non-limiting examples of homogenous populations include those containing a single type of polysaccharide molecule, such as that with the same structure and molecular weight. Non-limiting examples of heterogeneous populations include those containing more than one type of polysaccharide molecule, such as a mixture of polysaccharides having a molecular weight (MW) within a range or a MW above or below a MW value. In some cases, the polysaccharide has an average molecular weight above 2 million Daltons. For example, the *Porphyridium* sp. exopolysaccharide is typically produced in a range of sizes from 3-5 million Daltons. Of course a polysaccharide containing composition of the invention may be optionally protease treated, or reduced in the amount of protein, as described above.

In some embodiments, a composition of the invention may comprise one or more polysaccharides produced by microalgae that have not been recombinantly modified. The microalgae may be those which are naturally occurring or those which have been maintained in culture in the absence of alteration by recombinant DNA techniques or genetic engineering.

In other embodiments, the polysaccharides are those from modified microalgae, such as, but not limited to, microalgae modified by recombinant techniques. Non-limiting examples of such techniques include introduction and/or expression of an exogenous nucleic acid sequence encoding a gene product; genetic manipulation to decrease or inhibit expression of an endogenous microalgal gene product; and/or genetic manipulation to increase expression of an endogenous microalgal gene product. The invention contemplates recombinant modification of the various microalgae species described herein. In some embodiments, the microalgae is from the genus *Porphyridium*.

Polysaccharides provided by the invention that are produced by genetically modified microalgae or microalgae that are provided with an exogenous carbon source can be distinct from those produced by microalgae cultured in minimal growth media under photoautotrophic conditions (ie: in the absence of a fixed carbon source) at least in that they contain a different monosaccharide content relative to polysaccharides from unmodified microalgae or microalgae cultured in minimal growth media under photoautotrophic conditions. Non-limiting examples include polysaccharides having an increased amount of arabinose (Ara), rhamnose (Rha), fucose (Fuc), xylose (Xyl), glucuronic acid (GlcA), galacturonic acid (GalA), mannose (Man), galactose (Gal), glucose (Glc), N-acetyl galactosamine (GalNAc), N-acetyl glucosamine (GlcNAc), and/or N-acetyl neuraminic acid (NANA), per unit mass (or per mole) of polysaccharide, relative to polysaccharides from either non-genetically modified microalgae or microalgae cultured photoautotrophically. An increased amount of a monosaccharide may also be expressed in terms of an increase relative to other monosaccharides rather than relative to the unit mass, or mole, of polysaccharide. An example of genetic modification leading to production of modified polysaccharides is transforming a microalgae with a carbohydrate transporter gene, and culturing a transformant in the presence of a monosaccharide which is transported into the cell from the culture media by the carbohydrate transporter protein encoded by the carbohydrate transporter gene. In some instances the culture can be in the dark, where the monosaccharide, such as glucose, is used as the sole energy source for the cell. In other instances the culture is in the light, where the cells undergo photosynthesis and therefore produce monosaccharides such as glucose in the chloroplast and transport the monosaccharides into the cytoplasm, while additional exogenously provided monosaccharides are transported into the cell by the carbohydrate transporter protein. In both instances monosaccharides from the cytoplasm are transported into the endoplasmic reticulum, where polysaccharide synthesis occurs. Novel polysaccharides produced by non-genetically engineered microalgae can therefore be generated by nutritional manipulation, ie: exogenously providing carbohydrates in the culture media that are taken up through endogenous transport mechanisms. Uptake of the exogenously provided carbohydrates can be induced, for example, by culturing the cells in the dark, thereby forcing the cells to utilize the exogenously provided carbon source. For example, *Porphyridium* cells cultured in the presence of 7% glycerol in the dark produce a novel polysaccharide because the intracellular carbon flux under these nutritionally manipulated conditions is different from that under photosynthetic conditions. Insertion of carbohydrate transporter genes into microalgae facilitates, but is not strictly necessary for, polysaccharide structure manipulation because expression of such genes can significantly increase the concentration of a particular monosaccharide in the cytoplasm of the cell. Many carbohydrate transporter genes encode proteins that transport more than one monosaccharide, albeit with different affinities for different monosaccharides (see for example Biochimica et Biophysica Acta 1465 (2000) 263-274). In some instances a microalgae species can be transformed with a carbohydrate transporter gene and placed under different nutritional conditions, wherein one set of conditions includes the presence of exogenously provided galactose, and the other set of conditions includes the presence of exogenously provided xylose, and the transgenic species produces structurally distinct polysaccharides under the two conditions. By altering the identity and concentration of monosaccharides in the cytoplasm of the microalgae, through genetic and/or nutritional manipulation, the invention provides novel polysaccharides. Nutritional manipulation can also be performed, for example, by culturing the microalgae in the presence of high amounts of sulfate, as described herein. In some instances nutritional manipulation includes addition of one or more exogenously provided carbon sources as well as one or more other non-carbohydrate culture component, such as 50 mM $MgSO_4$.

In some embodiments, the increase in one or more of the above listed monosaccharides in a polysaccharide may be from below to above detectable levels and/or by at least about 5%, to at least about 2000%, relative to a polysaccharide produced from the same microalgae in the absence of genetic or nutritional manipulation. Therefore an increase in one or more of the above monosaccharides, or other carbohydrates listed in Tables 2 or 3, by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 105%, at least about 110%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 1000%, at least about 1100%, at least about 1200%, at least about 1300%, at least about 1400%, at least about 1500%, at least about 1600%, at least about 1700%, at least about 1800%, or at least about 1900%, or more, may be used in the practice of the invention.

In cases wherein the polysaccharides from unmodified microalgae do not contain one or more of the above monosaccharides, the presence of the monosaccharide in a microalgal polysaccharide indicates the presence of a polysaccharide distinct from that in unmodified microalgae. Thus, using particular strains of *Porphyridium* sp. and *Porphyridium cruentum* as non-limiting examples, the invention includes modification of these microalgae to incorporate arabinose and/or fucose, because polysaccharides from two strains of these species do not contain detectable amounts of these monosaccharides (see Example 5 herein). In another non-limiting example, the modification of *Porphyridium* sp. to produce polysaccharides containing a detectable amount of glucuronic acid, galacturonic acid, or N-acetyl galactosamine, or more than a trace amount of N-acetyl glucosamine, is specifically included in the instant disclosure. In a further non-limiting example, the modification of *Porphyridium cruentum* to produce polysaccharides containing a detectable amount of rhamnose, mannose, or N-acetyl neuraminic acid, or more than a trace amount of N-acetylglucosamine, is also specifically included in the instant disclosure.

Put more generally, the invention includes a method of producing a polysaccharide comprising culturing a microalgae cell in the presence of at least about 0.01 micromolar of an exogenously provided fixed carbon compound, wherein the compound is incorporated into the polysaccharide produced by the cell. In some embodiments, the compound is selected from Table 2 or 3. The cells may optionally be selected from the species listed in Tables 1A or 1B, and cultured by modification, using the methods disclosed herein, or the culture conditions also listed in Table 1A.

The methods may also be considered a method of producing a glycopolymer by culturing a transgenic microalgal cell in the presence of at least one monosaccharide, wherein the monosaccharide is transported by the transporter into the cell and is incorporated into a microalgal polysaccharide.

In some embodiments, the cell is selected from Table 1A or 1B, such as where the cell is of the genus *Porphyridium*, as a non-limiting example. In some cases, the cell is selected from *Porphyridium* sp. and *Porphyridium cruentum*. Embodiments include those wherein the polysaccharide is enriched for the at least one monosaccharide compared to an endogenous polysaccharide produced by a non-transgenic cell of the same species. The monosaccharide may be selected from Arabinose, Fructose, Galactose, Glucose, Mannose, Xylose, Glucuronic acid, Glucosamine, Galactosamine, Rhamnose and N-acetyl glucosamine.

These methods of the invention are facilitated by use of non-transgenic cell expressing a sugar transporter, optionally wherein the transporter has a lower $K_m$ for glucose than at least one monosaccharide selected from the group consisting of galactose, xylose, glucuronic acid, mannose, and rhamnose. In other embodiments, the transporter has a lower $K_m$ for galactose than at least one monosaccharide selected from the group consisting of glucose, xylose, glucuronic acid, mannose, and rhamnose. In additional embodiments, the transporter has a lower $K_m$ for xylose than at least one monosaccharide selected from the group consisting of glucose, galactose, glucuronic acid, mannose, and rhamnose. In further embodiments, the transporter has a lower $K_m$ for glucuronic acid than at least one monosaccharide selected from the group consisting of glucose, galactose, xylose, mannose, and rhamnose. In yet additional embodiments, the transporter has a lower $K_m$ for mannose than at least one monosaccharide selected from the group consisting of glucose, galactose, xylose, glucuronic acid, and rhamnose. In yet further embodiments, the transporter has a lower $K_m$ for rhamnose than at least one monosaccharide selected from the group consisting of glucose, galactose, xylose, glucuronic acid, and mannose. Manipulation of the concentration and identity of monosaccharides provided in the culture media, combined with use of transporters that have a different $K_m$ for different monosaccharides, provides novel polysaccharides. These general methods can also be used in cells other than microalgae, for example, bacteria that produce polysaccharides.

In alternative embodiments, the cell is cultured in the presence of at least two monosaccharides, both of which are transporter by the transporter. In some cases, the two monosaccharides are any two selected from glucose, galactose, xylose, glucuronic acid, rhamnose and mannose.

In one non-limiting example, the method comprises providing a transgenic cell containing a recombinant gene encoding a monosaccharide transporter; and culturing the cell in the presence of at least one monosaccharide, wherein the monosaccharide is transported by the transporter into the cell and is incorporated into a polysaccharide of the cell. It is pointed out that transportation of a monosaccharide from the media into a microalgal cell allows for the monosaccharide to be used as an energy source, as disclosed below, and for the monosaccharide to be transported into the endoplasmic reticulum (ER) by cellular transporters. In the ER, polysaccharide production and glycosylation occurs such that in the presence of exogenously provided monosaccharides, the sugar content of the microalgal polysaccharides change.

In some aspects, the invention includes a novel microalgal polysaccharide, such as from microalgae of the genus *Porphyridium*, comprising detectable amounts of xylose, glucose, and galactose wherein the molar amount of one or more of these three monosaccharides in the polysaccharide is not present in a polysaccharide of *Porphyridium* that is not genetically or nutritionally modified. An example of a non-nutritionally and non-genetically modified *Porphyridium* polysaccharide can be found, for example, in Jones R., Journal of Cellular Comparative Physiology 60; 61-64 (1962). In some embodiments, the amount of glucose, in the polysaccharide, is at least about 65% of the molar amount of galactose in the same polysaccharide. In other embodiments, glucose is at least about 70%, at least about 75%, at least about 80%, at least about 85%, at least about 90%, at least about 95%, at least about 100%, at least about 105%, at least about 110%, at least about 120%, at least about 130%, at least about 140%, at least about 150%, at least about 200%, at least about 250%, at least about 300%, at least about 350%, at least about 400%, at least about 450%, at least about 500%, or more, of the molar amount of galactose in the polysaccharide. Further embodiments of the invention include those wherein the amount of glucose in a microalgal polysaccharide is equal to, or approximately equal to, the amount of galactose (such that the amount of glucose is about 100% of the amount of galactose). Moreover, the invention includes microalgal polysaccharides wherein the amount of glucose is more than the amount of galactose.

Alternatively, the amount of glucose in the polysaccharide is less than about 65% of the molar amount of galactose in the same polysaccharide. The invention thus provides for polysaccharides wherein the amount of glucose is less than about 60%, less than about 55%, less than about 50%, less than about 45%, less than about 40%, less than about 35%, less than about 30%, less than about 25%, less than about 20%, less than about 15%, less than about 10%, or less than about 5% of the molar amount of galactose in the polysaccharide.

In other aspects, the invention includes a microalgal polysaccharide, such as from microalgae of the genus *Porphyridium*, comprising detectable amounts of xylose, glucose, galactose, mannose, and rhamnose, wherein the molar amount of one or more of these five monosaccharides in the polysaccharide is not present in a polysaccharide of non-genetically modified and/or non-nutritionally modified microalgae. In some embodiments, the amount of rhamnose in the polysaccharide is at least about 100% of the molar amount of mannose in the same polysaccharide. In other embodiments, rhamnose is at least about 110%, at least about 120%, at least about 130%, at least about 140%, at least about 150%, at least about 200%, at least about 250%, at least about 300%, at least about 350%, at least about 400%, at least about 450%, or at least about 500%, or more, of the molar amount of mannose in the polysaccharide. Further embodiments of the invention include those wherein the amount of rhamnose in a microalgal polysaccharide is more than the amount of mannose on a molar basis.

Alternatively, the amount of rhamnose in the polysaccharide is less than about 75% of the molar amount of mannose in the same polysaccharide. The invention thus provides for polysaccharides wherein the amount of rhamnose is less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, or less than about 5% of the molar amount of mannose in the polysaccharide.

In additional aspects, the invention includes a microalgal polysaccharide, such as from microalgae of the genus *Porphyridium*, comprising detectable amounts of xylose, glucose, galactose, mannose, and rhamnose, wherein the amount of mannose, in the polysaccharide, is at least about 130% of the molar amount of rhamnose in the same polysaccharide. In other embodiments, mannose is at least about 140%, at least about 150%, at least about 200%, at least about 250%, at least about 300%, at least about 350%, at least about 400%, at least about 450%, or at least about 500%, or more, of the molar amount of rhamnose in the polysaccharide.

Alternatively, the amount of mannose in the polysaccharide is equal to or less than the molar amount of rhamnose in the same polysaccharide. The invention thus provides for polysaccharides wherein the amount of mannose is less than about 95%, less than about 90%, less than about 85%, less than about 80%, less than about 75%, less than about 70%, less than about 65%, less than about 60%, less than about 60%, less than about 55%, less than about 50%, less than about 45%, less than about 40%, less than about 35%, less than about 30%, less than about 25%, less than about 20%, less than about 15%, less than about 10%, or less than about 5% of the molar amount of rhamnose in the polysaccharide.

In further aspects, the invention includes a microalgal polysaccharide, such as from microalgae of the genus *Porphyridium*, comprising detectable amounts of xylose, glucose, and galactose, wherein the amount of galactose in the polysaccharide, is at least about 100% of the molar amount of xylose in the same polysaccharide. In other embodiments, rhamnose is at least about 105%, at least about 110%, at least about 120%, at least about 130%, at least about 140%, at least about 150%, at least about 200%, at least about 250%, at least about 300%, at least about 350%, at least about 400%, at least about 450%, or at least about 500%, or more, of the molar amount of mannose in the polysaccharide. Further embodiments of the invention include those wherein the amount of galactose in a microalgal polysaccharide is more than the amount of xylose on a molar basis.

Alternatively, the amount of galactose in the polysaccharide is less than about 55% of the molar amount of xylose in the same polysaccharide. The invention thus provides for polysaccharides wherein the amount of galactose is less than about 50%, less than about 45%, less than about 40%, less than about 35%, less than about 30%, less than about 25%, less than about 20%, less than about 15%, less than about 10%, or less than about 5% of the molar amount of xylose in the polysaccharide.

In yet additional aspects, the invention includes a microalgal polysaccharide, such as from microalgae of the genus *Porphyridium*, comprising detectable amounts of xylose, glucose, glucuronic acid and galactose, wherein the molar amount of one or more of these five monosaccharides in the polysaccharide is not present in a polysaccharide of unmodified microalgae. In some embodiments, the amount of glucuronic acid, in the polysaccharide, is at least about 50% of the molar amount of glucose in the same polysaccharide. In other embodiments, glucuronic acid is at least about 55%, at least about 60%, at least about 65%, at least about 70%, at least about 75%, at least about 80%, at least about 85%, at least about 90%, at least about 95%, at least about 100%, at least about 105%, at least about 110%, at least about 120%, at least about 130%, at least about 140%, at least about 150%, at least about 200%, at least about 250%, at least about 300%, at least about 350%, at least about 400%, at least about 450%, or at least about 500%, or more, of the molar amount of glucose in the polysaccharide. Further embodiments of the invention include those wherein the amount of glucuronic acid in a microalgal polysaccharide is more than the amount of glucose on a molar basis.

In other embodiments, the exopolysaccharide, or cell homogenate polysaccharide, comprises glucose and galactose wherein the molar amount of glucose in the exopolysaccharide, or cell homogenate polysaccharide, is at least about 55% of the molar amount of galactose in the exopolysaccharide or polysaccharide. Alternatively, the molar amount of glucose in the exopolysaccharide, or cell homogenate polysaccharide, is at least about 60%, at least about 65%, at least about 70%, at least about 75%, at least about 80%, at least about 85%, at least about 90%, or at least about 100% of the molar amount of galactose in the exopolysaccharide or polysaccharide.

In yet further aspects, the invention includes a microalgal polysaccharide, such as from microalgae of the genus *Porphyridium*, comprising detectable amounts of xylose, glucose, glucuronic acid, galactose, at least one monosaccharide selected from arabinose, fucose, N-acetyl galactosamine, and N-acetyl neuraminic acid, or any combination of two or more of these four monosaccharides.

In one embodiment, a method of determining the amount of phycoerythrin per dry gram of cells in a formulated skin care composition is to quantify the amount of certain molecules known to be present at certain levels or ranges of levels in *Porphyridium* cells. Such measurement is an indication of how many grams of dry *Porphyridium* biomass per gram of formulated skin care product are in a given formulation. For example, compounds listed in FIG. 7 are known to be present in *Porphyridium* cells at certain ranges of levels. The amounts of compounds, such as those listed in FIG. 7, were determined by analysis of *Porphyridium* cell biomass grown in nitrogen-replete media under outdoor daylight conditions, i.e., deep red cells containing quantities of phycoerythrin typically seen in cells grown in artificial seawater media such as those described in Example 1. Given a certain quantity of a compound in a formulated skin care composition, the skilled artisan can determine the number of dry grams of *Porphyridium* biomass are present per gram of formulated skin care product. The number of dry grams of *Porphyridium* cells present in the composition can then be used to determine if the cells contain less than or more than a certain amount of phycoerythrin per dry gram of cells.

V. Cosmeceutical Compositions and Topical Application

A. General

Compositions, comprising polysaccharides, whole cell extracts, or mixtures of polysaccharides and whole cell extracts, are provided for topical application or non-systemic administration. The polysaccharide may be any one or more of the microalgal polysaccharides disclosed herein, including those produced by a species, or a combination of two or more species, in Tables 1A or 1B. Similarly, a whole cell extract may be that prepared from a microalgal species, or a combination of two or more species, in Tables 1A or 1B. In some embodiments, polysaccharides, such as exopolysaccharides, and cell extracts from microalgae of the genus *Porphyridium* are used in the practice of the invention. A composition of the invention may comprise from between about 0.001% and about 100%, about 0.01% and about 90%, about 0.1% and about 80%, about 1% and about 70%, about 2% and about 60%, about 4% and about 50%, about 6% and about 40%, about 7% and about 30%, about 8% and about 20%, or about 10% polysaccharide, and/or cell extract, by weight.

In other embodiments, the composition comprises a carrier suitable for topical administration and/or a preservative suitable for topical administration; and Rhodophyte cells, optionally of the genus *Porphyridium*. The cells may contain reduced amounts of the red pigmentation by preparation methods described herein. In some cases, an aqueous extract of a composition comprising the *Porphyridium* cells contains no more than 75% to no more than about 1% of the absorbance per gram at 545 nm of a second composition formulated in identical fashion except containing cells of the same species of *Porphyridium* cells that were grown in a photobioreactor in ATCC 1495 ASW media in the presence of 50 microeinsteins of light per square meter per second. In further embodiments, the carrier is suitable for topical administration to humans, such as to human skin or a skin tissue.

In alternative embodiments, a composition for application to human skin may comprise a polysaccharide isolated from cells of the genus *Porphyridium*. Such a composition may further comprise a carrier and/or preservative suitable for topical administration as described herein. In some cases, the polysaccharide of the composition contains no more than about 10% protein by weight. In other embodiments, the polysaccharide contains no more than about 5%, no more than about 2%, or no more than about 1% protein by weight. The polysaccharide may also be essentially, or completely, free of protein, as detectable by assay methods as described herein after treatment to remove protein.

In further embodiments, the polysaccharide may comprise a molar amount of glucose that is at least about 50%, or at least about 60%, of the molar amount of galactose. Alternatively, the molar amount of glucose in the polysaccharide is greater than the molar amount of galactose. In additional embodiments, the polysaccharide contains less than a 0.1%, or less than a 0.01%, molar amount of at least one monosaccharide selected from the group consisting of arabinose, rhamnose, fucose, and N-acetyl glucosamine Optionally, the polysaccharide contains less than a 0.1%, or less than a 0.01%, molar amount of each of arabinose, rhamnose, fucose, and N-acetyl glucosamine.

In yet additional embodiments, a composition may comprise a polysaccharide comprising a molar amount of glucose that is at least about 30%, or at least about 40%, of the molar amount of xylose. In some cases, the polysaccharide comprises a molar amount of glucose between about 15.8% and about 25.8%; and a molar amount of xylose that is between about 37.5% and about 45.5%. Alternatively, the polysaccharide comprises a molar amount of glucose between about 17.8% and about 23.8%; and a molar amount of xylose that is between about 39.5% and about 43.5%.

In yet further embodiments, the polysaccharides are sulfated exopolysaccharides containing at least about 3.0% sulfur, at least about 3.5% sulfur, at least about 4.0% sulfur, at least about 4.5% sulfur, at least about 4.6% sulfur, at least about 4.75% sulfur, at least about 5.0% sulfur, at least about 5.25% sulfur, at least about 5.5% sulfur, at least about 5.75% sulfur, at least about 6.0% sulfur, at least about 6.25% sulfur, at least about 6.5% sulfur, at least about 6.75% sulfur, or at least about 7.0% sulfur by weight of the polysaccharide. The amount or level of sulfation in the polysaccharides may be analyzed and compared to the amount of sulfates used to culture the microalgae. Thus, the amount or level of sulfation in the polysaccharides of cells grown at about 100 mM, about 200 mM, about 300 mM, about 400 mM, about 500 mM, about 600 mM, or about 700 mM or higher, sulfate ($SO_4^{2-}$) may be determined by routine and repetitive methods disclosed herein. The amount or level of sulfur by weight in the polysaccharides of a sample of cells or cell material may be determined without knowledge of the amount of sulfate used to culture the cells.

As a further alternative, a composition for topical application to human skin may comprise microalgal cells. The cells may be those of genus *Porphyridium* or any other species or strain as disclosed herein. Optionally, the composition further comprises a carrier and/or preservative suitable for topical administration as described herein. In alternative embodiments, the cells are homogenized (such as by methods described herein) to generate or form a microalgal cell homogenate. In some cases, the cells or homogenate thereof, and therefore the composition, is essentially free of red and/or green coloration. Optionally, the cells or homogenate thereof, and therefore the composition, is completely free of red coloration. Thus, in some embodiments, the cells (and therefore the homogenate thereof) contains less than about 15, less than about 10, less than about 5, less than about 2, less than about 1, less than about 0.5, or less than about 0.1 milligrams of phycoerythrin per dry gram of cells.

Alternatively, the cells (and therefore a homogenate thereof) contains a sulfated polysaccharide having an amount of sulfur by weight of at least 3.0%, at least 3.5%, at least 4.0%, at least 4.5%, at least 4.6%, at least 4.75%, at least 5.0%, at least 5.25%, at least 5.5%, at least 5.75%, at least 6.0%, at least 6.25%, at least 6.5%, at least 6.75%, or at least 7.0% sulfur by weight of the polysaccharide as described herein. In additional embodiments, the microalgal cell homogenate contains at least two, at least three, at least five, at least ten, or at least twenty times the amount of solvent-available polysaccharide present in a quantity of unhomogenized cells needed to generate the microalgal cell homogenate.

In further embodiments, the disclosed invention includes a composition comprising particulate polysaccharides, such as microbeads or nanobeads comprising a disclosed polysaccharide. In some embodiments the polysaccharide particles are referred to as Marine Nanobeads™. The composition may be for improving the appearance of skin, such as human skin. The polysaccharides may have any level of sulfation described herein. The composition may be sterile and/or non-pyrogenic and optionally substantially free of endotoxins and/or proteins. In other embodiments, the composition further comprises hyaluronic acid or another agent suitable or desirable for treatment of skin. Non-limiting examples of such an agent include aloe vera, urea, alpha hydroxyl acid, vitamin E, glycyrrhizinic acid, methylsulfonylmethane (MSM), and collagen.

In some embodiments, the composition comprises an algal polysaccharide, wherein the polysaccharide: (a) has been made completely or partially insoluble in water through drying; and (b) has been homogenized or otherwise milled or disrupted to generate particles.

The polysaccharide may of course be that of a variety of microalgal cells, such as those described in Tables 1A and 1B and those of the genus *Porphyridium*. In some cases, the polysaccharide is contained in a non-aqueous material. As non-limiting examples, the material may be contained in an oil suitable for topical administration, with hexadecanoic acid or oil that is contained in an emulsion as representative examples. In one embodiment, the particulate polysaccharides from a species of the genus *Porphyridium* are formulated in at least one of the following compounds: Ceraphyl (Ethylhexyl Palmitate), Aerosil (silica dimethyl silylate), butylene glycol, and a preservative such as diocide, dowicil 200, and methyl paraben. In some embodiments the concentrations of formulated particulate polysaccharides from a species of the genus *Porphyridium* are between 50-97% Ceraphyl (Ethylhexyl Palmitate), 1-5% Aerosil (silica dimethyl silylate), 0.1-3 butylene glycol, and 0.1-3% of a preservative such as diocide, dowicil 200, and methyl paraben. The composition may also comprise a carrier and/or preservative suitable for topical administration. The composition may also be substantially free of endotoxins and/or protein as well as sterile and/or non-pyrogenic. In further embodiments, the polysaccharide is encapsulated by a timed-release coating, such as one suitable for topical application to human skin.

Optionally, the composition is prepared by a manufacturing or preparation method as described herein, such as a method disclosed in the following Methods of Formulation section. In some cases, the composition comprises a polysaccharide that is partially or completely insoluble in water, such as by heating an aqueous suspension of the polysaccharide, thereby removing water from the suspension. The polysaccharide particulates may be partially soluble such that they are less than about 70%, less than about 60%, less than about 50%, less than about 40%, less than about 30%, less than about 20%, less than about 10%, less than about 5%, or less than about 2% soluble in water.

In other embodiments, the polysaccharide has been made partially or completely insoluble by a method selected from the group consisting of chemical cross-linking, chemical dehydration through displacement of bound water by an alcohol, precipitation from solution using an alcohol or a ketone or pH, and coating of particles by microencapsulation. Non-limiting examples of these methods are known to the skilled person and may be used in the practice of the invention. For examples, see Biomacromolecules. 2005 November-December; 6(6):3202-8; Arterioscler Thromb Vasc Biol. 2004 March; 24(3):613-7; J Biomed Mater Res. 2001 Sep. 15; 56(4):478-86; Dalton Trans. 2004 Sep. 7; (17):2621-34. Epub 2004 Jul. 28; Biomacromolecules. 2004 January-February; 5(1):126-36; Contraception. 2002 August; 66(2):137-40; Biomacromolecules. 2006 May; 7(5):1471-80; Biopolymers. 1999 September; 50(3):227-37; Biomaterials. 2003 May; 24(12):2083-96; Int J Pharm. 2003 Nov. 28; 267(1-2):13-25; Med Biol Eng Comput. 1998 January; 36(1):129-34 and Reprod Fertil Dev. 2002; 14(5-6):307-14. A representative example is chemical cross-linking to a pharmaceutically or cosmetically acceptable insoluble solid phase material, such as a polymer, microbead, or nanobead. The insoluble material need not precipitate when in a solution but includes a material that remains in suspension when in solution. Dehydration or precipitation with alcohol may be practiced with any alcohol suitable for pharmaceutical or cosmetic use. Non-limiting examples include ethanol or a fatty alcohol such as cetyl, stearyl, cetearyl, or lanolin alcohol. A non-limiting method of microencapsulating a cosmetic is described in U.S. Pat. No. 4,752,496.

The use of a disclosed method of the invention also includes milling of dried polysaccharide material (such as a film) into particles by any suitable method. Non-limiting examples of such methods are disclosed herein, and they produce particles with an average size that may range between about 400 and about 0.1 microns.

In some embodiments, the composition comprises polysaccharide particles that increase in volume on contact with water compared to their anhydrous or partially hydrated volume. In some embodiments, the particles increase in volume by an amount selected from at least about 5%, at least about 25%, at least about 50%, at least about 100%, at least about 200%, at least about 300%, by at least about 500%, at least about 1000%, or at least about 5000%.

In some embodiments, the polysaccharide of the method is associated with a fusion protein as described herein. In some cases, the fusion protein comprises a first protein with at least 60% amino acid identity with the protein of SEQ ID NO:15, and a second protein. Alternatively, the polysaccharide of the method contains an amount of sulfur by weight from at least about 3.0% sulfur to at least about 7.0% sulfur by weight as described herein, and optionally is also associated with a fusion protein. An example of an expression vector for expression in *Porphyridium* of a polysaccharide binding protein:superoxide dismutase fusion can be found in SEQ ID NO:36. In some embodiments a spacer of 1-15 amino acids is placed between the glycoprotein and second protein to enable flexibility between the two proteins. Expression of a fusion protein, wherein the second heterologous protein is a dimerizing or multimerizing protein (such as superoxide dismutase) can be advantageous when a higher viscosity or gelling property of the polysaccharide is desired because the dimmers serve to crosslink the polysaccharide. The reversibility of the crosslinking is in part dictated by the strength of the dimerization in such fusion proteins provided by the invention.

Topical compositions are usually formulated with a carrier, such as in an ointment or a cream, and may optionally include a fragrance. One non-limiting class of topical compositions is that of cosmeceuticals. Other non-limiting examples of topical formulations include gels, solutions, impregnated bandages, liposomes, or biodegradable microcapsules as well as lotions, sprays, aerosols, suspensions, dusting powder, impregnated bandages and dressings, biodegradable polymers, and artificial skin. Another non-limiting example of a topical formulation is that of an ophthalmic preparation. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water.

In some embodiments, the polysaccharides contain fucose moieties. In other embodiments, the polysaccharides are sulfated, such as exopolysaccharides from microalgae of the genus *Porphyridium*. In some embodiments, the polysaccharides will be those from a *Porphyridium* species, such as one that has been subject to genetic and/or nutritional manipulation to produce polysaccharides with altered monosaccharide content and/or altered sulfation.

In additional embodiments, a composition of the invention comprises a microalgal cell homogenate and a topical carrier. In some embodiments, the homogenate may be that of a species listed in Table 1A or 1B or may be material produced by a species in the tables.

In further embodiments, a composition comprising purified microalgal polysaccharide and a carrier suitable for topical administration also contains a fusion (or chimeric) protein associated with the polysaccharide. In some embodiments, the fusion protein comprises a first protein, or polypeptide region, with at least about 60% amino acid identity with the protein of SEQ ID NO:15. In other embodiments, the first protein has at least about 70%, at least about 75%, at least about 80%, at least about 85%, at least about 90%, at least about 95%, or at least about 98%, or higher, amino acid identity with the sequence of SEQ ID NO:15. Preferably the fusion protein binds to a sulfated exopolysaccharide from a cell of the genus *Porphyridium*. It is preferable that the binding of the fusion protein to the polysaccharide be selective and high affinity, though such is not required to practice the invention.

The fusion protein may comprise a second protein, or polypeptide region, with a homogenous or heterologous sequence. Non-limiting examples of the second protein include an antibody, an enzyme, or a structural protein of skin or a skin tissue, such as that of a human being. In some cases, the second protein is a peptide that binds to a surface on the exterior of a human body. In various embodiments, the peptide can be selected to bind human skin, human hair, or human fingernails or toenails. In optional embodiments, the enzyme is superoxide dismutase, such as that has at least about 60% amino acid identity with the sequence of SEQ ID NO:12, SEQ ID NO:13, or a protein from Table 21 and exhibit superoxide dismutase activity as non-limiting examples. In some embodiments, the superoxide dismutase has at least about 70%, at least about 75%, at least about 80%, at least about 85%, at least about 90%, at least about 95%, or at least about 98%, or higher, amino acid identity with the sequence of SEQ ID NO:12 or SEQ ID NO:13. In other embodiments, the second protein is a structural skin protein selected from the group consisting of elastin and a collagen chain, such as that of human skin. Sequences encoding elastin and a chain of collagen are known to the skilled person and may be incorporated into a fusion protein via routine methods. Examples of such human skin proteins are also disclosed herein in the sequence listing. In one embodiment, the second protein is keratin. Assays for superoxide dismutase activity are well known in the art. For examples see Song et al., Clin Sci (Lond). 2007 Jan. 8; Epub ahead of print, Oxidative stress, antioxidant status and DNA damage in patients with impaired glucose regulation and newly-diagnosed Type II diabetes; and Liu et al., Phytomedicine. 2006 Dec. 15 Protection of PC12 cells from hydrogen peroxide-induced cytotoxicity by salvianolic acid B, a new compound isolated from Radix Salviae miltiorrhizae. The presence of any exogenous or endogenous protein expressed in microalgae can be assayed for example, using well known methods such as western blotting and ELISA assays.

In other embodiments, the second protein is an antibody. Non-limiting examples of antibodies for use in this aspect of the invention include an antibody that selectively binds to an antigen from a pathogen selected from HIV, Herpes Simplex Virus, gonorrhea, *Chlamydia*, Human Papillomavirus, and Trichomoniasis. In some embodiments, the antibody is a humanized antibody.

B. Methods of Formulation

Polysaccharide compositions for topical application can be formulated by first preparing a purified preparation of polysaccharide. As a non-limiting example, the polysaccharide from aqueous growth media is precipitated with an alcohol, resuspended in a dilute buffer, and mixed with a carrier suitable for application to human skin or mucosal tissue, including the vaginal canal. Alternatively, the polysaccharide can be purified from growth media and concentrated by tangential flow filtration or other filtration methods, and formulated as described above. Intracellular polysaccharides can be also formulated in a similar or identical manner after purification from other cellular components.

As a non-limiting example, the invention includes a method of formulating a cosmeceutical composition, said method comprising culturing microalgal cells in suspension under conditions to allow cell division; separating the microalgal cells from culture media, wherein the culture media contains exopolysaccharide molecules produced by the microalgal cells; separating the exopolysaccharide molecules from other molecules present in the culture media; homogenizing the microalgal cells; and adding the separated exopolysaccharide molecules to the cells before, during, or after homogenization. In some embodiments, the microalgal cells are from the genus *Porphyridium*.

In other embodiments, the invention includes a method of manufacturing a composition comprising particles, the method comprising isolating a polysaccharide from microalgae; drying an aqueous suspension of the polysaccharide to a solid film wherein at least some proportion of the film has been made completely or partially insoluble in water; homogenizing or otherwise milling or disrupting the film into particles; and formulating the particles into a non-aqueous material.

The method may of course be practiced with a variety of microalgal cells, such as those described in Tables 1A or 1B and those of the genus *Porphyridium*.

As described herein, the resulting composition may be for improving the appearance of skin, such as human skin. In some embodiments, the formulating may be into the oil phase of an oil-in-water emulsion. In other embodiments, the non-aqueous material is an oil suitable for topical administration, with hexadecanoic acid and oil that is contained in an emulsion as non-limiting examples. In further embodiments, the method further comprises formulating the particles into a carrier and/or preservative suitable for topical administration. The resulting composition may also be substantially free of endotoxins and/or protein. In many embodiments, the composition is also made sterile and/or non-pyrogenic. Alternatively, the method further comprises formulating hyaluronic acid into the composition.

In other embodiments, the polysaccharide after the drying step is partially or completely insoluble in water. Optionally, the polysaccharide after the drying step is soluble in water at a percentage selected from the list consisting of less than about 70%, less than about 60%, less than about 50%, less than about 40%, less than about 30%, less than about 20%, less than about 10%, less than about 5%, and less than about 2%.

Embodiments of the drying step include drying performed at between about 40 and about 180° C., such as between about 80° C. and about 170° C., or between about 100° C. and about 160° C., between about 125° C. and about 155° C., between about 135° C. and about 152° C., between about 140° C. and about 150° C., or between about 145° C. and about 148° C. as non-limiting examples. Optionally, the drying is performed in two steps, wherein the first step comprises heating the suspension of the polysaccharide to no more than about 60° C. for a first period of time to produce a solid film followed by heating the solid film for a second period of time to no more than about 160° C. In alternative embodiments, the first and second steps comprise heating to no more than about 80° C. and no more than about 150° C., or to approximately 100° C. and no more than 148° C., respectively. In some embodiments, the suspension of the polysaccharide is heated during the first period of time in the presence of air to produce a solid film and the solid film is heated during the second period of time in at least a partial vacuum or otherwise under reduced pressure.

After the drying step, milling may be by any suitable method. Non-limiting examples include a method selected from the list consisting of jet milling, ball milling, Retsch® milling, and milling in a Quadro® device. The resulting particles of the composition may have an average size between about 400 and about 0.1 microns. In some embodiments, the particles of the composition have an average size between about 100 and about 0.1 microns, between about 50 and about 0.1 microns, between about 10 and about 0.1 microns, between about 10 and about 0.5 microns, or between about 5 and about 0.5 microns.

In some embodiments, the polysaccharide of the method is associated with a fusion protein as described herein. In some cases, the fusion protein comprises a first protein with at least 60% amino acid identity with the protein of SEQ ID NO:15, and a second protein. Alternatively, the polysaccharide of the method contains an amount of sulfur by weight from at least about 3.0% sulfur to at least about 7.0% sulfur by weight as described herein, and in some embodiments is associated with a fusion protein.

Examples of polysaccharides, both secreted and intracellular, that are suitable for formulation with a carrier for topical application are listed in Table 1A.

In further embodiments, polysaccharide is associated with a fusion (or chimeric) protein comprising a first protein (or polypeptide region) with at least about 60% amino acid identity with the protein of SEQ ID NO:15. In some cases, the first protein has at least about 70%, at least about 75%, at least about 80%, at least about 85%, at least about 90%, at least about 95%, or at least about 98%, or higher, amino acid identity with the sequence of SEQ ID NO:15.

The fusion protein may comprise a second protein, or polypeptide region, with a homogenous or heterologous sequence. One non-limiting example of the second protein is a superoxide dismutase enzyme.

Examples of carriers suitable for formulating polysaccharide are described above. Ratios of homogenate:carrier are typically in the range of about 0.001:1 to about 1:1 (volume:volume), although the invention comprises ratios outside of this range, such as, but not limited to, about 0.01:1 and about 0.1:1.

Microalgal cellular extracts can also be formulated for topical administration. It is preferable but not necessary that the cells are physically or chemically disrupted as part of the formulation process. For example, cells can be centrifuged from culture, washed with a buffer such as 1.0 mM phosphate buffered saline, pH 7.4, and sonicated. Preferably the cells are sonicated until the cell walls have been substantially disrupted, as can be determined under a microscope. For example, *Porphyridium* sp. cells can be sonicated using a Misonix sonicator as described in Example 3.

Cells can also be dried and ground using means such as mortar and pestle, colloid milling, ball milling, or other physical method of breaking cell walls.

After cell disruption, cell homogenate can be formulated with carrier and fragrance as described above for polysaccharides.

The compositions according to the present invention can also be used as hair treating agents such as hair dressings (e.g., hair creams, hair sprays, hair tonics, hair gels, hair lotions, hair oils, hair essences, hair waters, hair waxes, and hair mousses), shampoos, finishing rinses, hair treatments, hair creams, hair mousses, hair setting lotions, hair colors, hair dyes (e.g., hair colors, one-part hair dyes, and two-part hair dyes), perm solutions (e.g., permanent wave solutions, hair straightening solutions, and permanent wave holding agents), blood flow enhancers, scalp lotions, and anti-hair loss agents. Other applications of the compositions according to the present invention include, for example, skin care cosmetics such as toners, serums, whitening toners, milky lotions, whitening milky lotions, creams, whitening creams, ointments, whitening ointments, lotions, whitening lotions, oils, and facial packs. Furthermore, still other applications of the compositions according to the present invention include, for example, makeup cosmetics such as foundations, liquid foundations, lipsticks, lip glosses, moisturizing lip balms, eye shadows, powders, face powders, blushers, eye shadows, eye liners, mascaras, and eyebrow pencils. Other applications of the compositions according to the present invention include, for example, skin cleaners such as soap, cleansing creams, cleansing lotions, cleansing milks, cleansing pads, cosmetic compositions, facial washes, and body shampoos. Moreover, another application of the compositions according to the present invention is in finishing cosmetics for use in, e.g., manicures. Other applications of the compositions according to the present invention include, for example, cosmetic compositions in the form of bath agents, patches, perfumes, toothpastes, tooth washes, and mouthwashes.

Compositions in accordance with the present invention include finished cosmetic products for oral or topical administration. Combinations of various agents suitable or desirable for treatment of skin can be included in such finished cosmetic products. For example, compositions for topical administration can include algal polysaccharides, algal carotenoids, vitamins (e.g, vitamin C, vitamin E, vitamin D, or vitamin D precursors), salicylic acid, amino acids (e.g., tyrosine), amino acid derivatives (e.g., N-acetyl methionine), betaine, perfluoropolyethers, whole cell algae extracts, dihydroxyacetone, *Rhodiola rosea*, menthol, and tissue respiratory factor. Compositions for oral administration can include, for example, fish oils, algal oils, vitamins (e.g., vitamin C, vitamin D, vitamin E), carotenoids, asthaxanthin, zeoxanthin, amino acids (e.g., tyrosine), *Rhodiola rosea*, whole cell algal extracts, and betaine. These components can be combined with suitable carriers, as well as essential oils, fragrance oils, flavor oils, seed oils, botanicals, plant extracts, $CO_2$ extracts, soaps, clays, colorants, titanium dioxide, micas, tinting herbs, glitters, exfoliants, fruit seeds, fibers, grain powders, nut meals, seed meals, oil beads, wax beads, herbs, hydrosols, vitamins, milk powders, preservatives, antioxidants, tocopherols, salts, sugars, vegetable oils, waxes, glycerin, sea vegetables, nutritive oils, moisturizing oils, vegetable butters, propylene glycol, parabens, honey, bees wax, aloe, polysorbate, cornstarch, cocoa powder, coral powder, humectants, gums, emulsifying agents, and/or thickeners.

In some embodiments, compositions in accordance with the present invention include algal polysaccharides in combination with at least one other ingredient selected from the group consisting of beta carotene, lutein, astaxanthin, vitamin C, vitamin E, vitamin A, coenzyme Q10, a peptide, an aceylated peptide, oil soluble α-hydroxy acid, an alkyl lactate, and salicylic acid. The polysaccharides and other ingredients can be combined and subjected to processing (e.g., drying, heating, micronization, milling, and the like) to form particles comprising the multiple components for use in cosmetic, skin care, nutraceutical, or other products.

In one aspect, the invention is directed to cosmetic ingredients, including algal polysaccharides encapsulated in microspheres and aqueous solutions of such microencapsulated algal polysaccharides. In some embodiments, the aqueous solutions can include from 0.1% to 10% w/w microencapsulated algal polysaccharides. The microspheres can be formulated to release the algal polysaccharide contents upon topical application to, e.g., human skin, wherein the polysaccharides swell in contact with the skids moisture to reduce the appearance of wrinkles on the skin.

C. Co-Administered Compositions

Topical compositions can comprise a portion of a complete composition sold as a single unit. Other portions of the complete compositions can comprise an oral supplement intended for administration as part of a regime for altering skin appearance. Because the top layers of the skin contain dead cells, nutrients delivered via capillaries cannot reach the outer layers of cells. The outer layers of cells must be provided with nutrients though topical administration. However, topical administration is not always an effective method of providing nutrients to deep layers of skin that contain living cells. The compositions provided herein comprise both topical compositions that contain algal polysaccharides and/or cellular extracts as well as oral compositions comprising nutraceutical molecules such as purified polysaccharides, whole cell extracts, carotenoids, polyunsaturated fatty acids, and other molecules that are delivered to the skin via capillaries. The combined effect of the topical and oral administration of these molecules and extracts provides a benefit to skin health that is additive or synergistic compared to the use of only a topical or only an orally delivered product.

Examples of the topical components of the composition include exopolysaccharide from *Porphyridium cruentum*, *Porphyridium* sp., or other microalgae, e.g., those listed in Tables 1A and 1B. Other components of the topical composition can include polysaccharides and/or cell extracts from species listed in Table 1A and/or Table 1B.

Cellular extracts for topical administration can also include cellular homogenates from microalgae that have been genetically engineered. For example, homogenates of *Porphyridium* sp. that have been engineered to express an exogenous gene encoding superoxide dismutase can be formulated for topical administration. Other genes that can be expressed include carotenoid biosynthesis enzymes and polyunsaturated fatty acid biosynthesis enzymes.

Examples of compositions for oral administration include one or more of the following: DHA, EPA, ARA, lineoileic acid, lutein, lycopene, beta carotene, braunixanthin, zeaxanthin, astaxanthin, linoleic acid, alpha carotene, vitamin C and superoxide dismutase. Compositions for oral administration usually include a carrier such as those described above. Oral compositions can be formulated in tablet or capsule form. Oral compositions can also be formulated in an ingestible form such as a food, tea, liquid, etc. Oral compositions can, for example, comprise at least 50 micrograms, at least 100 micrograms, at least 50 milligrams, at least 100 milligrams, at least 500 milligrams, and at least one gram of a small molecule such as a carotenoids or a polyunsaturated fatty acid.

In another aspect, the invention includes orally administered nutraceutical compositions comprising one or more polysaccharides, or microalgal cell extract or homogenate, of the invention. A nutraceutical composition serves as a nutritional supplement upon consumption. In other embodiments, a nutraceutical may be bioactive and serve to affect, alter, or regulate a bioactivity of an organism.

A nutraceutical may be in the form of a solid or liquid formulation. In some embodiments, a solid formulation includes a capsule or tablet formulation as described above. In other embodiments, a solid nutraceutical may simply be a dried microalgal extract or homogenate, as well as dried polysaccharides per se. In liquid formulations, the invention includes suspensions, as well as aqueous solutions, of polysaccharides, extracts, or homogenates. In some embodiments the nutraceutical is derived from microalgae, while in other embodiments the nutraceutical is derived from other sources such as, for example, plants, plant extracts, and chemically synthesized molecules. In a preferred embodiment a topical composition and an oral composition contain at least one molecule in common.

The methods of the invention include a method of producing a nutraceutical composition. Such a method may comprise drying a microalgal cell homogenate or cell extract. The homogenate may be produced by disruption of microalgae which has been separated from culture media used to propagate (or culture) the microalgae. Thus in one non-limiting example, a method of the invention comprises culturing red microalgae; separating the microalgae from culture media; disrupting the microalgae to produce a homogenate; and drying the homogenate. In similar embodiments, a method of the invention may comprise drying one or more polysaccharides produced by the microalgae.

In some embodiments, a method of the invention comprises drying by tray drying, spin drying, rotary drying, spin flash drying, or lyophilization. In other embodiments, methods of the invention comprise disruption of microalgae by a method selected from pressure disruption, sonication, and ball milling.

In additional embodiments, a method of the invention further comprises formulation of the homogenate, extract, or polysaccharides with a carrier suitable for human consumption. As described herein, the formulation may be that of tableting or encapsulation of the homogenate or extract.

In further embodiments, the methods comprise the use of microalgal homogenates, extracts, or polysaccharides wherein the cells contain an exogenous nucleic acid sequence, such as in the case of modified cells described herein. The exogenous sequence may encode a gene product capable of being expressed in the cells or be a sequence which increases expression of one or more endogenous microalgal gene product.

In a preferred embodiment, at the topical composition and the oral composition both contain at least one molecule or one type of molecule (such as carotenoids) in common. For example, the topical composition contains homogenate of *Porphyridium* cells that contain zeaxanthin, and the oral composition contains zeaxanthin. In another embodiment, the topical composition contains homogenate of *Porphyridium* cells that contain polysaccharide, and the oral composition contains polysaccharide purified from *Porphyridium* culture media. In another embodiment, the topical composition and the oral composition both contain lutein and/or zeaxanthin. Microalgae can be but need not be the source of either or both lutein and zeaxanthin. In some embodiments, the daily oral composition dosage is about 10 mg lutein and about 0.6 mg zeaxanthin per day, and the daily topical composition dosage is about 100 ppm lutein and about 12 ppm of zeaxanthin in an oil-free liquid. In other embodiments the oral and topical compositions both comprise carotenoids such as at least one of phytoene, phytofluene, beta carotene, lutein, zeaxanthin, and astaxanthin.

In one embodiment, the topical composition, optionally derived or partially derived from microalgae, comprises the carotenoids phytoene and phytofluene, and optionally also contains vitamin C, and vitamin E; the oral composition, optionally derived or partially derived from microalgae, comprises at least two of the following compounds: ascorbic acid, vitamin E succinate, lutein, zeaxanthin, beta carotene, EPA, DHA, and CoQ10. All components of the oral composition do not necessarily need to be formulated into the same tablet or capsule. In some compositions the oral composition comprises at least 3, at least 4, at least 5, at least 6, and at least 7 of the aforementioned compounds. Optionally, daily dosages of the topical composition are about 0.1-7% IBR-CLC® concentrate (phytoene/phytofluene combination; Israeli Biotechnology Research Corp.; U.S. Pat. No. 6,383,474), 1-20% vitamin C, 1-20% vitamin E. Optionally, daily doses for the oral composition are between 20-600 mg ascorbic acid, 20-600 mg vitamin E succinate, 0.1-50 mg lutein, 0.05-30 mg zeaxanthin, 0.1-50 mg beta carotene, 5-400 mg CoQ10, 50-750 mg EPA, and 20-750 mg DHA.

Some of the compositions described herein are packaged for sale as a single unit. For example, a unit for sale comprises a first container holding a composition for topical administration, a second container holding individual doses of a composition for oral administration, and optionally, directions for co-administration of the topical and oral composition.

Some embodiments of the invention include a combination product comprising 1) a first composition comprising a microalgal extract and a carrier suitable for topical application to skin; and 2) a second composition comprising at least one compound and a carrier suitable for human consumption; wherein the first and second compositions are packaged for sale as a single unit. Thus the invention includes co-packaging of the two compositions, optionally with a instructions and/or a label indicating the identity of the contents and/or their proper use.

Other combination products are including in the invention. In some embodiments, the first composition may be a topical formulation or non-systemic formulation, optionally a cosmeceutical, as described herein. Preferably, the first composition comprises a carrier suitable for topical application to skin, such as human skin. Non-limiting examples of the second composition include a food composition or nutraceutical as described herein. Preferably, the second composition comprises at least one carrier suitable for human consumption, such as that present in a food product or composition. Combination products of the invention may be packaged separately for subsequent use together by a user or packaged together to facilitate purchase and use by a consumer. Packaging of the first and second compositions may be for sale as a single unit.

D. Methods of Cosmetic Enhancement

In a further aspect, the invention includes a method to cosmetically enhance skin or its appearance or texture. In some cases, the enhancement is due to increased or improved skin elasticity. The skin may be that of a human being, such as the skin of the face, hands, feet, or other parts of the human body. In other embodiments, the enhancement may be in the appearance or texture of human lips. The method may comprise administration of a polysaccharide composition suitable for injection into skin or lip tissue to improve the appearance thereof. The composition may be any as described herein suitable for the method of administration or application. In some embodiments, the injection is made to alleviate or eliminate wrinkles. In other embodiments, the treatment reduces the visible signs of aging and/or wrinkles.

As known to the skilled person, human skin, as it ages, gradually loses skin components that keep skin pliant and youthful-looking. The skin components include collagen, elastin, and hyaluronic acid, which have been the subject of interest and use to improve the appearance of aging skin.

The invention includes compositions of microalgal polysaccharides, microalgal cell extracts, and microalgal cell homogenates for use in the same manner as collagen and hyaluronic acid. In some embodiments, the polysaccharides will be those of from a *Porphyridium* species, such as one that has been subject to genetic and/or nutritional manipulation to produce polysaccharides with altered monosaccharide content and/or altered sulfation. In some embodiments, the polysaccharides are formulated as a fluid, optionally elastic and/or viscous, suitable for injection. The compositions may be used as injectable dermal fillers as one non-limiting example. The injections may be made into skin to fill-out facial lines and wrinkles. In other embodiments, the injections may be used for lip enhancement. These applications of polysaccharides are non-limiting examples of non-pharmacological therapeutic methods of the invention.

In further embodiments, the microalgal polysaccharides, cell extracts, and cell homogenates of the invention may be co-formulated with collagen and/or hyaluronic acid (such as the Restylane® and Hylaform® products) and injected into facial tissue. Non-limiting examples of such tissue include under the skin in areas of wrinkles and the lips. In a preferred embodiment, the polysaccharide is substantially free of protein. The injections may be repeated as deemed appropriate by the skilled practitioner, such as with a periodicity of about three, about four, about six, about nine, or about twelve months. In another preferred embodiment, a hyaluronic acid material is mixed with a polysaccharide from the genus *Porphyridium* prior to co-administration. The invention in this particular embodiment provides longer half-life to the hyaluronic acid due to the potent inhibition of hyaluronidase by polysaccharides isolated from microalgae from the genus *Porphyridium*. This allows for less injections to a patient. Preferably the polysaccharide from the genus *Porphyridium* is at least substantially free of protein. Preferably the mixture of polysaccharide from the genus *Porphyridium* and hyaluronic acid is sterile.

Thus, the invention includes a method of cosmetic enhancement comprising injecting a polysaccharide produced by microalgae into mammalian skin. The injection may be of an effective amount to produce a cosmetic improvement, such as decreased wrinkling or decreased appearance of wrinkles as non-limiting examples. Alternatively, the injection may be of an amount which produces relief in combination with a series of additional injections. In some methods, the polysaccharide is produced by a microalgal species, or two or more species, listed in Tables 1A or 1B. In one non-limiting example, the microalgal species is of the genus *Porphyridium* and the polysaccharide is substantially free of protein.

The invention further includes a method to inhibit hyaluronidase activity comprising contacting the hyaluronidase with a disclosed polysaccharide. In some embodiments, the hyaluronidase activity is in the skin or a skin tissue of a human subject and the contacting comprises administering the polysaccharide to the subject. The administering may comprise injection of the polysaccharide, or a polysaccharide containing composition of the invention, to the skin or skin tissue and/or to the lips or a lip tissue. The amount of polysaccharide administered may be any that is sufficient or effective to inhibit hyaluronidase activity to a level as desired by a skilled person. The level of reduction in hyaluronidase activity may be determined by routine methods, including a comparative method wherein the activity in the presence of polysaccharide is compared to the activity in the absence thereof. Thus the amount of reduction may be at least about 10%, about 20%, about 30%, about 40%, about 50%, about 60%, about 70%, about 80%, or about 90% or higher than that observed in the absence of polysaccharide. In a preferred embodiment the polysaccharide used to inhibit hyaluronidase is from a species of the genus *Porphyridium*.

The invention also includes a method to stimulate procollagen and/or collagen synthesis or production in a cell, such as a human fibroblast, by contacting the cell with a disclosed polysaccharide. In some embodiments, the cell is in the skin of a human subject and the contacting comprises administering the polysaccharide to the subject. The administering may comprise injection of the polysaccharide, or a polysaccharide containing composition of the invention, to the skin or a skin tissue and/or to the lips or a lip tissue. The amount of polysaccharide administered may be any that is sufficient or effective to stimulate procollagen or collagen synthesis to a level desired by a skilled person, such as an increase of at least about 5%, 10%, about 20%, or about 30% or higher than that observed in the absence of polysaccharide. In a related manner, the polysaccharide may be used to inhibit collagenase activity. The inhibition may be sufficient to result in an increase of procollagen or collagen levels as described above.

Additionally, the invention includes a method to stimulate elastin synthesis or production in a cell, such as a fibroblast, by contacting the cell with a disclosed polysaccharide. In a related manner, the polysaccharide may also inhibit elastase activity produced by a cell, such as, but not limited to, a fibroblast. In some embodiments, the cell is in the skin of a human subject and the contacting comprises administering the polysaccharide to the subject. The administering may comprise injection of the polysaccharide, or a polysaccharide containing composition of the invention, to the skin or a skin tissue. The amount of polysaccharide administered may be any that is sufficient or effective to stimulate elastin synthesis to a level desired by a skilled person, such as an increase of at least about 50%, 100%, about 200%, or about 300% or higher than that observed in the absence of polysaccharide. In a preferred embodiment the polysaccharide stimulating elastin secretion contains at least 5.0% sulfur by weight. Similarly, the polysaccharide may decrease elastase activity by about 10%, about 20%, about 30%, about 40%, about 50%, or about 60% or higher than that observed in the absence of polysaccharide.

The invention further includes the use of the disclosed polysaccharides based on their observed anti-oxidant activity. Thus the invention includes a method of providing anti-oxidant activity to skin or a skin tissue, such as that of a human subject, by administering a polysaccharide. In some embodiments, the method inhibits reactive oxygen species (ROS) formation and/or activity in the skin. The invention thus includes a method to prevent or treat a disease or unwanted condition associated with ROS or oxidative stress. Non-limiting examples of such a disease or unwanted condition include reducing inflammation or irritation of human skin or lips. In some embodiments, the polysaccharide composition comprises one or more other agents or compounds with anti-oxidant activity. Non-limiting examples of other agents include vitamin A (retinyl palmitate), vitamin C (such as one or more of ascorbyl palmitate, sodium ascorbyl palmitate, and tetrahexyldecyl ascorbate), vitamin D (cholecalciopherol), vitamin E (such as tocopheryl acetate and tocopherol/D-alpha tocopherol), alpha lipoic acid, coenzyme, L-selenomethionine, and beta glucan.

In a related manner, a polysaccharide is used based on its anti-inflammatory in skin or a skin tissue. In some embodiments, the method inhibits polymorphonuclear (PMN) leukocytes in chemotaxis, such as to sites of inflammation in skin. The level of inhibition may be about 10%, about 20%, about 30%, about 40%, or about 50% or more than that seen in the absence of polysaccharide. In other embodiments, the method inhibits the synthesis or release of a pro-inflammatory cytokine, such as interferon-gamma or interleukin-1-alpha. With interferon-gamma as an example, the inhibition may be at least about 10%, about 20%, about 30%, about 40%, about 50%, about 60%, about 70%, about 80%, or about 90% or more than that observed in the absence of polysaccharide. With interleukin-1-alpha as an example, the inhibition may be at least about 10%, about 20%, about 30%, about 40%, about 50%, about 60%, about 70%, or about 80% or more than that observed in the absence of polysaccharide. In further embodiments, the method inhibits proliferation of peripheral blood mononuclear cells, including lymphocytes, monocytes, and macrophages. The level of inhibition may be about 10%, about 20%, about 30%, about 40%, about 50%, about 60%, about 70%, or about 80% or more than that observed in the absence of polysaccharide.

The above described methods may be individually part of a method to reduce the signs of aging or reduce the appearance of aging in human skin as described herein. The methods may also be based upon the insight that the microalgal biomass and polysaccharides of the invention also reduce the effects of UV light or radiation. In some embodiments, the polysaccharide reduces thymidine dimer formation in DNA caused by exposure to UVB irradiation. The reduction may be at least about 10%, about 20%, about 30%, about 40%, about 50%, about 60%, about 70%, or about 80% or more than that observed in the absence of polysaccharide.

In a related manner, the disclosed methods can be used to shield human skin or lip tissue from UV light radiation. The UV radiation may comprise UVA and/or UVB. The method may comprise applying a composition of the disclosed invention to skin or a skin tissue in an effective or sufficient amount to shield, at least in part, the skin from UV radiation. In some embodiments, the amount is that which reduces thymidine dimer formation and/or sunburn. In an alternative embodiment, a composition of the invention may be applied in an effective or sufficient amount, such as that which reduces further UV-mediated damage, to treat skin that has been damaged by UV radiation. An additional non-limiting example is a method of for treating skin to reduce the risk of skin cancer induced by sunlight or UV radiation.

The polysaccharide compositions may be in the form of a sterile and/or non-pyrogenic injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringers solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

Sterile injectable polysaccharide compositions preferably contain less than 1% protein as a function of dry weight of the composition, more preferably less than 0.1% protein, more preferably less than 0.01% protein, less than 0.001% protein, less than 0.0001% protein, more preferably less than 0.00001% protein, more preferably less than 0.000001% protein.

VI. Gene Expression in Microalgae

Genes can be expressed in microalgae by providing, for example, coding sequences in operable linkage with promoters.

An exemplary vector design for expression of a gene in microalgae contains a first gene in operable linkage with a promoter active in algae, the first gene encoding a protein that imparts resistance to an antibiotic or herbicide. Exemplary antibiotic resistance genes include, without limitation, a *Porphyridium* sp. sulfometuron resistance gene (SEQ ID NO:10), and a zeocin resistance gene (SEQ ID NO:24). Optionally, the first gene is followed by a 3' untranslated sequence containing a polyadenylation signal. The vector may also contain a second promoter active in algae in operable linkage with a second gene. The second gene can encode any protein, for example an enzyme that produces small molecules or a mammalian growth hormone that can be advantageously present in a nutraceutical.

It is preferable to use codon-optimized cDNAs: for methods of recoding genes for expression in microalgae, see for example US patent application 20040209256.

It has been shown that many promoters in expression vectors that are active in algae, including both promoters that are endogenous to the algae being transformed algae as well as promoters that are not endogenous to the algae being transformed (i.e., promoters from other algae, promoters from plants, and promoters from plant viruses or algae viruses). Suitable promoters include, without limitation, *Chlamydomonas reinhardtii* RBCS2 promoters (SEQ ID NO:1 and SEQ ID NO:16), *Chlamydomonas reinhardtii* β-2 tubulin promoter (SEQ ID NO:2), *Chlorella* virus promoter #1 (SEQ ID NO:3), *Chlorella* virus promoter #2 (SEQ ID NO:4), *Chlorella* virus promoter #3 (SEQ ID NO:5), *Rhodella* reticulate phycoerythrin beta subunit promoter (SEQ ID NO:6), *Porphyridium* AHAS promoter (SEQ ID NO:7), *Porphyridium purpureum* carbonic anhydrase pca2 promoter (SEQ ID NO:8), and *Porphyridium purpureum* carbonic anhydrase pca1 promoter (SEQ ID NO:9).

Exemplary methods for transforming microalgae, in addition to those demonstrated in the Examples section below, including methods comprising the use of exogenous and/or endogenous promoters that are active in microalgae, and antibiotic resistance genes functional in microalgae, have been described. See for example; Curr Microbiol. 1997 December; 35(6):356-62 (*Chlorella vulgaris*); Mar Biotechnol (NY). 2002 January; 4(1):63-73 (*Chlorella ellipsoidea*); Mol Gen Genet. 1996 Oct. 16; 252(5):572-9 (*Phaeodactylum tricornutum*); Plant Mol Biol. 1996 April; 31(1):1-12 (*Volvox carteri*); Proc Natl Acad Sci USA. 1994 Nov. 22; 91(24):11562-6 (*Volvox carteri*); Falciatore A, Casotti R, Leblanc C, Abrescia C, Bowler C, PMID: 10383998, 1999 May; 1(3):239-251 (Laboratory of Molecular Plant Biology, Stazione Zoologica, Villa Comunale, 1-80121 Naples, Italy) (*Phaeodactylum tricornutum* and *Thalassiosira weissflogii*); Plant Physiol. 2002 May; 129(1):7-12. (*Porphyridium* sp.); Proc Natl Acad Sci USA. 2003 Jan. 21; 100(2):438-42. (*Chlamydomonas reinhardtii*); Proc Natl Acad Sci USA. 1990 February; 87(3):1228-32. (*Chlamydomonas reinhardtii*); Nucleic Acids Res. 1992 Jun. 25; 20(12):2959-65; Mar Biotechnol (NY). 2002 January; 4(1):63-73 (*Chlorella*); Biochem Mol Biol Int. 1995 August; 36(5):1025-35 (*Chlamydomonas reinhardtii*); J Microbiol. 2005 August; 43(4):361-5 (*Dunaliella*); Yi Chuan Xue Bao. 2005 April; 32(4):424-33 (*Dunaliella*); Mar Biotechnol (NY). 1999 May; 1(3):239-251. (*Thalassiosira* and *Phaedactylum*); Koksharova, Appl Microbiol Biotechnol 2002 February; 58(2):123-37 (various species); Mol Genet Genomics. 2004 February; 271(1):50-9 (*Thermosynechococcus elongates*); J. Bacteriol. (2000), 182, 211-215; FEMS Microbiol Lett. 2003 Apr. 25; 221(2):155-9; Plant Physiol. 1994 June; 105(2):635-41; Plant Mol Biol. 1995 December; 29(5):897-907 (*Synechococcus* PCC 7942); Mar Pollut Bull. 2002; 45(1-12):163-7 (*Anabaena* PCC 7120); Proc Natl Acad Sci USA. 1984 March; 81(5):1561-5 (*Anabaena* (various strains)); Proc Natl Acad Sci USA. 2001 Mar. 27; 98(7): 4243-8 (*Synechocystis*); Wirth, Mol Gen Genet 1989 March; 216(1):175-7 (various species); Mol Microbiol, 2002 June; 44(6):1517-31 and Plasmid, 1993 September; 30(2):90-105 (*Fremyella diplosiphon*); Hall et al. (1993) Gene 124: 75-81 (*Chlamydomonas reinhardtii*); Gruber et al. (1991). Current Micro. 22: 15-20; Jarvis et al. (1991) Current Genet. 19: 317-322 (*Chlorella*); for additional promoters see also Table 1 from U.S. Pat. No. 6,027,900).

Suitable promoters may be used to express a nucleic acid sequence in microalgae. In some embodiments, the sequence is that of an exogenous gene or nucleic acid. In some embodiments the exogenous gene can encode a superoxide dismutase (SOD) or an SOD fusion. In cases of an exogenous nucleic acid coding sequence, the codon usage may be optionally optimized in whole or in part to facilitate expression in microalgae.

In some embodiments the invention includes cells of the genus *Porphyridium* that have been stably transformed with a vector containing a selectable marker gene in operable linkage with a promoter active in microalgae. In other embodiments the invention includes cells of the genus *Porphyridium* that have been stably transformed with a vector containing a selectable marker gene in operable linkage with a promoter endogenous to a member of the Rhodophyte order. Such promoters include SEQ ID NO:6, SEQ ID NO:20 and SEQ ID NO:21, promoters from the genome of *Chondrus crispus* (Genbank accession number Z47547), promoters from the genome of *Cyanidioschyzon merolae* (see for example Matsuzaki, M. et al. Nature 428, 653-657 (2004); Plant Physiology 137:567-585 (2005); entire sequence available at http://merolae.biol.s.u-tokyo.ac.jp/db/chromosome.cgi). In other embodiments the invention includes cells of the genus *Porphyridium* that have been stably transformed with a vector containing a selectable marker gene in operable linkage with a promoter other than a CMV promoter such as that found in PCT application WO2006013572.

In other embodiments, the invention provides for the expression of a protein sequence found to be tightly associated with microalgal polysaccharides. One non-limiting example is the protein of SEQ ID NO:15, which has been shown to be tightly associated with, but not covalently bound to, the polysaccharide from *Porphyridium* sp. (see J. Phycol. 40: 568-580 (2004)). When *Porphyridium* culture media is subjected to tangential flow filtration using a filter containing a pore size well in excess of the molecular weight of the protein of SEQ ID NO:15, the polysaccharide in the retentate contains detectable amounts of the protein, indicating its tight association with the polysaccharide. The calculated molecular weight of the protein is approximately 58 kD, however with glycosylation the protein is approximately 66 kD.

Such a protein may be expressed directly such that it will be present with the polysaccharides of the invention or expressed as part of a fusion or chimeric protein as described herein. As a fusion protein, the portion that is tightly associated with a microalgal polysaccharide effectively links the other portion(s) to the polysaccharide. A fusion protein may comprise a second protein or polypeptide, with a homogenous or heterologous sequence. A homogenous sequence would result in a dimer or multimer of the protein while a heterologous sequence can introduce a new functionality, including that of a bioactive protein or polypeptide.

Non-limiting examples of the second protein include an enzyme. In optional embodiments, the enzyme is superoxide dismutase, such as that has at least about 60% amino acid identity with the sequence of SEQ ID NO:12, SEQ ID NO:13, and proteins from Table 21 as non-limiting examples. Exemplary fusion proteins include superoxide dismutase fused to a polysaccharide binding protein (SEQ ID NO:14 or SEQ ID NO:17). In some embodiments, the superoxide dismutase has at least about 70%, at least about 75%, at least about 80%, at least about 85%, at least about 90%, at least about 95%, or at least about 98%, or higher, amino acid identity with the sequence of SEQ ID NO:12 or SEQ ID NO:13 or a protein from Table 21. In other embodiments, the enzyme is a phytase (such as GenBank accession number CAB91845 and U.S. Pat. Nos. 6,855,365 and 6,110,719). Other examples of second proteins include structural proteins from mammalian skin such as collagen and elastin. Exemplary fusion proteins include a glycoprotein-collagen fusion (SEQ ID NO:22), and a glycoprotein-elastin fusion (SEQ ID NO:23). Assays such as wesytern blot and ELISAs can be used to confirm the presence of the second protein in the biomass as well as when it is attached to a purified polysaccharide. Polysaccharides with fusion proteins bound can be purified as in Example 2. Activity assays for proteins such as phytases and superoxide dismutase are well known in the art.

One advantage to a fusion is that the bioactivity of the polysaccharide and the bioactivity from the protein can be combined in a product without increasing the manufacturing cost over only purifying the polysaccharide. As a non-limiting example, the potent antioxidant properties of a *Porphyridium* polysaccharide can be combined with the potent antioxidant properties of superoxide dismutase in a fusion, however the polysaccharide:superoxide dismutase combination can be isolated to a high level of purity using tangential flow filtration. In another non-limiting example, the potent antiviral properties of a *Porphyridium* polysaccharide can be added to the potent neutralizing activity of recombinant antibodies fused to the protein (SEQ ID NO:15) that tightly associates with the polysaccharide.

Another preferred fusion is between a protein with 50-100% amino acid identity with SEQ ID NO:15, which retains the ability to bind a *Porphyridium* polysaccharide, and a peptide that bind to an external surface on a human body, such as hair, skin, fingernails, or toenails. Nucleic acid sequences encoding such peptides are cloned in-frame with the polysaccharide binding protein, such as at the C-terminus. In some embodiments a linker peptide can be placed between the skin-binding, hair-binding, or fingernail-binding peptide and the protein that binds the polysaccharide. An example of such a linker is SEQ ID NO:41, or a subsegment thereof. Flexible linker proteins are well known in the art. See Appl Microbiol Biotechnol (2002) 58:658-662 for examples. In one embodiment, the fusion protein contains a linker of 1-50 amino acids between the first protein and the second protein.

Examples of peptides for use in the invention described herein that bind exterior surfaces of the human body can be found, for example, in U.S. Pat. Nos. 7,129,326 and 7,220,405. For example, the peptides LESTPKMK and LESTPKM (SEQ ID NO:42 and SEQ ID NO:43) bind tightly to human hair and thus serve to anchor polysaccharide from *Porphyridium* to human hair. The peptide FTQSLPP (SEQ ID NO:44) binds tightly to human skin and thus serves to anchor polysaccharide from *Porphyridium* to human skin. The peptide ALPRIANTWSPS (SEQ ID NO:45) binds tightly to human fingernails and thus serves to anchor polysaccharide from *Porphyridium* to human fingernails. An example of a skin-binding peptide fusion with a flexible linker between the skin-binding peptide and the protein that binds the *Porphyridium* polysaccharide is SEQ ID NO:46.

Preferred carbohydrate transporters for expression in *Porphyridium* are SEQ ID NO:33, SEQ ID NO:34, SEQ ID NO:35, SEQ ID NO:38, SEQ ID NO:39, and SEQ ID NO:40.

In other embodiments, the invention includes genetic expression methods comprising the use of an expression vector. In one method, a microalgal cell, such as a *Porphyridium* cell, is transformed with a dual expression vector under conditions wherein vector mediated gene expression occurs. The expression vector may comprise a resistance cassette comprising a gene encoding a protein that confers resistance to an antibiotic such as zeocin, operably linked to a promoter active in microalgae. The vector may also comprise a second expression cassette comprising a second protein to a promoter active in microalgae. The two cassettes are physically linked in the vector. The transformed cells may be optionally selected based upon the ability to grow in the presence of the antibiotic or other selectable marker under conditions wherein cells lacking the resistance cassette would not grow, such as in the dark. The resistance cassette, as well as the expression cassette, may be taken in whole or in part from another vector molecule.

In one non-limiting example, a method of expressing an exogenous gene in a cell of the genus *Porphyridium* is provided. The method may comprise operably linking a gene encoding a protein that confers resistance to the antibiotic zeocin to a promoter active in microalgae to form a resistance cassette; operably linking a gene encoding a second protein to a promoter active in microalgae to form a second expression cassette, wherein the resistance cassette and second expression cassette are physically connected to form a dual expression vector; transforming the cell with the dual expression vector; and selecting for the ability to survive in the presence of at least 2.5 ug/ml zeocin, preferably at least 3.0 ug/ml zeocin, and more preferably at least 3.5 ug/ml zeocin, more preferably at least 5.0 ug/ml zeocin.

In additional aspects, the expression of a protein that produces small molecules in microalgae is included and described. Some genes that can be expressed using the methods provided herein encode enzymes that produce nutraceutical small molecules such as lutein, zeaxanthin, and DHA. Preferably the genes encoding the proteins are synthetic and are created using preferred codons on the microalgae in which the gene is to be expressed. For example, enzyme capable of turning EPA into DHA are cloned into the microalgae *Porphyridium* sp. by recoding genes to adapt to *Porphyridium* sp. preferred codons. For examples of such enzymes see Nat Biotechnol. 2005 August; 23(8):1013-7. For examples of enzymes in the carotenoid pathway see SEQ ID NO:18 and SEQ ID NO:19 and Table 22. The advantage to expressing such genes is that the nutraceutical value of the cells increases without increasing the manufacturing cost of producing the cells.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

It should be apparent to one skilled in the art that various embodiments and modifications may be made to the invention disclosed in this application without departing from the scope and spirit of the invention. All publications mentioned herein are cited for the purpose of describing and disclosing reagents, methodologies and concepts that may be used in connection with the present invention. Nothing herein is to be construed as an admission that these references are prior art in relation to the inventions described herein.

U.S. Pat. No. 7,135,290 is hereby incorporated by reference in its entirety for all purposes. The following applications are also incorporated by reference in their entirety for all purposes: U.S. patent application Ser. No. 11/336,426, filed Jan. 19, 2006, entitled "Polysaccharide Compositions and Methods of Administering, Producing, and Formulating Polysaccharide Compositions"; U.S. patent application Ser. No. 11/337,103, filed Jan. 19, 2006, entitled "Methods and Compositions for Improving the Health and Appearance of Skin"; U.S. patent application Ser. No. 11/336,656, filed Jan. 19, 2006, entitled "Devices and Solutions for Prevention of Sexually Transmitted Diseases"; U.S. patent application Ser. No. 11/336,428, filed Jan. 19, 2006, entitled "Methods and Compositions for Cholesterol Reduction in Mammals"; U.S. patent application Ser. No. 11/337,171, filed Jan. 19, 2006, entitled "Methods and Compositions for Reducing Inflammation and Preventing Oxidative Damage"; U.S. patent application Ser. No. 11/336,431, filed Jan. 19, 2006, entitled "Methods and Compositions for Thickening, Stabilizing and Emulsifying Foods"; U.S. patent application Ser. No. 11/336,430, filed Jan. 19, 2006, entitled "Methods and Compositions for Joint Lubrication"; U.S. Patent Application No. 60/832,091, filed Jul. 20, 2006, entitled "Decolorized Microalgal Compositions for Skin Care Products"; U.S. Patent Application No. 60/838,452, filed Aug. 17, 2006, entitled "Polysaccharide Compositions and Methods of Administering, Producing, and Formulating Polysaccharide Compositions"; U.S. Patent Application No. 60/816,967, filed Jun. 28, 2006, entitled "Zeaxanthin Production Methods and Novel Compositions Containing Zeaxanthin"; U.S. Patent Application No. 60/872,072, filed Nov. 30, 2006, entitled "Polysaccharide Compositions and Methods of Administering, Producing, and Formulating Polysaccharide Compositions"; and PCT Patent Application No: PCT/US2007/001319, filed Jan. 19, 2007, entitled "Nutraceutical Compositions from Microalgae and Related Methods of Production and Administration".

VII. Examples

Example 1

Growth of *Porphyridium cruentum* and *Porphyridium* sp.

*Porphyridium* sp. (strain UTEX 637) and *Porphyridium cruentum* (strain UTEX 161) were inoculated into autoclaved 2 liter Erlenmeyer flasks containing an artificial seawater media:

| 1495 ASW medium recipe from the American Type Culture Collection (components are per 1 liter of media) | |
|---|---|
| NaCl | 27.0 g |
| $MgSO_4 \cdot 7H_2O$ | 6.6 g |
| $MgCl_2 \cdot 6H_2O$ | 5.6 g |
| $CaCl_2 \cdot 2H_2O$ | 1.5 g |
| $KNO_3$ | 1.0 g |
| $KH_2PO_4$ | 0.07 g |
| $NaHCO_3$ | 0.04 g |
| 1.0M Tris-HCl buffer, pH 7.6 | 20.0 ml |
| Trace Metal Solution (see below) | 1.0 ml |
| Chelated Iron Solution (see below) | 1.0 ml |
| Distilled water | bring to 1.0 L |
| Trace Metal Solution: | |
| $ZnCl_2$ | 4.0 mg |
| $H_3BO_3$ | 60.0 mg |
| $CoCl_2 \cdot 6H_2O$ | 1.5 mg |
| $CuCl2 \cdot 2H_2O$ | 4.0 mg |
| $MnCl_2 \cdot 4H_2O$ | 40.0 mg |
| $(NH_4)_6Mo_7O_{24} \cdot 4H_2O$ | 37.0 mg |
| Distilled water | 100.0 ml |
| Chelated Iron Solution: | |
| $FeCl_3 \cdot 4H_2O$ | 240.0 mg |
| 0.05M EDTA, pH 7.6 | 100.0 ml |

Media was autoclaved for at least 15 minutes at 121° C.

Inoculated cultures in 2 liter flasks were maintained at room temperature on stir plates. Stir bars were placed in the flasks before autoclaving. A mixture of 5% $CO_2$ and air was bubbled into the flasks. Gas was filter sterilized before entry. The flasks were under 24 hour illumination from above by standard fluorescent lights (approximately 150 uE/m$^{-1}$/s$^{-1}$). Cells were grown for approximately 12 days, at which point the cultures contained approximately of $4 \times 10^6$ cells/mL.

Example 2

Dense *Porphyridium* sp. and *Porphyridium cruentum* cultures were centrifuged at 4000 rd. The supernatant was subjected to tangential flow filtration in a Millipore Pellicon 2 device through a 1000 kD regenerated cellulose membrane (filter catalog number P2C01MC01). Approximately 4.1 liters of *Porphyridium cruentum* and 15 liters of *Porphyridium* sp. supernatants were concentrated to a volume of approximately 200 ml in separate experiments. The concentrated exopolysaccharide solutions were then diafiltered with 10 liters of 1 mM Tris (pH 7.5). The retentate was then flushed with 1 mM Tris (pH 7.5), and the total recovered polysaccharide was lyophilized to completion. Yield calculations were performed by the dimethylmethylene blue (DMMB) assay. The lyophilized polysaccharide was resuspended in deionized water and protein was measured by the bicinchoninic acid (BCA) method. Total dry product measured after lyophilization was 3.28 g for *Porphyridium* sp. and 2.0 g for *Porphyridium cruentum*. Total protein calculated as a percentage of total dry product was 12.6% for *Porphyridium* sp. and 15.0% for *Porphyridium cruentum*.

Example 3

Increasing Solvent-Available Polysaccharide

A measured mass (approximately 125 grams) of freshly harvested *Porphyridium* sp. cells, resuspended in a minimum amount of $dH_2O$ sufficient to allow the cells to flow as a liquid, was placed in a container. The cells were subjected to increasing amounts of sonication over time at a predetermined sonication level. Samples were drawn at predetermined time intervals, suspended in measured volume of $dH_2O$ and diluted appropriately to allow visual observation under a microscope and measurement of polysaccharide concentration of the cell suspension using the DMMB assay. A plot was made of the total amount of time for which the biomass was sonicated and the polysaccharide concentration of the biomass suspension. Two experiments were conducted with different time intervals and total time the sample was subjected to sonication. The first data set from sonication experiment 1 was obtained by subjecting the sample to sonication for a total time period of 60 minutes in 5 minute increments. The second data set from sonication experiment 2 was obtained by subjecting the sample to sonication for a total time period of 6 minutes in 1-minute increments. The data, observations and experimental details are described below. Standard curves were generated using TFF-purified, lyophilized, weighed, resuspended *Porphyridium* sp. exopolysaccharide.

General Parameters of Sonication Experiments 1 and 2

Cells were collected and volume of the culture was measured. The biomass was separated from the culture solution by centrifugation. The centrifuge used was a Forma Scientific Centra-GP8R refrigerated centrifuge. The parameters used for centrifugation were 4200 rpm, 8 minutes, rotor#218. Following centrifugation, the biomass was washed with $dH_2O$. The supernatant from the washings was discarded and the pelleted cell biomass was collected for the experiment.

A sample of 100 μL of the biomass suspension was collected at time point 0 (OTP) and suspended in 900 μL $dH_2O$. The suspension was further diluted ten-fold and used for visual observation and DMMB assay. The time point 0 sample represents the solvent-available polysaccharide concentration in the cell suspension before the cells were subjected to sonication. This was the baseline polysaccharide value for the experiments.

The following sonication parameters were set: power level=8, 20 seconds ON/20 seconds OFF (Misonix 3000 Sonicator with flat probe tip). The container with the biomass was placed in an ice bath to prevent overheating and the ice was replenished as necessary. The sample was prepared as follows for visual observation and DMMB assay: 100 μL of the biomass sample+900 μL dH$_2$O was labeled as dilution 1. 100 μL of (i) dilution 1+900 μL dH$_2$O for cell observation and DMMB assay.

Sonication Experiment 1

In the first experiment the sample was sonicated for a total time period of 60 minutes, in 5-minute increments (20 seconds ON/20 seconds OFF). The data is presented in Tables 4, 5 and 6. The plots of the absorbance results are presented in FIG. 4.

TABLE 4

Sonication record for experiment 1.

| Ser# | Time point (min) | Observations (TP = time point) |
|---|---|---|
| 1 | 0 | Healthy red cells |
| 2 | 5 | Red color disappeared, small greenish circular particles |
| 3 | 10 | Small particle, smaller than 5 minute TP |
| 4 | 15 | Small particle, smaller than 10 minute TP. Same observation as 10 minute time |
| 5 | 20 | Similar to 15 minute TP. Small particles; empty circular shells in the field of vision |
| 6 | 25 | Similar to 20 minute TP |
| 7 | 30 | Similar to 25 minute TP, particles less numerous |
| 8 | 35 | Similar to 30 minute TP |
| 9 | 40 | Similar to 35 minute TP |
| 10 | 45 | Similar to 40 minute TP |
| 11 | 50 | Very few shells, mostly fine particles |
| 12 | 55 | Similar to 50 minute TP. |
| 13 | 60 | Fine particles, hardly any shells |

TABLE 5

Standard curve record for sonication experiment 1.

| Absorbance (AU) | Concentration (μg) |
|---|---|
| 0 | Blank, 0 |
| 0.02 | 0.25 |
| 0.03 | 0.5 |
| 0.05 | 0.75 |
| 0.07 | 1.0 |
| 0.09 | 1.25 |

TABLE 6

Record of sample absorbance versus time points for sonication experiment 1.

| SAMPLE TIME POINT (MIN) | Solvent-Available Polysaccharide (μg) |
|---|---|
| 0 | 0.23 |
| 5 | 1.95 |
| 10 | 2.16 |
| 15 | 2.03 |
| 20 | 1.86 |
| 25 | 1.97 |
| 30 | 1.87 |
| 35 | 2.35 |
| 40 | 1.47 |
| 45 | 2.12 |
| 50 | 1.84 |
| 55 | 2.1 |
| 60 | 2.09 |

Figure 4:
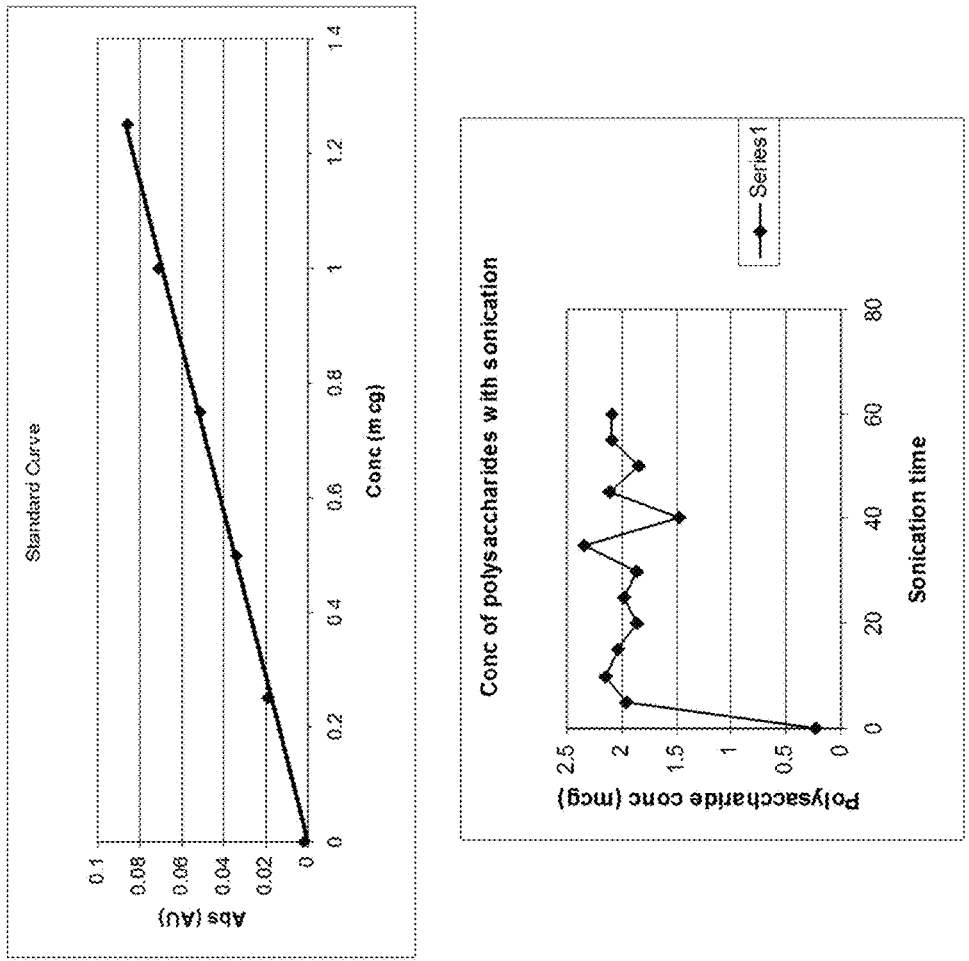
FIG. 4 shows levels of solvent-accessible polysaccharide in *Porphyridium* sp. homogenates subjected to various amounts of physical disruption from Sonication Experiment 1.

The plot of polysaccharide concentration versus sonication time points is displayed above and in FIG. 4. Solvent-available polysaccharide concentration of the biomass (cell) suspension reaches a maximum value after 5 minutes of sonication. Additional sonication in 5-minute increments did not result in increased solvent-available polysaccharide concentration.

Homogenization by sonication of the biomass resulted in an approximately 10-fold increase in solvent-available polysaccharide concentration of the biomass suspension, indicating that homogenization significantly enhances the amount of polysaccharide available to the solvent. These results demonstrate that physically disrupted compositions of *Porphyridium* for oral or other administration provide novel and unexpected levels or polysaccharide bioavailability compared to compositions of intact cells. Visual observation of the samples also indicates rupture of the cell wall and thus release of insoluble cell wall-bound polysaccharides from the cells into the solution that is measured as the increased polysaccharide concentration in the biomass suspension.

Sonication Experiment 2

In the second experiment the sample was sonicated for a total time period of 6 minutes in 1-minute increments. The data is presented in Tables 7, 8 and 9. The plots of the absorbance results are presented in FIG. 5.

TABLE 7

Sonication record for experiment 2.

| Ser# | Time point (min) | Observations |
|---|---|---|
| 1 | 0 | Healthy red-brown cells appear circular |
| 2 | 1 | Circular particles scattered in the field of vision with few healthy cells. Red color has mostly disappeared from cell bodies. |
| 3 | 2 | Observation similar to time point 2 minute. |
| 4 | 3 | Very few healthy cells present. Red color has disappeared and the concentration of particles closer in size to whole cells has decreased dramatically. |
| 5 | 4 | Whole cells are completely absent. The particles are smaller and fewer in number. |
| 6 | 5 | Observation similar to time point 5 minute. |
| 7 | 6 | Whole cells are completely absent. Large particles are completely absent. |

TABLE 8

Standard curve record for sonication experiment 2.

| Absorbance (AU) | Concentration (μg) |
|---|---|
| −0.001 | Blank, 0 |
| 0.017 | 0.25 |
| 0.031 | 0.5 |
| 0.049 | 0.75 |
| 0.0645 | 1.0 |
| 0.079 | 1.25 |

TABLE 9

Record of sample absorbance versus time points for sonication experiment 2.

| SAMPLE TIME POINT (MIN) | Solvent-Available Polysaccharide (μg) |
|---|---|
| 0 | 0.063 |
| 1 | 0.6 |

TABLE 9-continued

Record of sample absorbance versus time points for sonication experiment 2.

| SAMPLE TIME POINT (MIN) | Solvent-Available Polysaccharide (μg) |
|---|---|
| 2 | 1.04 |
| 3 | 1.41 |
| 4 | 1.59 |
| 5 | 1.74 |
| 6 | 1.78 |

Figure 5:
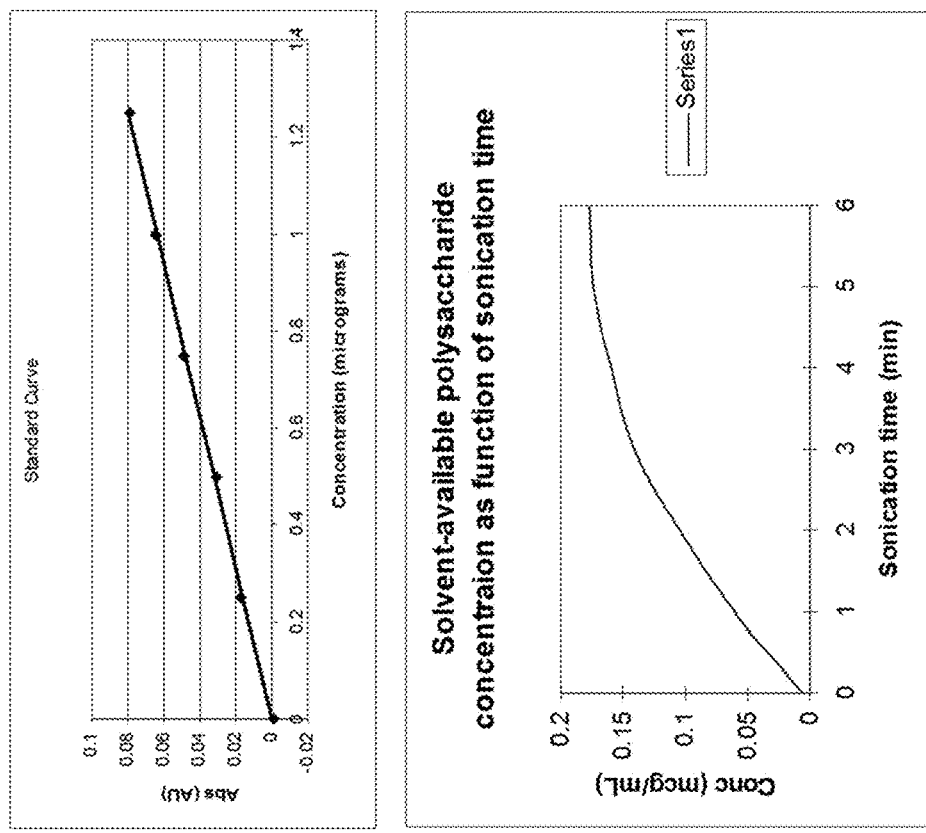
FIG. 5 shows levels of solvent-accessible polysaccharide in *Porphyridium* sp. homogenates subjected to various amounts of physical disruption from Sonication Experiment 2.

The value of the solvent-available polysaccharide increases gradually up to the 5 minute time point as shown in Table 9 and FIG. 5.

Example 4

Alcohol Precipitation

*Porphyridium* sp. culture was centrifuged at 4000 rcf and supernatant was collected. The supernatant was divided into six 30 ml aliquots. Three aliquots were autoclaved for 15 min at 121° C. After cooling to room temperature, one aliquot was mixed with methanol (58.3% vol/vol), one was mixed with ethanol (47.5% vol/vol) and one was mixed with isopropanol (50% vol/vol). The same concentrations of these alcohols were added to the three supernatant aliquots that were not autoclaved. Polysaccharide precipitates from all six samples were collected immediately by centrifugation at 4000 rcf at 20° C. for 10 min and pellets were washed in 20% of their respective alcohols. Pellets were then dried by lyophilization and resuspended in 15 ml deionized water by placement in a 60° C. water bath. Polysaccharide pellets from non-autoclaved samples were partially soluble or insoluble. Polysaccharide pellets from autoclaved ethanol and methanol precipitation were partially soluble. The polysaccharide pellet obtained from isopropanol precipitation of the autoclaved supernatant was completely soluble in water.

Example 5

Monosaccharide Analysis

Approximately 10 milligrams of purified polysaccharide from *Porphyridium* sp. and *Porphyridium cruentum* (described in Example 3) were subjected to monosaccharide analysis.

Monosaccharide analysis was performed by combined gas chromatography/mass spectrometry (GC/MS) of the per-O-trimethylsilyl (TMS) derivatives of the monosaccharide methyl glycosides produced from the sample by acidic methanolysis.

Methyl glycosides prepared from 500 μg of the dry sample provided by the client by methanolysis in 1 M HCl in methanol at 80° C. (18-22 hours), followed by re-N-acetylation with pyridine and acetic anhydride in methanol (for detection of amino sugars). The samples were then per-O-trimethylsilylated by treatment with Tri-Sil (Pierce) at 80° C. (30 mins) These procedures were carried out as previously described in Merkle and Poppe (1994) Methods Enzymol. 230: 1-15; York, et al. (1985) Methods Enzymol. 118:3-40. GC/MS analysis of the TMS methyl glycosides was performed on an HP 5890 GC interfaced to a 5970 MSD, using a Supelco DB-1 fused silica capillary column (30 m 0.25 mm ID).

Monosaccharide compositions were determined as follows:

TABLE 10

*Porphyridium* sp. monosaccharide analysis.

| Glycosyl residue | Mass (μg) | Mole % |
|---|---|---|
| Arabinose (Ara) | n.d. | n.d. |
| Rhamnose (Rha) | 2.7 | 1.6 |
| Fucose (Fuc) | n.d. | n.d. |
| Xylose (Xyl) | 70.2 | 44.2 |
| Glucuronic acid (GlcA) | n.d. | n.d. |
| Galacturonic acid (GalA) | n.d. | n.d. |
| Mannose (Man) | 3.5 | 1.8 |
| Galactose (Gal) | 65.4 | 34.2 |
| Glucose (Glc) | 34.7 | 18.2 |
| N-acetyl galactosamine (GalNAc) | n.d. | n.d. |
| N-acetyl glucosamine (GlcNAc) | trace | trace |

$\Sigma = 176.5$

TABLE 11

*Porphyridium cruentum* monosaccharide analysis.

| Glycosyl residue | Mass (μg) | Mole % |
|---|---|---|
| Arabinose (Ara) | n.d. | n.d. |
| Rhamnose (Rha) | n.d. | n.d. |
| Fucose (Fuc) | n.d. | n.d. |
| Xylose (Xyl) | 148.8 | 53.2 |
| Glucuronic Acid (GlcA) | 14.8 | 4.1 |
| Mannose (Man) | n.d. | n.d. |
| Galactose (Gal) | 88.3 | 26.3 |
| Glucose (Glc) | 55.0 | 16.4 |
| N-acetyl glucosamine (GlcNAc) | trace | trace |
| N-acetyl neuraminic acid (NANA) | n.d. | n.d. |

$\Sigma = 292.1$

Mole % values are expressed as mole percent of total carbohydrate in the sample. n.d.=none detected.

Example 6

Protein Measurement

*Porphyridium* sp. was grown as described. 2 liters of centrifuged *Porphyridium* sp. culture supernatant were autoclaved at 121° C. for 20 minutes and then treated with 50% isopropanol to precipitate polysaccharides. Prior to autoclaving the 2 liters of supernatant contained 90.38 mg polysaccharide. The pellet was washed with 20% isopropanol and dried by lyophilization. The dried material was resuspended in deionized water. The resuspended polysaccharide solution was dialyzed to completion against deionized water in a Spectra/Por cellulose ester dialysis membrane (25,000 MWCO). 4.24% of the solid content in the solution was proteins as measured by the BCA assay.

Example 7

Generation of Protein-Free Polysaccharide

Figure 6:
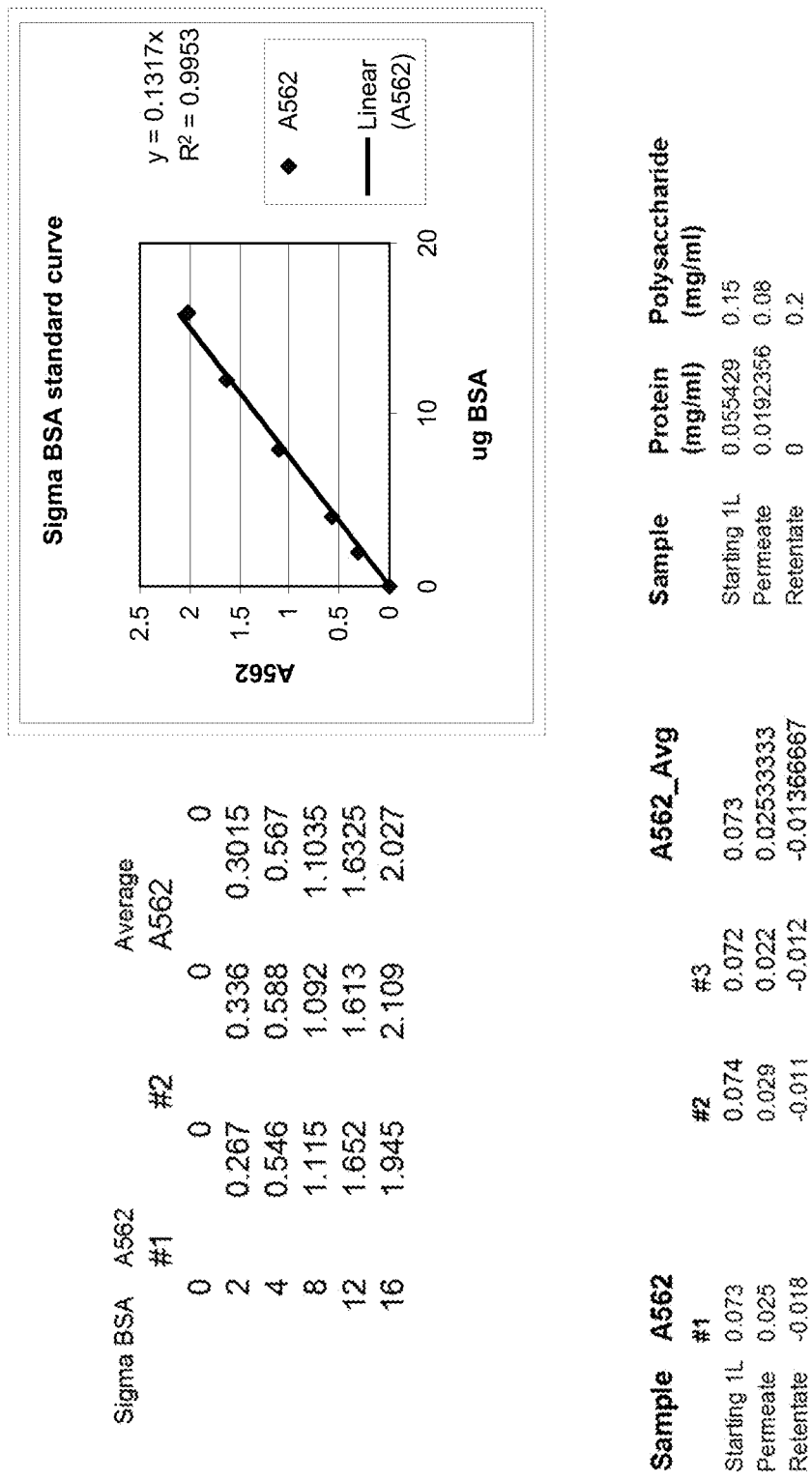
FIG. 6 shows protein concentration measurements of autoclaved, protease-treated, and diafiltered exopolysaccharide.

*Porphyridium* sp. was grown as described. 1 liters of centrifuged *Porphyridium* sp. culture supernatant was autoclaved at 121° C. for 15 minutes and then treated with 10% protease (Sigma catalog number P-5147; protease treatment amount relative to protein content of the supernatant as determined by BCA assay). The protease reaction proceeded for 4 days at 37° C. The solution was then subjected to tangential flow filtration in a Millipore Pellicon® cassette system using a 0.1 micrometer regenerated cellulose membrane. The retentate was diafiltered to completion with deionized water. No protein was detected in the diafiltered retentate by the BCA assay. See FIG. 6.

Optionally, the retentate can be autoclaved to achieve sterility if the filtration system is not sterile. Optionally the sterile retentate can be mixed with pharmaceutically acceptable carrier(s) and filled in vials for injection.

Optionally, the protein free polysaccharide can be fragmented by, for example, sonication to reduce viscosity for parenteral injection as, for example, an antiviral compound. Preferably the sterile polysaccharide is not fragmented when prepared for injection as a joint lubricant.

Example 8

Heterotrophic Growth of *Porphyridium*

Cultures of *Porphyridium* sp. (UTEX 637) and *Porphyridium cruentum* (strain UTEX 161) were grown, to a density of $4 \times 10^6$ cells/mL, as described in Example 1. For each strain, about $2 \times 10^6$ cells/mL cells per well (~500 uL) were transferred to 11 wells of a 24 well microtiter plate. These wells contained ATCC 1495 media supplemented with varying concentration of glycerol as follows: 0%, 0.1%, 0.25%, 0.5%, 0.75%, 1%, 2%, 3%, 5%, 7% and 10%. Duplicate microtiter plates were shaken (a) under continuous illumination of approximately 2400 lux as measured by a VWR Traceable light meter (cat #21800-014), and (b) in the absence of light. After 5 days, the effect of increasing concentrations of glycerol on the growth rate of these two species of *Porphyridium* in the light was monitored using a hemocytometer. The results are given in FIG. 2 and indicate that in light, 0.25 to 0.75 percent glycerol supports the highest growth rate, with an apparent optimum concentration of 0.5%.

Cells in the dark were observed after about 3 weeks of growth. The results are given in FIG. 3 and indicate that in complete darkness, 5.0 to 7.0% glycerol supports the highest growth rate, with an apparent optimum concentration of 7.0%.

Example 9

Cosmeceutical Compositions

*Porphyridium* sp. (UTEX 637) was grown to a density of approximately $4 \times 10^6$ cells/mL, as described in Example 1. Approximately 50 grams of wet pelleted, and washed cells were completely homogenized using approximately 20 minutes of sonication as described. The homogenized biomass was mixed with carriers including, water, butylene glycol, mineral oil, petrolatum, glycerin, cetyl alcohol, propylene glycol dicaprylate/dicaprate, PEG-40 stearate, C11-13 isoparaffin, glyceryl stearate, tri (PPG-3 myristyl ether) citrate, emulsifying wax, dimethicone, DMDM hydantoin, methylparaben, carbomer 940, ethylparaben, propylparaben, titanium dioxide, disodium EDTA, sodium hydroxide, butylparaben, and xanthan gum. The mixture was then further homogenized to form a composition suitable for topical administration. The composition was applied to human skin daily for a period of one week.

Example 10

Antibiotic Sensitivity

Approximately 4500 cells (300 ul of $1.5 \times 10^5$ cells per ml) of *Porphyridium* sp. and *Porphyridium cruentum* cultures in liquid ATCC 1495 ASW media were plated onto ATCC 1495 ASW agar plates (1.5% agar). The plates contained varying amounts of zeocin, sulfometuron, hygromycin and spectinomycin. The plates were put under constant artificial fluorescent light of approximately 480 lux. After 14 days, plates were checked for growth.

Results were as follows:

Zeocin

| Conc. (ug/ml) | Growth |
| --- | --- |
| 0.0 | ++++ |
| 2.5 | + |
| 5.0 | − |
| 7.0 | − |

Hygromycin

| Conc.(ug/ml) | Growth |
| --- | --- |
| 0.0 | + + + + |
| 5.0 | + + + + |
| 10.0 | + + + + |
| 50.0 | + + + + |

Specinomycin

| Conc.(ug/ml) | Growth |
| --- | --- |
| 0.0 | + + + + |
| 100.0 | + + + + |
| 250.0 | + + + + |
| 750.0 | + + + + |

Figure 8:
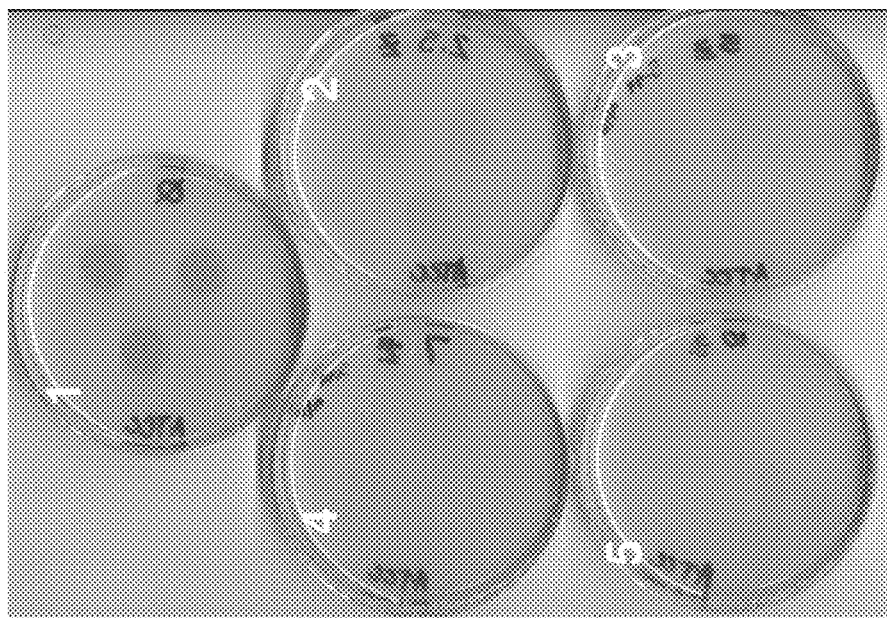
FIG. 8 shows *Porphyridium* sp. cultured on agar plates containing various concentrations of zeocin.
Figure 9:
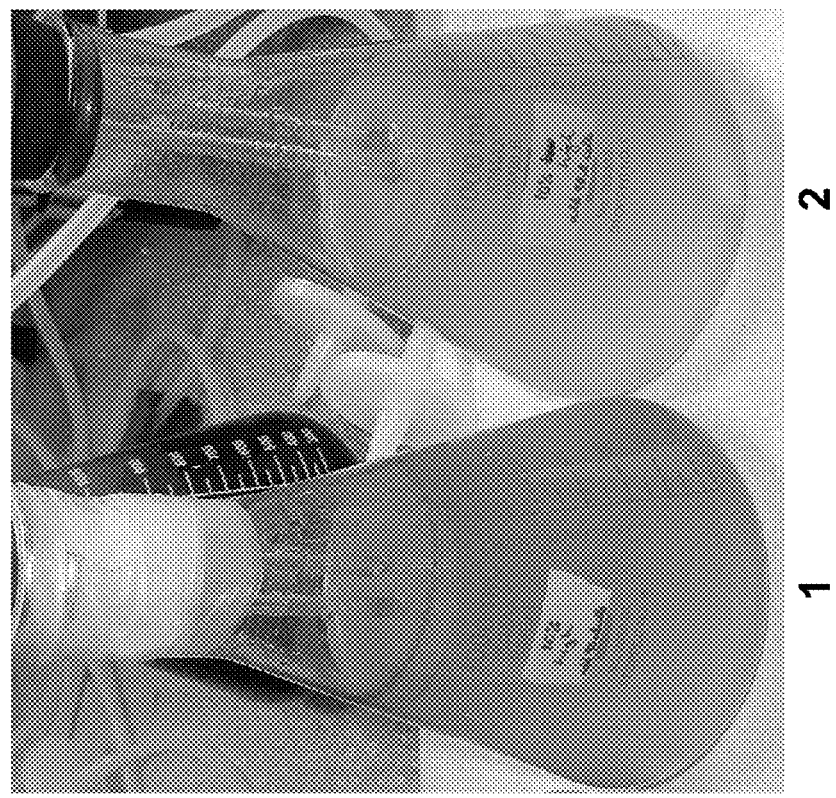
FIG. 9 shows cultures of nitrogen-replete (flask 1) and nitrogen-starved (flask 2) *Porphyridium cruentum*. The culture media in flask 1 is as described in Example 1. The culture media in flask 2 is as described in Example 1 except that the culture media contained no Tris and 0.125 g/L potassium nitrate, pH 7.6. Flasks 1 and 2 were inoculated with identical amounts of deep red colored cells taken from a culture grown in ATCC1495 ASW media. The cells in flask 2 are substantially free of red coloration.

After the initial results above were obtained, a titration of zeocin was performed to more accurately determine growth levels of *Porphyridium* in the presence of zeocin. *Porphyridium* sp. cells were plated as described above. Results are shown in FIG. 8.

Example 11

Nutritional Manipulation to Generate Novel Polysaccharides

Cells expressing an endogenous monosaccharide transporter, containing a monosaccharide transporter and capable of importing glucose, are cultured in ATCC 1495 media in the light in the presence of 1.0% glucose for approximately 12 days. Exopolysaccharide is purified as described in Example 2. Monosaccharide analysis is performed as described in Example 5.

Cells expressing an endogenous monosaccharide transporter, containing a monosaccharide transporter and capable of importing xylose, are cultured in ATCC 1495 media in the light in the presence of 1.0% xylose for approximately 12 days. Exopolysaccharide is purified as described in Example 2. Monosaccharide analysis is performed as described in Example 5.

Cells expressing an endogenous monosaccharide transporter, containing a monosaccharide transporter and capable of importing galactose, are cultured in ATCC 1495 media in the light in the presence of 1.0% galactose for approximately 12 days. Exopolysaccharide is purified as described in Example 2. Monosaccharide analysis is performed as described in Example 5.

Cells expressing an endogenous monosaccharide transporter, containing a monosaccharide transporter and capable of importing glucuronic acid, are cultured in ATCC 1495 media in the light in the presence of 1.0% glucuronic acid for approximately 12 days. Exopolysaccharide is purified as described in Example 2. Monosaccharide analysis is performed as described in Example 5.

Cells expressing an endogenous monosaccharide transporter, containing a monosaccharide transporter and capable of importing glucose, are cultured in ATCC 1495 media in the dark in the presence of 1.0% glucose for approximately 12 days. Exopolysaccharide is purified as described in Example 2. Monosaccharide analysis is performed as described in Example 5.

Cells expressing an endogenous monosaccharide transporter, containing a monosaccharide transporter and capable of importing xylose, are cultured in ATCC 1495 media in the dark in the presence of 1.0% xylose for approximately 12 days. Exopolysaccharide is purified as described in Example 2. Monosaccharide analysis is performed as described in Example 5.

Cells expressing an endogenous monosaccharide transporter, containing a monosaccharide transporter and capable of importing galactose, are cultured in ATCC 1495 media in the dark in the presence of 1.0% galactose for approximately 12 days. Exopolysaccharide is purified as described in Example 2. Monosaccharide analysis is performed as described in Example 5.

Cells expressing an endogenous monosaccharide transporter, containing a monosaccharide transporter and capable of importing glucuronic acid, are cultured in ATCC 1495 media in the dark in the presence of 1.0% glucuronic acid for approximately 12 days. Exopolysaccharide is purified as described in Example 2. Monosaccharide analysis is performed as described in Example 5.

Example 12

Increasing Solvent-Available Polysaccharide 128 mg of intact lyophilized *Porphyridium* sp. cells were ground with a mortar/pestle. The sample placed in the mortar pestle was ground for 5 minutes. 9.0 mg of the sample of the ground cells was placed in a micro centrifuge tube and suspended in 1000 µL of dH2O. The sample was vortexed to suspend the cells.

A second sample of 9.0 mg of intact, lyophilized *Porphyridium* sp. cells was placed in a micro centrifuge tube and suspended in 1000 µL of dH2O. The sample was vortexed to suspend the cells.

The suspensions of both cells were diluted 1:10 and polysaccharide concentration of the diluted samples was measured by DMMB assay. Upon grinding, the suspension of ground cells resulted in an approximately 10-fold increase in the solvent-accessible polysaccharide as measured by DMMB assay over the same quantity of intact cells.

TABLE 12

Results of dimethylmethylene blue (DMMB) assay.

| Sample Description | Read 1 (AU) | Read 2 (AU) | Avg. Abs (AU) | Conc. (µg/mL) |
| --- | --- | --- | --- | --- |
| Blank | 0 | −0.004 | −0.002 | 0 |
| 50 ng/µL Std., 10 µL; 0.5 µg | 0.03 | 0.028 | 0.029 | NA |
| 100 ng/µL Std., 10 µL; 1.0 µg | 0.056 | 0.055 | 0.0555 | NA |
| Whole cell suspension | 0.009 | 0.004 | 0.0065 | 0.0102 |
| Ground cell suspension | 0.091 | 0.072 | 0.0815 | 0.128 |

Reduction in the particle size of the lyophilized biomass by homogenization in a mortar/pestle results in better suspension and increase in the solvent-available polysaccharide concentration of the cell suspension.

Example 13

Decolorization of Biomass

A *Porphyridium* culture (UTEX 637) was grown as described in Example 1 except that the culture media contained no Tris and 0.125 g/L potassium nitrate, pH 7.6. The low nitrate culture was grown under approximately 130 µE m$^{-2}$ s$^{-1}$ until the color changed from red to yellow-brown, which took approximately 3 weeks. After waiting for a further three days, the yellow-brown cells were harvested by centrifugation, hereinafter referred to as "decolorized biomass" or "decolorized cell pellet". A deep red cell pellet generated from cells grown in normal ATCC 1495 ASW media was also generated as described in Example 1. The cell pellets were washed with 0.5 L of distilled water, shell frozen in a dry ice acetone bath and lyophilized.

Determination of Color

The decolorized cell pellet had a yellow-brown appearance (as opposed to cells grown in full ATCC 1495 ASW media which have a deep red appearance). The lyophilized decolorized cells and lyophilized red cells grown in full ATCC 1495 ASW media were treated identically. 100 mg of lyophilized cell-pellets were resuspended in 4 ml of 1M pH 7.6 Tris buffer by vigorous vortexing. The suspensions were sonicated on ice using a Misonix 3000 sonicator equipped with a micro-tip probe set at a power level of 6.5 for 90 seconds, pulsing for 30 seconds on 20 seconds off (3 cycles). The cell debris was pelleted by centrifugation in a micro-centrifuge at 14,000 rpm for 5 minutes and the supernatant decanted. This procedure was repeated twice more with 1M pH 7.6 Tris buffer, and finally with 6M urea. No red color was observed in cell pellets or supernatant from the decolorized biomass after the second extraction or from the cells grown in full ATCC 1495 ASW media after the fourth extraction. The respective supernatants were combined and brought to a final volume of 75 ml with distilled water.

Absorbance spectra of the supernatants from the decolorized pellet and the pellet from cells grown in full ATCC 1495 ASW media were recorded between 510 and 600 nM with a Pharmacia Ultraspec III spectrophotometer and a 1 cm path length cuvette.

The extinction coefficient for phycoerythrin is 5.26 ml·mg/cm at 545 nm (see for example Gantt and Lipschultz, Phycobilisomes of *Porphyridium cruentum*; Biochemistry, 13, 2960, 1974). The concentration phycoerythrin was calculated from the optical density at 545 nm (after subtracting the background due to scatter measured at 600 nm) as 46 mg/g dry-weight in cells grown in ATCC 1495 ASW media and 4.7 mg/g in the decolorized cells.

Example 14

Homogenization of Biomass

After *Porphyridium* biomass grown as described in Example 1 was recovered by centrifugation and washed in deionizer water, nitrogen was bubbled through the paste for 30 minutes to displace dissolved oxygen and minimize subsequent oxidation. The paste was then passed through a model 110Y Microfluidics Microfluidizer® at 22,000 PSI with cooling, and the process repeated until cell breakage was at least 50% as determined by microscopic examination. Nitrogen was once again bubbled through the paste, which was then lyophilized after shell freezing in dry ice ethanol. The dried cell mass was then ground to a fine powder with a Braun® kitchen homogenizer. This process can be performed with decolorized biomass generated as described herein. Optionally, preservative(s) and/or carrier(s) suitable for topical administration are added to the material, as well as fragrances and other materials used in the art of skin care product formulation.

Example 15

Hyaluronidase Inhibition

Biotinylated hyaluronic acid (bHA) was covalently attached to the wells of a 96-well plate. Samples containing hyaluronidase and various test materials were then added to the wells. The hyaluronidase degrades the bound hyaluronic acid, resulting in a decrease in the amount of biotin covalently linked to the well plate. At the end of the incubation period the reaction was stopped and the well plate was washed to remove the hyaluronidase. The remaining bHA was detected using an avidin bound peroxidase enzyme. When an appropriate substrate is added, the peroxidase enzyme generated a color signal in proportion to the amount of bHA. The color signal was measured spectrophotometrically, and was inversely proportional to the amount of hyaluronidase activity in the sample. Thus, materials that inhibited hyaluronidase resulted in a greater color signal, since more of the bHA remained intact. Also see Frost, G. I., Stern, R. A Microtiter-Based Assay for Hyaluronidase Activity Not Requiring Specialized Reagents. Analytical Biochemistry 251, 263-269: 1997.

Preparation of Test Material Extracts

Test Material A was supplied as a powder type material. For this study, 100 mg of this material was combined with either 5 ml of ethanol or 5 ml of ultrapure water in 15 ml centrifuge tubes. After combining, the mixtures were vortexed, then placed onto a rocking platform for approximately 30 minutes at room temperature, and then centrifuged at 1,000 RPM for 5 minutes. The supernatants were then used at the final concentrations listed in the results section. Test Material B was supplied as a thick, viscous solutions (3%).

Anti-Hyaluronidase Assay: Immobilization of bHA onto 96-Well Plates

A solution of sulfo-NHS (0.184 mg/ml) and bHA (0.2 mg/ml) was prepared in distilled water. 50 µl of this solution was then added to the wells of a 96-well Covalink-NH plate. A solution of EDC (0.123 mg/ml) was then prepared in distilled water and 50 µl of this solution was added to each well (which resulted in a final concentration of 10 µg/well bHA and 6.15 µg/well of EDC). The well plate was then incubated overnight at 4±2° C. or for 2 hours at room temperature. After the incubation the plate was washed three times with PBS containing 2 M NaCl and 50 mM MgSO$_4$.

Anti-Hyaluronidase Assay

Prior to the assay, the well plate was equilibrated with assay buffer (0.1 M formate [pH 4.5], 0.1 M NaCl, 1% Triton X-100, 5 mM saccharolactone). The test materials were prepared in assay buffer at 2× their final concentration (heparin was used as a positive control, 1 mg/ml final concentration). After removing the assay buffer from the well plate used for equilibration, 50 µl of each of the prepared test materials was added to three wells on the well plate, followed by the addition of 50 µl of assay buffer containing hyaluronidase will be added to each well (0.1 mg/ml). Three additional wells were treated with 100 µl of assay buffer alone (without test materials and without hyaluronidase) and served as an index of zero hyaluronidase activity. After the addition of the test materials and enzyme, the plate was incubated for 30 minutes at room temperature. At the end of the incubation period, 200 µl of 6 M guanidine-HCl was added to each well to terminate the reaction. The plate was then washed three times with PBS containing 2 M NaCl, 50 mM MgSO$_4$ and 0.05% Tween 20.

During the 30 minute incubation, an avidin/biotin-peroxidase complex was prepared in 10.5 ml of PBS containing 0.1% Tween 20 using an ABC kit. This mixture was incubated for at least 30 minutes prior to use. After the plate was washed, 100 µl of the avidin/biotin-peroxidase solution was added to each well and the plate was incubated for another 30 minutes at room temperature. The plate was washed three times with PBS containing 2 M NaCl, 50 mM MgSO$_4$ and 0.05% Tween 20. After the final wash, 100 µl of substrate solution (one 10 mg tablet of OPD in 10 ml of 0.1 M citrate-PO$_4$ buffer supplemented with 7.5 µl of 30% H$_2$O$_2$) was added to each well. The plate was incubated in the dark for 10-20 minutes and then read at 460 nm using a plate reader. The substrate solution was also added to three wells that were not treated with test materials or the avidin/biotin-peroxidase solution and were used as a blank for the absorbance measurements.

TABLE 13

Results of anti-hyaluronidase assay.

| Treatment | Percent Inhibition |
| --- | --- |
| 10% A Water Extract | 86 |
| 5% MATERIAL A Water Extract | 67 |
| 1% MATERIAL A Water Extract | 29 |
| 1.5% MATERIAL B | 93 |
| 0.5% MATERIAL B | 81 |
| 0.1% MATERIAL B | 70 |
| 0.1% Heparin | 74 |
| Negative Control | 0 |

Test Material Identification: MATERIAL A: *Porphyridium* sp. biomass homogenized (Quadro F10); cells grown as described in Example 1
Physical Description: Red/Purple powder
Concentrations Tested: 10%, 5%, 1% (Extracted in either ethanol or water)
Test Material Identification: 3% MATERIAL B: Exopolysaccahride from *Porphyridium* sp. purified as described in Example 2
Physical Description: Light tan, viscous liquid
Concentrations Tested: 1.5%, 1%, 0.5%, 0.1%

Example 16

Sulfated Derivative Polysaccharides

*Porphyridium cruentum* and *Porphyridium* sp. were grown in artificial seawater media essentially as described in Example 1 except that the amount of MgSO$_4$ was varied. *Porphyridium* sp. cells were grown in 17 mM MgSO$_4$. *Porphyridium cruentum* was grown in 120 mM, 600 mM, 750 mM, 1M, and 2M MgSO$_4$. Cell division occurred at all concentrations. Polysaccharide was purified essentially as described in Example 2 from the 120 and 600 mM cultures, to the point where all soluble protein and small molecules were removed. Sulfur content was analyzed according to US EPA SW846, Method 6010B, Inductively Coupled Plasma-Atomic Emission Spectrometry. The polysaccharide purified from the 17, 120 and 600 mM cultures contained 3.57, 4.23 and 5.57% sulfur, respectively. It was observed that polysaccharides with higher percent sulfate by weight exhibited stronger gelling properties than polysaccharides with a lower percent sulfate by weight when the two preparations were generated at the same polysaccharide concentration. For example, at a 1% concentration the polysaccharide containing 5.57% sulfur held its shape and moved as a gelatinous unit whereas the polysaccharide with a 3.57 percent sulfur by weight at 1% flowed as a viscous liquid. The increased gelling properties provide added benefits for skin care compositions as they can form gels in products at lower concentrations.

Example 17

Monosaccharide Analysis

*Porphyridium cruentum* was cultured as described in Example 1 except that (a) the amount of $KNO_3$ per liter of media was approximately 150 g/L; (b) the media contained no Tris; and (c) the media contained approximately 0.14 g/L $KH_2PO_4$. The cells lost all detectable red coloration after approximately three weeks of growth, and turned to a yellow shade. Exopolysaccharide was purified essentially as described in Example 2. Monosaccharide analysis was performed essentially as described in Example 5.

Monosaccharide composition of the exopolysaccharide was as follows:

| Glycosyl residue | Mass (μg) | Mole % |
| --- | --- | --- |
| Arabinose (Ara) | n.d. | n.d. |
| Rhamnose (Rha) | n.d. | n.d. |
| Fucose (Fuc) | n.d. | n.d. |
| Xylose (Xyl) | 137.8 | 41.5 |
| Glucuronic Acid (GlcA) | 18.7 | 4.3 |
| Mannose (Man) | trace | trace |
| Galactose (Gal) | 133.2 | 33.4 |
| Glucose (Glc) | 83.2 | 20.8 |
| Unknown Sugar | n.d. | n.d. |
| N-acetyl glucosamine (GlcNAc) | n.d. | n.d. |
| N-acetyl neuraminic acid (NANA) | n.d. | n.d. |
| $\Sigma$ = 372.9 | | |

The exopolysaccharide contained significantly different and more advantageous monosaccharide composition from those grown under standard conditions shown in Example 5. The composition is a preferred composition for skin care products. For example, the ratio of glucose to xylose is higher in the polysaccharide from bleached cells.

Example 18

Polysaccharide Bead Production

Two solutions of polysaccharide from *Porphyridium cruentum* (0.5% w/v) in water, prepared as described in Example 2 except flushed with distilled water rather than 1 mM Tris, were dried under air flow at 60° C. until converted to a solid translucent film. One sample was isolated from *Porphyridium cruentum* grown in ATCC 1495 media, while the other was from *Porphyridium cruentum* grown in ATCC 1495 media with the exception that the $KNO_3$ was approximately 0.15 g/L (labeled as "1495 low N"). The resulting films were then heated under vacuum (≥25 in Hg) at approximately 150° C. overnight to form dried polysaccharide. The dried polysaccharide was then ground in a pestle and mortar. A third polysaccharide sample (0.5% w/v) in water, isolated from *Porphyridium cruentum* grown in ATCC 1495 media, prepared as described in Example 2 except flushed with distilled water rather than 1 mM Tris, was lyophilized and not ground.

100 mg of dried, ground polysaccharide from each sample (FIG. 16(a)) was resuspended in 2.5 ml of water. 100 mg of lyophilized polysaccharide was also resuspended in 2.5 ml of water (FIG. 16(b)). The suspensions were centrifuged at 4,400 rpm in a Forma Scientific Centra-GP8R refrigerated centrifuge. The parameters used for centrifugation were 4200 rpm, rotor#218, 20 minute spin. As shown in FIG. 16(c), there was a swollen, insoluble gel layer and a clear supernatant in the samples that were dried at 150° C. but not in the samples that were lyophilized or dried at 105° C. The polysaccharide dried at 150° C. did not go into solution, but rather stayed insoluble despite significant swelling in size.

The percentage insoluble polysaccharide in the 150° C. dried samples was measured by separating the insoluble and supernatant fractions, lyophilizing the separated fractions, and weighing the dried residual polysaccharide from each fraction. The percentage insoluble polysaccharide was then calculated as a percentage of the total polysaccharide from both fractions. While the polysaccharide from the samples that were originally dried by lyophilization and drying at 105° C. were 100% soluble, the low N and ATCC 1495 polysaccharide samples dried at 150° C. were 75% and 86% insoluble, respectively. Independent experiments demonstrated that material dried at 125° C. was completely soluble.

Example 19

Polysaccharide Bead Properties

Insoluble polysaccharide preparations, prepared essentially as described in Example 18, were tested for (a) the ability to swell in size over time and (b) the ability to bind soluble polysaccharide and remove it from solution.

Figure 17A:
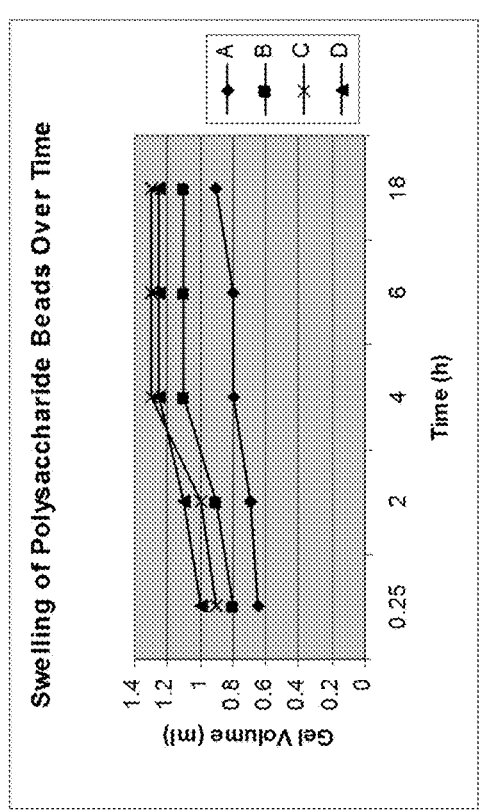
FIGS. 17(a) and (b)

Samples were resuspended in distilled water as described in Example 18. Samples were centrifuged as described in Example 18 at various time points. The volume of the insoluble gel layer was measured, followed by resuspension of the material and incubation at room temperature until the next centrifugation point. Results are shown in FIG. 17. The results demonstrate that the dried polysaccharide beads continue to swell in volume for at least 4 hours and as long as 18 hours after initial exposure to water.

Figure 17B:
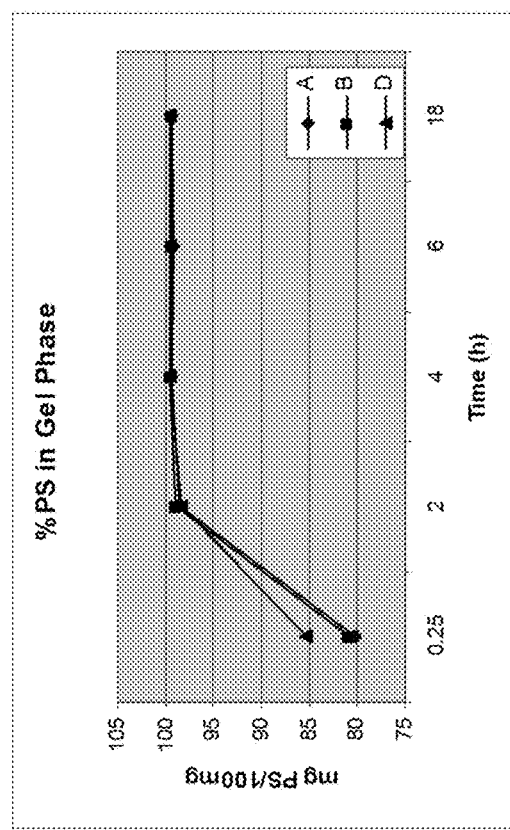
FIG. 17(b) shows percentages of polysaccharide in the insoluble gel phase over time.

The concentration of polysaccharide in solution in the supernatant was measured at each time point using the DMMB assay as described in Example 3. Results are shown in FIG. 17(b). The results demonstrate that the polysaccharide beads bind soluble polysaccharide and remove it from solution for at least 4 hours after initial exposure to water. The swelling and binding of soluble polysaccharide is a useful property for topical application to human skin and is stimulated by transepidermal water loss.

Example 20

Transformation of *Porphyridium* and Genotyping

The *Porphyridum* glycoprotein promoter, SEQ ID NO:21, was cloned in operable linkage with a zeocin resistance ble cDNA with small amounts of flanking sequence (SEQ ID NO:37), with the far 5' region of the glycoprotein promoter directly adjacent to the pBluescript SacI site and the far 3' region of the CMV 3'UTR (SEQ ID NO:32) adjacent to the pBlusecript KpnI site. The CMV 3'UTR was also in operable linkage with the ble cDNA. The plasmid was linearized by KpnI, which does cut in the promoter, ble cDNA, or 3'UTR, prior to transformation.

The biolistic particle delivery system PDS 1000/He (Bio-Rad, USA) was used for transformation. *Porphyridium* sp. culture was grown to logarithmic phase (~$2 \times 10^6$ cells/mL)

in liquid ATCC 1495 media under continuous light (approximately 75 umol/photons/m²). Cells from this culture were harvested at 4,000 rpm at room temperature. The cell pellet was washed twice with sterile distilled water. Cells were resuspended in fresh ATCC 1495 media to the same cell density i.e. ~2×10⁶ cells/mL and incubated in the dark for 16 hours. The dark adapted cells were then harvested at 4000 rpm at room temperature, resuspended in fresh ATCC 1495 media to a density of ~2×10⁸ cells/mL. Approximately 1×10⁸ cells were transferred to each ATCC 1495 agarose plate. Filter sterilized DNA from the plasmids was coated onto 550 nm gold particles (catalog number S04e, Seashell Technology, USA) according to the manufacturer's protocol. For each of the particle bombardments, 1 ug of plasmid DNA was used. The negative controls were bombarded in identical fashion with gold particles coated with a plasmid containing the *Porphyridum* glycoprotein promoter, SEQ ID NO:21, and the CMV 3'UTR, (SEQ ID NO:32), with no zeocin resistance gene. Each of the particle bombardments were performed using 1350 psi rupture disks, at bombardment distance of 9 cm, and under 28 in. Hg vacuum. The bombarded cells were scraped off the plates, and transferred to 100 ml of fresh ATCC 1495 media, and shaken under continuous light (approximately 75 umol/m²) for 3 days. Following recovery, the cells were harvested at 4,000 rpm at room temperature, and plated onto ATCC 1495 plates supplemented with 30 ug/mL Zeocin (Invitrogen, Carlsbad, Calif., USA) at a cell density of 1×10⁷ cells/plate. These plates were incubated under light (approximately 25 umol/m²) for 4-5 weeks. Zeocin resistant colonies growing on these plates were scored as transformants and transferred onto fresh ATCC 1495 plates supplemented with 30 ug/mL Zeocin (Invitrogen, Carlsbad, Calif., USA) for growth and analysis.

Zeocin resistant colonies appeared after 2-3 weeks. Genotyping with primers specific to the zeocin resistance gene was performed on genomic DNA isolated from zeocin resistant colonies. Results from genotyping of one strain (referred to herein and labeled as "transformant #2" in FIG. 14) indicated that the zeocin resistance gene was present. A band of the correct size was amplified. Results are shown in FIG. 14 and discussed in more detail in Example 20.

Example 21

Transformation of *Porphyridium*, Genotyping, and Southern Blot Analysis

The zeocin resistance plasmid described in Example 20 and a second plasmid that was identical with the exception that it contained a cDNA for a human GLUT1 glucose transporter (SEQ ID NO:25) instead of the ble cDNA were combined in a co-transformation experiment carried out essentially as described in Example 20 except that both the zeocin resistance and GLUT1 plasmids were both adhered to the gold beads. A zeocin resistant colony (referred to herein as transformant #1) was selected for further analysis. Genomic DNA was extracted from wild type *Porphyridium* sp. and transformant #1.

Genotyping was performed on genomic DNA extracted from wild type, transformant #1, and transformant #2 DNA with plasmid DNA used as a template positive control and water in place of DNA as a template negative control. A segment of the *Porphyridium* glycoprotein (GLP) gene promoter was used as a target positive control. The following primer sets were used for the genotyping PCR: Ble-FWD (SEQ ID NO:26) and Ble-REV (SEQ ID NO:27), GLP-FWD (SEQ ID NO:28) and (SEQ ID NO:29), GLUT1-FWD (SEQ ID NO:30) and GLUT1-REV (SEQ ID NO:31). The PCR profile used was as follows: 94° C. denaturation for 5 min; 35 cycles of 94° C. for 30 sec, 51° C. or 60° C. (51° C. for glycoprotein gene & GLUT1 and 60° C. for ble) for 30 sec, 72° C. for 2 min; 72° C. for 5 min Results are shown in FIG. 14. FIG. 14(*a*) demonstrates that the ble gene was present in both transformants, as the expected 300 bp product was generated. FIG. 14(*b*) demonstrates that the genomic DNA extraction and amplification was working, as the expected 948 bp glycoprotein promoter fragment was generated. FIG. 14(*c*) demonstrates that the GLUT1 gene was present transformant #1, as the expected 325 bp product was generated. DNA ladder was from BioNexus, Inc., All Purpose Hi-Lo DNA Marker, Catalog No: BN2050.

Specific bands can be amplified from residual plasmid DNA adhered to the outside of cells on transformation plates. Additionally, plasmids that have not been linearized can be maintained as episomes for a period of time before being degraded and can serve as template during PCR despite not having been integrated into a chromosome of a host organism. In both cases, microalgal strains may genotype positive despite the absence of stable chromosomal integration of the vector. Antibiotic resistant strains are known to arise due to mutagenesis caused by chromosomal damage from biolistic particles, electroporation conditions, and random genetic variation that is known to occur in microbial organisms. Southern blot analysis was performed to conclusively confirm the integration of the GLUT1 construct into the genome of transformant #1.

Figure 15:
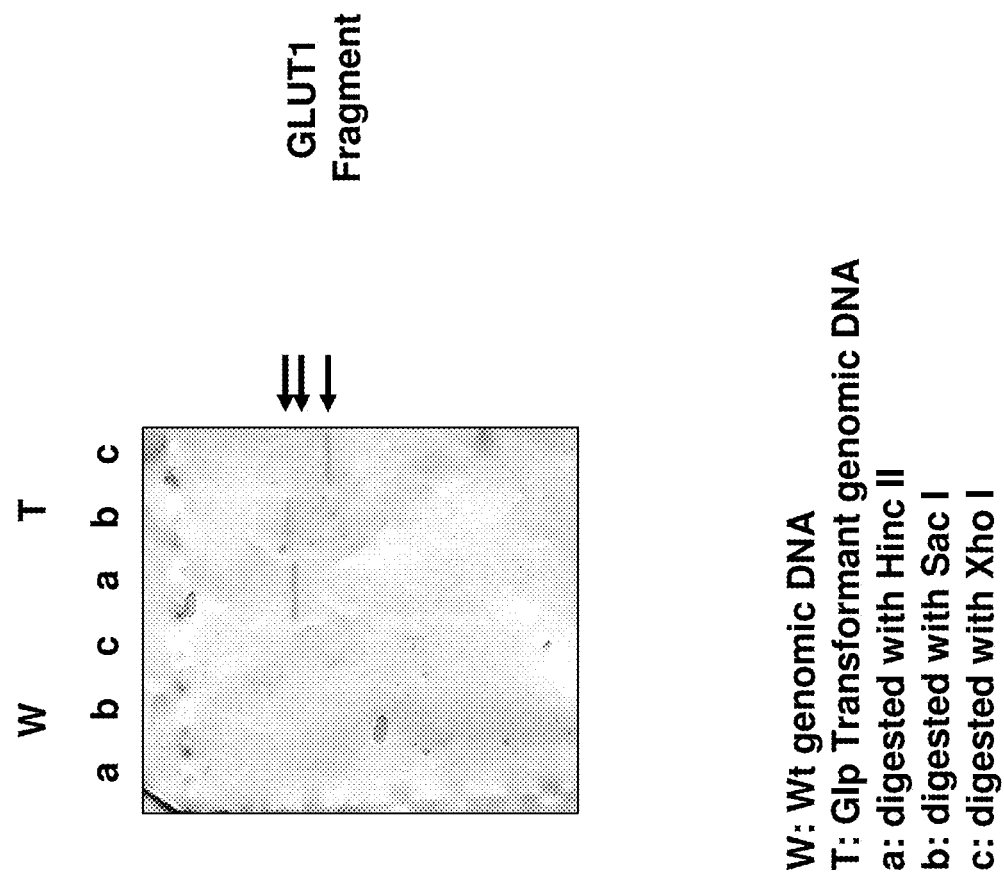
FIG. 15 shows a Southern blot indicating chromosomal integration of an exogenous gene encoding a recoded human GLUT1 transporter.

Southern blot analysis was performed on transformant #1. 20 μg genomic DNA from wild type and transformant #1 were individually digested with Hinc II, Sac I, Xho I and separated on a 1% agarose gel. DNA was transferred onto Nylon membrane (Hybond N+, Amersham Biosciences). A 1495 bp fragment containing the entire coding region of the GLUT1 gene was used as a probe. DIG labeled probes were generated for each probe fragment using the DIG High Prime DNA labeling and detection Kit according to the manufacturers instructions (Roche). The hybridizing bands were detected using the colorimetric detection reagents provided by the manufacturer. FIG. 15 demonstrates that the GLUT1 plasmid was stably integrated into the genome of transformant #1 while no detectable signal arose from wild type genomic DNA. As would be expected for a plasmid integrating into a chromosome of an organism, the specific band was in a different position for each different restriction enzyme used to digest the genomic DNA. This data conclusively demonstrates a species of the genus *Porphyridium* containing an exogenous gene encoding a carbohydrate transporter integrated into a chromosome of the organism. In this embodiment the carbohydrate transporter gene is in operable linkage with a promoter endogenous to a species of the genus *Porphyridium*. In some other embodiments embodiment the carbohydrate transporter gene is in operable linkage with a promoter endogenous to a Rhodophyte.

Example 22

Production of Materials from Microalgae

Materials from *Porphyridium* were generated to assess their utility as components of skin care compositions. Materials BM, LS PS, and HS PS were generated and tested as referenced in this and following Examples. BM is *Porphyridium* sp. biomass, grown essentially as described in Example 1, which was washed once with distilled water, run twice through a microfluidizer (Microfluidics Inc, Newton, Mass., U.S.A.), and lyophilized as follows: using a Microfluidics Microfluidizer® (model #110Y) pressurized with nitrogen, washed biomass material was pumped through an 87 um orifice at 22,000 psi twice. The product was kept on ice at all times. Nitrogen gas was bubbled through the final product while mixing for 10 min Snap freeze for storage or shell freeze and lyophilize. The BM material was then treated as described in each example.

LS PS was polysaccharide from *Porphyridium* sp. HS PS was polysaccharide from *Porphyridium cruentum*. Both were purified essentially as described in Example 2. The cells grown for preparation of LS PS and HS PS were grown essentially as described in Example 1 except that the sulfate in the media was 17 mM for the LS PS and 600 mM for the HS PS (also described in Example 16).

Example 23

UVB Protective Properties of Materials from Microalgae

TT dimer-UV exposure assay: The testing system used for this assay was the MatTek EpiDerm®, a skin model that consists of normal human-derived epidermal keratinocytes cultured to form a multilayered, highly differentiated model of the human epidermis. For this study, the tissues were treated topically overnight with either test materials, 1 mM Trolox (positive control), or left untreated (negative control). On the following day, the tissues were exposed to UVB (300 $mJ/cm^2$). Following the exposures the DNA was extracted from the EpiDerm tissues and assayed for thymine dimer content. Samples of the DNA were immobilized on a solid membrane support and incubated with an antibody that recognizes thymidine dimers in double stranded DNA. The primary antibody was detected using a secondary antibody conjugated to an alkaline phosphatase enzyme followed by the addition of a substrate that the alkaline phosphatase enzyme uses to generate a chemiluminescent signal. The light generated by this reaction was captured using film with the intensity of the light signal being proportional to the amount of the thymine dimers present in the sample.

Test material BM was *Porphyridium* sp. biomass that had been homogenized with a Microfluidizer® twice and then lyophilized. For this study, 100 mg of this material was combined with 5 ml of ultrapure water in 15 ml centrifuge tubes. After combining, the mixture was vortexed, then placed onto a rocking platform for approximately 30 minutes at room temperature, and then centrifuged at 1,000 RPM for 5 minutes. The supernatant was then used at a final concentration of 10% and 5%. The two remaining test materials, LS PS and HS PS were supplied as thick, viscous solutions (3 g/100 mL). LS PS53 was tested at the final concentrations of 1.5%, 0.5%, and 0.1%, while PS133 was tested at the final concentration of 0.1%.

Prior to use, the MatTek EpiDerm® tissues were removed from the agarose-shipping tray and placed into a 6-well plate containing 0.9 ml of culture medium (MatTek EPI-100 culture media) according to the manufacturer. The tissues were allowed to incubate for at least 1 hour at 37±2° C. and 5±1% $CO_2$. After this initial incubation, the culture media was replaced with fresh, pre-warmed EPI-100 media and 100 µl of test material, 1 mM Trolox or PBS (negative control) was applied. The tissues were then incubated overnight at 37±2° C. and 5±1% $CO_2$. On the following day, the tissues were exposed to 300 $mJ/cm^2$ of UVB energy at 300 nm. After the UVB exposure the tissues were collected and DNA was immediately extracted.

DNA extraction was performed using the Qiagen, DNEasy Kit. Single tissues were placed into 1.5 ml centrifuge tubes containing 180 µl of Lysis Buffer One. After mincing the tissues with a pair of fine tipped scissors, 20 µl of Proteinase K was added to the tube and the tube was incubated overnight at 55±2° C. with occasional mixing/vortexing. After the Proteinase K digestion, 200 µl of Lysis Buffer Two was added to the tube and the tube was incubated at 70±2° C. for approximately 10 minutes. Next, the DNA was precipitated by the addition of 200 µl of 100% ethanol. The precipitated DNA was washed to remove cellular debris by applying the mixture to a DNEasy Spin Column and centrifuging the sample in a 2 ml collection tube at 8,000 RPM for 1 minute. The flow through and collection tube was discarded, and 500 µl of Wash Buffer One was added to the spin column and the column was placed into a new collection tube and centrifuged at 8,000 RPM for 1 minute. The flow through and collection tube was again discarded, and 500 µl of Wash Buffer Two was added to the spin column and the column was placed into a new collection tube and centrifuged at 14,000 RPM for 3 minutes. The spin column was then placed into a new 1.5 ml centrifuge tube and 110 µl of Elution Buffer was added to the column. The column was incubated for 1 minute at room temperature and then centrifuged at 8,000 RPM for 1 minute.

Extracted DNA was quantified via a fluorometric assay. A 10 µl aliquot of the DNA sample was mixed with 1.0 ml of Assay Buffer (2 M NaCl, 50 mM sodium phosphate, pH 7.4) and 100 µl of this diluted sample was transferred to a well in a black 96-well plate. A series of DNA standards (0, 100, 200, 300, 400 and 500 ng) was also transferred to wells in a 96-well plate (in duplicate). Finally, 100 µl of dilute Hoechst 33258 dye (0.006 mg/ml in Assay Buffer) was added to each well and the fluorescence intensity of each well was determined using an excitation wavelength of 355 nm and an emission wavelength of 485 nm.

Aliquots of DNA (400 ng in 2×SSC [20× stock SSC: 3 M NaCl, 0.3 M sodium citrate, pH 7.0]) was loaded onto a membrane via microfiltration blotting. After loading, the membrane was washed once in 2×SSC and then baked for 30 minutes at 80° C. to crosslink the DNA to the membrane. The membrane was then incubated for 1 hour in blocking solution (TBS [20 mM Tris, pH 7.5, 500 mM NaCl] supplemented with 5% non-fat milk protein, 0.2% polyvinylpyrolidone, and 0.2% ficol), and then briefly washed twice in TBS-T (TBS with 0.1% non-fat milk protein and 0.1% Tween 20). The membrane was then incubated overnight (4° C.) with an antibody that recognizes thymine dimers diluted in TBS-T. On the following day, the membrane was washed 3 times with TBS-T (20 minutes per wash) and then incubated with an AP-conjugated secondary antibody for 1-2 hours at room temperature. After this incubation period the membrane was washed as described above.

Near the end of the final wash the chemiluminescence reagent was prepared. At the end of the last wash, all of the TBS-T was drained from the membrane and the chemiluminescent substrate was applied to the membrane and it was allowed to sit for approximately 1 minute. The membrane was then wrapped in Saran foil and taped inside of a film cassette. In a dark room a piece of film was inserted into the cassette and exposed for various amounts of time, starting with 10 seconds and increasing or decreasing in appropriate increments, until obtaining the necessary exposures. After exposure, the films were analyzed via densitometry. To quantify the amount of DNA present, a standard curve was generated using known concentrations of DNA and their respective fluorescence intensity (measured in RFUs or relative fluorescence units). A regression analysis was performed to establish the line that best fits these data points. The RFUs for each unknown sample were used to estimate the amount DNA. Mean densitometric values, expressed in optical density units, were determined for each treatment.

Figures 11A, 11B:
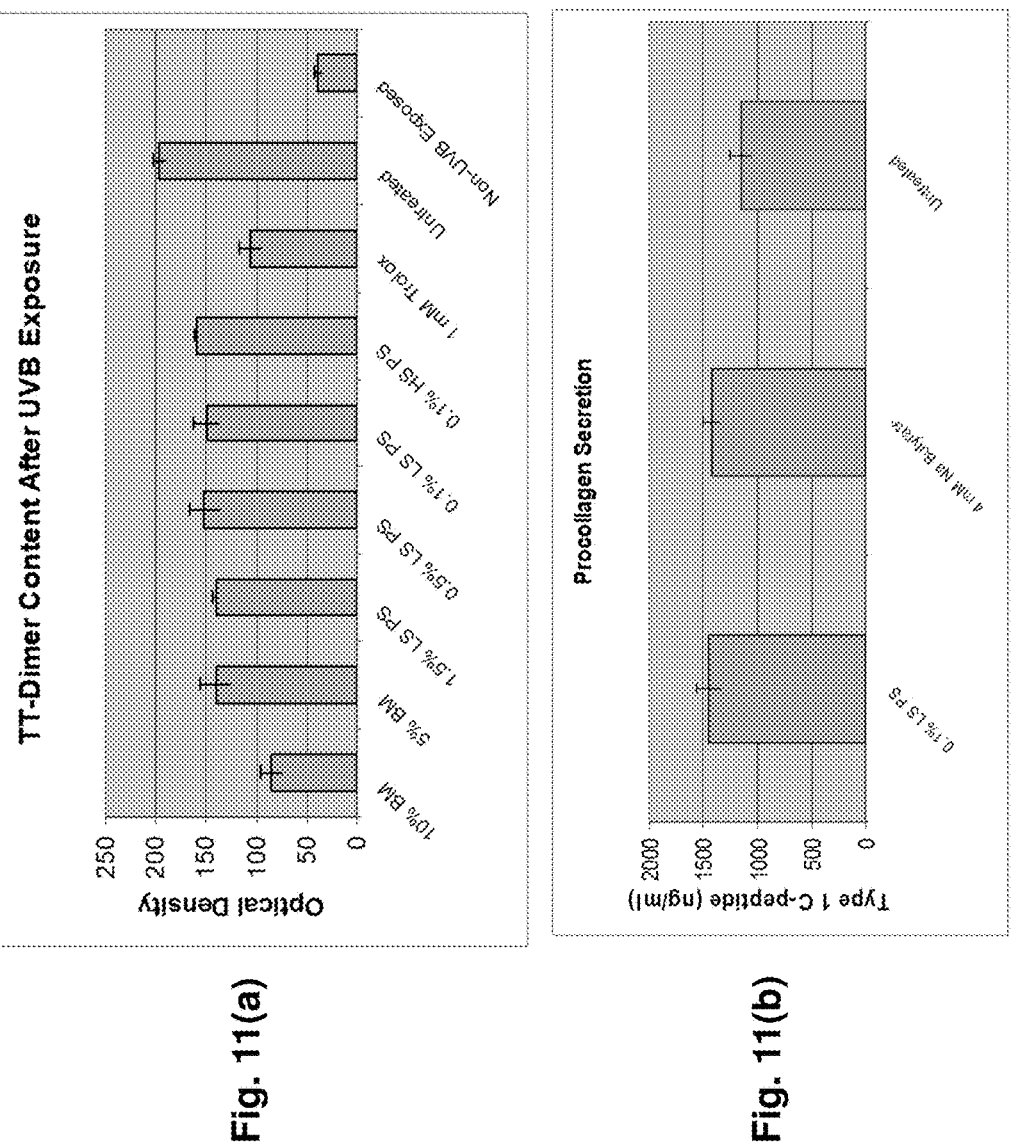
FIGS. 11(a) and (b)
FIG. 11(b) shows secretion of procollagen by human fibroblasts in the presence and absence of microalgae-derived materials.

The results for the thymidine dimer assay are presented in Table 14 and FIG. 11(a). The values are expressed as optical density units. The values are presented as mean values±standard deviation.

TABLE 14

Thymidine dimer assay.

| Treatment | Optical Density |
|---|---|
| 10% BM | 85 ± 11 |
| 5% BM | 140 ± 15 |
| 1.5% LS PS | 140 ± 3 |
| 0.5% LS PS | 152 ± 16 |
| 0.1% LS PS | 150 ± 13 |
| 0.1% HS PS | 160 ± 2 |
| 1 mM Trolox | 107 ± 1 |
| Untreated | 196 ± 6 |
| Non-UVB Exposed | 39 ± 4 |

The results of this study indicate that all three of the test materials significantly reduced the amount of TT dimer formation.

Example 24

Procollagen Synthesis Stimulating Properties of Materials from Microalgae

A fibroblast cell culture model was used to assess the ability of the polysaccharide from *Porphyridium* to exert an effect on procollagen synthesis. Fibroblasts are the main source of the extracelluar matrix peptides, including the structural protein collagen. Procollagen is a large peptide synthesized by fibroblasts in the dermal layer of the skin and is the precursor for collagen. As the peptide is processed to form a mature collagen protein, the propeptide portion is cleaved off (type I C-peptide). Both the mature collagen protein and the type I C-peptide fragment are then released into the extracellular environment. As collagen is synthesized the type I C-peptide fragment accumulates into the tissue culture medium. Since there is a 1:1 stoichiometric ratio between the two parts of the procollagen peptide, assaying for type I C-peptide reflects the amount of collagen synthesized. Type 1 C-peptide was assayed via an ELISA based method. Test material LS PS was supplied as a thick, viscous solution (3 g/100 mL). This material was used at a 0.1% final concentration. The anti-collagen antibody used was Procollagen Type I: N-18 antibody, catalog number sc-8785, Santa Cruz Biotechnology. The secondary antibody used was anti-goat conjugated with alkaline phosphatase catalog number sc-2355, Santa Cruz Biotechnology.

Fibroblasts were seeded into the individual wells of a 12 well plate in 1.0 ml of Fibroblast Growth Media (FGM: DMEM supplemented with 2% FBS, 5 ng/ml human recombinant growth factor, 5 ug/ml insulin, 50 ug/ml gentamicin, and 0.5 ug/ml Amphotericin-B) and incubated overnight at 37±2° C. and 5±1% $CO_2$. On the following day the media was removed via aspiration to eliminate any non-adherent cells and replaced with 1.0 ml of fresh FGM. The cells were grown until confluent with a media change every 48 to 72 hours. Upon reaching confluency the cells were treated for 24 hours with DMEM supplemented with 1.5% FBS to wash out any effects from the growth factors included in the normal culture media. After this 24-hour wash out period the cells were treated with 0.1% LS PS dissolved in FGM with 1.5% FBS. 4 mM sodium butyrate was used as a positive control. Untreated cells (negative controls) received FGM with 1.5% FBS. The cells were incubated for 48 hours and at the end of the incubation period cell culture medium was collected and either stored frozen (−75° C.) or assayed immediately. Materials were tested in triplicate.

A series of type I C-peptide standards was prepared ranging from 0 ng/ml to 640 ng/ml. Next, an ELISA microplate was prepared by removing any unneeded strips from the plate frame followed by the addition of 100 µl of peroxidase-labeled anti procollagen type I-C peptide antibody to each well used in the assay. Twenty (20) µl of either sample (collected tissue culture media) or standard was then added to appropriate wells and the microplate was covered and allowed to incubate for 3±0.25 hours at 37° C. After the incubation the wells were aspirated and washed three times with 400 µl of wash buffer. After the last wash was removed 100 µl of peroxidase substrate solution (hydrogen peroxide+ tetramethylbenzidine as a chromagen) was added to each well and the plate was incubated for 15±5 minutes at room temperature. After the incubation 100 µl of stop solution (1 N sulfuric acid) was added to each well and the plate was read using a microplate reader at 450 nm.

To quantify the amount of procollagen present, a standard curve was generated using known concentrations of procollagen. A regression analysis was be performed to establish the line that best fit the data points. Absorbance values for the test and positive control samples was used to determine the amount of procollagen present. The values are presented in mean ng/ml±the standard deviation of the mean. 0.1% LS PS increased procollagen synthesis compared to untreated cells, as seen below in Table 15 and in FIG. 11(b).

TABLE 15

Procollagen assay.

| Treatment | Type I C-Peptide ng/ml |
|---|---|
| 0.1% LS PS | 1448 ± 113 |
| 4 mM Na Butyrate | 1425 ± 81 |
| Untreated | 1151 ± 96 |

Example 25

Elastin Synthesis Stimulating Properties of Materials from Microalgae

A fibroblast cell culture model was used to assess elastin synthesis. Elastin is the main component of a network of elastic fibers that give tissues their ability to recoil after a transient stretch. This protein is released by fibroblasts (soluble elastin) into the extracellular space where it is then cross-linked to other elastin proteins to form an extensive network of fibers and sheets (insoluble elastin). Soluble elastin can be readily measured from cell culture medium via a competitive ELISA based method.

Test material BM was supplied as a powder type material. 100 mg of BM was combined with 5 ml of ultrapure water in 15 ml centrifuge tubes. After combining, the mixtures were vortexed, then placed onto a rocking platform for approximately 30 minutes at room temperature, and then centrifuged at 1,000 RPM for 5 minutes. The supernatant for each mixture was then used at final concentrations indicated in FIG. 12(a). LS PS and HS PS was supplied as a thick, viscous solution (3 g/100 mL). This material was used at final concentrations indicated in FIG. 12(a).

Fibroblasts were seeded into the individual wells of a 12 well plate in 1.0 ml of Fibroblast Growth Media (FGM) and incubated overnight at 37±2° C. and 5±1% $CO_2$. On the following day the media was removed via aspiration to eliminate any non-adherent cells and replaced with 1.0 ml of fresh FGM. The cells were grown until confluent, with a media change every 48 to 72 hours. Upon reaching confluency the cells were treated for 24 hours with DMEM supplemented with 1.5% FBS to wash out any effects from the growth factors included in the normal culture media. After this 24-hour wash out period the cells were treated with the test materials at the specified concentrations dissolved in FGM with 1.5% FBS. 4 mM sodium butyrate was used as a positive control for elastin synthesis. Untreated cells (negative controls) received FGM with 1.5% FBS. The cells were incubated for 48 hours and at the end of the incubation period cell culture medium was collected and either stored frozen (−75° C.) or assayed immediately. Materials were tested in triplicate.

Soluble α-elastin was dissolved in 0.1 M sodium carbonate (pH 9.0) at a concentration of 1.25 µg/ml. 150 µl of this solution was then applied to the wells of a 96-well maxisorp Nunc plate and the plate was incubated overnight at 4° C. On the following day the wells were saturated with PBS containing 0.25% BSA and 0.05% Tween 20. The plate was then incubated with this blocking solution for 1 hour at 37° C. and then washed two times with PBS containing 0.05% Tween 20.

A set of α-elastin standards was generated ranging from 0 to 100 ng/ml. 180 µl of either standard or sample was then transferred to a 650 µl microcentrifuge tube. The anti-elastin antibody was the C-21 antibody, catalog number sc-17581, from Santa Cruz Biotechnology. The secondary antibody used was anti-goat conjugated with alkaline phosphatase catalog number sc-2355, Santa Cruz Biotechnology. An anti-elastin antibody solution was prepared (the antibody was diluted 1:100 in PBS containing 0.25% BSA and 0.05% Tween 20) and 20 µl of the solution was added to the tube. The tubes were then incubated overnight at 4±2° C. On the following day, 150 µl was transferred from each tube to the 96-well elastin ELISA plate, and the plate was incubated for 1 hour at room temperature. The plate was then washed 3 times with PBS containing 0.05% Tween 20. After washing, 200 µl of a solution containing a peroxidase linked secondary antibody diluted in PBS containing 0.25% BSA and 0.05% Tween 20 was added, and the plate was incubated for 1 hour at room temperature. After washing the plate three times as described above, 200 µl of a substrate solution was added and the plate was incubated for 10 to 30 minutes in the dark at room temperature. After this final incubation the plate was read at 460 nm using a plate reader.

To quantify the amount of elastin present, a standard curve was generated using known concentrations of elastin. A regression analysis was performed to establish the line that best fit these data points. Absorbance values for the test and control samples was used to determine the amount of elastin present in each sample. Both the 0.5% and 0.1% concentrations of LS PS and HS PS induced an increase in elastin synthesis.

Example 26

Antiinflammatory Properties of Materials from Microalgae

Microalgal polysaccharide materials were tested for their ability to influence the migration of polymorphonucelar (PMN) leukocytes in response to chemotractant substances. Leukocyte migration is essential for leukocyte accumulation at sites of inflammation. During the inflammatory response, leukocytes migrate towards the source of a chemotractant substance in a process called chemotaxis. In vitro methods to study chemotaxis often use a membrane based approach, where a chemoattractant is placed on one side of a membrane and PMN leukocytes are placed on the other. Chemotaxis is then measured by quantifying the number of leukocytes which then migrate through the filter towards the chemotractant substance.

For this study, human PMN leukocytes were isolated via density centrifugation from freshly drawn blood. The PMN cells were loaded with a Calcein AM, a fluorescent dye. While the PMN cells were being labeled, the bottom chamber of a chemotaxis chamber was filled with PBS containing FMLP, a chemotractant substance. A membrane filter was placed over the bottom wells, after which a small aliquot of fluorescently labeled PMN cells was placed on top, along with the LS PS and HS PS test materials and positive control materials. The chemotaxis chamber was be incubated and at the end of the incubation period the fluorescence of the bottom wells was read and used as an index of PMN migration. Test material LS PS and HS PS, were supplied as thick, viscous solutions (3 g/100 mL). These materials were used at a final concentration of 1.5%, 0.5% and 0.1%.

Heparinized whole blood (20-30 ml) was collected from a healthy human donor, layered over a density gradient (Histopaque 1077 and Histopaque 1119) and centrifuged at 400 g for 30 min. The PMN rich fraction was removed, washed twice in with phosphate buffered saline (PBS) and then resuspended in 5.0 ml RPMI-1640 without phenol red supplemented with 10% heat-treated fetal calf serum (RPMI-FCS). Calcein AM (5 µg/ml final) was added to the cell suspension and then the cells were incubated for 30 min at 37° C. After the incubation, the PMN cells were washed twice with PBS, counted and resuspended in RPMI-FCS at $1-5 \times 10^6$ cells/ml.

A disposable 96-well chemotaxis chamber was used to measure PMN migration (chemotaxis chambers manufactured by Neuroprobe Inc., Gaithersburg, Md., catalog number 101-5). To set up the 96-well chamber, the wells in the microplate (bottom chamber) were filled with 29 µl of FMLP (0.1 µM) diluted in PBS with 0.1% serum albumin Negative control wells were prepared with PBS and albumin (no FMLP added). Amphotericin B (2 µg/ml) was used as a positive control (inhibits PMN migration). In addition, 3 wells were filled with 12.5 µl of fluorescently labeled PMN cells and 12.5 µl of PBS with 0.1% albumin. These latter wells were used as an index to represent 100% migration by the PMN cells.

Test materials were prepared in RPMI-FCS at 2× their desired final concentration. RPMI-FCS without test materials was used as another negative control. Aliquots of the test materials were combined with an equal volume of the fluorescently labeled PMN cells. A chemotaxis membrane was then placed over the bottom wells of the chemotaxis chamber and anchored into place. 25 µl of the PMN/test material combination was then spotted onto the membrane above each of the bottom wells (materials were tested in triplicate) and the well plate was incubated for 1 hour at 37±2° C. and 5% $CO_2$. At the end of the incubation, the top of the chemotaxis membrane was wiped clean with a tissue to remove any non-migrating cells and the bottom wells of the chemotaxis chamber were read using a fluorescent plate reader (485 nm excitation, 530 nm emission).

The mean fluorescence of the three wells filled directly with fluorescent PMN cells was determined and used to represent 100% migration. The mean fluorescence of the test material treated PMN cells were then determined (Test Material Migration). The fluorescent values were corrected for non-chemotaxis migration by subtracting the mean fluorescent measurements for the wells where FMLP was not present as a chemotractant. Percent PMN migration was then calculated using the following equation: ((Test Material Migration (mean RFU))/(100% Migration (mean RFU)))× 100

The results for the PMN migration assay are presented in Table 16 and FIG. 12(b). The values are expressed as mean percent of maximal (100%) migrating cells±standard deviation. The LS PS and HS PS samples reduced PMN migration at all concentrations tested.

TABLE 16

PMN migration.

| Treatment | Percent of Maximal Migration |
|---|---|
| 1.5% LS PS | 7.3 ± 1.0 |
| 0.5% LS PS | 7.7 ± 0.7 |
| 0.1% LS PS | 11.1 ± 0.6 |
| 1.5% HS PS | 6.0 ± 0.8 |
| 0.5% HS PS | 9.0 ± 0.4 |
| 0.1% HS PS | 10.6 ± 1.3 |
| 2 ug/ml Amphotericin B | 9.4 ± 0.6 |
| Untreated | 13.5 ± 0.9 |

Example 27

Antiinflammatory Properties of Materials from Microalgae

The pro-inflammatory cytokine interferon-gamma, which is released by activated T-lymphocytes, plays a role in human inflammatory responses. Interferon-gamma also stimulates the enzyme indoleamine-2,3-dioxygenase, which degrades tryptophan to kynurenine. In concert with other pro-inflammatory cytokines, interferon-gamma is the most important trigger for the formation and release of reactive oxygen species (ROS). Interleukin-1 alpha (IL1-α) is a cytokine that also plays a major role in inflammatory responses. Microalgal materials were tested for their ability to suppress secretion of gamma interferon and IL1-α by human peripheral blood mononuclear cells.

Heparinized whole blood (20-30 ml) was collected from a healthy human donor, layered over a density gradient (Histopaque 1077 and Histopaque 1119) and centrifuged at 400 g for 30 min. The PBMC rich fraction was removed and washed twice in with 5.0 ml RPMI-1640 without phenol red supplemented with 5% heat-treated fetal calf serum (RPMI-FCS). After washing, the cells were resuspended in RPMI-FCS at a final density of $1 \times 10^6$ cells/ml.

Fifty microliters of PBMC cells were added to wells in a 96-well plate (each treatment was tested in triplicate). Next, 50 μl of RPMI-FCS supplemented with 2 μg/ml phytohemagglutinin (PHA) and the respective test materials was added to the wells. Cyclosporin A (2.5 μg/ml) was used as a positive control, while untreated cells served as a negative control (Untreated). One set of wells was not treated with PHA (Untreated-PHA). After the wells had been prepared, the plates were incubated for approximately 68 hours at 37±2° C. and 5% $CO_2$. After the incubation, 20 μl of a 20:1 solution of MTS:PMS (Promega) was added to each well and the 96-well plate was returned to the incubator for an additional 4 hours. The plate was then read at 490 nm using a plate reader. At the end of the incubation period the cell culture supernatant was assayed for IL-1α and gamma interferon.

Prior to the assay, all buffers and reagents were prepared according to the ELISA kit instructions (IL-1α: Cayman Chemicals (catalog number 583301); γ-IFN: R&D Systems (catalog number DIF50)) and allowed to reach room temperature. The 96-well plate was prepared by removing any unneeded well strips and by rinsing the plate once with Wash Buffer followed by blotting it dry. Next, a series of IL-1α standards was prepared ranging from 0 to 250 pg/ml and 100 μl of each of these standards was dispensed into two wells (duplicates) in the 96-well plate. Subsequently, 50 μl of each sample+50 μl of culture media was added to additional wells (the samples were diluted to bring their IL-1α levels within the range of the standard curve), followed by the addition of 100 μl of acetylcholinesterase:Interleukin-1α FAB' Conjugate solution. After reserving two empty wells to serve as blanks, the 96-well plate was incubated overnight at 2-8° C. On the following day the wells were aspirated and washed 5-6 times with Wash Buffer. After the last wash was removed 200 μl of fresh Ellman's Reagent was added to each well. The plate was incubated at room temperature with periodic checks of the absorbance readings (405 nm) using a plate reader.

A series of gamma interferon standards was prepared ranging from 15.6 pg/ml to 1000 pg/ml using human gamma interferon. Next, an ELISA microplate was prepared by removing any unneeded strips from the plate frame. 100 μl of Assay Diluent RD1F was added to each well, followed by the addition of 100 μl of sample (diluted in culture media if necessary to bring the gamma interferon values within the range of the standard curve) or 100 μl of standard per well. The microplate was covered and allowed to incubate for 2±0.25 hours at room temperature. After the incubation the plate was aspirated and washed three times with 400 μl of wash buffer. After the last wash was removed 200 μl of anti-gamma interferon antibody/horseradish peroxidase conjugate solution was added to each well and the plate was incubated for 1±0.25 hour at room temperature. The wells were aspirated and washed again as described above. After the last wash was removed 200 μl of horseradish peroxidase substrate solution (hydrogen peroxide+tetramethylbenzidine as a chromagen) was added to each well and the plate was incubated for 20±5 minutes at room temperature. After the incubation 50 μl of stop solution (2 N sulfuric acid) was added to each well and the plate was read using a microplate reader at 450 nm.

As demonstrated by Tables 17 and 18 and FIGS. 13(a) and 13(b), all materials tested at all concentrations reduced gamma interferon and IL1-α by human PBMC cells.

TABLE 17

IL-1α assay.

| Treatment | pg/ml |
|---|---|
| 1.5% LS PS | 689 ± 69.3 |
| 0.5% LS PS | 1530 ± 79.7 |
| 0.1% LS PS | 1715 ± 69.3 |
| 1.5% HS PS | 563 ± 38.5 |
| 0.5% HS PS | 1462 ± 99.9 |
| 0.1% HS PS | 1663 ± 54.1 |
| 2.5 ug/ml Cyclosporin A | 1561 ± 77.5 |
| Untreated | 2402 ± 146.2 |
| Untreated -PHA | 1512 ± 88.8 |

TABLE 18

Gamma interferon assay.

| Treatment | pg/ml |
|---|---|
| 1.5% LS PS | 1116 ± 109.7 |
| 0.5% LS PS | 3924 ± 425.8 |
| 0.1% LS PS | 4626 ± 305.5 |
| 1.5% HS PS | 997 ± 159.7 |
| 0.5% HS PS | 3509 ± 203.0 |
| 0.1% HS PS | 4125 ± 131.4 |
| 2.5 ug/ml Cyclosporin A | 3259 ± 326.8 |
| Untreated | 11078 ± 315.0 |
| Untreated -PHA | 83 ± 7.0 |

TABLE 19

Proliferation assay.

| Treatment | Stimulation Index |
|---|---|
| 1.5% LS PS | 32 ± 16.0 |
| 0.5% LS PS | 106 ± 6.9 |
| 0.1% LS PS | 111 ± 12.0 |
| 1.5% HS PS | 50 ± 13.6 |
| 0.5% HS PS | 117 ± 14.4 |
| 0.1% HS PS | 126 ± 34.4 |
| 2.5 ug/ml Cyclosporin A | 123 ± 6.5 |
| Untreated | 183 ± 13.9 |
| Untreated -PHA | 100 ± 5.2 |

Example 28

Antiinflammatory Properties of Materials from Microalgae

When presented with certain antigens, lymphocytes, which are the main cell type in PBMCs, respond by proliferating. This massive proliferation reaction forms the initial step in the immune response of this cell type. In vitro were used methods to study human lymphocyte proliferation using the antigen phytohemagglutinin (PHA) to stimulate a proliferation response. The ability of microalgal materials to inhibit this proliferation was tested.

Heparinized whole blood (20-30 ml) was collected from a healthy human donor, layered over a density gradient (Histopaque 1077 and Histopaque 1119) and centrifuged at 400 g for 30 min. The PBMC rich fraction was removed and washed twice in with 5.0 ml RPMI-1640 without phenol red supplemented with 5% heat-treated fetal calf serum (RPMI-FCS). After washing, the cells were resuspended in RPMI-FCS at a final density of $1 \times 10^6$ cells/ml.

Fifty microliters of PBMC cells were added to wells in a 96-well plate (each treatment was tested in triplicate). Next, 50 µl of RPMI-FCS supplemented with 2 µg/ml PHA and the respective test materials was added to the wells. Cyclosporin A (2.5 µg/ml) was used as a positive control, while untreated cells served as a negative control (Untreated). One set of wells was not treated with PHA and served as an index of non-stimulated proliferation (Untreated-PHA); all samples but this sample were treated with PHA. After the wells had been prepared, the plates were incubated for approximately 68 hours at 37±2° C. and 5% $CO_2$. After the incubation, 20 µl of a 20:1 solution of MTS:PMS (Promega) was added to each well and the 96-well plate was returned to the incubator for an additional 4 hours. The plate was then read at 490 nm using a plate reader.

The mean absorbance of the three wells of PBMC not treated with PHA was determined and used to represent non-stimulated proliferation. The absorbance values for the PBMC from each treatment group were also then determined A stimulated proliferation index for each treatment was calculated using the following equations: ((Mean absorbance of treatment with PHA)/(Mean Absorbance without PHA))×100

Figure 18:
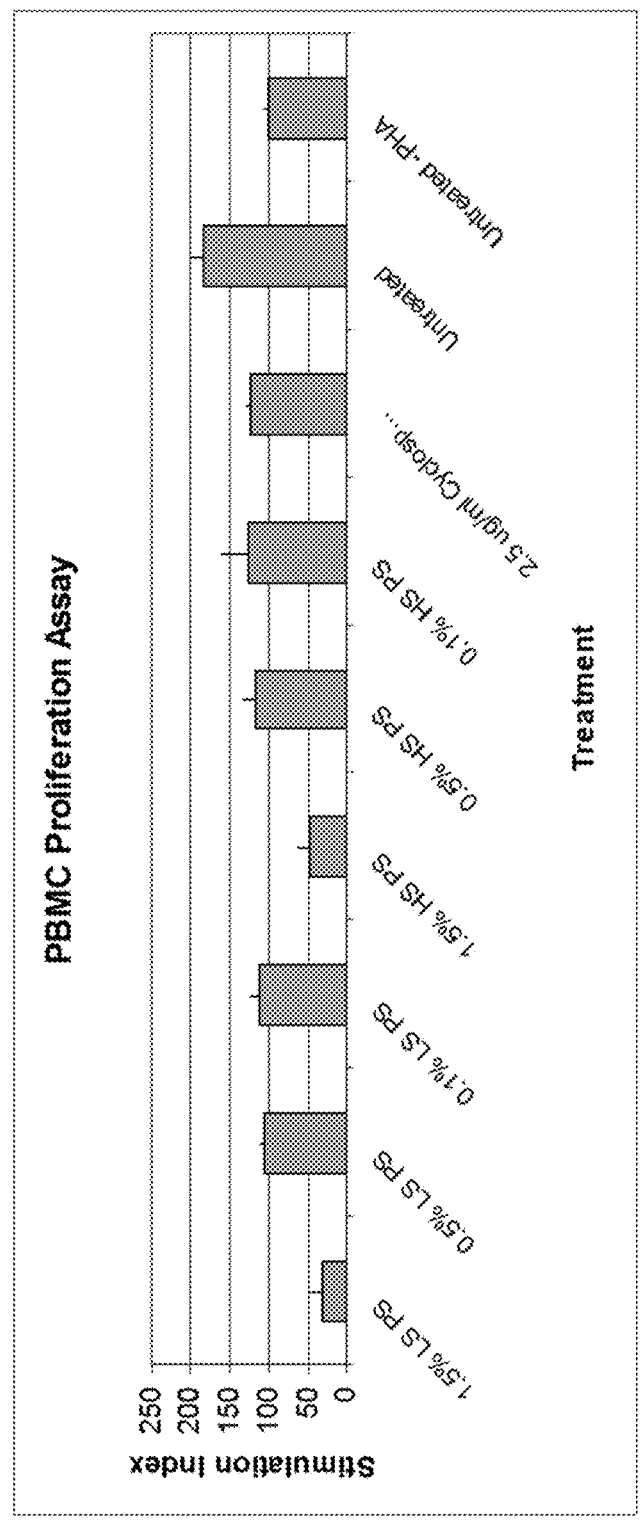
FIG. 18 shows PBMC proliferation in the presence and absence of microalgae-derived materials.
Figure 20B:
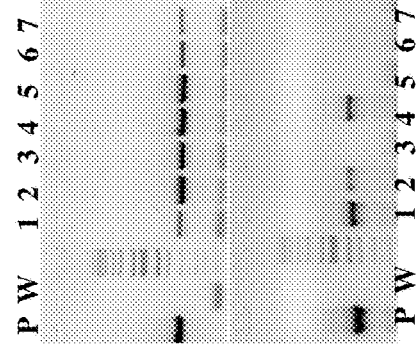
FIGS. 20(a), (b), (c) and (d) show transformation of exogenous genes into *Porphyridium* sp.
Figure 20D:
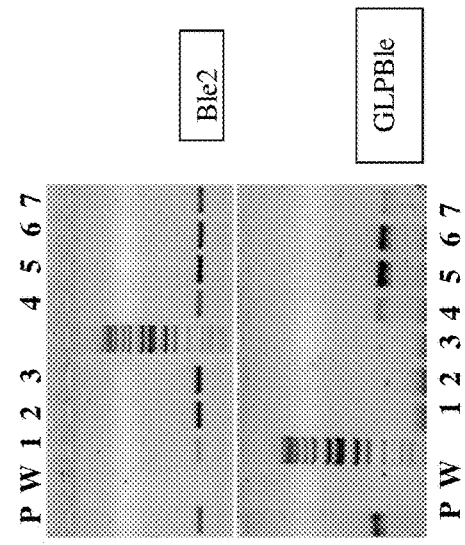
Figure 20A:
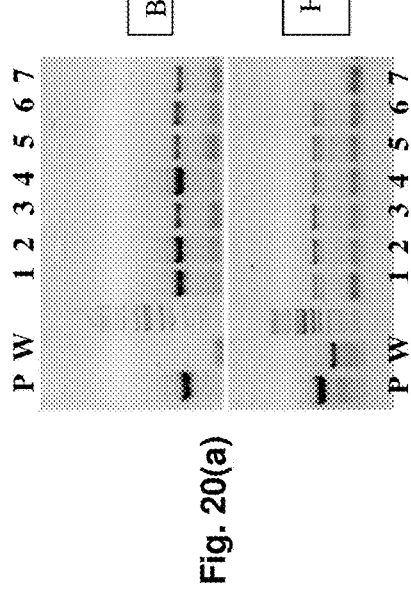
Figure 20C:
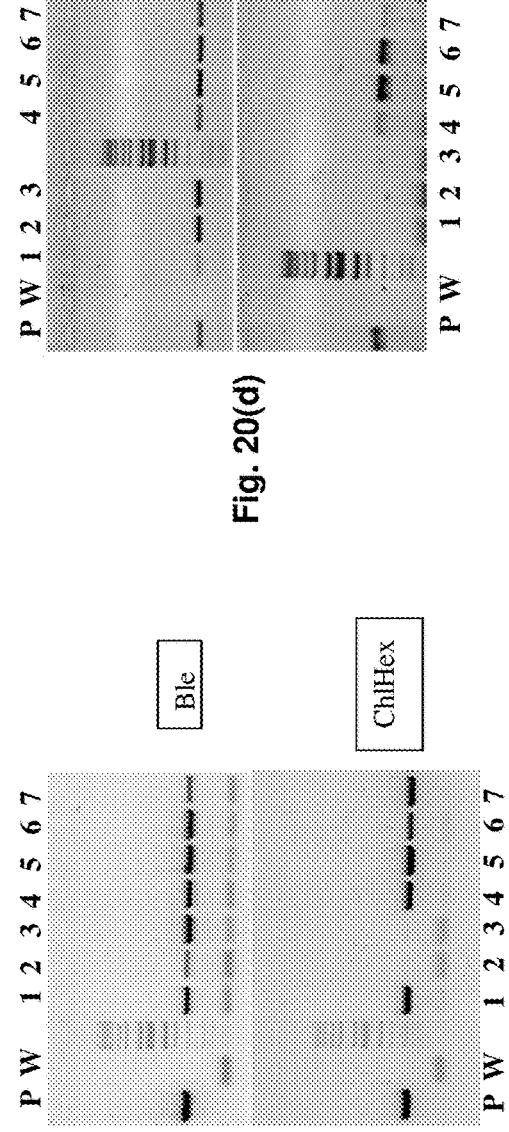

The results for the PBMC proliferation assay are presented in Table 19 and FIG. 18. The values are expressed as a stimulation index, using the untreated PBMC not exposed to PHA to represent 100%. As can be seen in Table 19 and FIG. 18, all materials tested reduced PBMC proliferation compared to PHA stimulated cells that were untreated by the test materials.

Example 29

Elastase Inhibition

Human dermal fibroblasts were cultured and used as a source of the elastase enzyme. This enzyme was be partially purified from the fibroblasts by lysing the cells in an elastase buffer and retaining the soluble portion of the lysate. Portions of this fibroblast lysate were then be incubated with test materials a synthetic elastase substrate, Suc-$(Ala_3)$-p-Nitroaniline (STANA). Elastase acts upon this substrate to release p-nitroaniline, which is detected with a spectrophotometer by measuring the absorbance at a wavelength of 405 nm. An inhibition of the elastase enzyme is identified by a decrease in the amount of released p-nitroaniline when compared to uninhibited enzyme.

Test material BM was supplied as a powder. 100 mg of BM was combined with either 5 ml of ethanol or 5 ml of ultrapure water in 15 ml centrifuge tubes. After combining, the mixtures were vortexed, then placed onto a rocking platform for approximately 30 minutes at room temperature, and then centrifuged at 1,000 RPM for 5 minutes. The supernatants were then used at the final concentrations listed in Table 20. The two additional materials used in this study, PS53 and PS133, were supplied as thick, viscous solutions (3%). These materials were also used at the final concentrations listed in the results section.

Human neonatal dermal fibroblasts were obtained and cultured per the vendor's specifications using sterile technique at all times (Cascade Biologics, catalog # C-004-5C). The cells were seeded in a 75-$cm^2$ flask and grown in Fibroblast Growth Medium (FGM: DMEM supplemented with 2% FBS, 5 ng/ml human recombinant growth factor, 5 ug/ml insulin, 50 ug/ml gentamicin, and 0.5 ug/ml Amphotericin-B) and subcultured until a sufficient number of cells had been grown.

After washing the cells twice with PBS, approximately 7.5 ml of PBS was added to each culture flask and the cells were detached using a cell scraper. The detached cells were transferred to a 15 ml centrifuge tube and the flask was rinsed with a second application of 7.5 ml of PBS, which was also transferred to the 15 ml tube. After centrifuging the tube for 5 minutes at 1,200 RPM (4° C.), the supernatant was removed and discarded while the pellet was resuspended in 2 ml of ice cold 2× elastase buffer (400 mM Tris-HCl [pH 8.0], 0.2% Triton X-100) and sonicated 3× for 10 seconds or until the lysate became clear. The lysed cells were centrifuged at 2,200 RPM for 10 minutes (4° C.) to remove any cellular debris. The supernatants from all of the preparations were pooled into a single container, mixed, and then aliquoted into 2 ml portions and stored at −75±5° C. until used.

One of the aliquots was used to determine the protein concentration (BCA Protein Assay) and elastase activity level of the batch.

A Bicinchoninic Acid assay (Pierce, Inc., BCA Protein Assay Kit, catalog#23227) Fifty volumes of Reagent A (Bicinchoninic Acid BCA was combined with 1 volume of Reagent B (4% (w/v) $CuSO_4$-5 $H_2O$) in a 15-ml centrifuge tube. For the assay, proteins can reduce Cu(II) to Cu(I) in a concentration dependent manner. BCA can then react with the Cu(I) to form a purple colored complex with a maximum absorbance at 562 nm. Two hundred microliters of this combined reagent was dispensed into a 96-well plate. Next, 10 µl of each of the standards was added into their respective wells (standards were made using 2 mg/ml bovine serum albumin dissolved in PBS, and then making a series of 50% dilutions down to 0.0078 mg/ml). Next, 10 µl of 2× elastase buffer (used as a blank) or cell lysate sample was added. The plate was covered and incubated at 37±2° C. for 30±5 minutes. At the end of the incubation the absorbance of each well was measured at 540 nm using a microplate reader.

After measuring the protein concentration of the lysate, a small sample was obtained and the elastase activity of the lysate was determined at 100%, 50% and 25% concentrations using 2× elastase buffer to make the dilutions. To determine the activity, 100 µl of the three different lysate concentrations was loaded into a 96 well plate (each concentration tested in triplicate), while 100 ul of 2× Elastase buffer was added to three additional wells to serve as blanks. Next, 100 µl of deionized water was added to all wells and the 96-well plate will be allowed to incubate with the samples for 15 minutes at 37±2° C. Next, 4 µl of STANA (62.5 mM Suc-$(Ala_3)$-p-Nitroaniline in DMSO) was added to each well, and the 96-well plate was returned to the incubator for 1 hour. After the incubation the well plate was read at 405 nm using a microplate reader. The mean absorbance for each concentration of the lysate was plotted versus its respective concentration. These values were used to estimate a concentration that will produce a spectrophotometric measurement of 0.4 to 0.5 using a linear regression analysis of the best-fit line through all three (100%, 50%, and 25%) data points. The stored fibroblast lysates was diluted to the appropriate concentration to elicit the desired level of activity.

Test materials were prepared at 2× their final desired concentration in deionized water. If solvents were present in the test materials then appropriate solvent controls were also prepared. 100 µl of distilled water served as a negative control while 100 µl of 0.2 mM Phosphoramidon served as a positive control. After all of the wells had been prepared the well plate was sealed with an adhesive cover and incubated for 15 minutes at 37±2° C. to allow the inhibitors time to interact with elastase. After this preliminary 15 minute incubation, 4 µl of STANA was added; the plate was resealed and then incubated for 1 hour at 37±2° C. At the end of the incubation the plate was read at 405 nm using a microplate reader.

TABLE 20

Anti-elastase assay.

| Treatment | Percent Inhibition |
|---|---|
| 10% BM water extraction | 59 |
| 5% BM water extraction | 40 |
| 10% BM Ethanol extraction | 28 |
| 5% BM Ethanol extraction | 16 |
| 1% LS PS | 29 |

TABLE 20-continued

Anti-elastase assay.

| Treatment | Percent Inhibition |
|---|---|
| 0.5% LS PS | 23 |
| 1% LS PS | 31 |
| 0.5% HS PS | 19 |
| 100 µM Phosphoramidon | 94 |

Example 30

Microalgal materials were tested to assess their ability to relieve redness and pain associated with sunburn. Informed consent was obtained from human subjects. A 1.5% preparation of polysaccharide from *Porphyridium cruentum*, purified essentially as described in Example 2, was formulated with 1% Germaben II and 0.15% sodium EDTA. A patch of arm skin was exposed to UV radiation from a Solar Ultraviolet Simulator model 14S with a dose controller system model DCS-1 and a 150 watt xenon arc lamp #1122200 (Hanovia) having a continuous emission spectrum in the UV-B range of 290-320 nanometers. The dose was tested on each subject prior to the experiment to determine the minimal erythema dose (MED) necessary to achieve a level 2 response in each subject. Erythema was scored by a trained evaluator using the following scale: 0=no reaction; +=minimal erythema; 1=slight erythema; 2 moderate erythema; 3=marked erythema with or without edema; 4=severe erythema with or without edema. Subjects were them exposed to a UVB dose sufficient to generate a level 2 erythema at three sites on the skin. One site was treated with the polysaccharide before and after irradiation. One site was treated with polysaccharide only after irradiation. One site was left untreated as a control. After 4, 24, 48, 72, and 96 hours, follow-up examination was performed. Polysaccharide was applied once daily to the two treated sites following daily examinations and was also treated once per day at home by each subject.

Mean erythema scores were the same on all three sites tested through the 4 and 24 hour evaluation points. At the 48 hour evaluation the mean erythema score decreased 5% on the site treated pre and post irradiation and stayed the same on the other two sites. At the 72 hour evaluation the mean erythema scores decreased by 30% on both sites treated with the polysaccharide and decreased 13% on the untreated site. At the 96 hour evaluation the mean erythema scores decreased by 40% on both sites treated with the polysaccharide and decreased 22% on the untreated site. There was no edema observed at any time on any site. The polysaccharide treatment was associated with a clinically significant decrease in erythema compared to no treatment.

Example 31

Polysaccharide was prepared essentially as described in Example 2 was tested for the ability to protect a skin model from TT dimer formation. The MatTek EpiDerm® tissue skin model was generate as described in Example 23, as well as polysaccharide application and UV exposure.

After fixing the tissues overnight in 10% neutral buffered Formalin the tissues were processed as follows: 1. tissues were washed in 80% ethanol, (15-20 minutes); 2. tissues were washed in 95% ethanol, (3 times, 15-20 minutes); 3. tissues were washed in Absolute ethanol (3 times, 15-20 minutes); 4. tissues were washed in 50% absolute ethanol/

50% xylene (15-20 minutes); 5. tissues were washed in Xylene (2 times, 15-20 minutes each); 6. tissues were washed in Paraffin (3 changes, 15 minutes each); 7. tissues were embedded and sectioned (4-6 mm sections) onto microscope slides.

Immunohistochemistry: Tissue Hydration and Pre-Immunohistochemical Processing: 1. tissues were washed with Xylene (3 times, 5 minutes each); 2. tissues were washed with Absolute ethanol (2 times, 10 minutes each); 3. tissues were washed with 95% ethanol (2 times, 10 minutes each); 4. tissues were washed with 80% ethanol (1 time, 5 minutes); 5. tissues were washed with Distilled water (1 time, 1 minute); 6. Antigen unmasking was performed by washing with 10 mM sodium citrate buffer (pH 6.0) at 95° C. for 10 minutes and then rinsing in distilled water 3 times, 2 minutes each; 7. endogenous peroxide activity was quenched (0.5% hydrogen peroxide for 5-10 minutes and then rinse in PBS 2×, 5 minutes each).

Immunohistochemistry: Immunoperoxidase Staining: 1. sections were incubated for 1 hour in 1.5% goat serum in PBS. 2. primary antibody (anti-thymine dimer antibody, clone KTM53, Kamiya Biomedical Company) was incubated for 30 minutes at room temperature or overnight at 4° C. Primary antibody was diluted in 1.5% goat serum in PBS. 3. Sections were washed 3× with PBS, 5 minutes per wash. 4. Sections were incubated for 30 minutes with biotin-conjugated secondary antibody (goat anti-mouse, Santa Cruz Biotechnology). Secondary antibody was diluted in 1.5% normal blocking serum. 5. sections were washed 3× with PBS, 5 minutes per wash. 6. Sections were incubated for 30 minutes with the avidin/HRP enzyme complex (ABC Staining System, Santa Cruz Biotechnology) and then wash the sections 3× with PBS, 5 minutes per wash. 7. Sections were incubated in HRP substrate solution for about 5 minutes. 8. Sections were washed 1× in distilled water for 5 minutes. 9. sections were counter-stained in hematoxylin for 5-10 seconds and then rinsed through several changes of distilled water. 10. Sections were dehydrated as follows: a. sections were washed in 95% ethanol (2×, 10 seconds each); b. sections were washed in 100% ethanol (2×, 10 seconds each) c. sections were washed in xylene (3×, 10 seconds each). Mounting medium (Shurmount, Triangle Biomedical Sciences, Inc.) was applied, followed by a microscope cover slip.

Example 32

Polysaccharide was tested on human volunteers obtained for various skin parameters. The study was conducted in compliance with CFR Title 21, Part 50 (Informed Consent of Human Subjects). Informed Consent was obtained from each subject in the study and documented in writing before participation in the study. Twenty-seven (27) female subjects ranging in age from 38 to 60 years were impaneled for the 12 week testing procedure.

Subjects reported to the testing facility for a baseline visit. A trained technician evaluated the presence of crow's feet fine lines/wrinkles on the face of each subject and evaluated pore size and skin texture. The elasticity of the skin was measured using the Cutometer® (Courage+Khazaka, Germany) and the moisture content of the skin was measured using the Corneometer® (Courage+Khazaka, Germany). Skin replicas were taken at the crow's feet area to evaluate fine lines/wrinkles and on the cheek to evaluate pore size. Subjects were given a 1.5% (w/w) polysaccharide solution prepared essentially as described in Example 2, which also contained 1% (w/w) Germaben II® and 0.15% (w/w) disodium EDTA.

Subjects applied a sufficient quantity of polysaccharide to cover the entire face, including eye area, in the morning and evening, and rubbed the polysaccharide in until it was completely absorbed by the skin. The twice daily application occurred for a period of 12 weeks.

Fine lines and wrinkles/crows feet were evaluated reduced by 3.1% after 4 weeks, 4.6% after 8 weeks, and 3.1% after Skin elasticity, measured by Cutometer®, demonstrated an average 4.4% increase in elasticity after 8 weeks and an average 3.4% increase in elasticity after 12 weeks.

Skin moisturization level, measured by a Corneometer®, increased an average of 7.4% after 8 weeks, and 8.8% after 12 weeks. Skin moisturization level was also measured 15 minutes after the initial application, and averaged an increase of 4.2%.

Transepidermal water loss was measured using a Tewameter®. Average decrease in transepidermal water loss was 13.9% after 12 weeks.

Additionally, skin replica analysis indicated a smoothing effect in coarse lines as well as a reduction in the number. 76% of subjects responded their skin was less rough and 68% felt that the overall quality of their skin improved. 81% of subjects responded that their skin felt tighter immediately after application, and 85% of subjects responded that their skin felt tighter 30 minutes after application.

Example 33

Glucose transporters and a gene encoding a fusion of the *Porphyridium* polysaccharide-binding protein:ble protein were cloned into pBluescript and were used to transform *Porphyridium* sp.

Plasmid Constructs: All the plasmid constructs were designed to have the expression of the heterologous gene driven by endogenous promoter Glp (which drives the expression of the glycoprotein gene). The GlpBle construct has the Ble gene cloned as a fusion downstream of the Glp gene.

The architecture of the constructs is as follows:

| | | |
|---|---|---|
| Plasmid 1: | Ble: (SEQ ID NO: 11) | 5' Glp:: Ble::cmv 3' |
| Plasmid 2: | Human Glut1 (HuGlut): | 5' Glp:: HuGlut::cmv 3' |
| Plasmid 3: | *Chlorella* hexose (ChlHex): | 5' Glp:: ChlHex::cmv 3' |
| Plasmid 4: | Yeast Hxt2 (YeHxt2): | 5' Glp:: YeHxt2::cmv 3' |
| Plasmid 5: | Ble Fused to GLPcDNA (GLPBle): | 5' Glp:: GLPBle::cmv 3' |

GLP:BLE is (SEQ ID NO:15:SEQ ID NO:11); 5' Glp is the glycoprotein promoter (SEQ ID NO:21); Transporter sequences are documented in applications cited herein, such as PCT Patent application No: PCT/US2007/001319, filed Jan. 19, 2007, entitled "Nutraceutical Compositions from Microalgae and Related Methods of Production and Administration". Cmv 3' is the 3'UTR listed in SEQ ID NO:32.

Biolistic Transformation: All transformations were performed as co-transformations using plasmid 1 in combination with one of plasmids 2-5. The biolistic particle delivery system PDS 1000/He (Bio-Rad, USA) was used for transformation. *Porphyridium* sp. culture was grown to logarithmic phase (~2×10$^6$ cells/mL) in ASW (ATCC) media, under continuous light (~75 umol/m$^2$). Cells from this culture were harvested at 4000 rpm at room temperature. The cell pellet was washed twice with sterile distilled water. Cells were resuspended in fresh ASW (ATCC) media to the same cell density i.e. ~2×10⁶ cells/mL and incubated in the dark for 16 hours. The dark adapted cells were then harvested at 4000 rpm at room temperature, resuspended to a density of ~2×10⁸ cells/mL in fresh ASW (ATCC) media. About ~1×10⁸ cells were transferred to each plate. The plasmid DNA was coated onto 550 nm gold particles (S04e, Seashell Technology, Inc). Ten uL gold particles coated with co-transforming plasmid DNA were delivered to each plate using a 1350 psi rupture disc, under a vacuum of 28 in. Hg. The transformed cells were recovered for a day in non selective medium, and then harvested, resuspended in ASW (ATCC) media and transferred to ASW (ATCC) agar plates supplemented with 15 ug/mL Zeocin. These plates were incubated under 75 umol/m² light conditions for 10-14 days. Colonies growing on these plates were transferred to fresh ASW (ATCC) plates supplemented with 15 ug/mL Zeocin. The resistant colonies were selected for further analysis.

Genotyping: Genotyping was done on genomic DNA extracted from WT, the transformants and plasmid DNA. For each co-transformation set, seven transformants (numbered 1 to 7) were genotyped for the resistant marker, ble and the corresponding co-transforming plasmid. The following primer sets were used to genotype for the different plasmids:

| Construct | Primer set (SEQ ID NOs) |
| --- | --- |
| Ble | SEQ ID NO: 49 + SEQ ID NO: 48 |
| Ble2 | SEQ ID NO: 47 + SEQ ID NO: 48 |
| HuGlut1 | SEQ ID NO: 49 + SEQ ID NO: 50 |
| Chl Hex | SEQ ID NO: 49 + SEQ ID NO: 51 |
| Ye Hxt2 | SEQ ID NO: 49 + SEQ ID NO: 52 |
| GLPBLE | SEQ ID NO: 53 + SEQ ID NO: 48 |

The PCR profile used was as follows: 94° C. denaturation for 5 min; 35 cycles of 94° C.—30 sec, 58° C. or 62° C. or 66° C. (58° C. for ble2, 62° C. for GLPBle and 66° C. for ble, HuGlut and Chl Hex)—30 sec, 72° C.—2 min; 72° C.—5 min.

Results are shown in FIG. 20. In each of the four panels, the top gel shows genotyping of individual transformants for the ble gene (plasmid 1), while the bottom gel shows genotypoing of the same transformants for plasmids 2-5. P is plasmid DNA template showing the expected size of the genotyping PCR product; W is wild type DNA. 1-7 are 7 independent transformants. Panel (a) shows integration of plasmid 2 into the genome of 6 transformants. Panel (b) shows integration of plasmid 4 into the genome of 3 transformants. Panel (c) shows integration of plasmid 3 into the genome of 5 transformants. Panel (d) shows integration of plasmid 5 into the genome of 4 transformants.

TABLE 21

Genbank accession numbers of superoxide dismutases.

CAA42737; AA43859; AA29934; AA02655; P__625295;
H004200; AC14367; P__001003721; BM60577; AM08755;
P__966270; P__963716; ABM37237; ABM35060; ABM33234;
AAY48900; NP__000445; AAH12423; AAA62278; ABM33141;
NP__407488; NP__405922; YP__932026; ZP__01641300;
ZP__01638301; ZP__01637188; EAX24391; EAX23794;
EAX23720; EAX23627; EAX20859; EAX19390; EAX16596;
CAL93139; YP__914326; YP__747424; ABI59459; ZP__01610569;
ZP__01605216; ZP__01600343; ZP__01584712; ZP__01581863;
ZP__01581157; ZP__01575777; ZP__01569848; ZP__01559998;
EAW01367; EAW01065; EAV97274; EAV95856; EAV80568;
EAV73624; EAV73531; EAV70130; EAV66456; EAV61854;
ZP__01532079; ZP__01516088; EAV26209; YP__845889;
YP__822355; YP__843115; YP__836186; and ABK17454

TABLE 22

Genbank accession numbers of beta-carotene hydroxylases.

NP__682690; YP__172377; NP__440788; YP__475340;
YP__475340; BAB75708; ZP__01084736; ZP__01080915;
ZP__01123496; ABB27016; NP__895643; NP__896386;
ABB34062; YP__292794; AAP99312; ZP__01006041;
ABB49299; NP__848964; ZP__01040435; NP__049051;
YP__457405; and AAT38625

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A gel, lotion, cream or ointment composition suitable for topical administration comprising microalgal exopolysaccharide particles, the exopolysaccharide produced by microalgae of the genus *Parachlorella*, wherein the exopolysaccharide particles are made by:

culturing microalgae cells in a culture medium so that exopolysaccharide is secreted by the microalgal cells into the culture medium;

separating the exopolysaccharide from the microalgal cells to create a purified exopolysaccharide;

heating, in two parts, the purified exopolysaccharide, the first part being performed at a temperature in the range of 60° C. to 100° C. and the second part being performed at a temperature range of 148° C.-160° C. so as to render it partially insoluble in water, and so that it forms a polysaccharide gel in water; and generating particles having an average size of between 0.1 and 400 microns from the heated exopolysaccharide, wherein the particles increase in volume on contact with water by at least 100% compared to their anhydrous volume; and the particles increase in volume for at least 4 hours, and wherein the composition when applied to mammalian skin reduces the presence of crow's feet fine lines/wrinkles, increases skin elasticity, increases skin moisture, or decreases transepidermal water loss.

2. The composition of claim 1, wherein the particles increase in volume on contact with water by at least 200% compared to their anhydrous volume.

3. The composition of claim 1, wherein the composition further comprises between 50-97% ethylhexyl palmitate, 1-5% silica dimethyl silylate, 0.1-3% butylene glycol, and 0.1-3% of one or more preservative selected from the group consisting of diocide, dowicil 200, and methyl paraben.

4. The composition of claim 1, wherein the particles are generated by milling the heated purified exopolysaccharide.

5. The composition of claim 1, further comprising at least one ingredient selected from the group consisting of beta carotene, lutein, astaxanthin, vitamin C, vitamin E, vitamin A, and coenzyme Q10, a peptide, an acetylated peptide, oil soluble a-hydroxy acid, an alkyl lactate, and salicylic acid.

6. A gel, lotion, cream or ointment composition suitable for topical administration comprising microalgal exopolysaccharide particles, the exopolysaccharide produced by microalgae of the genus *Parachlorella*, wherein the exopolysaccharide particles are made by:

culturing microalgae cells in a culture medium so that exopolysaccharide is secreted by the microalgal cells into the culture medium;

separating the exopolysaccharide from the microalgal cells to create a purified exopolysaccharide;

heating, in two parts, the purified exopolysaccharide, the first part being performed at a temperature in the range of 60° C. to 100° C. and the second part being performed at a temperature of 148° C.-160° C. so as to render it partially insoluble in water, and so that it forms a polysaccharide gel in water; and generating particles having an average size of between 0.1 and 400 microns from the heated exopolysaccharide, wherein the particles increase in volume on contact with water by at least 100% compared to their anhydrous volume; and the particles increase in volume for at least 4 hours, and wherein the composition when applied to mammalian skin cells stimulates an anti-inflammatory response in the mammalian cell, the anti-inflammatory response selected from the group consisting of reducing lymphocyte proliferation, reducing gamma interferon production, reducing interleukin 1a production, and reducing erythema.

7. The composition of claim 6, wherein the particles increase in volume on contact with water by at least 200% compared to their anhydrous volume.

8. The composition of claim 6, wherein the composition further comprises between 50-97% ethylhexyl palmitate, 1-5% silica dimethyl silylate, 0.1-3% butylene glycol, and 0.1-3% of one or more preservative selected from the group consisting of diocide, dowicil 200, and methyl paraben.

9. The composition of claim 6, wherein the particles are generated by milling the heated purified exopolysaccharide.

10. The composition of claim 6, further comprising at least one ingredient selected from the group consisting of beta carotene, lutein, astaxanthin, vitamin C, vitamin E, vitamin A, and coenzyme Q10, a peptide, an acetylated peptide, oil soluble a-hydroxy acid, an alkyl lactate, and salicylic acid.

11. A gel, lotion, cream or ointment composition suitable for topical administration comprising microalgal exopolysaccharide particles, the exopolysaccharide produced by microalgae of the genus *Parachlorella*, wherein the exopolysaccharide particles are made by:

culturing microalgae cells in a culture medium so that exopolysaccharide is secreted by the microalgal cells into the culture medium;

separating the exopolysaccharide from the microalgal cells to create a purified exopolysaccharide;

heating, in two parts, the purified exopolysaccharide, the first part being performed at a temperature in the range of 60° C. to 100° C. and the second part being performed at a temperature of 148° C.-160° C. so as to render it partially insoluble in water, and so that it forms a polysaccharide gel in water; and generating particles having an average size of between 0.1 and 400 microns from the heated exopolysaccharide, wherein the particles increase in volume on contact with water by at least 100% compared to their anhydrous volume; and the particles increase in volume for at least 4 hours, and wherein the composition when applied to mammalian skin cells stimulates the synthesis of procollagen and/or elastin in the mammalian cell.

12. The composition of claim 11, wherein the particles increase in volume on contact with water by at least 200% compared to their anhydrous volume.

13. The composition of claim 11, wherein the composition further comprises between 50-97% ethylhexyl palmitate, 1-5% silica dimethyl silylate, 0.1-3% butylene glycol, and 0.1-3% of one or more preservative selected from the group consisting of diocide, dowicil 200, and methyl paraben.

14. The composition of claim 11, wherein the particles are generated by milling the heated purified exopolysaccharide.

15. The composition of claim 11, further comprising at least one ingredient selected from the group consisting of beta carotene, lutein, astaxanthin, vitamin C, vitamin E, vitamin A, and coenzyme Q10, a peptide, an acetylated peptide, oil soluble a-hydroxy acid, an alkyl lactate, and salicylic acid.

* * * * *

SEQUENCE LISTING

<160> NUMBER OF SEQ ID NOS: 53

<210> SEQ ID NO 1
<211> LENGTH: 253
<212> TYPE: DNA
<213> ORGANISM: Artificial
<220> FEATURE:
<223> OTHER INFORMATION: Synthetic RBCS2 Chlamydomonas reinhardtii

<400> SEQUENCE: 1
cgcttagaag atttcgataa ggcgccagaa ggagcgcagc caaaccagga tgatgtttga      60
tggggtattt gagcacttgc aacccttatc cggaagcccc ctggcccaca aaggctaggc     120

| | |
|---|---|
| gccaatgcaa gcagttcgca tgcagcccct ggagcggtgc cctcctgata aaccggccag | 180 |
| ggggcctatg ttctttactt ttttacaaga gaagtcactc aacatcttaa acggtcttaa | 240 |
| gaagtctatc cgg | 253 |

<210> SEQ ID NO 2
<211> LENGTH: 312
<212> TYPE: DNA
<213> ORGANISM: Artificial
<220> FEATURE:
<223> OTHER INFORMATION: Synthetic Beta2 tubulin Chlamydomonas
      reinhardtii

<400> SEQUENCE: 2

| | |
|---|---|
| ctttcttgcg ctatgacact tccagcaaaa ggtagggcgg gctgcgagac ggcttcccgg | 60 |
| cgctgcatgc aacaccgatg atgcttcgac cccccgaagc tccttcgggg ctgcatgggc | 120 |
| gctccgatgc cgctccaggg cgagcgctgt ttaaatagcc aggcccccga ttgcaaagac | 180 |
| attatagcga gctaccaaag ccatattcaa acacctagat cactaccact tctacacagg | 240 |
| ccactcgagc ttgtgatcgc actccgctaa ggggcgcct cttcctcttc gtttcagtca | 300 |
| caacccgcaa ac | 312 |

<210> SEQ ID NO 3
<211> LENGTH: 356
<212> TYPE: DNA
<213> ORGANISM: Artificial
<220> FEATURE:
<223> OTHER INFORMATION: Synthetic Chlorella virus promoter #1

<400> SEQUENCE: 3

| | |
|---|---|
| cggggatcgc agggcatggg cattaaaaga actttatgga atcaaaaatc ttagtgaatt | 60 |
| tccaccacag gtatatagtc ttcaggacgc taacgatgat atcaacgatt gtatcaaagg | 120 |
| ttatcgtttg aggcactcat atcaggtagt ttctacacag aaacttgaac aacgcctggg | 180 |
| aaaagatcct gagcatagta acttatatac tagcagatgt tgtaacgatg ctttatatga | 240 |
| atatgaatta gcacaacgac aactacaaaa acaacttgat gaatttgacg aagatgggta | 300 |
| tgatttttt caggcacgta taaatacatt agatccgtcg acctgcagcc aagctt | 356 |

<210> SEQ ID NO 4
<211> LENGTH: 207
<212> TYPE: DNA
<213> ORGANISM: Artificial
<220> FEATURE:
<223> OTHER INFORMATION: Synthetic Chlorella virus promoter #2

<400> SEQUENCE: 4

| | |
|---|---|
| cccggggatc atcgaaagca actgccgcat tcgaaacttc gactgcctcg ttataaaggt | 60 |
| tagtgaaagc cattgtatgt tattactgag ttatttaatt tagcttgctt aaatgcttat | 120 |
| cgtgttgata tgataaatga caaatgatac gctgtatcaa catctcaaaa gattaatacg | 180 |
| aagatccgtc gacctgcagc caagctt | 207 |

<210> SEQ ID NO 5
<211> LENGTH: 277
<212> TYPE: DNA
<213> ORGANISM: Artificial
<220> FEATURE:
<223> OTHER INFORMATION: Synthetic Chlorella virus promoter #3

<400> SEQUENCE: 5

```
cccggggatc tgcgtattgc gggacttttg agcattttcc agaacggatt gccgggacgt      60
atactgaacc tccagtccct ttgctcgtcg tatttcccat aatatacata tacactattt     120
taattattta caccggttgt tgctgagtga tacaatgcaa attccctcca ccgaggagga    180
tcgcgaactg tccaaatgtc ttctttctgc agctccatac ggagtcgtta ggaaacattc    240
acttaattat aggatccgtc gacctgcagc caagctt                             277
```

<210> SEQ ID NO 6
<211> LENGTH: 489
<212> TYPE: DNA
<213> ORGANISM: Artificial
<220> FEATURE:
<223> OTHER INFORMATION: Synthetic Rhodella reticulata phycoerythrin
      beta subunit promoter from AF114823

<400> SEQUENCE: 6

```
tttttataga tcatccaatt attttttcat tagatattgt atatcaataa tttggcatat    60
gttttgtagt atacgggtta tgatattgca atatatgtac aacattggta atttttggac   120
ttacatatat atcaattata tcaatgacaa tgtaatatat tggttgatag atcaataaac   180
atctttaata agatctgtta aaattcaaat atagactttc tgtattataa gtagttttct    240
tatattacta tagacgtaga acgatcaaaa aaaaataaat atggacatga cttgattcaa    300
tatggaagac ggggtatgag aaatatcgtg ttgcactcaa tatagaattg acgtattttt    360
aatgcagtgc ccgttatata ttgcgtaaca aagattaaaa gtatattata tattataata    420
ctagtagacc agcaaatata aaattatgct gaaacaataa tacccttaaa agttttaagg    480
agcctttc                                                             489
```

<210> SEQ ID NO 7
<211> LENGTH: 543
<212> TYPE: DNA
<213> ORGANISM: Artificial
<220> FEATURE:
<223> OTHER INFORMATION: Synthetic AHAS promoter from Porphyridium from
      AJ224709

<400> SEQUENCE: 7

```
attatttaac aattggaaac ttagttaatt agggtaaatt atattaaccc ttatgaacca    60
aaataatttg gtttcaaaaa aaactaactt atgaattaaa attgaaatat tttctacatc   120
ataataattt taattctaaa tagaatttta gataagggat ctaagataac aaaaaaatca   180
atttaagtaa taagaaaat gtgattacaa aattttgat attaaactat agtatttaca    240
aattattatc aaaaattact tatccatttg aggaaaagac tgaacctta aacatatttg   300 tttatgcgat tttagatcat tcaagttagc gagctgtatg aaatgaaagt ttcatgtaca   360
gttcttaagt agagatgtat atatgttaat agaaatatta tttgcatcga ctataatcaa   420
ttctgaagac ttcaaaataa aacctgttat acgtgctata ctagagatgg ttgatgaaat   480
aaatcaacca ggtattatta cagactgaac tgaactaaaa aaattcatat aatttagcgt   540
act                                                                 543
```

<210> SEQ ID NO 8
<211> LENGTH: 799
<212> TYPE: DNA
<213> ORGANISM: Artificial
<220> FEATURE:
<223> OTHER INFORMATION: Synthetic carbonic anhydrase pca2 promoter
      AB040136 from Porphyridium purpureum

<400> SEQUENCE: 8

```
gcacacgagt gttgtggcgt tgtcgcagca ggtttggggg cgcgagagcg cacgacgctt     60
gtgtgtgtgt gtgtgtgtgg accgcaacca ccctcgcgac gcggcattgc cgtgcgtgcc    120
gtcgcggctg cgtggttcgt ggtgtgatat tctaaacgca tgtgggttgg gtgtgggtgt    180
tgttctgtgt ccatcaggcg atggacacag ccgccactga agtgtcactg aattaagcgc    240
ggtgcatttt gcacgtggct tttgtgtggg tgtgtgtgta tgtgtcctgc tcggcttgta    300
tcgacatcct ccttcgtttt tctcgtacgg ggcttttgtg tttcctttgg tacgtggtga    360
gcgttttttg gggtgttgcc ggacatgatg gtgttgtgtt tgtgagtttg ggagtgtgag    420
actgggagcg acggtgaagc cgcatgaatc gtggagcgca aaatgcaagt tgactggagc    480
catcgcgatg cttttggcgt tttgcgcatg tgatcacaat ctcctcggaa tggtccaaaa    540
tggatcgaac tggctcgccc cccaatctgt gcgctttcgg cctgttcgga catgccggtt    600
tcgcggtgcg cagcatgtgg ctcgcgcatg gtagggggatg ttggcgcggg gcataaatag    660
gctgcgacaa cttgccgctt ccccttcatc gcacacctca ggcaggagga agtggtggaa    720
aagactggtg caggagagga ttttgcagga gaggaaggag agggagaggc gtgtcgtgct    780
tgccactgcg atagtcacc                                                  799
```

<210> SEQ ID NO 9
<211> LENGTH: 848
<212> TYPE: DNA
<213> ORGANISM: Artificial
<220> FEATURE:
<223> OTHER INFORMATION: Synthetic carbonic anhydrase pca1 promoter AB040135 from Porphyridium purpureum

<400> SEQUENCE: 9

```
gcgtgcgtca agcacattgg ggcaactcgg gcaaccgacg cagccacgca cacgagtgtt     60
gtggcgttgt cgtagcaggt ttgggggcgc gagagcgcac gacgcgtgtg tgtgtgtgtg    120
tgtgtggacc gcaaccaccc tcgcgacgcg gcattgccgt gcctgccgtt gcggctgcgt    180
ggttcgtggt gtgatattct aaacgcatgt gggttgggtg ttggtgttgt tctgtgtcca    240
tcaggcgatg gacacagccg ccactgaagt gtcactgaat taagcgcggt gcattttgca    300
cgtggctttt gtgtgtgtgt gtttgtgtct atgtgtcctg ctcggtttgt atcgacgtcc    360
tccttcgttt ttttcgcacg gggcttttgt ctttcctttg gtacgtggtg agcgtttttt    420
ggggtgttgc cggacatgat ggtgttgtgt ttgtgagttt gagagtgaga ctgggagcga    480
cggtgaagcc gcatgaatcg tggagcgcaa aatgcaagtt gactggagcc atcgcgatgc    540
ttttggcgtt ttgcgcatgt gatcacaatc tcctcggaat ggtccaaaat ggatcgaact    600
ggctcgcccc ccaatctgtg cgctttcggc ctgttcggac atgccggttt cgtggtgcgc    660
agcatgtggc tcgcgcatgg tagggggatgt tggcgcgggg cataaatagg ctgcgacaac    720
ttgccgcttc cccttccctg cacgcctcag gcaggaagaa gtggtggaaa agactggtgc    780
aggagaggat cttgcaggag aggaaggaga gggagaggcg tgtcgtgctt gccactgcaa    840
tcgtcacc                                                              848
```

<210> SEQ ID NO 10
<211> LENGTH: 587
<212> TYPE: PRT
<213> ORGANISM: Artificial
<220> FEATURE:
<223> OTHER INFORMATION: Synthetic sulfometuron resistance- acetohydroxy acid synthase [Porphyridium sp.]

<400> SEQUENCE: 10

```
Met Thr His Ile Glu Lys Ser Asn Tyr Gln Glu Gln Thr Gly Ala Phe
1               5                   10                  15

Ala Leu Leu Asp Ser Leu Val Arg His Lys Val Lys His Ile Phe Gly
            20                  25                  30

Tyr Pro Gly Gly Ala Ile Leu Pro Ile Tyr Asp Glu Leu Tyr Lys Trp
        35                  40                  45

Glu Glu Gln Gly Tyr Ile Lys His Ile Leu Val Arg His Glu Gln Gly
    50                  55                  60

Ala Ala His Ala Ala Asp Gly Tyr Ala Arg Ala Thr Gly Glu Val Gly
65                  70                  75                  80

Val Cys Phe Ala Thr Ser Gly Pro Gly Ala Thr Asn Leu Val Thr Gly
                85                  90                  95

Ile Ala Thr Ala His Met Asp Ser Ile Pro Ile Val Ile Thr Gly
            100                 105                 110

Gln Val Gly Arg Ser Phe Ile Gly Thr Asp Ala Phe Gln Glu Val Asp
        115                 120                 125

Ile Phe Gly Ile Thr Leu Pro Ile Val Lys His Ser Tyr Val Ile Arg
130                 135                 140

Asp Pro Arg Asp Ile Pro Arg Ile Val Ala Glu Ala Phe Ser Ile Ala
145                 150                 155                 160

Lys Gln Gly Arg Pro Gly Pro Val Leu Ile Asp Val Pro Lys Asp Val
                165                 170                 175

Gly Leu Glu Thr Phe Glu Tyr Gln Tyr Val Asn Pro Gly Glu Ala Arg
            180                 185                 190

Ile Pro Gly Phe Arg Asp Leu Val Ala Pro Ser Ser Arg Gln Ile Ile
        195                 200                 205

His Ser Ile Gln Leu Ile Gln Glu Ala Asn Gln Pro Leu Leu Tyr Val
    210                 215                 220

Gly Gly Gly Ala Ile Thr Ser Gly Ala His Asp Leu Ile Tyr Lys Leu
225                 230                 235                 240

Val Asn Gln Tyr Lys Ile Pro Ile Thr Thr Thr Leu Met Gly Lys Gly
                245                 250                 255

Ile Ile Asp Glu Gln Asn Pro Leu Ala Leu Gly Met Leu Gly Met His
            260                 265                 270

Gly Thr Ala Tyr Ala Asn Phe Ala Val Ser Glu Cys Asp Leu Leu Ile
        275                 280                 285

Thr Leu Gly Ala Arg Phe Asp Asp Arg Val Thr Gly Lys Leu Asp Glu
    290                 295                 300

Phe Ala Cys Asn Ala Lys Val Ile His Val Asp Ile Asp Pro Ala Glu
305                 310                 315                 320

Val Gly Lys Asn Arg Ile Pro Gln Val Ala Ile Val Gly Asp Ile Ser
                325                 330                 335

Leu Val Leu Glu Gln Trp Leu Leu Tyr Leu Asp Arg Asn Leu Gln Leu
            340                 345                 350

Asp Asp Ser His Leu Arg Ser Trp His Glu Arg Ile Phe Arg Trp Arg
        355                 360                 365

Gln Glu Tyr Pro Leu Ile Val Pro Lys Leu Val Gln Thr Leu Ser Pro
    370                 375                 380

Gln Glu Ile Ile Ala Asn Ile Ser Gln Ile Met Pro Asp Ala Tyr Phe
385                 390                 395                 400

Ser Thr Asp Val Gly Gln His Gln Met Trp Ala Ala Gln Phe Val Lys
```

```
                    405                 410                 415
Thr Leu Pro Arg Arg Trp Leu Ser Ser Ser Gly Leu Gly Thr Met Gly
            420                 425                 430

Tyr Gly Leu Pro Ala Ala Ile Gly Ala Lys Ile Ala Tyr Pro Glu Ser
        435                 440                 445

Pro Val Val Cys Ile Thr Gly Asp Ser Ser Phe Gln Met Asn Ile Gln
    450                 455                 460

Glu Leu Gly Thr Ile Ala Gln Tyr Lys Leu Asp Ile Lys Ile Ile Ile
465                 470                 475                 480

Ile Asn Asn Lys Trp Gln Gly Met Val Arg Gln Ser Gln Gln Ala Phe
                485                 490                 495

Tyr Gly Ala Arg Tyr Ser His Ser Arg Met Glu Asp Gly Ala Pro Asn
            500                 505                 510

Phe Val Ala Leu Ala Lys Ser Phe Gly Ile Asp Gly Gln Ser Ile Ser
        515                 520                 525

Thr Arg Gln Glu Met Asp Ser Leu Phe Asn Thr Ile Ile Lys Tyr Lys
    530                 535                 540

Gly Pro Met Val Ile Asp Cys Lys Val Ile Glu Asp Glu Asn Cys Tyr
545                 550                 555                 560

Pro Met Val Ala Pro Gly Lys Ser Asn Ala Gln Met Ile Gly Leu Asp
                565                 570                 575

Lys Ser Asn Asn Glu Ile Ile Lys Ile Lys Glu
            580                 585

<210> SEQ ID NO 11
<211> LENGTH: 129
<212> TYPE: PRT
<213> ORGANISM: Artificial
<220> FEATURE:
<223> OTHER INFORMATION: Synthetic zeocin resistance- ble protein

<400> SEQUENCE: 11

Met Ala Arg Met Ala Lys Leu Thr Ser Ala Val Pro Val Leu Thr Ala
1               5                   10                  15

Arg Asp Val Ala Gly Ala Val Glu Phe Trp Thr Asp Arg Leu Gly Phe
            20                  25                  30

Ser Arg Asp Phe Val Glu Asp Phe Ala Gly Val Arg Asp Asp
        35                  40                  45

Val Thr Leu Phe Ile Ser Ala Val Gln Asp Gln Asp Gln Val Val Pro
50                  55                  60

Asp Asn Thr Leu Ala Trp Val Trp Val Arg Gly Leu Asp Glu Leu Tyr
65                  70                  75                  80

Ala Glu Trp Ser Glu Val Val Ser Thr Asn Phe Arg Asp Ala Ser Gly
                85                  90                  95

Pro Ala Met Thr Glu Ile Gly Glu Gln Pro Trp Gly Arg Glu Phe Ala
            100                 105                 110

Leu Arg Asp Pro Ala Gly Asn Cys Val His Phe Val Ala Glu Glu Gln
        115                 120                 125

Asp

<210> SEQ ID NO 12
<211> LENGTH: 144
<212> TYPE: PRT
<213> ORGANISM: Artificial
<220> FEATURE:
<223> OTHER INFORMATION: Synthetic Superoxide Dismutase From AAB60930
```

```
<400> SEQUENCE: 12

Gly Tyr Val Asn Gly Leu Glu Ser Ala Glu Glu Thr Leu Ala Glu Asn
1               5                   10                  15

Arg Glu Ser Gly Asp Phe Gly Ser Ala Ala Ala Met Gly Asn Val
            20                  25                  30

Thr His Asn Gly Cys Gly His Tyr Leu His Thr Leu Phe Trp Glu Asn
            35                  40                  45

Met Asp Pro Asn Gly Gly Gly Glu Pro Glu Gly Glu Leu Leu Asp Arg
    50                  55                  60

Ile Glu Glu Asp Phe Gly Ser Tyr Glu Gly Trp Lys Gly Glu Phe Glu
65                  70                  75                  80

Ala Ala Ala Ser Ala Ala Gly Gly Trp Ala Leu Leu Val Tyr Asp Pro
                85                  90                  95

Val Ala Lys Gln Leu Arg Asn Val Pro Val Asp Lys His Asp Gln Gly
            100                 105                 110

Ala Leu Trp Gly Ser His Pro Ile Leu Ala Leu Asp Val Trp Glu His
            115                 120                 125

Ser Tyr Tyr Tyr Asp Tyr Gly Pro Ala Arg Gly Asp Phe Ile Asp Ala
            130                 135                 140

<210> SEQ ID NO 13
<211> LENGTH: 154
<212> TYPE: PRT
<213> ORGANISM: Artificial
<220> FEATURE:
<223> OTHER INFORMATION: Synthetic Superoxide Dismutase from NP_000445

<400> SEQUENCE: 13

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150

<210> SEQ ID NO 14
<211> LENGTH: 711
<212> TYPE: PRT
<213> ORGANISM: Artificial
<220> FEATURE:
<223> OTHER INFORMATION: Synthetic Superoxide Dismutase-Polysaccharide
      binding protein fusion AAV48590-NP_000445

<400> SEQUENCE: 14
```

```
Met Ala Arg Met Val Ala Ala Val Ala Val Met Ala Val Leu Ser
1               5                   10                  15

Val Ala Leu Ala Gln Phe Ile Pro Asp Val Asp Ile Thr Trp Lys Val
            20                  25                  30

Pro Met Thr Leu Thr Val Gln Asn Leu Ser Ile Phe Thr Gly Pro Asn
        35                  40                  45

Gln Phe Gly Arg Gly Ile Pro Ser Pro Ser Ala Ile Gly Gly Asn
50                      55                  60

Gly Leu Asp Ile Val Gly Gly Gly Ser Leu Tyr Ile Ser Pro Thr
65                  70                  75                  80

Gly Gly Gln Val Gln Tyr Ser Arg Gly Ser Asn Asn Phe Gly Asn Gln
                85                  90                  95

Val Ala Phe Thr Arg Val Arg Lys Asn Gly Asn Asn Glu Ser Asp Phe
                100                 105                 110

Ala Thr Val Phe Val Gly Gly Thr Thr Pro Ser Phe Val Ile Val Gly
                115                 120                 125

Asp Ser Thr Glu Asn Glu Val Ser Phe Trp Thr Asn Asn Lys Val Val
        130                 135                 140

Val Asn Ser Gln Gly Phe Ile Pro Pro Asn Gly Asn Ser Ala Gly Gly
145                 150                 155                 160

Asn Ser Gln Tyr Thr Phe Val Asn Gly Ile Thr Gly Thr Ala Gly Ala
                165                 170                 175

Pro Val Gly Gly Thr Val Ile Arg Gln Val Ser Ala Trp Arg Glu Ile
                180                 185                 190

Phe Asn Thr Ala Gly Asn Cys Val Lys Ser Phe Gly Leu Val Val Arg
                195                 200                 205

Gly Thr Gly Asn Gln Gly Leu Val Gln Gly Val Glu Tyr Asp Gly Tyr
                210                 215                 220

Val Ala Ile Asp Ser Asn Gly Ser Phe Ala Ile Ser Gly Tyr Ser Pro
225                 230                 235                 240

Ala Val Asn Asn Ala Pro Gly Phe Gly Lys Asn Phe Ala Ala Ala Arg
                245                 250                 255

Thr Gly Asn Phe Phe Ala Val Ser Ser Glu Ser Gly Val Ile Val Met
                260                 265                 270

Ser Ile Pro Val Asp Asn Ala Gly Cys Thr Leu Ser Phe Ser Val Ala
                275                 280                 285

Tyr Thr Ile Thr Pro Gly Ala Gly Arg Val Ser Gly Val Ser Leu Ala
                290                 295                 300

Gln Asp Asn Glu Phe Tyr Ala Ala Val Gly Ile Pro Gly Ala Gly Pro
305                 310                 315                 320

Gly Glu Val Arg Ile Tyr Arg Leu Asp Gly Gly Ala Thr Thr Leu
                325                 330                 335

Val Gln Thr Leu Ser Pro Pro Asp Asp Ile Pro Glu Leu Pro Ile Val
                340                 345                 350

Ala Asn Gln Arg Phe Gly Glu Met Val Arg Phe Gly Ala Asn Ser Glu
                355                 360                 365

Thr Asn Tyr Val Ala Val Gly Ser Pro Gly Tyr Ala Ala Glu Gly Leu
                370                 375                 380

Ala Leu Phe Tyr Thr Ala Glu Pro Gly Leu Thr Pro Asn Asp Pro Asp
385                 390                 395                 400

Glu Gly Leu Leu Thr Leu Leu Ala Tyr Ser Asn Ser Glu Ile Pro
                405                 410                 415
```

```
Ala Asn Gly Gly Leu Gly Glu Phe Met Thr Ala Ser Asn Cys Arg Gln
            420                 425                 430

Phe Val Phe Gly Glu Pro Ser Val Asp Ser Val Thr Phe Leu Ala
        435                 440                 445

Ser Ile Gly Ala Tyr Tyr Glu Asp Tyr Cys Thr Cys Glu Arg Glu Asn
450                 455                 460

Ile Phe Asp Gln Gly Ile Met Phe Pro Val Pro Asn Phe Pro Gly Glu
465                 470                 475                 480

Ser Pro Thr Thr Cys Arg Ser Ser Ile Tyr Glu Phe Arg Phe Asn Cys
            485                 490                 495

Leu Met Glu Gly Ala Pro Ser Ile Cys Thr Tyr Ser Gly Arg Pro Thr
            500                 505                 510

Tyr Glu Trp Thr Glu Glu Val Val Asp Pro Asp Asn Thr Pro Cys Glu
            515                 520                 525

Leu Val Ser Arg Ile Gln Arg Arg Leu Ser Gln Ser Asn Cys Phe Gln
            530                 535                 540

Asp Tyr Val Thr Leu Gln Val Val Gly Ala Gly Ala Gly Met Ala Thr
545                 550                 555                 560

Lys Ala Val Cys Val Leu Lys Gly Asp Gly Pro Val Gln Gly Ile Ile
                565                 570                 575

Asn Phe Glu Gln Lys Glu Ser Asn Gly Pro Val Lys Val Trp Gly Ser
            580                 585                 590

Ile Lys Gly Leu Thr Glu Gly Leu His Gly Phe His Val His Glu Phe
            595                 600                 605

Gly Asp Asn Thr Ala Gly Cys Thr Ser Ala Gly Pro His Phe Asn Pro
610                 615                 620

Leu Ser Arg Lys His Gly Gly Pro Lys Asp Glu Glu Arg His Val Gly
625                 630                 635                 640

Asp Leu Gly Asn Val Thr Ala Asp Lys Asp Gly Val Ala Asp Val Ser
                645                 650                 655

Ile Glu Asp Ser Val Ile Ser Leu Ser Gly Asp His Cys Ile Ile Gly
            660                 665                 670

Arg Thr Leu Val Val His Glu Lys Ala Asp Asp Leu Gly Lys Gly Gly
            675                 680                 685

Asn Glu Glu Ser Thr Lys Thr Gly Asn Ala Gly Ser Arg Leu Ala Cys
690                 695                 700

Gly Val Ile Gly Ile Ala Gln
705                 710

<210> SEQ ID NO 15
<211> LENGTH: 552
<212> TYPE: PRT
<213> ORGANISM: Artificial
<220> FEATURE:
<223> OTHER INFORMATION: Synthetic protein associated with
      polysaccharide from Porphyridium from AAV48590

<400> SEQUENCE: 15

Met Ala Arg Met Val Val Ala Val Ala Val Met Ala Val Leu Ser
1               5                   10                  15

Val Ala Leu Ala Gln Phe Ile Pro Asp Val Asp Ile Thr Trp Lys Val
            20                  25                  30

Pro Met Thr Leu Thr Val Gln Asn Leu Ser Ile Phe Thr Gly Pro Asn
            35                  40                  45

Gln Phe Gly Arg Gly Ile Pro Ser Pro Ser Ala Ile Gly Gly Gly Asn
50                  55                  60
```

```
Gly Leu Asp Ile Val Gly Gly Gly Ser Leu Tyr Ile Ser Pro Thr
 65                  70                  75                  80

Gly Gly Gln Val Gln Tyr Ser Arg Gly Ser Asn Asn Phe Gly Asn Gln
             85                      90                  95

Val Ala Phe Thr Arg Val Arg Lys Asn Gly Asn Asn Glu Ser Asp Phe
            100                 105                 110

Ala Thr Val Phe Val Gly Gly Thr Thr Pro Ser Phe Val Ile Val Gly
            115                 120                 125

Asp Ser Thr Glu Asn Glu Val Ser Phe Trp Thr Asn Asn Lys Val Val
            130                 135                 140

Val Asn Ser Gln Gly Phe Ile Pro Pro Asn Gly Asn Ser Ala Gly Gly
145                 150                 155                 160

Asn Ser Gln Tyr Thr Phe Val Asn Gly Ile Thr Gly Thr Ala Gly Ala
                165                 170                 175

Pro Val Gly Gly Thr Val Ile Arg Gln Val Ser Ala Trp Arg Glu Ile
                180                 185                 190

Phe Asn Thr Ala Gly Asn Cys Val Lys Ser Phe Gly Leu Val Val Arg
                195                 200                 205

Gly Thr Gly Asn Gln Gly Leu Val Gln Gly Val Glu Tyr Asp Gly Tyr
    210                 215                 220

Val Ala Ile Asp Ser Asn Gly Ser Phe Ala Ile Ser Gly Tyr Ser Pro
225                 230                 235                 240

Ala Val Asn Asn Ala Pro Gly Phe Gly Lys Asn Phe Ala Ala Ala Arg
                245                 250                 255

Thr Gly Asn Phe Phe Ala Val Ser Ser Glu Ser Gly Val Ile Val Met
                260                 265                 270

Ser Ile Pro Val Asp Asn Ala Gly Cys Thr Leu Ser Phe Ser Val Ala
                275                 280                 285

Tyr Thr Ile Thr Pro Gly Ala Gly Arg Val Ser Gly Val Ser Leu Ala
    290                 295                 300

Gln Asp Asn Glu Phe Tyr Ala Ala Val Gly Ile Pro Gly Ala Gly Pro
305                 310                 315                 320

Gly Glu Val Arg Ile Tyr Arg Leu Asp Gly Gly Ala Thr Thr Leu
                325                 330                 335

Val Gln Thr Leu Ser Pro Pro Asp Asp Ile Pro Glu Leu Pro Ile Val
                340                 345                 350

Ala Asn Gln Arg Phe Gly Glu Met Val Arg Phe Gly Ala Asn Ser Glu
                355                 360                 365

Thr Asn Tyr Val Ala Val Gly Ser Pro Gly Tyr Ala Ala Glu Gly Leu
    370                 375                 380

Ala Leu Phe Tyr Thr Ala Glu Pro Gly Leu Thr Pro Asn Asp Pro Asp
385                 390                 395                 400

Glu Gly Leu Leu Thr Leu Leu Ala Tyr Ser Asn Ser Ser Glu Ile Pro
                405                 410                 415

Ala Asn Gly Gly Leu Gly Glu Phe Met Thr Ala Ser Asn Cys Arg Gln
                420                 425                 430

Phe Val Phe Gly Glu Pro Ser Val Asp Ser Val Thr Phe Leu Ala
                435                 440                 445

Ser Ile Gly Ala Tyr Tyr Glu Asp Tyr Cys Thr Cys Glu Arg Glu Asn
    450                 455                 460

Ile Phe Asp Gln Gly Ile Met Phe Pro Val Pro Asn Phe Pro Gly Glu
465                 470                 475                 480
```

```
Ser Pro Thr Thr Cys Arg Ser Ser Ile Tyr Glu Phe Arg Phe Asn Cys
            485                 490                 495

Leu Met Glu Gly Ala Pro Ser Ile Cys Thr Tyr Ser Glu Arg Pro Thr
        500                 505                 510

Tyr Glu Trp Thr Glu Glu Val Val Asp Pro Asp Asn Thr Pro Cys Glu
        515                 520                 525

Leu Val Ser Arg Ile Gln Arg Arg Leu Ser Gln Ser Asn Cys Phe Gln
        530                 535                 540

Asp Tyr Val Thr Leu Gln Val Val
545                 550

<210> SEQ ID NO 16
<211> LENGTH: 207
<212> TYPE: DNA
<213> ORGANISM: Artificial
<220> FEATURE:
<223> OTHER INFORMATION: Synthetic RBCS2 promoter from Chlamydomonas
      reinhardtii

<400> SEQUENCE: 16
gccagaagga gcgcagccaa accaggatga tgtttgatgg ggtatttgag cacttgcaac      60
ccttatccgg aagcccctg gcccacaaag gctaggcgcc aatgcaagca gttcgcatgc     120 agccctgga gcggtgccct cctgataaac cggccagggg gcctatgttc tttactttt     180 tacaagagaa gtcactcaac atcttaa                                         207

<210> SEQ ID NO 17
<211> LENGTH: 706
<212> TYPE: PRT
<213> ORGANISM: Artificial
<220> FEATURE:
<223> OTHER INFORMATION: Synthetic Superoxide Dismutase-Polysaccharide
      binding protein fusion AAV48590-NP_000445

<400> SEQUENCE: 17

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Met Ala Arg Met Val Val
145                 150                 155                 160

Ala Ala Val Ala Val Met Ala Val Leu Ser Val Ala Leu Ala Gln Phe
                165                 170                 175

Ile Pro Asp Val Asp Ile Thr Trp Lys Val Pro Met Thr Leu Thr Val
```

```
                180              185              190
    Gln Asn Leu Ser Ile Phe Thr Gly Pro Asn Gln Phe Gly Arg Gly Ile
                    195              200              205
    Pro Ser Pro Ser Ala Ile Gly Gly Asn Gly Leu Asp Ile Val Gly
            210              215              220
    Gly Gly Gly Ser Leu Tyr Ile Ser Pro Thr Gly Gln Val Gln Tyr
    225              230              235              240
    Ser Arg Gly Ser Asn Asn Phe Gly Asn Gln Val Ala Phe Thr Arg Val
                    245              250              255
    Arg Lys Asn Gly Asn Asn Glu Ser Asp Phe Ala Thr Val Phe Val Gly
                    260              265              270
    Gly Thr Thr Pro Ser Phe Val Ile Val Gly Asp Ser Thr Glu Asn Glu
                275              280              285
    Val Ser Phe Trp Thr Asn Lys Val Val Asn Ser Gln Gly Phe
                290              295              300
    Ile Pro Pro Asn Gly Asn Ser Ala Gly Gly Asn Ser Gln Tyr Thr Phe
    305              310              315              320
    Val Asn Gly Ile Thr Gly Thr Ala Gly Ala Pro Val Gly Gly Thr Val
                    325              330              335
    Ile Arg Gln Val Ser Ala Trp Arg Glu Ile Phe Asn Thr Ala Gly Asn
                    340              345              350
    Cys Val Lys Ser Phe Gly Leu Val Val Arg Gly Thr Gly Asn Gln Gly
                    355              360              365
    Leu Val Gln Gly Val Glu Tyr Asp Gly Tyr Val Ala Ile Asp Ser Asn
                370              375              380
    Gly Ser Phe Ala Ile Ser Gly Tyr Ser Pro Ala Val Asn Asn Ala Pro
    385              390              395              400
    Gly Phe Gly Lys Asn Phe Ala Ala Arg Thr Gly Asn Phe Phe Ala
                    405              410              415
    Val Ser Ser Glu Ser Gly Val Ile Val Met Ser Ile Pro Val Asp Asn
                    420              425              430
    Ala Gly Cys Thr Leu Ser Phe Ser Val Ala Tyr Thr Ile Thr Pro Gly
                    435              440              445
    Ala Gly Arg Val Ser Gly Val Ser Leu Ala Gln Asp Asn Glu Phe Tyr
                450              455              460
    Ala Ala Val Gly Ile Pro Gly Ala Gly Pro Gly Glu Val Arg Ile Tyr
    465              470              475              480
    Arg Leu Asp Gly Gly Ala Thr Thr Leu Val Gln Thr Leu Ser Pro
                    485              490              495
    Pro Asp Asp Ile Pro Glu Leu Pro Ile Val Ala Asn Gln Arg Phe Gly
                    500              505              510
    Glu Met Val Arg Phe Gly Ala Asn Ser Glu Thr Asn Tyr Val Ala Val
                    515              520              525
    Gly Ser Pro Gly Tyr Ala Ala Glu Gly Leu Ala Leu Phe Tyr Thr Ala
                530              535              540
    Glu Pro Gly Leu Thr Pro Asn Asp Pro Asp Glu Gly Leu Leu Thr Leu
    545              550              555              560
    Leu Ala Tyr Ser Asn Ser Ser Glu Ile Pro Ala Asn Gly Gly Leu Gly
                    565              570              575
    Glu Phe Met Thr Ala Ser Asn Cys Arg Gln Phe Val Phe Gly Glu Pro
                    580              585              590
    Ser Val Asp Ser Val Val Thr Phe Leu Ala Ser Ile Gly Ala Tyr Tyr
                595              600              605
```

Glu Asp Tyr Cys Thr Cys Glu Arg Glu Asn Ile Phe Asp Gln Gly Ile
            610                 615                 620

Met Phe Pro Val Pro Asn Phe Pro Gly Glu Ser Pro Thr Thr Cys Arg
625                 630                 635                 640

Ser Ser Ile Tyr Glu Phe Arg Phe Asn Cys Leu Met Glu Gly Ala Pro
            645                 650                 655

Ser Ile Cys Thr Tyr Ser Glu Arg Pro Thr Tyr Glu Trp Thr Glu Glu
            660                 665                 670

Val Val Asp Pro Asp Asn Thr Pro Cys Glu Leu Val Ser Arg Ile Gln
            675                 680                 685

Arg Arg Leu Ser Gln Ser Asn Cys Phe Gln Asp Tyr Val Thr Leu Gln
            690                 695                 700

Val Val
705

<210> SEQ ID NO 18
<211> LENGTH: 763
<212> TYPE: PRT
<213> ORGANISM: Artificial
<220> FEATURE:
<223> OTHER INFORMATION: Synthetic Zeaxanthin epoxidase from AAO34404

<400> SEQUENCE: 18

Met Leu Ala Ser Thr Tyr Thr Pro Cys Gly Val Arg Gln Val Ala Gly
1               5                   10                  15

Arg Thr Val Ala Val Pro Ser Ser Leu Val Ala Pro Val Ala Val Ala
            20                  25                  30

Arg Ser Leu Gly Leu Ala Pro Tyr Val Pro Val Cys Glu Pro Ser Ala
            35                  40                  45

Ala Leu Pro Ala Cys Gln Gln Pro Ser Gly Arg Arg His Val Gln Thr
    50                  55                  60

Ala Ala Thr Leu Arg Ala Asp Asn Pro Ser Ser Val Ala Gln Leu Val
65                  70                  75                  80

His Gln Asn Gly Lys Gly Met Lys Val Ile Ile Ala Gly Ala Gly Ile
                85                  90                  95

Gly Gly Leu Val Leu Ala Val Ala Leu Leu Lys Gln Gly Phe Gln Val
            100                 105                 110

Gln Val Phe Glu Arg Asp Leu Thr Ala Ile Arg Gly Glu Gly Lys Tyr
            115                 120                 125

Arg Gly Pro Ile Gln Val Gln Ser Asn Ala Leu Ala Ala Leu Glu Ala
    130                 135                 140

Ile Asp Pro Glu Val Ala Ala Glu Val Leu Arg Glu Gly Cys Ile Thr
145                 150                 155                 160

Gly Asp Arg Ile Asn Gly Leu Cys Asp Gly Leu Thr Gly Glu Trp Tyr
                165                 170                 175

Val Lys Phe Asp Thr Phe His Pro Ala Val Ser Lys Gly Leu Pro Val
            180                 185                 190

Thr Arg Val Ile Ser Arg Leu Thr Leu Gln Gln Ile Leu Ala Lys Ala
            195                 200                 205

Val Glu Arg Tyr Gly Gly Pro Gly Thr Ile Gln Asn Gly Cys Asn Val
    210                 215                 220

Thr Glu Phe Thr Glu Arg Arg Asn Asp Thr Thr Gly Asn Asn Glu Val
225                 230                 235                 240

Thr Val Gln Leu Glu Asp Gly Arg Thr Phe Ala Ala Asp Val Leu Val
            245                 250                 255

```
Gly Ala Asp Gly Ile Trp Ser Lys Ile Arg Lys Gln Leu Ile Gly Glu
            260                 265                 270

Thr Lys Ala Asn Tyr Ser Gly Tyr Thr Cys Tyr Thr Gly Ile Ser Asp
            275                 280                 285

Phe Thr Pro Ala Asp Ile Asp Ile Val Gly Tyr Arg Val Phe Leu Gly
            290                 295                 300

Asn Gly Gln Tyr Phe Val Ser Ser Asp Val Gly Asn Gly Lys Met Gln
305                 310                 315                 320

Trp Tyr Gly Phe His Lys Glu Pro Ser Gly Gly Thr Asp Pro Glu Gly
                325                 330                 335

Ser Arg Lys Ala Arg Leu Leu Gln Ile Phe Gly His Trp Asn Asp Asn
            340                 345                 350

Val Val Asp Leu Ile Lys Ala Thr Pro Glu Glu Asp Val Leu Arg Arg
            355                 360                 365

Asp Ile Phe Asp Arg Pro Pro Ile Phe Thr Trp Ser Lys Gly Arg Val
    370                 375                 380

Ala Leu Leu Gly Asp Ser Ala His Ala Met Gln Pro Asn Leu Gly Gln
385                 390                 395                 400

Gly Gly Cys Met Ala Ile Glu Asp Ala Tyr Glu Leu Ala Ile Asp Leu
            405                 410                 415

Ser Arg Ala Val Ser Asp Lys Ala Gly Asn Ala Ala Val Asp Val
            420                 425                 430

Glu Gly Val Leu Arg Ser Tyr Gln Asp Ser Arg Ile Leu Arg Val Ser
            435                 440                 445

Ala Ile His Gly Met Ala Gly Met Ala Ala Phe Met Ala Ser Thr Tyr
    450                 455                 460

Lys Cys Tyr Leu Gly Glu Gly Trp Ser Lys Trp Val Glu Gly Leu Arg
465                 470                 475                 480

Ile Pro His Pro Gly Arg Val Val Gly Arg Leu Val Met Leu Leu Thr
            485                 490                 495

Met Pro Ser Val Leu Glu Trp Val Leu Gly Gly Asn Thr Asp His Val
            500                 505                 510

Ala Pro His Arg Thr Ser Tyr Cys Ser Leu Gly Asp Lys Pro Lys Ala
            515                 520                 525

Phe Pro Glu Ser Arg Phe Pro Glu Phe Met Asn Asn Asp Ala Ser Ile
            530                 535                 540

Ile Arg Ser Ser His Ala Asp Trp Leu Leu Val Ala Glu Arg Asp Ala
545                 550                 555                 560

Ala Thr Ala Ala Ala Ala Asn Val Asn Ala Thr Gly Ser Ser Ala
            565                 570                 575

Ala Ala Ala Ala Ala Asp Val Asn Ser Ser Cys Gln Cys Lys Gly
            580                 585                 590

Ile Tyr Met Ala Asp Ser Ala Ala Leu Val Gly Arg Cys Gly Ala Thr
            595                 600                 605

Ser Arg Pro Ala Leu Ala Val Asp Asp Val His Val Ala Glu Ser His
            610                 615                 620

Ala Gln Val Trp Arg Gly Leu Ala Gly Leu Pro Pro Ser Ser Ser
625                 630                 635                 640

Ala Ser Thr Ala Ala Ala Ser Ala Ser Ala Ala Ser Ser Ala Ala Ser
            645                 650                 655

Gly Thr Ala Ser Thr Leu Gly Ser Ser Glu Gly Tyr Trp Leu Arg Asp
            660                 665                 670
```

```
Leu Gly Ser Gly Arg Gly Thr Trp Val Asn Gly Lys Arg Leu Pro Asp
            675                 680                 685

Gly Ala Thr Val Gln Leu Trp Pro Gly Asp Ala Val Glu Phe Gly Arg
    690                 695                 700

His Pro Ser His Glu Val Phe Lys Val Lys Met Gln His Val Thr Leu
705                 710                 715                 720

Arg Ser Asp Glu Leu Ser Gly Gln Ala Tyr Thr Thr Leu Met Val Gly
                725                 730                 735

Lys Ile Arg Asn Asn Asp Tyr Val Met Pro Glu Ser Arg Pro Asp Gly
            740                 745                 750

Gly Ser Gln Gln Pro Gly Arg Leu Val Thr Ala
            755                 760
```

<210> SEQ ID NO 19
<211> LENGTH: 524
<212> TYPE: PRT
<213> ORGANISM: Artificial
<220> FEATURE:
<223> OTHER INFORMATION: Synthetic lycopene epsilon cyclase from BAA97033

<400> SEQUENCE: 19

```
Met Glu Cys Val Gly Ala Arg Asn Phe Ala Ala Met Ala Val Ser Thr
1               5                   10                  15

Phe Pro Ser Trp Ser Cys Arg Arg Lys Phe Pro Val Val Lys Arg Tyr
            20                  25                  30

Ser Tyr Arg Asn Ile Arg Phe Gly Leu Cys Ser Val Arg Ala Ser Gly
        35                  40                  45

Gly Gly Ser Ser Gly Ser Glu Ser Cys Val Ala Val Arg Glu Asp Phe
    50                  55                  60

Ala Asp Glu Glu Asp Phe Val Lys Ala Gly Ser Glu Ile Leu Phe
65                  70                  75                  80

Val Gln Met Gln Gln Asn Lys Asp Met Asp Glu Gln Ser Lys Leu Val
                85                  90                  95

Asp Lys Leu Pro Pro Ile Ser Ile Gly Asp Gly Ala Leu Asp Leu Val
            100                 105                 110

Val Ile Gly Cys Gly Pro Ala Gly Leu Ala Leu Ala Ala Glu Ser Ala
        115                 120                 125

Lys Leu Gly Leu Lys Val Gly Leu Ile Gly Pro Asp Leu Pro Phe Thr
    130                 135                 140

Asn Asn Tyr Gly Val Trp Glu Asp Glu Phe Asn Asp Leu Gly Leu Gln
145                 150                 155                 160

Lys Cys Ile Glu His Val Trp Arg Glu Thr Ile Val Tyr Leu Asp Asp
                165                 170                 175

Asp Lys Pro Ile Thr Ile Gly Arg Ala Tyr Gly Arg Val Ser Arg Arg
            180                 185                 190

Leu Leu His Glu Glu Leu Leu Arg Arg Cys Val Glu Ser Gly Val Ser
        195                 200                 205

Tyr Leu Ser Ser Lys Val Asp Ser Ile Thr Glu Ala Ser Asp Gly Leu
    210                 215                 220

Arg Leu Val Ala Cys Asp Asp Asn Val Ile Pro Cys Arg Leu Ala
225                 230                 235                 240

Thr Val Ala Ser Gly Ala Ala Ser Gly Lys Leu Leu Gln Tyr Glu Val
                245                 250                 255

Gly Gly Pro Arg Val Cys Val Gln Thr Ala Tyr Gly Val Glu Val Glu
            260                 265                 270
```

Val Glu Asn Ser Pro Tyr Asp Pro Asp Gln Met Val Phe Met Asp Tyr
    275                 280                 285

Arg Asp Tyr Thr Asn Glu Lys Val Arg Ser Leu Glu Ala Glu Tyr Pro
    290                 295                 300

Thr Phe Leu Tyr Ala Met Pro Met Thr Lys Ser Arg Leu Phe Phe Glu
305                 310                 315                 320

Glu Thr Cys Leu Ala Ser Lys Asp Val Met Pro Phe Asp Leu Leu Lys
                325                 330                 335

Thr Lys Leu Met Leu Arg Leu Asp Thr Leu Gly Ile Arg Ile Leu Lys
                340                 345                 350

Thr Tyr Glu Glu Glu Trp Ser Tyr Ile Pro Val Gly Gly Ser Leu Pro
        355                 360                 365

Asn Thr Glu Gln Lys Asn Leu Ala Phe Gly Ala Ala Ala Ser Met Val
    370                 375                 380

His Pro Ala Thr Gly Tyr Ser Val Val Arg Ser Leu Ser Glu Ala Pro
385                 390                 395                 400

Lys Tyr Ala Ser Val Ile Ala Glu Ile Leu Arg Glu Thr Thr Lys
                405                 410                 415

Gln Ile Asn Ser Asn Ile Ser Arg Gln Ala Trp Asp Thr Leu Trp Pro
            420                 425                 430

Pro Glu Arg Lys Arg Gln Arg Ala Phe Phe Leu Phe Gly Leu Ala Leu
        435                 440                 445

Ile Val Gln Phe Asp Thr Glu Gly Ile Arg Ser Phe Phe Arg Thr Phe
    450                 455                 460

Phe Arg Leu Pro Lys Trp Met Trp Gln Gly Phe Leu Gly Ser Thr Leu
465                 470                 475                 480

Thr Ser Gly Asp Leu Val Leu Phe Ala Leu Tyr Met Phe Val Ile Ser
                485                 490                 495

Pro Asn Asn Leu Arg Lys Gly Leu Ile Asn His Leu Ile Ser Asp Pro
            500                 505                 510

Thr Gly Ala Thr Met Ile Lys Thr Tyr Leu Lys Val
        515                 520

<210> SEQ ID NO 20
<211> LENGTH: 828
<212> TYPE: DNA
<213> ORGANISM: Artificial
<220> FEATURE:
<223> OTHER INFORMATION: Synthetic Porphyra EF1 promoter

<400> SEQUENCE: 20
aagcttcgct gccaggctct ccatcagcga cttgcggtcg gtgctgtttg gggaccggcg    60
ggaagcgcac cagaatgtgg ggggagacag gcagggctca gagacacgag tggagagcat   120
tgatcagtaa cagtcgcacg tcagactggg tctgcgtggg gccacgaaag cgcaaaaatg   180
ggcctagcag gcgccgtcaa ccttctcaag ctcagagcgc cgccaggctg cacaccccg    240 aggcgacggc cagtagcacc tgcgccacgg agacaccgtc tcctgctaac atacggttgt   300
tcgtccgcca tcgagaacag ctaggtacaa ataccacga ggaagggaag aaaagccttg    360
aatggcaaag ggtggtcgaa ggcaagccag agagggacgt tctacatgca ccaaagccag   420
taggagcgca ctacgcggta agcggtcgcc gaaagagggg gggcgaccca cgctcgtcac   480
tgcaggttgt attgtgccgg tccgcaactg ccactggcgg tgtttgtcaa gcggccacca   540
cgagtctcga gggctcagca attgcaccgc tggcacgcag aatgtggcct tccccgagtt   600

```
tacagtggtc cttttccccg aaagcatccc taaaaaaagg aattgagcga cggcgacgcc    660
gaccgacgtc cgcggcggcg gccacaggcg agggacggag gaccaccggc cttttaaatg    720
ggcgtcgaag accacgtgct cggcacacca ccccgtcgac atcgctatcg tacccgtctt    780
ccccgccgat tgacgtcttg agtttacctg ttcacctagc ctttcatc                 828

<210> SEQ ID NO 21
<211> LENGTH: 1759
<212> TYPE: DNA
<213> ORGANISM: Artificial
<220> FEATURE:
<223> OTHER INFORMATION: Synthetic Glycoprotein promoter from
      Porphyridium sp.

<400> SEQUENCE: 21
cgtcattagc gaagcgtccg cgttcacagc gttcgatgga ggtggcaggg acaatgatgg     60
tggagcctct tcgcacctca gcgcggcata caccacaaaa ccaccgtcta actcgaggga    120
cagcgcctgg cgcacgttgg atttcagggt cgcgtaccgc gccaggtcaa agtggatctt    180
accgaccagt ttttcgttgt cactgctagc cgcggtcacc gactttgccg agtctgtgtg    240
gtacagctgc agcacggcaa agcgctggtg gcgatcttca aagtttcggt ccgatgcgcg    300
tctcgacagg cgcgcaggaa cgctgaaggt ctcgttccac acggccacgt tgggctgatg    360
gtcgaaactg acgaatgcgc ttggttttcg tcccggccg tccgagcacc tgctggtctc     420
catacgcgag tcgaaagcga tacgtgccat ccactttcat gcgggtcact ttctccactt    480
cgagcgtaaa tatgaacgta tgcgagcaga ggtgcccacc gccactcacg ttcgtgccgg    540
tgtcgacgcc attcgtcgcc catgacgagg aagagagcaa gacgacgttt ccagccctgc    600
tcgccgactt gctctgcgcc gacgacgcgg acgcctgcgt cacactggag gagtttgagg    660
cgttggacgc gcgcacgctg gactctcgct tcactagcaa gccactcccg ctgcgatcga    720
gcgacggcga gcgcgagccc ttcctactct cactgcgcga cgaggcggtc gagtccgagc    780
gactcacctg gcttaagcgt ctctcgctca tgacgcgctt gacgagcacc ttgcgagtag    840
ccagccgcac ctctaccgc gcatgccaac ctcactccag tgtctcgcaa gcaaccacga    900
tgctccttcc cagtcgaatg cgacacgcga ccacgttcgc cgcgcaactt tttttccac    960 cgcagaaatt ggcgcggacg aagtacagct gacccgcacc aacggtacag tcatgagctt   1020
gtaactgcca cttcgcactt ttgtaacgta taaaataacg atacaaaggt ggattaatta   1080
tttcattttt tcatgttcca gatgtttcaa gctctcatgc tttgtgagtg ttttggatg    1140 tgtagccggc aaccctactt gttcgggcaa cgaaacagat tgttcgtgcg gttggcgcgg   1200
ttgacgcggt tgatgacaac tggatgacga aaccagtgc gcaagaaggg ggggggggtt    1260
aagtatagtg tgtttagtca acgaacgcg tgtgaattta aatgctttgg ggtgtagtca    1320
aacgggtgtg gtttacaagg cgctgccaag cagcgggagt acagcgctgt acgccgccga   1380
tttcaaaagg agacacgcgc gagcaacaaa atcacgaatc gggtggattt tgcgtggtgc   1440
gttcgttggg gtgtgtgtgt ggcgctggcg gttggacacg cgtaacaaat gcaggctgtt   1500
ttactataaa gtcgggcgag aagcggatgg ctggtgcggt gtgatgggcg cgcacgacgc   1560
cacgcagtgc ctctatgcaa tcgagaggga gatgcgaaaa aaaggggggcg gtctggtata   1620 aagtgcgcgg gcacgtcgta ggtacttaaa tgctgtgggg acggtgaaaa gagtgcgtga   1680
gtgaggtgtg tggacgaaag ggagagggaa gagggagtgg gtggccgctg tagagaacac   1740
ggtcgggtgc agtaacgaa                                                1759
```

<210> SEQ ID NO 22
<211> LENGTH: 1712
<212> TYPE: PRT
<213> ORGANISM: Artificial
<220> FEATURE:
<223> OTHER INFORMATION: Synthetic Glycoprotein-collagen fusion
      AAV48590-CAA34683

<400> SEQUENCE: 22

| | | | | | | | | | | | | | | |
|---|---|---|---|---|---|---|---|---|---|---|---|---|---|---|
| Met | Ala | Arg | Met | Val | Val | Ala | Val | Ala | Val | Met | Ala | Val | Leu | Ser |
| 1 | | | | 5 | | | | | 10 | | | | | 15 |
| Val | Ala | Leu | Ala | Gln | Phe | Ile | Pro | Asp | Val | Asp | Ile | Thr | Trp | Lys | Val |
| | | | 20 | | | | | 25 | | | | | 30 | | |
| Pro | Met | Thr | Leu | Thr | Val | Gln | Asn | Leu | Ser | Ile | Phe | Thr | Gly | Pro | Asn |
| | | | 35 | | | | | 40 | | | | | 45 | | |
| Gln | Phe | Gly | Arg | Gly | Ile | Pro | Ser | Pro | Ser | Ala | Ile | Gly | Gly | Gly | Asn |
| | | | 50 | | | | | 55 | | | | | 60 | | |
| Gly | Leu | Asp | Ile | Val | Gly | Gly | Gly | Ser | Leu | Tyr | Ile | Ser | Pro | Thr |
| 65 | | | | | 70 | | | | | 75 | | | | | 80 |
| Gly | Gly | Gln | Val | Gln | Tyr | Ser | Arg | Gly | Ser | Asn | Asn | Phe | Gly | Asn | Gln |
| | | | | 85 | | | | | 90 | | | | | 95 | |
| Val | Ala | Phe | Thr | Arg | Val | Arg | Lys | Asn | Gly | Asn | Asn | Glu | Ser | Asp | Phe |
| | | | | 100 | | | | | 105 | | | | | 110 | |
| Ala | Thr | Val | Phe | Val | Gly | Gly | Thr | Thr | Pro | Ser | Phe | Val | Ile | Val | Gly |
| | | | | 115 | | | | | 120 | | | | | 125 | |
| Asp | Ser | Thr | Glu | Asn | Glu | Val | Ser | Phe | Trp | Thr | Asn | Asn | Lys | Val | Val |
| | | | | 130 | | | | | 135 | | | | | 140 | |
| Val | Asn | Ser | Gln | Gly | Phe | Ile | Pro | Pro | Asn | Gly | Asn | Ser | Ala | Gly | Gly |
| 145 | | | | | 150 | | | | | 155 | | | | | 160 |
| Asn | Ser | Gln | Tyr | Thr | Phe | Val | Asn | Gly | Ile | Thr | Gly | Thr | Ala | Gly | Ala |
| | | | | 165 | | | | | 170 | | | | | 175 | |
| Pro | Val | Gly | Gly | Thr | Val | Ile | Arg | Gln | Val | Ser | Ala | Trp | Arg | Glu | Ile |
| | | | | 180 | | | | | 185 | | | | | 190 | |
| Phe | Asn | Thr | Ala | Gly | Asn | Cys | Val | Lys | Ser | Phe | Gly | Leu | Val | Val | Arg |
| | | | | 195 | | | | | 200 | | | | | 205 | |
| Gly | Thr | Gly | Asn | Gln | Gly | Leu | Val | Gln | Gly | Val | Glu | Tyr | Asp | Gly | Tyr |
| | | | | 210 | | | | | 215 | | | | | 220 | |
| Val | Ala | Ile | Asp | Ser | Asn | Gly | Ser | Phe | Ala | Ile | Ser | Gly | Tyr | Ser | Pro |
| 225 | | | | | 230 | | | | | 235 | | | | | 240 |
| Ala | Val | Asn | Asn | Ala | Pro | Gly | Phe | Gly | Lys | Asn | Phe | Ala | Ala | Arg |
| | | | | 245 | | | | | 250 | | | | | 255 |
| Thr | Gly | Asn | Phe | Phe | Ala | Val | Ser | Ser | Glu | Ser | Gly | Val | Ile | Val | Met |
| | | | | 260 | | | | | 265 | | | | | 270 | |
| Ser | Ile | Pro | Val | Asp | Asn | Ala | Gly | Cys | Thr | Leu | Ser | Phe | Ser | Val | Ala |
| | | | | 275 | | | | | 280 | | | | | 285 | |
| Tyr | Thr | Ile | Thr | Pro | Gly | Ala | Gly | Arg | Val | Ser | Gly | Val | Ser | Leu | Ala |
| | | | | 290 | | | | | 295 | | | | | 300 | |
| Gln | Asp | Asn | Glu | Phe | Tyr | Ala | Ala | Val | Gly | Ile | Pro | Gly | Ala | Gly | Pro |
| 305 | | | | | 310 | | | | | 315 | | | | | 320 |
| Gly | Glu | Val | Arg | Ile | Tyr | Arg | Leu | Asp | Gly | Gly | Ala | Thr | Thr | Leu |
| | | | | 325 | | | | | 330 | | | | | 335 |
| Val | Gln | Thr | Leu | Ser | Pro | Pro | Asp | Asp | Ile | Pro | Glu | Leu | Pro | Ile | Val |
| | | | | 340 | | | | | 345 | | | | | 350 | |
| Ala | Asn | Gln | Arg | Phe | Gly | Glu | Met | Val | Arg | Phe | Gly | Ala | Asn | Ser | Glu |
| | | | | 355 | | | | | 360 | | | | | 365 | |

```
Thr Asn Tyr Val Ala Val Gly Ser Pro Gly Tyr Ala Ala Glu Gly Leu
    370             375                 380

Ala Leu Phe Tyr Thr Ala Glu Pro Gly Leu Thr Pro Asn Asp Pro Asp
385                 390                 395                 400

Glu Gly Leu Leu Thr Leu Leu Ala Tyr Ser Asn Ser Ser Glu Ile Pro
                405                 410                 415

Ala Asn Gly Gly Leu Gly Glu Phe Met Thr Ala Ser Asn Cys Arg Gln
            420                 425                 430

Phe Val Phe Gly Glu Pro Ser Val Asp Ser Val Val Thr Phe Leu Ala
        435                 440                 445

Ser Ile Gly Ala Tyr Tyr Glu Asp Tyr Cys Thr Cys Glu Arg Glu Asn
    450                 455                 460

Ile Phe Asp Gln Gly Ile Met Phe Pro Val Pro Asn Phe Pro Gly Glu
465                 470                 475                 480

Ser Pro Thr Thr Cys Arg Ser Ser Ile Tyr Glu Phe Arg Phe Asn Cys
                485                 490                 495

Leu Met Glu Gly Ala Pro Ser Ile Cys Thr Tyr Ser Glu Arg Pro Thr
            500                 505                 510

Tyr Glu Trp Thr Glu Glu Val Val Asp Pro Asp Asn Thr Pro Cys Glu
        515                 520                 525

Leu Val Ser Arg Ile Gln Arg Arg Leu Ser Gln Ser Asn Cys Phe Gln
530                 535                 540

Asp Tyr Val Thr Leu Gln Val Val Met Ile Arg Leu Gly Ala Pro Gln
545                 550                 555                 560

Ser Leu Val Leu Leu Thr Leu Leu Val Ala Ala Val Leu Arg Cys Gln
                565                 570                 575

Gly Gln Asp Val Arg Gln Pro Gly Pro Lys Gly Gln Lys Gly Glu Pro
            580                 585                 590

Gly Asp Ile Lys Asp Ile Val Gly Pro Lys Gly Pro Pro Gly Pro Gln
        595                 600                 605

Gly Pro Ala Gly Glu Gln Gly Pro Arg Gly Asp Arg Gly Asp Lys Gly
        610                 615                 620

Glu Lys Gly Ala Pro Gly Pro Arg Gly Arg Asp Gly Glu Pro Gly Thr
625                 630                 635                 640

Pro Gly Asn Pro Gly Pro Pro Gly Pro Pro Gly Pro Pro Gly Pro Pro
                645                 650                 655

Gly Leu Gly Gly Asn Phe Ala Ala Gln Met Ala Gly Gly Phe Asp Glu
            660                 665                 670

Lys Ala Gly Gly Ala Gln Leu Gly Val Met Gln Gly Pro Met Gly Pro
        675                 680                 685

Met Gly Pro Arg Gly Pro Pro Gly Pro Ala Gly Ala Pro Gly Pro Gln
        690                 695                 700

Gly Phe Gln Gly Asn Pro Gly Glu Pro Gly Glu Pro Gly Val Ser Gly
705                 710                 715                 720

Pro Met Gly Pro Arg Gly Pro Pro Gly Pro Pro Gly Lys Pro Gly Asp
                725                 730                 735

Asp Gly Glu Ala Gly Lys Pro Gly Lys Ala Gly Glu Arg Gly Pro Pro
            740                 745                 750

Gly Pro Gln Gly Ala Arg Gly Phe Pro Gly Thr Pro Gly Leu Pro Gly
        755                 760                 765

Val Lys Gly His Arg Gly Tyr Pro Gly Leu Asp Gly Ala Lys Gly Glu
        770                 775                 780
```

```
Ala Gly Ala Pro Gly Val Lys Gly Glu Ser Gly Ser Pro Gly Glu Asn
785                 790                 795                 800

Gly Ser Pro Gly Pro Met Gly Pro Arg Gly Leu Pro Gly Glu Arg Gly
                805                 810                 815

Arg Thr Gly Pro Ala Gly Ala Gly Ala Arg Gly Asn Asp Gly Gln
            820                 825                 830

Pro Gly Pro Ala Gly Pro Pro Gly Pro Val Gly Pro Ala Gly Gly Pro
        835                 840                 845

Gly Phe Pro Gly Ala Pro Gly Ala Lys Gly Glu Ala Gly Pro Thr Gly
    850                 855                 860

Ala Arg Gly Pro Glu Gly Ala Gln Gly Pro Arg Gly Glu Pro Gly Thr
865                 870                 875                 880

Pro Gly Ser Pro Gly Pro Ala Gly Ala Ser Gly Asn Pro Gly Thr Asp
            885                 890                 895

Gly Ile Pro Gly Ala Lys Gly Ser Ala Gly Ala Pro Gly Ile Ala Gly
        900                 905                 910

Ala Pro Gly Phe Pro Gly Pro Arg Gly Pro Pro Gly Pro Gln Gly Ala
    915                 920                 925

Thr Gly Pro Leu Gly Pro Lys Gly Gln Thr Gly Glu Pro Gly Ile Ala
930                 935                 940

Gly Phe Lys Gly Glu Gln Gly Pro Lys Gly Glu Pro Gly Pro Ala Gly
945                 950                 955                 960

Pro Gln Gly Ala Pro Gly Pro Ala Gly Glu Glu Gly Lys Arg Gly Ala
            965                 970                 975

Arg Gly Glu Pro Gly Gly Val Gly Pro Ile Gly Pro Pro Gly Glu Arg
        980                 985                 990

Gly Ala Pro Gly Asn Arg Gly Phe Pro Gly Gln Asp Gly Leu Ala Gly
    995                 1000                1005

Pro Lys Gly Ala Pro Gly Glu Arg Gly Pro Ser Gly Leu Ala Gly
    1010                1015                1020

Pro Lys Gly Ala Asn Gly Asp Pro Gly Arg Pro Gly Glu Pro Gly
    1025                1030                1035

Leu Pro Gly Ala Arg Gly Leu Thr Gly Arg Pro Gly Asp Ala Gly
    1040                1045                1050

Pro Gln Gly Lys Val Gly Pro Ser Gly Ala Pro Gly Glu Asp Gly
    1055                1060                1065

Arg Pro Gly Pro Pro Gly Pro Gln Gly Ala Arg Gly Gln Pro Gly
    1070                1075                1080

Val Met Gly Phe Pro Gly Pro Lys Gly Ala Asn Gly Glu Pro Gly
    1085                1090                1095

Lys Ala Gly Glu Lys Gly Leu Pro Gly Ala Pro Gly Leu Arg Gly
    1100                1105                1110

Leu Pro Gly Lys Asp Gly Glu Thr Gly Ala Ala Gly Pro Pro Gly
    1115                1120                1125

Pro Ala Gly Pro Ala Gly Glu Arg Gly Glu Gln Gly Ala Pro Gly
    1130                1135                1140

Pro Ser Gly Phe Gln Gly Leu Pro Gly Pro Pro Gly Pro Pro Gly
    1145                1150                1155

Glu Gly Gly Lys Pro Gly Asp Gln Gly Val Pro Gly Glu Ala Gly
    1160                1165                1170

Ala Pro Gly Leu Val Gly Pro Arg Gly Glu Arg Gly Phe Pro Gly
    1175                1180                1185

Glu Arg Gly Ser Pro Gly Ala Gln Gly Leu Gln Gly Pro Arg Gly
```

-continued

```
            1190                1195                1200
Leu Pro Gly Thr Pro Gly Thr Asp Gly Pro Lys Gly Ala Ser Gly
        1205                1210                1215
Pro Ala Gly Pro Pro Gly Ala Gln Gly Pro Pro Gly Leu Gln Gly
        1220                1225                1230
Met Pro Gly Glu Arg Gly Ala Ala Gly Ile Ala Gly Pro Lys Gly
        1235                1240                1245
Asp Arg Gly Asp Val Gly Glu Lys Gly Pro Gly Ala Pro Gly
        1250                1255                1260
Lys Asp Gly Gly Arg Gly Leu Thr Gly Pro Ile Gly Pro Pro Gly
        1265                1270                1275
Pro Ala Gly Ala Asn Gly Glu Lys Gly Glu Val Gly Pro Pro Gly
        1280                1285                1290
Pro Ala Gly Ser Ala Gly Ala Arg Gly Ala Pro Gly Glu Arg Gly
        1295                1300                1305
Glu Thr Gly Pro Pro Gly Pro Ala Gly Phe Ala Gly Pro Pro Gly
        1310                1315                1320
Ala Asp Gly Gln Pro Gly Ala Lys Gly Glu Gln Gly Glu Ala Gly
        1325                1330                1335
Gln Lys Gly Asp Ala Gly Ala Pro Gly Pro Gln Gly Pro Ser Gly
        1340                1345                1350
Ala Pro Gly Pro Gln Gly Pro Thr Gly Val Thr Gly Pro Lys Gly
        1355                1360                1365
Ala Arg Gly Ala Gln Gly Pro Pro Gly Ala Thr Gly Phe Pro Gly
        1370                1375                1380
Ala Ala Gly Arg Val Gly Pro Pro Gly Ser Asn Gly Asn Pro Gly
        1385                1390                1395
Pro Pro Gly Pro Pro Gly Pro Ser Gly Lys Asp Gly Pro Lys Gly
        1400                1405                1410
Ala Arg Gly Asp Ser Gly Pro Pro Gly Arg Ala Gly Glu Pro Gly
        1415                1420                1425
Leu Gln Gly Pro Ala Gly Pro Pro Gly Glu Lys Gly Glu Pro Gly
        1430                1435                1440
Asp Asp Gly Pro Ser Gly Ala Glu Gly Pro Pro Gly Pro Gln Gly
        1445                1450                1455
Leu Ala Gly Gln Arg Gly Ile Val Gly Leu Pro Gly Gln Arg Gly
        1460                1465                1470
Glu Arg Gly Phe Pro Gly Leu Pro Gly Pro Ser Gly Glu Pro Gly
        1475                1480                1485
Lys Gln Gly Ala Pro Gly Ala Ser Gly Asp Arg Gly Pro Pro Gly
        1490                1495                1500
Pro Val Gly Pro Pro Gly Leu Thr Gly Pro Ala Gly Glu Pro Gly
        1505                1510                1515
Arg Gln Gly Ser Pro Gly Ala Asp Gly Pro Pro Gly Arg Asp Gly
        1520                1525                1530
Ala Ala Gly Val Lys Gly Asp Arg Gly Glu Thr Gly Ala Val Gly
        1535                1540                1545
Ala Pro Gly Thr Pro Gly Pro Pro Gly Ser Pro Gly Pro Ala Gly
        1550                1555                1560
Pro Thr Gly Lys Gln Gly Asp Arg Gly Glu Ala Gly Ala Gln Gly
        1565                1570                1575
Pro Met Gly Pro Ser Gly Pro Ala Gly Ala Arg Gly Ile Gln Gly
        1580                1585                1590
```

```
Pro Gln Gly Pro Arg Gly Asp Lys Gly Glu Ala Gly Glu Pro Gly
    1595                1600                1605

Glu Arg Gly Leu Lys Gly His Arg Gly Phe Thr Gly Leu Gln Gly
    1610                1615                1620

Leu Pro Gly Pro Pro Gly Pro Ser Gly Asp Gln Gly Ala Ser Gly
    1625                1630                1635

Pro Ala Gly Pro Ser Gly Pro Arg Gly Pro Pro Gly Pro Val Gly
    1640                1645                1650

Pro Ser Gly Lys Asp Gly Ala Asn Gly Ile Pro Gly Pro Ile Gly
    1655                1660                1665

Pro Pro Gly Pro Arg Gly Arg Ser Gly Glu Thr Gly Pro Ala Gly
    1670                1675                1680

Pro Pro Gly Asn Pro Gly Pro Pro Gly Pro Pro Gly Pro Pro Gly
    1685                1690                1695

Pro Gly Ile Asp Met Ser Ala Phe Ala Gly Leu Gly Pro Arg
    1700                1705                1710
```

<210> SEQ ID NO 23
<211> LENGTH: 1309
<212> TYPE: PRT
<213> ORGANISM: Artificial
<220> FEATURE:
<223> OTHER INFORMATION: Synthetic glycoprotein-elastin fusion AAV48590- NP_000492

<400> SEQUENCE: 23

```
Met Ala Arg Met Val Ala Val Ala Val Met Ala Val Leu Ser
1               5                   10                  15

Val Ala Leu Ala Gln Phe Ile Pro Asp Val Asp Ile Thr Trp Lys Val
                20                  25                  30

Pro Met Thr Leu Thr Val Gln Asn Leu Ser Ile Phe Thr Gly Pro Asn
        35                  40                  45

Gln Phe Gly Arg Gly Ile Pro Ser Pro Ser Ala Ile Gly Gly Gly Asn
    50                  55                  60

Gly Leu Asp Ile Val Gly Gly Gly Ser Leu Tyr Ile Ser Pro Thr
65                  70                  75                  80

Gly Gly Gln Val Gln Tyr Ser Arg Gly Ser Asn Asn Phe Gly Asn Gln
                85                  90                  95

Val Ala Phe Thr Arg Val Arg Lys Asn Gly Asn Asn Glu Ser Asp Phe
            100                 105                 110

Ala Thr Val Phe Val Gly Gly Thr Thr Pro Ser Phe Val Ile Val Gly
        115                 120                 125

Asp Ser Thr Glu Asn Glu Val Ser Phe Trp Thr Asn Asn Lys Val Val
    130                 135                 140

Val Asn Ser Gln Gly Phe Ile Pro Pro Asn Gly Asn Ser Ala Gly Gly
145                 150                 155                 160

Asn Ser Gln Tyr Thr Phe Val Asn Gly Ile Thr Gly Thr Ala Gly Ala
                165                 170                 175

Pro Val Gly Gly Thr Val Ile Arg Gln Val Ser Ala Trp Arg Glu Ile
            180                 185                 190

Phe Asn Thr Ala Gly Asn Cys Val Lys Ser Phe Gly Leu Val Val Arg
        195                 200                 205

Gly Thr Gly Asn Gln Gly Leu Val Gln Gly Val Glu Tyr Asp Gly Tyr
    210                 215                 220

Val Ala Ile Asp Ser Asn Gly Ser Phe Ala Ile Ser Gly Tyr Ser Pro
```

```
                225                 230                 235                 240
        Ala Val Asn Asn Ala Pro Gly Phe Gly Lys Asn Phe Ala Ala Arg
                        245                 250                 255

Thr Gly Asn Phe Phe Ala Val Ser Ser Glu Ser Gly Val Ile Val Met
                        260                 265                 270

Ser Ile Pro Val Asp Asn Ala Gly Cys Thr Leu Ser Phe Ser Val Ala
                        275                 280                 285

Tyr Thr Ile Thr Pro Gly Ala Gly Arg Val Ser Gly Val Ser Leu Ala
                        290                 295                 300

Gln Asp Asn Glu Phe Tyr Ala Ala Val Gly Ile Pro Gly Ala Gly Pro
        305                 310                 315                 320

Gly Glu Val Arg Ile Tyr Arg Leu Asp Gly Gly Ala Thr Thr Leu
                        325                 330                 335

Val Gln Thr Leu Ser Pro Pro Asp Asp Ile Pro Glu Leu Pro Ile Val
                        340                 345                 350

Ala Asn Gln Arg Phe Gly Glu Met Val Arg Phe Gly Ala Asn Ser Glu
                        355                 360                 365

Thr Asn Tyr Val Ala Val Gly Ser Pro Gly Tyr Ala Ala Glu Gly Leu
                        370                 375                 380

Ala Leu Phe Tyr Thr Ala Glu Pro Gly Leu Thr Pro Asn Asp Pro Asp
        385                 390                 395                 400

Glu Gly Leu Leu Thr Leu Leu Ala Tyr Ser Asn Ser Glu Ile Pro
                        405                 410                 415

Ala Asn Gly Gly Leu Gly Glu Phe Met Thr Ala Ser Asn Cys Arg Gln
                        420                 425                 430

Phe Val Phe Gly Glu Pro Ser Val Asp Ser Val Val Thr Phe Leu Ala
                        435                 440                 445

Ser Ile Gly Ala Tyr Tyr Glu Asp Tyr Cys Thr Cys Glu Arg Glu Asn
                        450                 455                 460

Ile Phe Asp Gln Gly Ile Met Phe Pro Val Pro Asn Phe Pro Gly Glu
        465                 470                 475                 480

Ser Pro Thr Thr Cys Arg Ser Ser Ile Tyr Glu Phe Arg Phe Asn Cys
                        485                 490                 495

Leu Met Glu Gly Ala Pro Ser Ile Cys Thr Tyr Ser Glu Arg Pro Thr
                        500                 505                 510

Tyr Glu Trp Thr Glu Glu Val Val Asp Pro Asp Asn Thr Pro Cys Glu
                        515                 520                 525

Leu Val Ser Arg Ile Gln Arg Arg Leu Ser Gln Ser Asn Cys Phe Gln
        530                 535                 540

Asp Tyr Val Thr Leu Gln Val Val Met Ala Gly Leu Thr Ala Ala Ala
        545                 550                 555                 560

Pro Arg Pro Gly Val Leu Leu Leu Leu Ser Ile Leu His Pro Ser
                        565                 570                 575

Arg Pro Gly Gly Val Pro Gly Ala Ile Pro Gly Gly Val Pro Gly Gly
                        580                 585                 590

Val Phe Tyr Pro Gly Ala Gly Leu Gly Ala Leu Gly Gly Gly Ala Leu
                        595                 600                 605

Gly Pro Gly Gly Lys Pro Leu Lys Pro Val Pro Gly Gly Leu Ala Gly
                        610                 615                 620

Ala Gly Leu Gly Ala Gly Leu Gly Ala Phe Pro Ala Val Thr Phe Pro
        625                 630                 635                 640

Gly Ala Leu Val Pro Gly Gly Val Ala Asp Ala Ala Ala Tyr Lys
                        645                 650                 655
```

```
Ala Ala Lys Ala Gly Ala Gly Leu Gly Gly Val Pro Gly Val Gly
            660                 665                 670

Leu Gly Val Ser Ala Gly Ala Val Pro Gln Pro Gly Ala Gly Val
        675                 680                 685

Lys Pro Gly Lys Val Pro Gly Val Gly Leu Pro Gly Val Tyr Pro Gly
690                 695                 700

Gly Val Leu Pro Gly Ala Arg Phe Pro Gly Val Gly Val Leu Pro Gly
705                 710                 715                 720

Val Pro Thr Gly Ala Gly Val Lys Pro Lys Ala Pro Gly Val Gly Gly
                725                 730                 735

Ala Phe Ala Gly Ile Pro Gly Val Gly Pro Phe Gly Gly Pro Gln Pro
                740                 745                 750

Gly Val Pro Leu Gly Tyr Pro Ile Lys Ala Pro Lys Leu Pro Gly Gly
                755                 760                 765

Tyr Gly Leu Pro Tyr Thr Thr Gly Lys Leu Pro Tyr Gly Tyr Gly Pro
            770                 775                 780

Gly Gly Val Ala Gly Ala Ala Gly Lys Ala Gly Tyr Pro Thr Gly Thr
785                 790                 795                 800

Gly Val Gly Pro Gln Ala Ala Ala Ala Ala Ala Lys Ala Ala Ala
                805                 810                 815

Lys Phe Gly Ala Gly Ala Ala Gly Val Leu Pro Gly Val Gly Gly Ala
                820                 825                 830

Gly Val Pro Gly Val Pro Gly Ala Ile Pro Gly Ile Gly Gly Ile Ala
                835                 840                 845

Gly Val Gly Thr Pro Ala Ala Ala Ala Ala Ala Ala Ala Ala Lys
                850                 855                 860

Ala Ala Lys Tyr Gly Ala Ala Gly Leu Val Pro Gly Gly Pro Gly
865                 870                 875                 880

Phe Gly Pro Gly Val Val Gly Val Pro Gly Ala Gly Val Pro Gly Val
                885                 890                 895

Gly Val Pro Gly Ala Gly Ile Pro Val Val Pro Gly Ala Gly Ile Pro
                900                 905                 910

Gly Ala Ala Val Pro Gly Val Val Ser Pro Glu Ala Ala Ala Lys Ala
                915                 920                 925

Ala Ala Lys Ala Ala Lys Tyr Gly Ala Arg Pro Gly Val Gly Val Gly
            930                 935                 940

Gly Ile Pro Thr Tyr Gly Val Gly Ala Gly Gly Phe Pro Gly Phe Gly
945                 950                 955                 960

Val Gly Val Gly Gly Ile Pro Gly Val Ala Gly Val Pro Ser Val Gly
                965                 970                 975

Gly Val Pro Gly Val Gly Gly Val Pro Gly Val Gly Ile Ser Pro Glu
                980                 985                 990

Ala Gln Ala Ala Ala Ala Lys Ala Ala Lys Tyr Gly Val Gly Thr
                995                 1000                1005

Pro Ala Ala Ala Ala Ala Lys Ala Ala Lys Ala Ala Gln Phe
        1010                1015                1020

Gly Leu Val Pro Gly Val Gly Val Ala Pro Gly Val Gly Val Ala
        1025                1030                1035

Pro Gly Val Gly Val Ala Pro Gly Val Gly Leu Ala Pro Gly Val
        1040                1045                1050

Gly Val Ala Pro Gly Val Gly Val Ala Pro Gly Val Gly Val Ala
        1055                1060                1065
```

-continued

```
Pro Gly Ile Gly Pro Gly Gly Val Ala Ala Ala Lys Ser Ala
    1070            1075            1080

Ala Lys Val Ala Ala Lys Ala Gln Leu Arg Ala Ala Ala Gly Leu
1085                1090                1095

Gly Ala Gly Ile Pro Gly Leu Gly Val Gly Val Gly Val Pro Gly
    1100            1105            1110

Leu Gly Val Gly Ala Gly Val Pro Gly Leu Gly Val Gly Ala Gly
    1115            1120            1125

Val Pro Gly Phe Gly Ala Gly Ala Asp Glu Gly Val Arg Arg Ser
    1130            1135            1140

Leu Ser Pro Glu Leu Arg Glu Gly Asp Pro Ser Ser Ser Gln His
    1145            1150            1155

Leu Pro Ser Thr Pro Ser Ser Pro Arg Val Pro Gly Ala Leu Ala
    1160            1165            1170

Ala Ala Lys Ala Ala Lys Tyr Gly Ala Ala Val Pro Gly Val Leu
    1175            1180            1185

Gly Gly Leu Gly Ala Leu Gly Gly Val Gly Ile Pro Gly Gly Val
    1190            1195            1200

Val Gly Ala Gly Pro Ala Ala Ala Ala Ala Ala Lys Ala Ala
    1205            1210            1215

Ala Lys Ala Ala Gln Phe Gly Leu Val Gly Ala Ala Gly Leu Gly
    1220            1225            1230

Gly Leu Gly Val Gly Gly Leu Gly Val Pro Gly Val Gly Gly Leu
    1235            1240            1245

Gly Gly Ile Pro Pro Ala Ala Ala Ala Lys Ala Ala Lys Tyr Gly
    1250            1255            1260

Ala Ala Gly Leu Gly Gly Val Leu Gly Gly Ala Gly Gln Phe Pro
    1265            1270            1275

Leu Gly Gly Val Ala Ala Arg Pro Gly Phe Gly Leu Ser Pro Ile
    1280            1285            1290

Phe Pro Gly Gly Ala Cys Leu Gly Lys Ala Cys Gly Arg Lys Arg
    1295            1300            1305

Lys
```

<210> SEQ ID NO 24
<211> LENGTH: 375
<212> TYPE: DNA
<213> ORGANISM: Artificial
<220> FEATURE:
<223> OTHER INFORMATION: Synthetic zeocin resistance gene

<400> SEQUENCE: 24

```
atggccaagt tgaccagtgc cgttccggtg ctcaccgcgc gcgacgtcgc cggagcggtc    60
gagttctgga ccgaccggct cgggttctcc cgggacttcg tggaggacga cttcgccggt   120
gtggtccggg acgacgtgac cctgttcatc agcgcggtcc aggaccaggt ggtgccggac   180
aacaccctgg cctgggtgtg ggtgcgcggc ctggacgagc tgtacgccga gtggtcggag   240
gtcgtgtcca cgaacttccg ggacgcctcc gggccggcca tgaccgagat cggcgagcag   300
ccgtggggc gggagttcgc cctgcgcgac ccggccggca actgcgtgca cttcgtggcc   360
gaggagcagg actga                                                    375
```

<210> SEQ ID NO 25
<211> LENGTH: 1479
<212> TYPE: DNA
<213> ORGANISM: Artificial
<220> FEATURE:
<223> OTHER INFORMATION: Synthetic human GLUT1 protein in Porphyridium
    codons

<400> SEQUENCE: 25

| | | | | | |
|---|---|---|---|---|---|
| atggagccga | gcagcaagaa | gctgaccggc | cgcctgatgc | tggcggttgg | cggcgccgtt | 60 |
| ctgggcagcc | tccagttcgg | ctacaacacc | ggcgtgatta | acgccccaca | gaaggtgatc | 120 |
| gaggagttct | acaaccagac | ctgggtccac | cgctacggcg | agagcattct | gccgaccacc | 180 |
| ctgaccacgc | tgtggagcct | gagcgtggcg | attttcagcg | tgggcggcat | gattggcagc | 240 |
| ttctcggtgg | gcctgttcgt | gaaccgcttc | ggccgccgca | acagcatgct | gatgatgaac | 300 |
| ctgctggcct | tcgtgtcggc | ggtgctgatg | ggcttcagca | agctgggcaa | gagcttcgag | 360 |
| atgctgattc | tgggccgctt | cattattggc | gtgtactgcg | gcctgaccac | cggcttcgtg | 420 |
| ccgatgtacg | tgggcgaggt | gtcgccaacg | cgttccgcg | gcgcgctggg | caccctccat | 480 |
| cagctgggca | ttgttgtggg | cattctgatt | gcccaggtgt | tcggcctgga | cagcattatg | 540 |
| ggcaacaagg | acctgtggcc | gctgctgctg | tcgattattt | tcattccggc | gctgctccag | 600 |
| tgcattgtgc | tgccgttctg | cccagagagc | ccacgcttcc | tgctgattaa | ccgcaacgag | 660 |
| gagaaccgcg | cgaagagcgt | gctgaagaag | ctgcgcggca | cggcggacgt | tacccacgac | 720 |
| ctccaggaga | tgaaggagga | gagccgccag | atgatgcgcg | agaagaaggt | gaccattctg | 780 |
| gagctgttcc | gctcgccagc | gtaccgccag | ccgattctga | tcgccgtggt | gctccagctg | 840 |
| tcccagcagc | tgtcgggcat | taacgccgtg | ttctactaca | gcaccagcat | tttcgagaag | 900 |
| gcgggcgtcc | agcagccagt | gtacgccacc | attggcagcg | gcattgtgaa | caccgccttc | 960 |
| accgtggtgt | cgctgttcgt | ggttgagcgc | gcgggccgcc | gcacgctcca | tctgattggc | 1020 |
| ctggcgggca | tggcgggctg | cgcgattctg | atgaccattg | ccctggcgct | gctggagcag | 1080 |
| ctgccgtgga | tgagctacct | gagcattgtg | gcgatcttcg | gcttcgtggc | gttcttcgag | 1140 |
| gttggcccag | gcccgattcc | gtggttcatt | gtggcggagc | tgttcagcca | gggcccacgc | 1200 |
| ccagcggcga | ttgccgttgc | cggcttctcg | aactggacca | gcaacttcat | tgtgggcatg | 1260 |
| tgcttccagt | acgtcgagca | gctgtgcggc | ccgtacgtgt | tcattatctt | caccgtgctg | 1320 |
| ctggtcctct | tcttcatctt | cacctacttc | aaggtgccgg | agaccaaggg | ccgcaccttc | 1380 |
| gacgagattg | ccagcggctt | ccgccagggc | ggcgccagcc | agagcgacaa | gaccccggag | 1440 |
| gagctgttcc | atccactggg | cgccgacagc | caggtgtaa | | | 1479 |

<210> SEQ ID NO 26
<211> LENGTH: 27
<212> TYPE: DNA
<213> ORGANISM: Artificial
<220> FEATURE:
<223> OTHER INFORMATION: Synthetic primer

<400> SEQUENCE: 26
gccaagttga ccagtgccgt tccggtg                                        27

<210> SEQ ID NO 27
<211> LENGTH: 26
<212> TYPE: DNA
<213> ORGANISM: Artificial
<220> FEATURE:
<223> OTHER INFORMATION: Synthetic primer

<400> SEQUENCE: 27
cggctgctcg ccgatctcgg tcatgg                                         26

-continued

<210> SEQ ID NO 28
<211> LENGTH: 17
<212> TYPE: DNA
<213> ORGANISM: Artificial
<220> FEATURE:
<223> OTHER INFORMATION: Synthetic primer

<400> SEQUENCE: 28
atacgcgagt cgaaagc                                                      17

<210> SEQ ID NO 29
<211> LENGTH: 16
<212> TYPE: DNA
<213> ORGANISM: Artificial
<220> FEATURE:
<223> OTHER INFORMATION: Synthetic primer

<400> SEQUENCE: 29
acagcgctgt actccc                                                       16

<210> SEQ ID NO 30
<211> LENGTH: 23
<212> TYPE: DNA
<213> ORGANISM: Artificial
<220> FEATURE:
<223> OTHER INFORMATION: Synthetic primer

<400> SEQUENCE: 30
tgctgatgat gaacctgctg gcc                                               23

<210> SEQ ID NO 31
<211> LENGTH: 22
<212> TYPE: DNA
<213> ORGANISM: Artificial
<220> FEATURE:
<223> OTHER INFORMATION: Synthetic primer

<400> SEQUENCE: 31
agcacaatgc actggagcag cg                                                22

<210> SEQ ID NO 32
<211> LENGTH: 185
<212> TYPE: DNA
<213> ORGANISM: Artificial
<220> FEATURE:
<223> OTHER INFORMATION: Synthetic CMV 3' UTR

<400> SEQUENCE: 32
tttctccata ataatgtgtg agtagttccc agataaggga attagggttc ctatagggtt       60
tcgctcatgt gttgagcata taagaaaccc ttagtatgta tttgtatttg taaaatactt      120
ctatcaataa aatttctaat tcctaaaacc aaaatccagt actaaaatcc agatccccccg    180 aatta                                                                  185

<210> SEQ ID NO 33
<211> LENGTH: 672
<212> TYPE: PRT
<213> ORGANISM: Artificial
<220> FEATURE:
<223> OTHER INFORMATION: Synthetic Cyanidioschyzon merolae Na+/glucose
      co-transporter c05f0001

<400> SEQUENCE: 33

Met Ala Ser Thr Ala Pro Ala Asn Thr Ala Val Ala Leu Asn Thr Leu

```
1               5                   10                  15
Asp Trp Val Leu Val Ile Val Tyr Phe Ser Ala Leu Val Leu Ala Ile
                20                  25                  30
Trp Leu Ser Thr Arg Lys Ser Ser Arg Ala Gly Ser Gly Thr Gln Ser
                35                  40                  45
Lys Pro Ala Ser Glu Met Phe Phe Leu Ala Gly Arg Ser Thr Thr Phe
                50                  55                  60
Phe Ala Val Gly Ala Ser Leu Phe Met Ser Asn Ile Gly Ser Glu His
 65                 70                  75                  80
Phe Ile Ala Leu Ala Ala Ala Gly Ala Thr Ser Gly Leu Ala Val Ala
                85                  90                  95
Ser Phe Glu Trp Met Ala Ser Ile Phe Val Gly Val Val Leu Gly Arg
                100                 105                 110
Val Phe Ala Pro Phe Tyr Leu Arg Asn Ser Leu His Thr Val Pro Lys
                115                 120                 125
Phe Leu Glu Leu Arg Tyr Ala Ala Gly Ala Arg Arg Tyr His Ala Leu
130                 135                 140
Ala Thr Ile Met Met Ala Ile Leu Thr Lys Val Ser Ala Thr Leu Tyr
145                 150                 155                 160
Ser Gly Ala Ile Ile Leu Arg Val Leu Leu Gly Trp Pro Val Trp Phe
                165                 170                 175
Ser Leu Ile Met Ile Leu Val Leu Thr Thr Leu Tyr Thr Ser Leu Gly
                180                 185                 190
Gly Leu Arg Ala Val Ile Trp Thr Glu Val Leu Gln Ala Phe Val Leu
                195                 200                 205
Leu Ala Gly Gly Leu Ala Leu Ala Val Arg Ser Leu Gln Ala Val Gly
210                 215                 220
Ser Leu Ala Gly Leu Ser Glu Leu Leu Ala Ala Gln Asn Arg Arg Gln
225                 230                 235                 240
Met Leu Asp Leu Leu Gln Trp Pro Ser Thr Thr Pro Trp Val Glu
                245                 250                 255
Tyr Pro Trp Pro Gly Ile Ile Phe Gly Leu Pro Ala Leu Glu Val Phe
                260                 265                 270
Tyr Trp Cys Thr Asp Gln Val Val Gln Arg Val Leu Ser Ala Lys
                275                 280                 285
Ser Glu Ala His Ala Arg Gly Gly Ser Leu Leu Cys Gly Phe Leu Lys
                290                 295                 300
Thr Leu Val Pro Phe Met Met Val Ile Pro Gly Leu Cys Ala Phe Leu
305                 310                 315                 320
Leu Phe Pro Glu Val Ala Ala Asn Pro Asn Gln Ala Tyr Pro Thr Ala
                325                 330                 335
Val Ala Arg Leu Leu Pro His Gly Leu Gly Leu Met Val Ser Ala
                340                 345                 350
Met Leu Ala Ala Leu Met Ser Ser Leu Ala Ser Thr Phe Asn Ser Thr
                355                 360                 365
Ser Thr Val Val Tyr Asp Phe Val Ile Glu Cys Cys Gly Leu Ser
                370                 375                 380
Arg Leu Ser Asp Lys Thr Leu Val Leu Leu Gly Arg Ile Ala Asn Ile
385                 390                 395                 400
Val Leu Cys Ala Phe Ser Leu Ala Trp Ile Pro Ile Val Glu Gly Met
                405                 410                 415
Gly Glu Glu Leu Tyr Phe Tyr Ile Gln Ser Val Ile Ser Tyr Ile Ala
                420                 425                 430
```

```
Pro Pro Ile Ala Val Val Phe Val Ala Gly Ile Ala Trp Arg Arg Ala
        435                 440                 445

Thr Ala Thr Gly Ala Leu Cys Thr Leu Leu Val Gly Gly Ala Leu Gly
    450                 455                 460

Leu Val Arg Phe Val Val Glu Val Ala Leu Arg Leu Ala His Arg Glu
465                 470                 475                 480

Ala Pro Leu Gly Ala Leu Gly Lys Ile Phe Phe Gln Ser Asn Phe Leu
                485                 490                 495

Tyr Phe Ala Ile Phe Ser Trp Val Phe Ser Ser Leu Leu Leu Val Thr
            500                 505                 510

Val Ser Leu Phe Thr Glu Pro Pro Ser Glu Gln Gln Leu Gly Leu Leu
        515                 520                 525

Phe Gln Glu Ala Gly Ala Ser Gly Ser His Val Arg Thr Thr Ala Gly
        530                 535                 540

Asn Gln Ile Gly Glu Ala Ser Ser Lys Gln Val Val Gly Ala Ser Arg
545                 550                 555                 560

Tyr Val Ala Asp Glu Pro Ser Ser Asp Pro Ala Ala Arg Gln Gln
                565                 570                 575

Thr Val Glu Leu Glu Ile Glu Ser Phe Ser Gly Thr Glu Asn Ser Asp
            580                 585                 590

Glu Ala Phe Ser Val Asp Pro Glu His Thr Ala Pro Ser Met Lys Arg
        595                 600                 605

Val Ala Ser Arg Asp Thr Leu Leu Ala Gly Glu Ala Ala Ser Gln Glu
        610                 615                 620

Pro Leu Phe Ser Pro Gln Gly Glu Phe Ser Ala Ala Gln Glu Thr Phe
625                 630                 635                 640

Ser Ser Ala Ala Pro Ser Arg Leu Thr Ser Ala Ala Leu Asp Val Leu
                645                 650                 655

Ser Val Val Leu Val Ala Glu Ile Leu Ala Phe Tyr Ile Gln Phe Arg
            660                 665                 670

<210> SEQ ID NO 34
<211> LENGTH: 541
<212> TYPE: PRT
<213> ORGANISM: Artificial
<220> FEATURE:
<223> OTHER INFORMATION: Synthetic Cyanidioschyzon merolae arabinose
      permease CMK066C

<400> SEQUENCE: 34

Met Glu Thr Val Thr Val Arg Trp Lys Arg Phe Leu Ser Thr Phe Gly
1               5                   10                  15

Ala Arg Pro Cys Leu Leu Ser Cys Leu Leu Gly Gly Leu Leu Phe Gly
            20                  25                  30

Tyr His Leu Ala Val Phe Ser Thr Val Thr Thr Phe Arg Ser Phe Gln
        35                  40                  45

Asp Trp Phe Gly Ser Trp Pro Ser Gly Glu Gln Val Leu Leu Gly Ser
    50                  55                  60

Tyr Phe Val Gly Ala Phe Val Gly Cys Leu Tyr Gln Arg Val Leu Pro
65                  70                  75                  80

Phe Leu Ala His Gly Ala Gly Thr Ala Ala Trp Arg Arg Tyr Leu Trp
                85                  90                  95

Leu Arg Trp Ser Ser Val Phe Phe Cys Leu Gly Ser Gly Leu Pro Phe
            100                 105                 110

Leu Ile Lys Arg Glu Arg Met Leu Thr Gly Arg Phe Gln Met Gly Ala
```

```
                115                 120                 125
Phe Leu Val Leu Leu Ile His Arg Leu Leu Ile Gly Ile Ala Gly
            130                 135                 140
Ile Val Asn Val Leu Gly Pro Ala Leu Cys Leu Glu Val Ala Pro Ser
145                 150                 155                 160
Thr Ser Arg Gly Ala Phe Val Phe Leu Tyr Gln Leu Ala Ile Thr Ile
                165                 170                 175
Gly Ile Leu Met Ala Asn Leu Val Asn Leu Ala Thr Gly His Glu Asp
            180                 185                 190
Val His Arg Gln Val Asp Pro Val Ala Gly Ala Gly Ile Asp Met
        195                 200                 205
Arg Gly Asn Phe Leu Arg Pro Leu Arg Tyr Pro Leu Val Pro Ala Ile
    210                 215                 220
Leu Met Cys Ile Gly Leu Leu Arg Tyr Gln Ser Ser Met Gly Val Ser
225                 230                 235                 240
Ala Tyr Arg Asp Ala Thr Ser Ala Asp Met Leu Glu Thr Gly Lys Pro
                245                 250                 255
Met Ser Gln Arg Lys Glu Arg Glu His Ser Met Val Ala Ser Ala Arg
            260                 265                 270
Ala Leu Arg Pro Asp Ala Ala Glu Ala Gly His Ser Phe Asn Val Ile
        275                 280                 285
Ser Arg Pro Ser Leu Gln Asn Glu Ser Leu Ser Leu Lys Asp Val Glu
    290                 295                 300
Ser Phe Ala Met Tyr Ala Val Leu Ala Arg Gly Ser Ser Pro Thr Ala
305                 310                 315                 320
Arg Ser Arg Ala Ser Val Trp Leu Leu Leu Arg Asp Pro Arg Ile Gln
                325                 330                 335
Ile Cys Met Ile Leu Gln Leu Leu Gln Gln Leu Thr Gly Ile Asn Val
            340                 345                 350
Val Leu Val Tyr Gly Val Gln Ile Leu Glu Gln Val Gln Ser Ser Ala
        355                 360                 365
Met Gly Ser Ser Arg Arg Leu Ala Arg Leu Ser Gly Pro Leu Tyr Gly
    370                 375                 380
Ala Val Leu Leu Ser Val Met Asn Val Ile Ala Thr Leu Val Ala Val
385                 390                 395                 400
Gly Ile Ile Asp Arg Thr Cys Arg Arg Lys Leu Tyr Leu Phe Ser Thr
                405                 410                 415
Pro Val Leu Ala Ala Cys His Leu Ala Leu Ala Arg Ala Thr Arg Ala
            420                 425                 430
Glu Asn Gly Ser Ser Ser Val Ala Phe Thr Gly Phe Leu Ala Leu Met
        435                 440                 445
Leu Phe Val Ala Val Phe Ala Val Ser His Gly Pro Leu Ala Val Leu
    450                 455                 460
Val Ala Asn Glu Leu Phe Ser Pro Glu Ala Arg Ala Ser Ala Asn Ser
465                 470                 475                 480
Ile Gly Met Val Val Asn Ala Val Ala Thr Thr Ala Val Ser Ile Gly
                485                 490                 495
Phe Pro Leu Leu Gln Arg Glu Leu Phe Gly Ile Ala Gly Thr Phe Leu
            500                 505                 510
Phe Phe Ala Leu Ile Leu Met Gly Gly Glu Tyr Trp Leu Trp Arg Tyr
        515                 520                 525
Leu Pro Glu Thr Arg Gln Pro Thr Ser Ala Asp Ser Ser
    530                 535                 540
```

<210> SEQ ID NO 35
<211> LENGTH: 640
<212> TYPE: PRT
<213> ORGANISM: Artificial
<220> FEATURE:
<223> OTHER INFORMATION: Synthetic Galdieria sulphuraria myo-inositol transporter EAL84263

<400> SEQUENCE: 35

```
Met Val Glu Lys Ser Ser Asp Pro Glu Val Pro Ser Leu Ser His His
 1               5                  10                  15

Glu Ser Ser Ile Ser Ile Glu Lys Gln Gly Asp Ala Ala Thr Ala Arg
            20                  25                  30

Glu Trp Ala Gln Asp Val Asn Ser Thr Thr Asn Thr Lys Leu Lys
        35                  40                  45

Asn Pro Leu Ala Gly Leu Thr Arg Glu Gln Leu Leu Asn Asp Val Glu
    50                  55                  60

Ala Phe Ala Lys Glu Lys Asp Leu Glu His Ile Leu Asp Asp Leu Arg
65                  70                  75                  80

Lys Gly Ala Leu Val Ala Gln Asp Pro Arg Glu Phe Glu Gln Met Asp
                85                  90                  95

Ala Leu Thr Glu Ser Glu Lys Glu Leu Leu Arg Arg Glu Lys Thr His
            100                 105                 110

Arg Trp Ser Gln Pro Phe Met Met Tyr Phe Met Thr Ser Glu Ser Ser
        115                 120                 125

Arg Tyr Pro Pro Thr Glu Phe Gly Phe Asn Pro Ala Cys Gln Ser Ser
    130                 135                 140

Val Leu Asp Leu Leu Ser Cys Arg Glu Trp Ile Arg Leu Leu Ser Thr
145                 150                 155                 160

Val Arg Arg Ser Met Tyr Ser Ser Ile Thr His Leu Ser Tyr Ala Lys
                165                 170                 175

Gln Ser Arg Phe Tyr Phe Ala Glu Phe Asn Val Thr Asp Thr Trp Met
            180                 185                 190

Gln Gly Leu Leu Asn Gly Ala Pro Tyr Leu Cys Ser Ala Val Ile Gly
        195                 200                 205

Cys Trp Thr Thr Ala Pro Leu Asn Arg Trp Phe Gly Arg Arg Gly Cys
    210                 215                 220

Ile Phe Ile Ser Cys Phe Ile Ser Phe Ala Ser Ser Phe Trp Met Ala
225                 230                 235                 240

Ala Ala His Thr Trp Trp Asn Leu Leu Leu Gly Arg Phe Leu Leu Gly
                245                 250                 255

Phe Ala Val Gly Ala Lys Ser Thr Thr Thr Pro Val Tyr Gly Ala Glu
            260                 265                 270

Cys Ser Pro Ala Asn Ile Arg Gly Ala Leu Val Met Met Trp Gln Met
        275                 280                 285

Trp Thr Ala Phe Gly Ile Met Leu Gly Tyr Ile Ala Ser Val Ala Phe
    290                 295                 300

Met Asp Val Thr His Pro Thr Ile Pro Gly Phe Asn Trp Arg Leu Met
305                 310                 315                 320

Leu Gly Ser Thr Ala Ile Pro Pro Phe Val Cys Ile Gln Val Tyr
                325                 330                 335

Phe Cys Pro Glu Ser Pro Arg Trp Tyr Met Met Arg Asn Arg Tyr His
            340                 345                 350

Asp Ala Tyr Lys Ala Leu Cys Lys Phe Arg Pro Ser Thr Phe Gln Ala
```

| | | 355 | | | 360 | | | 365 | | | |
|---|---|---|---|---|---|---|---|---|---|---|---|

Ala Arg Asp Leu Tyr Tyr Ile His Ala Ala Leu Lys Val Glu Glu Lys
370 375 380

Leu Arg Glu Gly Lys His Leu Phe Arg Glu Met Phe Thr Ile Pro Arg
385 390 395 400

Asn Arg Arg Ala Ala Gln Ser Ser Phe Val Met Phe Met Gln Gln
405 410 415

Phe Cys Gly Val Asn Ala Ile Met Tyr Tyr Ser Ser Met Phe Arg
420 425 430

Glu Ala Gly Phe Asp Thr Arg Met Ala Leu Ile Thr Ser Leu Gly Cys
435 440 445

Gly Ile Thr Asn Trp Ile Phe Ala Leu Pro Ala Val Tyr Thr Ile Asp
450 455 460

Thr Phe Gly Arg Arg Asn Leu Leu Leu Thr Thr Phe Pro Leu Met Cys
465 470 475 480

Ile Phe Leu Leu Phe Thr Gly Phe Ser Phe Tyr Ile Pro Asp Gln Thr
485 490 495

Ser Arg Thr Ala Cys Val Ala Thr Gly Ile Tyr Leu Phe Met Ile Val
500 505 510

Tyr Ser Pro Gly Glu Gly Pro Val Pro Phe Thr Tyr Ser Ala Glu Ala
515 520 525

Phe Pro Leu Tyr Ile Arg Asp Ile Gly Met Ser Phe Ala Thr Ala Thr
530 535 540

Thr Trp Gly Phe Asn Phe Ile Val Ser Leu Thr Trp Pro Ser Leu Asn
545 550 555 560

Lys Ser Phe Thr Pro Thr Gly Ala Phe Gly Trp Tyr Ala Ala Trp Asn
565 570 575

Phe Phe Gly Trp Ile Phe Cys Tyr Phe Cys Leu Pro Glu Thr Lys Ala
580 585 590

Leu Ser Leu Glu Glu Leu Asp Gln Val Phe Ser Val Pro Thr Thr Lys
595 600 605

His Val Asn His Tyr Arg Ala Met Leu Pro Trp Tyr Val Lys Lys Tyr
610 615 620

Leu Leu Arg Arg Asp Val Pro Pro Gln Asn Gln Leu Tyr Asp Tyr Tyr
625 630 635 640

<210> SEQ ID NO 36
<211> LENGTH: 4080
<212> TYPE: DNA
<213> ORGANISM: Artificial
<220> FEATURE:
<223> OTHER INFORMATION: Synthetic glp promoter - glp-SOD fusion- CMV
    3'UTR

<400> SEQUENCE: 36

| | | |
|---|---|---|
| cgtcattagc gaagcgtccg cgttcacagc gttcgatgga ggtggcaggg acaatgatgg | 60 |
| tggagcctct tcgcacctca gcgcggcata caccacaaaa ccaccgtcta actcgaggga | 120 |
| cagcgcctgg cgcacgttgg atttcagggt cgcgtaccgc gccaggtcaa agtggatctt | 180 |
| accgaccagt ttttcgttgt cactgctagc gcggtcacc gactttgccg agtctgtgtg | 240 |
| gtacagctgc agcacggcaa agcgctggtg gcgatcttca aagtttcggt ccgatgcgcg | 300 |
| tctcgacagg cgcgcaggaa cgctgaaggt ctcgttccac acggccacgt tgggctgatg | 360 |
| gtcgaaactg acgaatgcgc ttggttttcg tcccgggccg tccgagcacc tgctggtctc | 420 |
| catacgcgag tcgaaagcga tacgtgccat ccactttcat gcgggtcact ttctccactt | 480 |

```
cgagcgtaaa tatgaacgta tgcgagcaga ggtgcccacc gccactcacg ttcgtgccgg    540
tgtcgacgcc attcgtcgcc catgacgagg aagagagcaa gacgacgttt ccagccctgc    600
tcgccgactt gctctgcgcc gacgacgcgg acgcctgcgt cacactggag gagtttgagg    660
cgttggacgc gcgcacgctg gactctcgct tcactagcaa gccactcccg ctgcgatcga    720
gcgacggcga gcgcgagccc ttcctactct cactgcgcga cgaggcggtc gagtccgagc    780
gactcacctg gcttaagcgt ctctcgctca tgacgcgctt gacgagcacc ttgcgagtag    840
ccagccgcac ctctacccgc gcatgccaac ctcactccag tgtctcgcaa gcaaccacga    900
tgctccttcc cagtcgaatg cgacacgcga ccacgttcgc cgcgcaactt ttttttccac    960
cgcagaaatt ggcgcggacg aagtacagct gacccgcacc aacggtacag tcatgagctt   1020
gtaactgcca cttcgcactt tgtaacgta taaaataacg atacaaaggt ggattaatta   1080
tttcattttt tcatgttcca gatgtttcaa gctctcatgc tttgtgagtg tttttggatg   1140
tgtagccggc aaccctactt gttcgggcaa cgaaacagat tgttcgtgcg gttggcgcgg   1200
ttgacgcggt tgatgacaac tggatgacga aaccagtgc gcaagaaggg ggggggggtt   1260
aagtatagtg tgtttagtca acgaacggcg tgtgaattta aatgctttgg ggtgtagtca   1320
aacgggtgtg gtttacaagg cgctgccaag cagcgggagt acagcgctgt acgccgccga   1380
tttcaaaagg agacacgcgc gagcaacaaa atcacgaatc gggtggattt tgcgtggtgc   1440
gttcgttggg gtgtgtgtgt ggcgctggcg gttggacacg cgtaacaaat gcaggctgtt   1500
ttactataaa gtcgggcgag aagcggatgg ctggtgcggt gtgatgggcg cgcacgacgc   1560
cacgcagtgc ctctatgcaa tcgagaggga gatgcgaaaa aaggggggcg gtctggtata   1620
aagtgcgcgg gcacgtcgta ggtacttaaa tgctgtgggg acggtgaaaa gagtgcgtga   1680
gtgaggtgtg tggacgaaag ggagagggaa gagggagtgg gtggccgctg tagagaacac   1740
ggtcgggtgc agtaacgaaa tggcccgcat ggtggtggcc gccgtggccg tgatggccgt   1800
gctgtcggtg gccctggccc agttcattcc ggacgtggac attacgtgga aggtgccgat   1860
gacgctgacg gtgcagaacc tgtcgatttt cacgggcccg aaccagttcg gccgcggcat   1920
tccgtcgccg tcggccattg gcggcggcaa cggcctggac attgtgggcg gcggcggctc   1980
gctgtacatt tcgccgacgg gcggccaggt gcagtactcg cgcggctcga caacttcgg   2040
caaccaggtg gccttcacgc gcgtgcgcaa gaacggcaac aacgagtcgg acttcgccac   2100
ggtgttcgtg ggcggcacga cgccgtcgtt cgtgattgtg ggcgactcga cggagaacga   2160
ggtgtcgttc tggacgaaca acaaggtggt ggtgaactcg cagggcttca ttccgccgaa   2220
cggcaactcg gccggcggca actcgcagta cacgttcgtg aacggcatta cgggcacggc   2280
cggcgccccg gtgggcggca cggtgattcg ccaggtgtcg gcctggcgcg agattttcaa   2340
cacggccggc aactgcgtga agtcgttcgg cctggtggtg cgcggcacgg gcaaccaggg   2400
cctggtgcag ggcgtggagt acgacggcta cgtggccatt gactcgaacg gctcgttcgc   2460
catttcgggc tactcgccgg ccgtgaacaa cgccccgggc ttcggcaaga acttcgccgc   2520
cgcccgcacg ggcaacttct cgccgtgtc gtcggagtcg ggcgtgattg tgatgtcgat   2580
tccggtggac aacgccggct gcacgctgtc gttctcggtg gcctacacga ttacgccggg   2640
cgccggccgc gtgtcgggcg tgtcgctggc ccaggacaac gagttctacg ccgccgtggg   2700
cattccgggc gccggcccgg gcgaggtgcg catttaccgc ctggacggcg gcggcgccac   2760
gacgctggtg cagacgctgt cgccgccgga cgacattccg gagctgccga ttgtggccaa   2820
```

```
ccagcgcttc ggcgagatgg tgcgcttcgg cgccaactcg gagacgaact acgtggccgt    2880
gggctcgccg ggctacgccg ccagggcct ggccctgttc tacacggccg agccgggcct    2940
gacgccgaac gacccggacg agggcctgct gacgctgctg gcctactcga actcgtcgga    3000
gattccggcc aacggcggcc tgggcgagtt catgacggcc tcgaactgcc gcagttcgt    3060 gttcggcgag ccgtcggtgg actcggtggt gacgttcctg gcctcgattg gcgcctacta    3120
cgaggactac tgcacgtgcg agcgcgagaa cattttcgac cagggcatta tgttcccggt    3180
gccgaacttc ccgggcgagt cgccgacgac gtgccgctcg tcgatttacg agttccgctt    3240
caactgcctg atggagggcg ccccgtcgat ttgcacgtac tcggagcgcc cgacgtacga    3300
gtggacggag gaggtggtgg acccggacaa cacgccgtgc gagctggtgt cgcgcattca    3360
gcgccgcctg tcgcagtcga actgcttcca ggactacgtg acgctgcagg tggtgggcgc    3420
cggcgccggc atggccacga aggccgtgtg cgtgctgaag ggcgacggcc cggtgcaggg    3480
cattattaac ttcgagcaga aggagtcgaa cggcccggtg aaggtgtggg gctcgattaa    3540
gggcctgacg gagggcctgc acggcttcca cgtgcacgag ttcggcgaca cacggccgg    3600 ctgcacgtcg gccggcccgc acttcaaccc gctgtcgcgc aagcacggcg gcccgaagga    3660
cgaggagcgc cacgtgggcg acctgggcaa cgtgacggcc gacaaggacg gcgtggccga    3720
cgtgtcgatt gaggactcgg tgatttcgct gtcgggcgac cactgcatta ttggccgcac    3780
gctggtggtg cacgagaagg ccgacgacct gggcaagggc ggcaacgagg agtcgacgaa    3840
gacgggcaac gccggctcgc gcctggcctg cggcgtgatt ggcattgccc agtaatttct    3900
ccataataat gtgtgagtag ttcccagata agggaattag ggttcctata gggtttcgct    3960
catgtgttga gcatataaga aacccttagt atgtatttgt atttgtaaaa tacttctatc    4020
aataaaattt ctaattccta aaaccaaaat ccagtactaa aatccagatc ccccgaatta    4080
```

<210> SEQ ID NO 37
<211> LENGTH: 408
<212> TYPE: DNA
<213> ORGANISM: Artificial
<220> FEATURE:
<223> OTHER INFORMATION: Synthetic ble cDNA with small flanking regions on both sides

<400> SEQUENCE: 37

```
atacgacaag gtgaggaact aaaccatggc caagttgacc agtgccgttc cggtgctcac     60
cgcgcgcgac gtcgccggag cgtcgagtt ctggaccgac cggctcgggt tctcccggga    120
cttcgtggag gacgacttcg ccggtgtggt ccggacgac gtgaccctgt tcatcagcgc    180
ggtccaggac caggtggtgc cggacaacac cctggcctgg gtgtgggtgc gcggcctgga    240
cgagctgtac gccgagtggt cggaggtcgt gtccacgaac ttcccgggacg cctccgggcc    300 ggccatgacc gagatcggcg agcagccgtg ggggcgggag ttcgccctgc gcgacccggc    360
cggcaactgc gtgcacttcg tggccgagga gcaggactga cacggacc                 408
```

<210> SEQ ID NO 38
<211> LENGTH: 534
<212> TYPE: PRT
<213> ORGANISM: Artificial
<220> FEATURE:
<223> OTHER INFORMATION: Synthetic chlorella hexose transporter from Q39525 Parachlorella kessleri

<400> SEQUENCE: 38

Met Ala Gly Gly Ala Ile Val Ala Ser Gly Gly Ala Ser Arg Ser Ser

-continued

```
1               5                   10                  15
Glu Tyr Gln Gly Gly Leu Thr Ala Tyr Val Leu Leu Val Ala Leu Val
                20                  25                  30

Ala Ala Cys Gly Gly Met Leu Leu Gly Tyr Asp Asn Gly Val Thr Gly
                35                  40                  45

Gly Val Ala Ser Met Glu Gln Phe Glu Arg Lys Phe Phe Pro Asp Val
            50                  55                  60

Tyr Glu Lys Lys Gln Gln Ile Val Glu Thr Ser Pro Tyr Cys Thr Tyr
65                  70                  75                  80

Asp Asn Pro Lys Leu Gln Leu Phe Val Ser Ser Leu Phe Leu Ala Gly
                85                  90                  95

Leu Ile Ser Cys Ile Phe Ser Ala Trp Ile Thr Arg Asn Trp Gly Arg
                100                 105                 110

Lys Ala Ser Met Gly Ile Gly Gly Ile Phe Phe Ile Ala Ala Gly Gly
                115                 120                 125

Leu Val Asn Ala Phe Ala Gln Asp Ile Ala Met Leu Ile Val Gly Arg
            130                 135                 140

Val Leu Leu Gly Phe Gly Val Gly Leu Gly Ser Gln Val Val Pro Gln
145                 150                 155                 160

Tyr Leu Ser Glu Val Ala Pro Phe Ser His Arg Gly Met Leu Asn Ile
                165                 170                 175

Gly Tyr Gln Leu Phe Val Thr Ile Gly Ile Leu Ile Ala Gly Leu Val
                180                 185                 190

Asn Tyr Gly Val Arg Asn Trp Asp Asn Gly Trp Arg Leu Ser Leu Gly
                195                 200                 205

Leu Ala Ala Val Pro Gly Leu Ile Leu Leu Gly Ala Ile Val Leu
210                 215                 220

Pro Glu Ser Pro Asn Phe Leu Val Glu Lys Gly Arg Thr Asp Gln Gly
225                 230                 235                 240

Arg Arg Ile Leu Glu Lys Leu Arg Gly Thr Ser His Val Glu Ala Glu
                245                 250                 255

Phe Ala Asp Ile Val Ala Ala Val Glu Ile Ala Arg Pro Ile Thr Met
            260                 265                 270

Arg Gln Ser Trp Arg Ser Leu Phe Thr Arg Arg Tyr Met Pro Gln Leu
                275                 280                 285

Leu Thr Ser Phe Val Ile Gln Phe Phe Gln Gln Phe Thr Gly Ile Asn
            290                 295                 300

Ala Ile Ile Phe Tyr Val Pro Val Leu Phe Ser Ser Leu Gly Ser Ala
305                 310                 315                 320

Ser Ser Ala Ala Leu Leu Asn Thr Val Val Val Gly Ala Val Asn Val
                325                 330                 335

Gly Ser Thr Met Ile Ala Val Leu Leu Ser Asp Lys Phe Gly Arg Arg
            340                 345                 350

Phe Leu Leu Ile Glu Gly Gly Ile Thr Cys Cys Leu Ala Met Leu Ala
                355                 360                 365

Ala Gly Ile Thr Leu Gly Val Glu Phe Gly Gln Tyr Gly Thr Glu Asp
            370                 375                 380

Leu Pro His Pro Val Ser Ala Gly Val Leu Ala Val Ile Cys Ile Phe
385                 390                 395                 400

Ile Ala Gly Phe Ala Trp Ser Trp Gly Pro Met Gly Trp Leu Ile Pro
                405                 410                 415

Ser Glu Ile Phe Thr Leu Glu Thr Arg Pro Ala Gly Thr Ala Val Ala
            420                 425                 430
```

```
Val Met Gly Asn Phe Leu Phe Ser Phe Val Ile Gly Gln Ala Phe Val
            435                 440                 445

Ser Met Leu Cys Ala Met Lys Phe Gly Val Phe Leu Phe Phe Ala Gly
        450                 455                 460

Trp Leu Val Ile Met Val Leu Cys Ala Ile Phe Leu Leu Pro Glu Thr
465                 470                 475                 480

Lys Gly Val Pro Ile Glu Arg Val Gln Ala Leu Tyr Ala Arg His Trp
                485                 490                 495

Phe Trp Lys Lys Val Met Gly Pro Ala Ala Gln Glu Ile Ile Ala Glu
            500                 505                 510

Asp Glu Lys Arg Val Ala Ala Ser Gln Ala Ile Met Lys Glu Glu Arg
            515                 520                 525

Ile Ser Gln Thr Met Lys
            530
```

<210> SEQ ID NO 39
<211> LENGTH: 541
<212> TYPE: PRT
<213> ORGANISM: Artificial
<220> FEATURE:
<223> OTHER INFORMATION: Synthetic yeast hxt2 from P23585
      Saccharomyces cerevisiae

<400> SEQUENCE: 39

```
Met Ser Glu Phe Ala Thr Ser Arg Val Glu Ser Gly Ser Gln Gln Thr
1               5                   10                  15

Ser Ile His Ser Thr Pro Ile Val Gln Lys Leu Glu Thr Asp Glu Ser
            20                  25                  30

Pro Ile Gln Thr Lys Ser Glu Tyr Thr Asn Ala Glu Leu Pro Ala Lys
        35                  40                  45

Pro Ile Ala Ala Tyr Trp Thr Val Ile Cys Leu Cys Leu Met Ile Ala
    50                  55                  60

Phe Gly Gly Phe Val Phe Gly Trp Asp Thr Gly Thr Ile Ser Gly Phe
65                  70                  75                  80

Val Asn Gln Thr Asp Phe Lys Arg Arg Phe Gly Gln Met Lys Ser Asp
            85                  90                  95

Gly Thr Tyr Tyr Leu Ser Asp Val Arg Thr Gly Leu Ile Val Gly Ile
            100                 105                 110

Phe Asn Ile Gly Cys Ala Phe Gly Gly Leu Thr Leu Gly Arg Leu Gly
        115                 120                 125

Asp Met Tyr Gly Arg Arg Ile Gly Leu Met Cys Val Val Leu Val Tyr
    130                 135                 140

Ile Val Gly Ile Val Ile Gln Ile Ala Ser Ser Asp Lys Trp Tyr Gln
145                 150                 155                 160

Tyr Phe Ile Gly Arg Ile Ile Ser Gly Met Gly Val Gly Gly Ile Ala
                165                 170                 175

Val Leu Ser Pro Thr Leu Ile Ser Glu Thr Ala Pro Lys His Ile Arg
            180                 185                 190

Gly Thr Cys Val Ser Phe Tyr Gln Leu Met Ile Thr Leu Gly Ile Phe
        195                 200                 205

Leu Gly Tyr Cys Thr Asn Tyr Gly Thr Lys Asp Tyr Ser Asn Ser Val
    210                 215                 220

Gln Trp Arg Val Pro Leu Gly Leu Asn Phe Ala Phe Ala Ile Phe Met
225                 230                 235                 240

Ile Ala Gly Met Leu Met Val Pro Glu Ser Pro Arg Phe Leu Val Glu
```

245                 250                 255
Lys Gly Arg Tyr Glu Asp Ala Lys Arg Ser Leu Ala Lys Ser Asn Lys
            260                 265                 270

Val Thr Ile Glu Asp Pro Ser Ile Val Ala Glu Met Asp Thr Ile Met
        275                 280                 285

Ala Asn Val Glu Thr Glu Arg Leu Ala Gly Asn Ala Ser Trp Gly Glu
    290                 295                 300

Leu Phe Ser Asn Lys Gly Ala Ile Leu Pro Arg Val Ile Met Gly Ile
305                 310                 315                 320

Met Ile Gln Ser Leu Gln Gln Leu Thr Gly Asn Asn Tyr Phe Phe Tyr
            325                 330                 335

Tyr Gly Thr Thr Ile Phe Asn Ala Val Gly Met Lys Asp Ser Phe Gln
        340                 345                 350

Thr Ser Ile Val Leu Gly Ile Val Asn Phe Ala Ser Thr Phe Val Ala
    355                 360                 365

Leu Tyr Thr Val Asp Lys Phe Gly Arg Arg Lys Cys Leu Leu Gly Gly
370                 375                 380

Ser Ala Ser Met Ala Ile Cys Phe Val Ile Phe Ser Thr Val Gly Val
385                 390                 395                 400

Thr Ser Leu Tyr Pro Asn Gly Lys Asp Gln Pro Ser Ser Lys Ala Ala
                405                 410                 415

Gly Asn Val Met Ile Val Phe Thr Cys Leu Phe Ile Phe Phe Phe Ala
            420                 425                 430

Ile Ser Trp Ala Pro Ile Ala Tyr Val Ile Val Ala Glu Ser Tyr Pro
        435                 440                 445

Leu Arg Val Lys Asn Arg Ala Met Ala Ile Ala Val Gly Ala Asn Trp
    450                 455                 460

Ile Trp Gly Phe Leu Ile Gly Phe Phe Thr Pro Phe Ile Thr Ser Ala
465                 470                 475                 480

Ile Gly Phe Ser Tyr Gly Tyr Val Phe Met Gly Cys Leu Val Phe Ser
            485                 490                 495

Phe Phe Tyr Val Phe Phe Phe Val Cys Glu Thr Lys Gly Leu Thr Leu
        500                 505                 510

Glu Glu Val Asn Glu Met Tyr Val Glu Gly Val Lys Pro Trp Lys Ser
    515                 520                 525

Gly Ser Trp Ile Ser Lys Glu Lys Arg Val Ser Glu Glu
530                 535                 540

<210> SEQ ID NO 40
<211> LENGTH: 492
<212> TYPE: PRT
<213> ORGANISM: Artificial
<220> FEATURE:
<223> OTHER INFORMATION: Synthetic human GLUT1 from AAA52571 Homo
      sapiens

<400> SEQUENCE: 40

Met Glu Pro Ser Ser Lys Lys Leu Thr Gly Arg Leu Met Leu Ala Val
1               5                   10                  15

Gly Gly Ala Val Leu Gly Ser Leu Gln Phe Gly Tyr Asn Thr Gly Val
            20                  25                  30

Ile Asn Ala Pro Gln Lys Val Ile Glu Glu Phe Tyr Asn Gln Thr Trp
        35                  40                  45

Val His Arg Tyr Gly Glu Ser Ile Leu Pro Thr Thr Leu Thr Thr Leu
    50                  55                  60

```
Trp Ser Leu Ser Val Ala Ile Phe Ser Val Gly Met Ile Gly Ser
 65                  70                  75                  80

Phe Ser Val Gly Leu Phe Val Asn Arg Phe Gly Arg Arg Asn Ser Met
                 85                  90                  95

Leu Met Met Asn Leu Leu Ala Phe Val Ser Ala Val Leu Met Gly Phe
                100                 105                 110

Ser Lys Leu Gly Lys Ser Phe Glu Met Leu Ile Leu Gly Arg Phe Ile
            115                 120                 125

Ile Gly Val Tyr Cys Gly Leu Thr Thr Gly Phe Val Pro Met Tyr Val
        130                 135                 140

Gly Glu Val Ser Pro Thr Ala Phe Arg Gly Ala Leu Gly Thr Leu His
145                 150                 155                 160

Gln Leu Gly Ile Val Val Gly Ile Leu Ile Ala Gln Val Phe Gly Leu
                165                 170                 175

Asp Ser Ile Met Gly Asn Lys Asp Leu Trp Pro Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
210                 215                 220

Lys Ser Val Leu Lys Lys Leu Arg Gly Thr Ala Asp Val Thr His Asp
225                 230                 235                 240

Leu Gln Glu Met Lys Glu Glu Ser Arg Gln Met Met Arg Glu Lys Lys
                245                 250                 255

Val Thr Ile Leu Glu Leu Phe Arg Ser Pro Ala Tyr Arg Gln Pro Ile
            260                 265                 270

Leu Ile Ala Val Val Leu Gln Leu Ser Gln Gln Leu Ser Gly Ile Asn
        275                 280                 285

Ala Val Phe Tyr Tyr Ser Thr Ser Ile Phe Glu Lys Ala Gly Val Gln
        290                 295                 300

Gln Pro Val Tyr Ala Thr Ile Gly Ser Gly Ile Val Asn Thr Ala Phe
305                 310                 315                 320

Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
            340                 345                 350

Ile Ala Leu Ala Leu Leu Glu Gln Leu Pro Trp Met Ser Tyr Leu Ser
        355                 360                 365

Ile Val Ala Ile Phe Gly Phe Val Ala Phe Phe Glu Val Gly Pro Gly
        370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
                405                 410                 415

Ile Val Gly Met Cys Phe Gln Tyr Val Glu Gln Leu Cys Gly Pro Tyr
            420                 425                 430

Val Phe Ile Ile Phe Thr Val Leu Leu Val Leu Phe Phe Ile Phe Thr
        435                 440                 445

Tyr Phe Lys Val Pro Glu Thr Lys Gly Arg Thr Phe Asp Glu Ile Ala
        450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
```

```
                        485                 490

<210> SEQ ID NO 41
<211> LENGTH: 36
<212> TYPE: PRT
<213> ORGANISM: Artificial
<220> FEATURE:
<223> OTHER INFORMATION: Synthetic flexible linker

<400> SEQUENCE: 41

Thr Ser Thr Ser Lys Ala Ser Thr Thr Thr Ser Ser Lys Thr Thr
1               5                   10                  15

Thr Thr Ser Ser Lys Thr Thr Thr Thr Ser Lys Thr Ser Thr Thr
            20                  25                  30

Ser Ser Ser Thr
        35

<210> SEQ ID NO 42
<211> LENGTH: 8
<212> TYPE: PRT
<213> ORGANISM: Artificial
<220> FEATURE:
<223> OTHER INFORMATION: Synthetic peptide

<400> SEQUENCE: 42

Leu Glu Ser Thr Pro Lys Met Lys
1               5

<210> SEQ ID NO 43
<211> LENGTH: 7
<212> TYPE: PRT
<213> ORGANISM: Artificial
<220> FEATURE:
<223> OTHER INFORMATION: Synthetic peptide

<400> SEQUENCE: 43

Leu Glu Ser Thr Pro Lys Met
1               5

<210> SEQ ID NO 44
<211> LENGTH: 7
<212> TYPE: PRT
<213> ORGANISM: Artificial
<220> FEATURE:
<223> OTHER INFORMATION: Synthetic peptide

<400> SEQUENCE: 44

Phe Thr Gln Ser Leu Pro Pro
1               5

<210> SEQ ID NO 45
<211> LENGTH: 12
<212> TYPE: PRT
<213> ORGANISM: Artificial
<220> FEATURE:
<223> OTHER INFORMATION: Synthetic peptide

<400> SEQUENCE: 45

Ala Leu Pro Arg Ile Ala Asn Thr Trp Ser Pro Ser
1               5                   10

<210> SEQ ID NO 46
<211> LENGTH: 595
<212> TYPE: PRT
<213> ORGANISM: Artificial
<220> FEATURE:
```

-continued

<223> OTHER INFORMATION: Synthetic skin binding fusion with linker

<400> SEQUENCE: 46

```
Met Ala Arg Met Val Val Ala Ala Val Ala Val Met Ala Val Leu Ser
1               5                   10                  15

Val Ala Leu Ala Gln Phe Ile Pro Asp Val Asp Ile Thr Trp Lys Val
            20                  25                  30

Pro Met Thr Leu Thr Val Gln Asn Leu Ser Ile Phe Thr Gly Pro Asn
        35                  40                  45

Gln Phe Gly Arg Gly Ile Pro Ser Pro Ser Ala Ile Gly Gly Gly Asn
    50                  55                  60

Gly Leu Asp Ile Val Gly Gly Gly Gly Ser Leu Tyr Ile Ser Pro Thr
65                  70                  75                  80

Gly Gly Gln Val Gln Tyr Ser Arg Gly Ser Asn Asn Phe Gly Asn Gln
                85                  90                  95

Val Ala Phe Thr Arg Val Arg Lys Asn Gly Asn Asn Glu Ser Asp Phe
            100                 105                 110

Ala Thr Val Phe Val Gly Gly Thr Thr Pro Ser Phe Val Ile Val Gly
        115                 120                 125

Asp Ser Thr Glu Asn Glu Val Ser Phe Trp Thr Asn Asn Lys Val Val
    130                 135                 140

Val Asn Ser Gln Gly Phe Ile Pro Pro Asn Gly Asn Ser Ala Gly Gly
145                 150                 155                 160

Asn Ser Gln Tyr Thr Phe Val Asn Gly Ile Thr Gly Thr Ala Gly Ala
                165                 170                 175

Pro Val Gly Gly Thr Val Ile Arg Gln Val Ser Ala Trp Arg Glu Ile
            180                 185                 190

Phe Asn Thr Ala Gly Asn Cys Val Lys Ser Phe Gly Leu Val Val Arg
        195                 200                 205

Gly Thr Gly Asn Gln Gly Leu Val Gln Gly Val Glu Tyr Asp Gly Tyr
    210                 215                 220

Val Ala Ile Asp Ser Asn Gly Ser Phe Ala Ile Ser Gly Tyr Ser Pro
225                 230                 235                 240

Ala Val Asn Asn Ala Pro Gly Phe Gly Lys Asn Phe Ala Ala Ala Arg
                245                 250                 255

Thr Gly Asn Phe Phe Ala Val Ser Ser Glu Ser Gly Val Ile Val Met
            260                 265                 270

Ser Ile Pro Val Asp Asn Ala Gly Cys Thr Leu Ser Phe Ser Val Ala
        275                 280                 285

Tyr Thr Ile Thr Pro Gly Ala Gly Arg Val Ser Gly Val Ser Leu Ala
    290                 295                 300

Gln Asp Asn Glu Phe Tyr Ala Ala Val Gly Ile Pro Gly Ala Gly Pro
305                 310                 315                 320

Gly Glu Val Arg Ile Tyr Arg Leu Asp Gly Gly Gly Ala Thr Thr Leu
                325                 330                 335

Val Gln Thr Leu Ser Pro Pro Asp Asp Ile Pro Glu Leu Pro Ile Val
            340                 345                 350

Ala Asn Gln Arg Phe Gly Glu Met Val Arg Phe Gly Ala Asn Ser Glu
        355                 360                 365

Thr Asn Tyr Val Ala Val Gly Ser Pro Gly Tyr Ala Ala Glu Gly Leu
    370                 375                 380

Ala Leu Phe Tyr Thr Ala Glu Pro Gly Leu Thr Pro Asn Asp Pro Asp
385                 390                 395                 400
```

Glu Gly Leu Leu Thr Leu Leu Ala Tyr Ser Asn Ser Glu Ile Pro
                        405                 410                 415

Ala Asn Gly Gly Leu Gly Glu Phe Met Thr Ala Ser Asn Cys Arg Gln
                        420                 425                 430

Phe Val Phe Gly Glu Pro Ser Val Asp Ser Val Thr Phe Leu Ala
                        435                 440                 445

Ser Ile Gly Ala Tyr Tyr Glu Asp Tyr Cys Thr Cys Glu Arg Asn
                450                 455                 460

Ile Phe Asp Gln Gly Ile Met Phe Pro Val Pro Asn Phe Pro Gly Glu
            465                 470                 475                 480

Ser Pro Thr Thr Cys Arg Ser Ser Ile Tyr Glu Phe Arg Phe Asn Cys
                        485                 490                 495

Leu Met Glu Gly Ala Pro Ser Ile Cys Thr Tyr Ser Glu Arg Pro Thr
                        500                 505                 510

Tyr Glu Trp Thr Glu Glu Val Val Asp Pro Asp Asn Thr Pro Cys Glu
                        515                 520                 525

Leu Val Ser Arg Ile Gln Arg Arg Leu Ser Gln Ser Asn Cys Phe Gln
                        530                 535                 540

Asp Tyr Val Thr Leu Gln Val Val Thr Ser Thr Ser Lys Ala Ser Thr
            545                 550                 555                 560

Thr Thr Thr Ser Ser Lys Thr Thr Thr Ser Ser Lys Thr Thr Thr
                        565                 570                 575

Thr Thr Ser Lys Thr Ser Thr Thr Ser Ser Ser Thr Phe Thr Gln Ser
                        580                 585                 590

Leu Pro Pro
                595

<210> SEQ ID NO 47
<211> LENGTH: 27
<212> TYPE: DNA
<213> ORGANISM: Artificial
<220> FEATURE:
<223> OTHER INFORMATION: Synthetic primer 2040

<400> SEQUENCE: 47
gccaagttga ccagtgccgt tccggtg                                       27

<210> SEQ ID NO 48
<211> LENGTH: 26
<212> TYPE: DNA
<213> ORGANISM: Artificial
<220> FEATURE:
<223> OTHER INFORMATION: Synthetic primer 2041

<400> SEQUENCE: 48
cggctgctcg ccgatctcgg tcatgg                                        26

<210> SEQ ID NO 49
<211> LENGTH: 29
<212> TYPE: DNA
<213> ORGANISM: Artificial
<220> FEATURE:
<223> OTHER INFORMATION: Synthetic primer 2053

<400> SEQUENCE: 49
gcggtgtgat gggcgcgcac gacgccacg                                     29

<210> SEQ ID NO 50
<211> LENGTH: 22
<212> TYPE: DNA

```
<213> ORGANISM: Artificial
<220> FEATURE:
<223> OTHER INFORMATION: Synthetic primer 1987

<400> SEQUENCE: 50
agcacaatgc actggagcag cg                                            22

<210> SEQ ID NO 51
<211> LENGTH: 25
<212> TYPE: DNA
<213> ORGANISM: Artificial
<220> FEATURE:
<223> OTHER INFORMATION: Synthetic primer 1989

<400> SEQUENCE: 51
ctggtagcca atgttgagca tgccg                                         25

<210> SEQ ID NO 52
<211> LENGTH: 27
<212> TYPE: DNA
<213> ORGANISM: Artificial
<220> FEATURE:
<223> OTHER INFORMATION: Synthetic primer 1991

<400> SEQUENCE: 52
ctcaatggtc accttgttgc tcttcgc                                       27

<210> SEQ ID NO 53
<211> LENGTH: 30
<212> TYPE: DNA
<213> ORGANISM: Artificial
<220> FEATURE:
<223> OTHER INFORMATION: Synthetic primer 2058

<400> SEQUENCE: 53
gccgggtgca ctctgtcctt ctcagtggcc                                    30
```